United States Patent
Lee et al.

(10) Patent No.: US 11,759,651 B2
(45) Date of Patent: Sep. 19, 2023

(54) IN VIVO VISUALIZATION AND CONTROL OF PATHOLOGICAL CHANGES IN NEURAL CIRCUITS

(71) Applicant: THE REGENTS OF THE UNIVERSITY OF CALIFORNIA, Oakland, CA (US)

(72) Inventors: Jin Hyung Lee, Los Angeles, CA (US); Zhongnan Fang, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 894 days.

(21) Appl. No.: 16/677,407

(22) Filed: Nov. 7, 2019

(65) Prior Publication Data

US 2020/0179717 A1  Jun. 11, 2020

Related U.S. Application Data

(63) Continuation of application No. 14/343,831, filed as application No. PCT/US2012/054516 on Sep. 10, 2012, now Pat. No. 10,478,639.

(60) Provisional application No. 61/533,108, filed on Sep. 9, 2011, provisional application No. 61/533,112, filed on Sep. 9, 2011.

(51) Int. Cl.
*A61N 5/06* (2006.01)
*A61B 5/055* (2006.01)
*A61B 5/00* (2006.01)
*A61B 5/369* (2021.01)
(Continued)

(52) U.S. Cl.
CPC .......... *A61N 5/0622* (2013.01); *A61B 5/0002* (2013.01); *A61B 5/0036* (2018.08); *A61B 5/055* (2013.01); *A61B 5/1468* (2013.01); *A61B 5/369* (2021.01); *A61B 5/4094* (2013.01); *A61N 5/062* (2013.01); *G01R 33/4806* (2013.01); *A61B 5/7232* (2013.01); *A61N 2005/0626* (2013.01); *A61N 2005/0663* (2013.01)

(58) Field of Classification Search
CPC .................. A61N 5/0622; A61N 5/062; A61N 2005/0663; A61B 5/055; A61B 5/1468; A61B 5/7232; G01R 33/4806
USPC ...................................................... 607/88–92
See application file for complete search history.

(56) References Cited

U.S. PATENT DOCUMENTS 5,876,337 A * 3/1999 Tsuda ................. G01R 33/3875
                                                          324/309
6,225,804 B1 * 5/2001 Lai ..................... G01R 33/5659
                                                          324/309
(Continued)

OTHER PUBLICATIONS

Xiong J, Parsons LM, Gao JH, Fox PT. Interregional connectivity to primary motor cortex revealed using MRI resting state images. Hum Brain Mapp. 1999;8(2-3):151-6. doi: 10.1002/(sici)1097-0193(1999)8:2/3<151::aid-hbm13>3.0.co;2-5. PMID: 10524607; PMCID: PMC6873334. (Year: 1999).*

(Continued)

*Primary Examiner* — John R Downey
(74) *Attorney, Agent, or Firm* — Morgan, Lewis & Bockius LLP

(57) ABSTRACT

Neurological Disease Mechanism Analysis for Diagnosis, Drug Screening, (Deep) Brain Stimulation Therapy design (Continued)

and monitoring, Stem Cell Transplantation therapy design and monitoring, Brain Machine Interface design, control, and monitoring.

19 Claims, 56 Drawing Sheets

(51) Int. Cl.
*A61B 5/1468* (2006.01)
*G01R 33/48* (2006.01)

(56) References Cited

U.S. PATENT DOCUMENTS

| | | | |
|---|---|---|---|
| 7,024,001 B1 | 4/2006 | Nakada | |
| 7,168,807 B2* | 1/2007 | Chernyak | A61B 3/1015 351/205 |
| 7,384,145 B2 | 6/2008 | Hetling | |
| 8,519,343 B1* | 8/2013 | Mihailescu | G01T 1/1647 250/367 |
| 2002/0034472 A1* | 3/2002 | Renshaw | A61B 5/4064 424/1.11 |
| 2002/0177771 A1* | 11/2002 | Guttman | G06T 15/08 128/920 |
| 2003/0153826 A1* | 8/2003 | Jack | A61B 5/7207 600/410 |
| 2005/0085705 A1 | 4/2005 | Rao | |
| 2005/0154290 A1 | 7/2005 | Langleben | |
| 2005/0197586 A1* | 9/2005 | Pearlman | A61B 5/7267 600/509 |
| 2006/0025658 A1 | 2/2006 | Newman | |
| 2006/0155348 A1 | 7/2006 | deCharms | |
| 2006/0190044 A1 | 8/2006 | Libbus | |
| 2008/0063135 A1* | 3/2008 | DeMan | A61B 6/482 378/4 |
| 2009/0054955 A1 | 2/2009 | Kopell | |
| 2009/0062660 A1 | 3/2009 | Chance | |
| 2009/0088680 A1* | 4/2009 | Aravanis | A61K 48/0058 604/21 |
| 2009/0093403 A1 | 4/2009 | Zhang | |
| 2009/0143668 A1* | 6/2009 | Harms | A61B 5/055 600/410 |
| 2011/0040356 A1 | 2/2011 | Schiffer | |
| 2011/0046473 A1 | 2/2011 | Pradeep et al. | |
| 2011/0125078 A1* | 5/2011 | Denison | A61N 5/0622 604/20 |
| 2011/0159562 A1* | 6/2011 | Deisseroth | C12N 5/0606 435/173.8 |
| 2011/0166440 A1* | 7/2011 | Harvey | A61B 5/0013 382/131 |
| 2011/0166632 A1* | 7/2011 | Delp | A61N 5/0622 607/88 |
| 2011/0178441 A1* | 7/2011 | Tyler | A61B 5/0036 601/2 |
| 2011/0188577 A1* | 8/2011 | Kishore | H04N 19/00 375/E7.123 |
| 2011/0202745 A1 | 8/2011 | Bordawekar | |
| 2011/0301431 A1 | 12/2011 | Greicius | |
| 2012/0165904 A1* | 6/2012 | Lee | A61N 5/0622 607/90 |
| 2012/0277572 A1 | 11/2012 | Hubbard | |
| 2012/0319686 A1 | 12/2012 | Jesmanowicz | |
| 2013/0019325 A1 | 1/2013 | Deisseroth | |
| 2013/0072775 A1 | 3/2013 | Rogers | |
| 2013/0281890 A1 | 10/2013 | Mishelevich | |
| 2014/0243714 A1 | 8/2014 | Ward | |
| 2014/0364721 A1 | 12/2014 | Lee | |
| 2015/0366482 A1 | 12/2015 | Lee | |

OTHER PUBLICATIONS

Eklund, Anders et al., "fMRI analysis on the GPU-Possibilities and challenges," Computer Methods and Programs in Biomedicine, vol. 105, No. 2, Aug. 20, 2011, 18 pgs.

Eklund, Anders et al., "Fast Random Permutation Tests Enable Objective Evaluation of Methods for Single-Subject fMRI Analysis," International Journal of Biomedical Imaging, vol. 2011, Article ID 627947, Jul. 14, 2011, 16 pgs.

Gembris, Daniel et al., "Correlation analysis on GPU systems using NVIDIA's CUDA," Journal of Real-Time Image Processing, Springer-verlag, Berlin/Heidelberg, vol. 6, No. 4, Jun. 17, 2010, 6 pgs.

Lee, Office Action, U.S. Appl. No. 14/343,831, dated Jul. 26, 2016, 18 pgs.

Lee, Final Office Action, U.S. Appl. No. 14/343,831, dated May 31, 2017, 17 pgs.

Lee, Office Action, U.S. Appl. No. 14/343,831, dated Dec. 6, 2017, 19 pgs.

Lee, et al., "Global and Local FMRI signals driven by neurons defined optogenetically by type and wiring," Nature, vol. 465, No. 10, pp. 788-792, Jun. 2010.

Huang, Teng-Yi et al., "Accelerating image registration of MRI by GPU-based parallel computation," Magnetic Resonance Imaging, Elsevier Science, Tarrytown, NY, US, vol. 29, No. 5, Feb. 20, 2011, 6 pgs.

Otazo, Ricardo et al., "Combination of compressed sensing and parallel imaging for highly accelerated first-pass cardiac perfusion MRI," Magnetic Resonance in Medicine, vol. 64, No. 3, Jun. 9, 2010, pp. 767-776, XP055236486, US ISSN:0740-3194, DOI: 10.1002/MRM.22463.

The Regents of the University of California, Extended European Search Report, EP12829753.8, dated Sep. 15, 2015, 10 pgs.

The Regents of the University of California, Communication Pursuant to Article 94(3), EP12829753.8, dated Jun. 7, 2017, 10 pgs.

Xuejun Gu et al., "GPU-based fast gamma index calculation," Physics in Medicine and Biology, Institute of Physics Publishing, Bristol GB, vol. 56, No. 5, Feb. 11, 2011, 12 pgs.

Zhang et al., "Non-invasive imaging of epileptic seizures in vivo using photoacoustic tomography," Phys. Med. Biol., vol. 53, pp. 1921-1932, 2008.

Lee, Notice of Allowance, U.S. Appl. No. 14/343,831, dated Mar. 26, 2019, 5 pgs.

Lee et al., Advisory Action, U.S. Appl. No. 14/343,831, dated Aug. 14, 2018, 7 pgs.

Jan Tonnesen, Andreas T. Sorensen, Karl Deisseroth, Cecilia Lundberg, and Merab Kokaia, "Optogenetic control of epileptiform activity", PNAS, 2009, 6 pgs.

J. Lee R. Durand, V. Gradinaru, F. Zhang, D-S. Kim, and K. Deisseroth, "Optogenetic Functional Magnetic Resonance Imaging'(ofMRI): Genetically Targeted In Vivo Brain Circuit Mapping", Proc. Intl. Soc. Mag. Reson. Med. 18 (2010), 1 pg.

Lee et al., Final Office Action, U.S. Appl. No. 14/343,831, dated Apr. 19, 2018, 21 pgs.

The Regents of the University of California, Partial European Search Report, EP19214958.1, dated Aug. 7, 2020, 7 pgs.

Viviana Gradinaru, "Mechanisms of Deep Brain Stimulation Revealed By Optogenetic Deconstruction of Diseased Brain Circuitry", Jun. 2010, 159 pgs. XP055718247 https://stacks.stanford.edu/file/druid:rj878dv3879/VivianaGradinaru_PhD_Thesis_final-augmented.pdf.

* cited by examiner https://www.ncbi.nlm.nih.gov/pmc/articles/PMC3200570/ modulator: ChR2 and NpHR
reporter: XFP and MR marker
X: promoter (tunable for specific neuron type)

a)

b)

a. rt-ofMRI system architecture b. rt-ofMRI processing parallel streamline a cortex stim.

b hippocampus stim.

a motor cortex stim.

b hippocampus stim.

IN VIVO VISUALIZATION AND CONTROL OF PATHOLOGICAL CHANGES IN NEURAL CIRCUITS

CROSS-REFERENCES TO RELATED APPLICATIONS

This application a continuation application of U.S. application Ser. No. 14/343,831, filed Aug. 28, 2014, which is a national phase application of PCT application PCT/US2012/054516, filed Sep. 10, 2012, which claims the benefit of priority under 35 USC 119(e) to U.S. Ser. No. 61/533,108, filed Sep. 9, 2011 and U.S. Ser. No. 61/533,112 filed Sep. 9, 2011, herein incorporated by reference in their entireties.

GOVERNMENT FUNDING

This invention was made with Government support of Grant No. 1056008, awarded by the National Science Foundation, Grant No. 4R00EB008738, awarded by the National Institutes of Health. The Government has certain rights in this invention.

FIELD OF THE INVENTION

The present invention relates to neural circuit analysis. The present invention also relates to motion correction methods for time-series imaging and its application to optogenetic fMRI (ofMRI).

BRIEF SUMMARY OF THE INVENTION

This invention allows brain circuit to be analyzed and debugged in a systematic manner. Examples of Commercial Application: Neurological Disease Mechanism Analysis for Diagnosis, Drug Screening, (Deep) Brain Stimulation Therapy design and monitoring, Stem Cell Transplantation therapy design and monitoring, Brain Machine Interface design, control, and monitoring.

(c) Passband SSFP hemodynamic response function was measured for flip angles ranging from 20° to 70°. However, no clear difference could be observed. (d) Since no apparent difference was observed, to improve the SNR, all 6 measurements were averaged and fitted with a two-gamma function. The two-gamma function fit resulted in a T-value of 17.5494, maximum amplitude of 0.5560 at 5.55 s. Rise to half time was 2.7 s.

Figure 43:
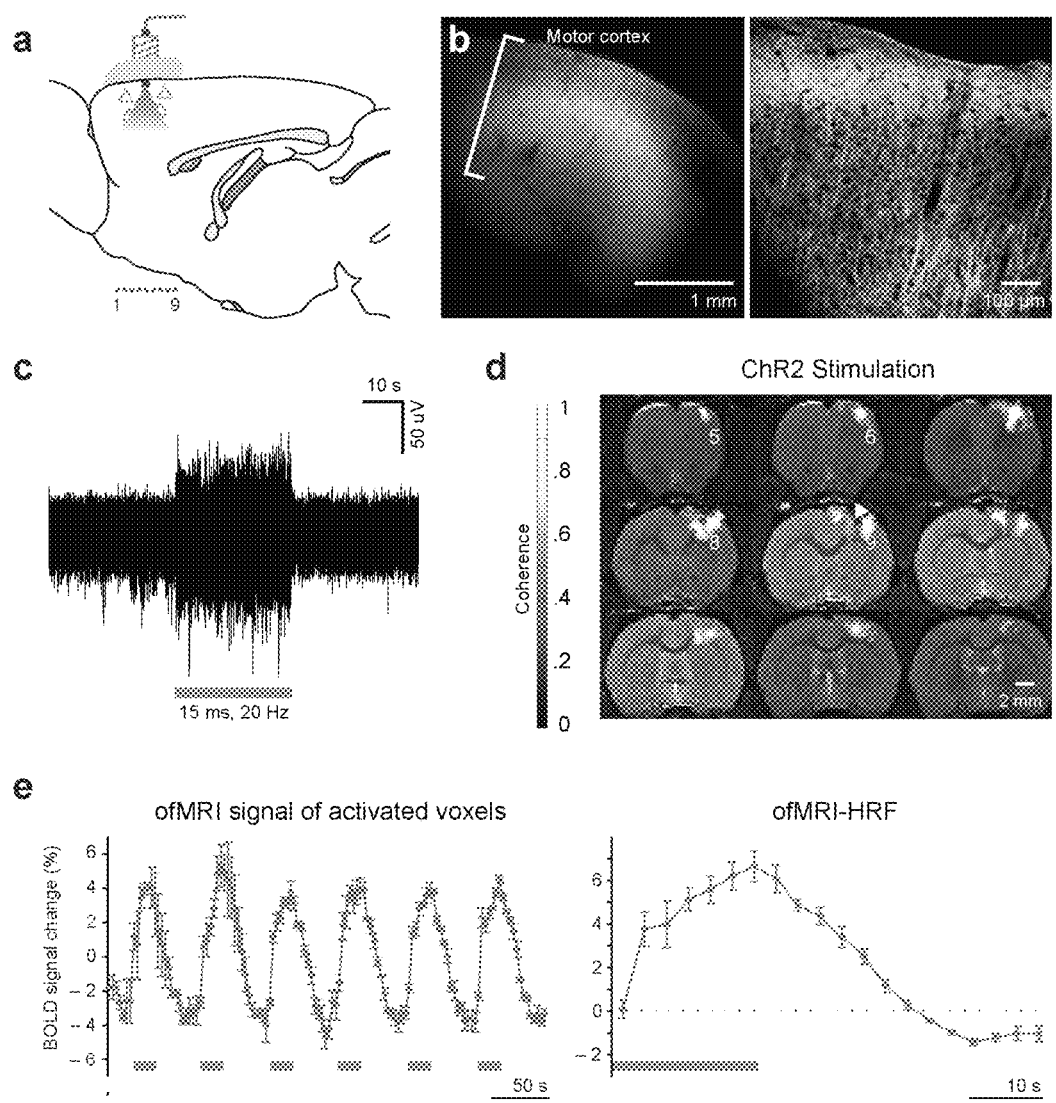

FIG. 43: ofMRI: optically-driven local excitation in defined rodent neocortical cells drives positive BOLD. a, Experimental schematic: transduced cells (triangles) and blue light delivery shown in M1 at cannula implantation and stimulation site. Coronal imaging slices shown in (d) marked as 1 . . . 9. b, Confocal images of ChR2-EYFP expression in M1 (left); higher magnification reveals transduced neuronal cell bodies and processes (right). c, Extracellular optrode recordings during 473 nm optical stimulation (20 Hz/15 ms pulsewidth). d, BOLD activation is observed at near the site of optical stimulation (right) in animals injected with AAV5-CaMKII::ChR2-EYFP ($p<0.001$; arrowhead: injection/stimulation site). Coronal slices are consecutive and 0.5 mm thick. e, ofMRI hemodynamic response during 6 consecutive epochs of optical stimulation (left); stimulus paradigm was 20 s of 20 Hz, 15 ms 473 nm light stimulation repeated every 60 s (blue bars). Hemodynamic response was averaged across all voxels with coherence coefficient>0.35 in motor cortex. Right, Mean of all stimulation epochs; baseline corresponds to mean pre-stimulation signal magnitude.

Figure 44:
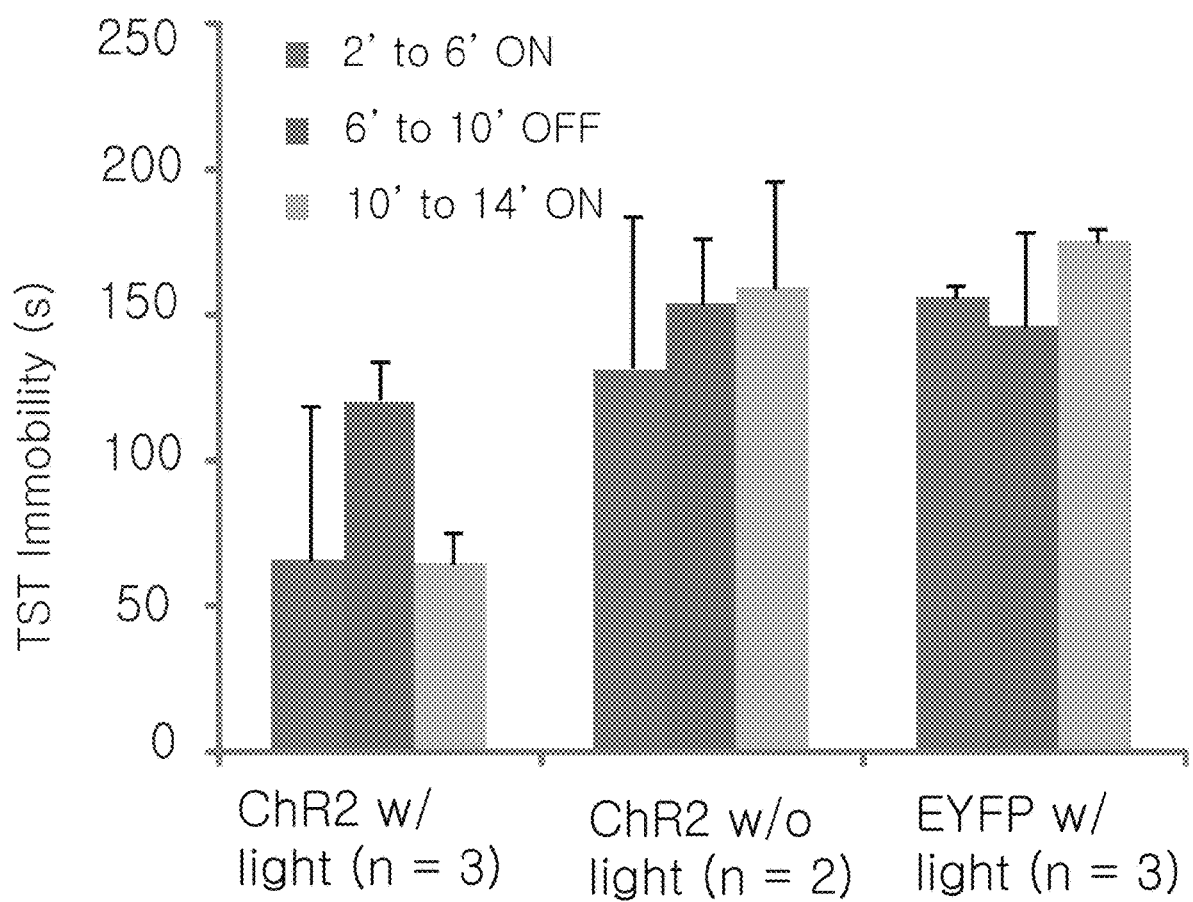

FIG. 44: The plot shows animals injected with a lentivirus carrying ChR2-EYFP or EYFP alone. The virus is specific for excitatory cells and were injected into the prefrontal cortex of C57BL/6 mice. The targeted region is the infralimbic and prelimbic prefrontal cortex. The experiment is done with fiber stimulation of the ChR2 expressing neurons during a tail-suspension test (TST). Light is turned on during 2 to 6 minutes and 10 to 14 minutes during the TST assay. Immobility during TST is reported in the plot. Error bar shows standard error of the mean.

Figure 45:
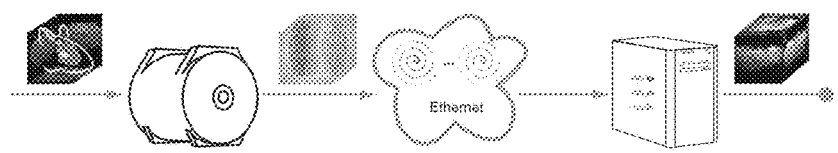
Figure 45:
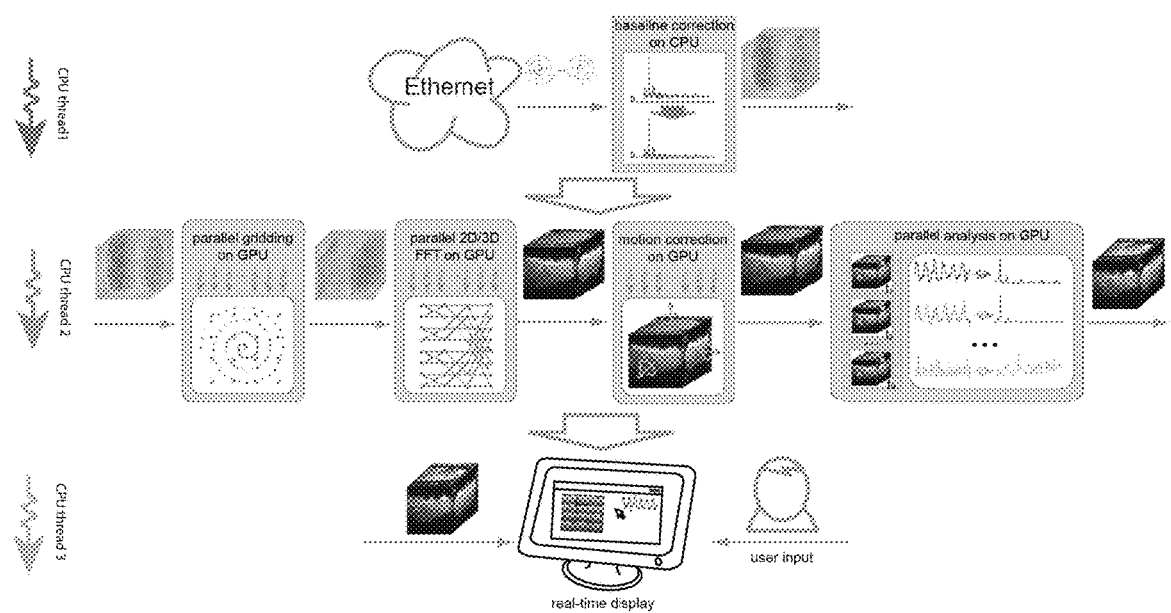

FIG. 45: Architecture of the parallel computation based real-time functional magnetic resonance imaging system. a. Real-time fMRI data acquisition, transmission and processing streamline. b. Detailed processing streamline of the system. There are three CPU threads running concurrently on the real-time processing workstation. The first thread is in charge of Ethernet communication with scanner and data preprocessing. Core processing is done on the second thread. Parallel computation on GPU is utilized by the second thread to achieve online processing. Image reconstruction, motion correction and analysis algorithms are largely paralyzed and optimized for maximum throughput. The thread 3 manages image rendering for display and handles input from users.

Figure 46:
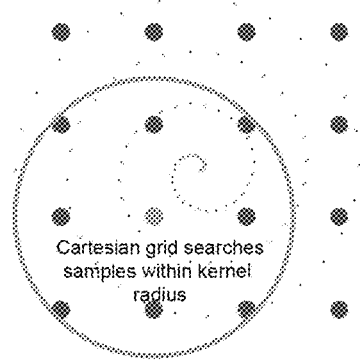

FIG. 46: Parallel grid based gridding method. Each thread on GPU is allocated a Cartesian grid. During gridding, each thread will look for spiral samples that are within the gridding kernel (the large circle in the figure). Eligible samples are then convoluted with the weighted kernel function separately and then summed together.

Figure 47:
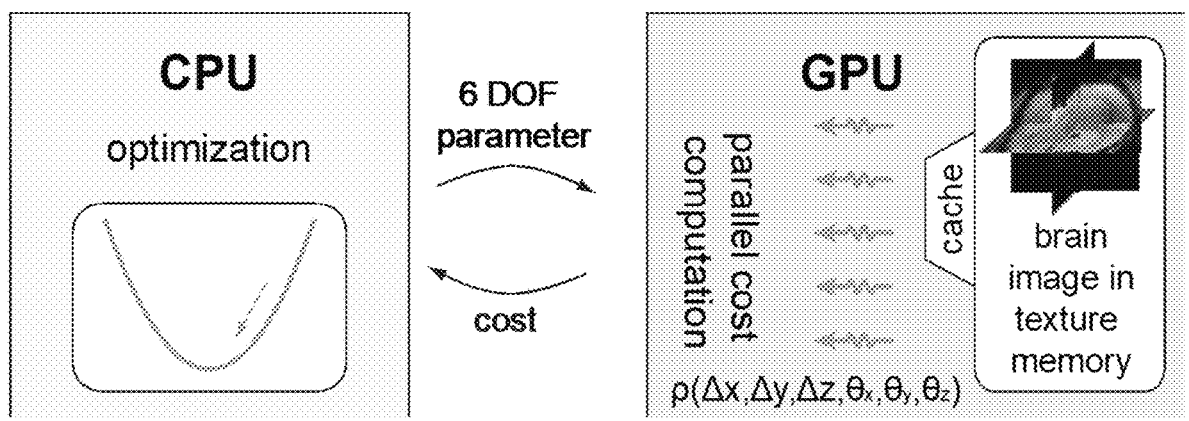

FIG. 47: GPU based parallel motion correction method. The method utilizes the GPU as a co-processor for the CPU. The CPU controls the optimization process while querying the GPU for the cost function value. The fMRI images are stored in the GPU texture memory that is cached for fast data retrieval and makes it possible to perform linear interpolation on the hardware without loss of speed. During each iteration, only motion correction parameters and cost function values are passed between the CPU and the GPU, which significantly reduces data transfer time.

Figure 48:
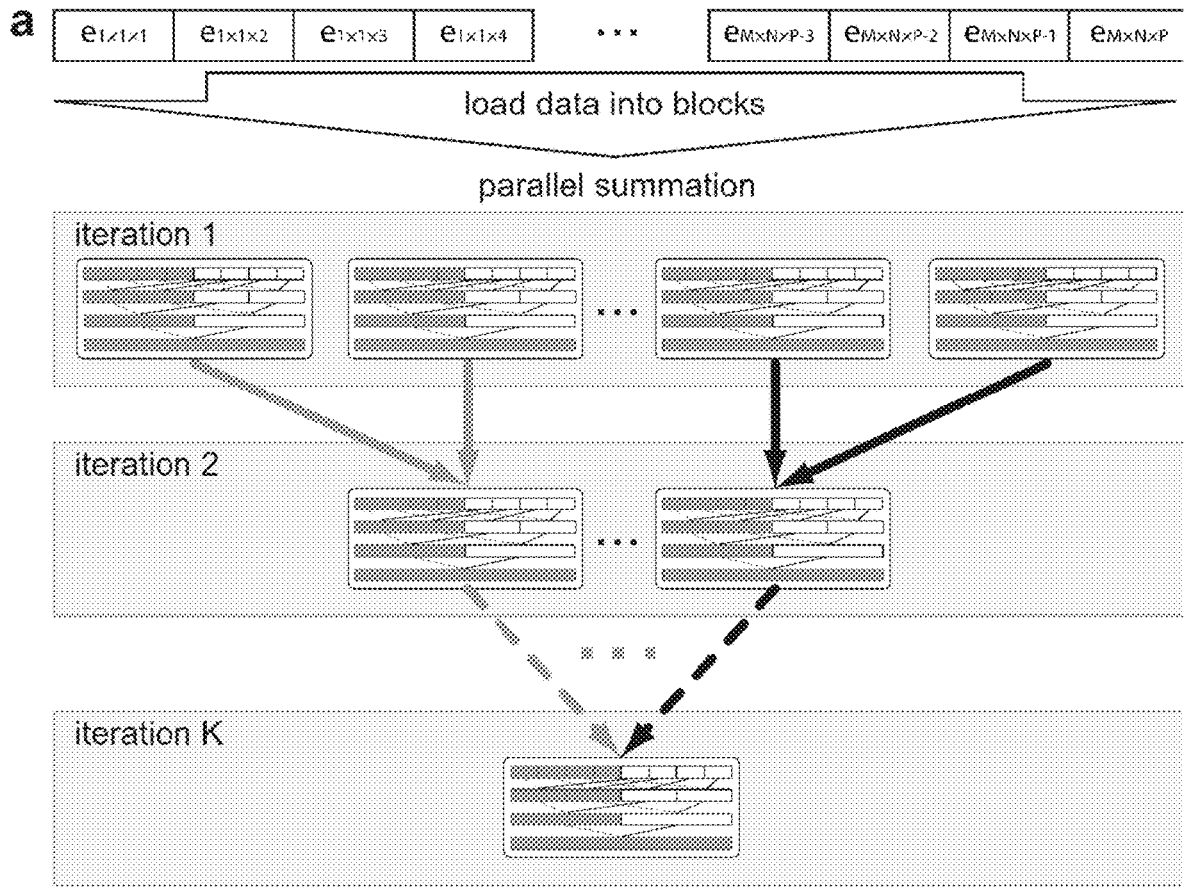
Figure 48:
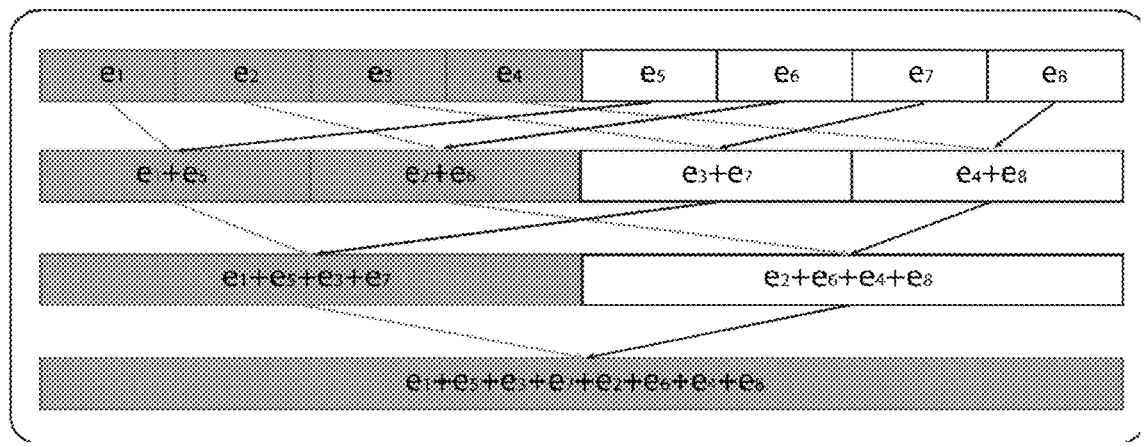

FIG. 48: Parallel GPU summation algorithm. a, Threads in the GPU are organized in blocks, and linear data (e.g. error $e_{m \times n \times p}$) are divided and allocated to each block. Each block sums the assigned data. After all blocks finish calculation, the next iteration starts and continues the summation in the same way until the final sum is calculated. Therefore, the total number of data values is required to be a power of two. b. Within each block, data values are stored and operated on shared memory. The first half of the data values are iteratively added to the second half (e.g. if eight data points are assigned to one block, the first four data points are added to the corresponding last four in parallel, in the first iteration. The iteration continues until the final convergence). By avoiding GPU thread divergence efficiency is significantly improved. Since the dimension of our error matrix between two images is 128×128×23, we allocated 2944 (128×23) blocks and 128 threads within each block. Because the number of blocks is not a power of two, after seven iterations ($2^7=128$), 23 partially summed errors remain, which are then summed on the CPU. The timing test reveals that the transfer time for 23 float variables does not add any significant overhead on the data transfer time because the transfer loading time dominates the overall transfer time when the data size is small.

Figure 49:
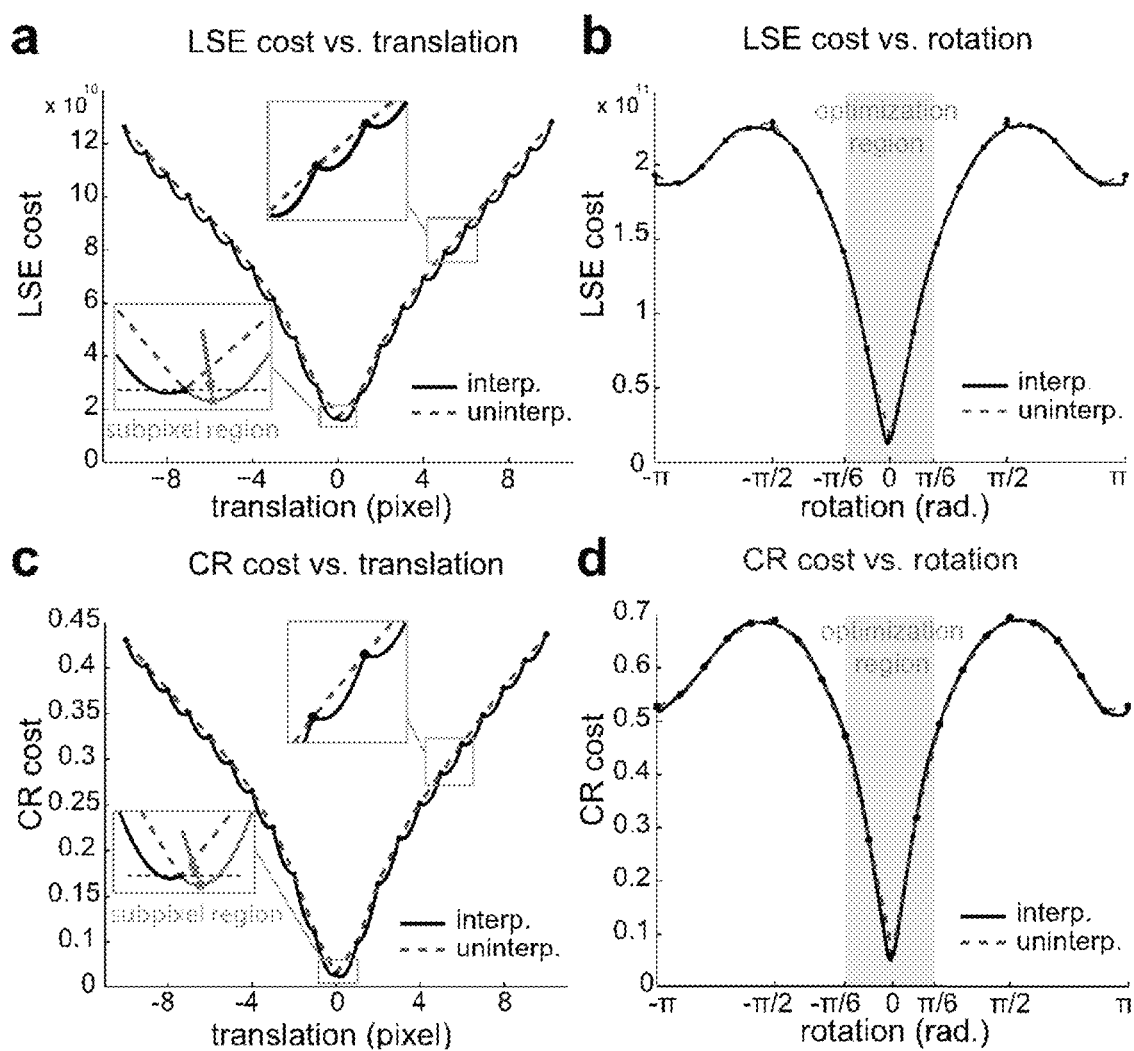

FIG. 49: Optimization in the presence of local minima introduced by interpolation. a. LSE cost variation with translation. b. LSE cost variation with rotation. c. CR cost variation with translation. d. CR cost variation with rotation. Many local minima appear in the translation vs. cost plot. To ensure that the global minimum can be reached during optimization, pixel level optimization is first conducted. This forces the optimization into the global optimal region, which is the region between the two smallest-cost pixels. Sub-pixel level optimization is then implemented to find the global minimum There are two minima for rotation. We limit our search range to $-\pi/6 - \pi/6$ to avoid the local minimum at $\pi$.

Figure 50:
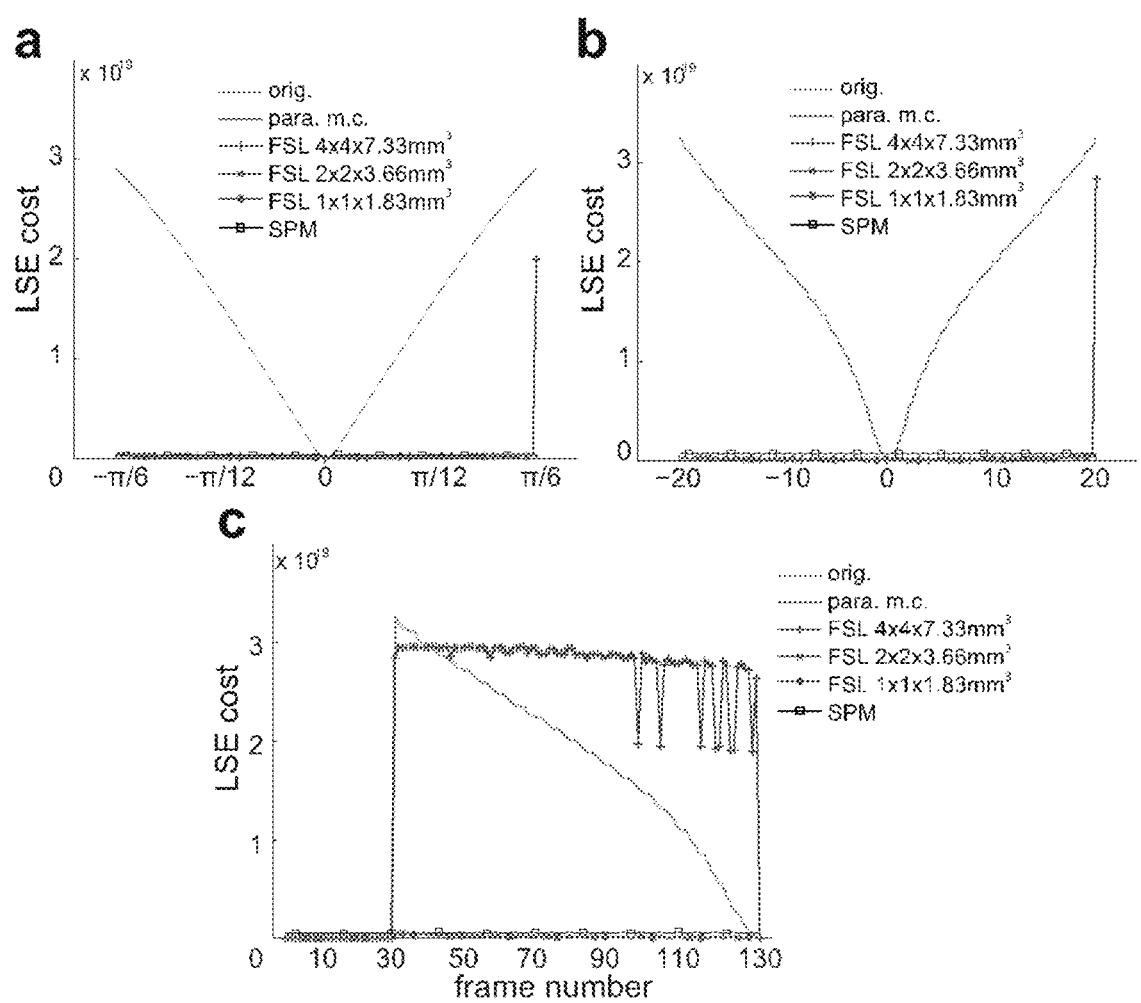

FIG. 50: Robustness test with large motion. a. The original test image has rotation from $-\pi/6$ to $\pi/6$ across 130 samples. All images, except the last frame of the 4×4×7.33 mm³ resolution FSL, are successfully corrected to their original position. b. The original test image is shifted from −20 to 20 voxels in the x-axis across 130 samples. FSL MCFLIRT gets trapped into a local minimum in the last frame of the 4×4×7.33 mm³ resolution dataset, while the parallel method and SPM successfully corrects for the motion. c. In this test image, abrupt motion is introduced at frame 30, after which the brain slowly moves back its original location. FSL MCFLIRT working at 4×4×7.33 mm³ fails to correct for the motion while FSL at lower resolution settings, SPM, and the proposed motion successfully corrects for the motion.

Figure 51:
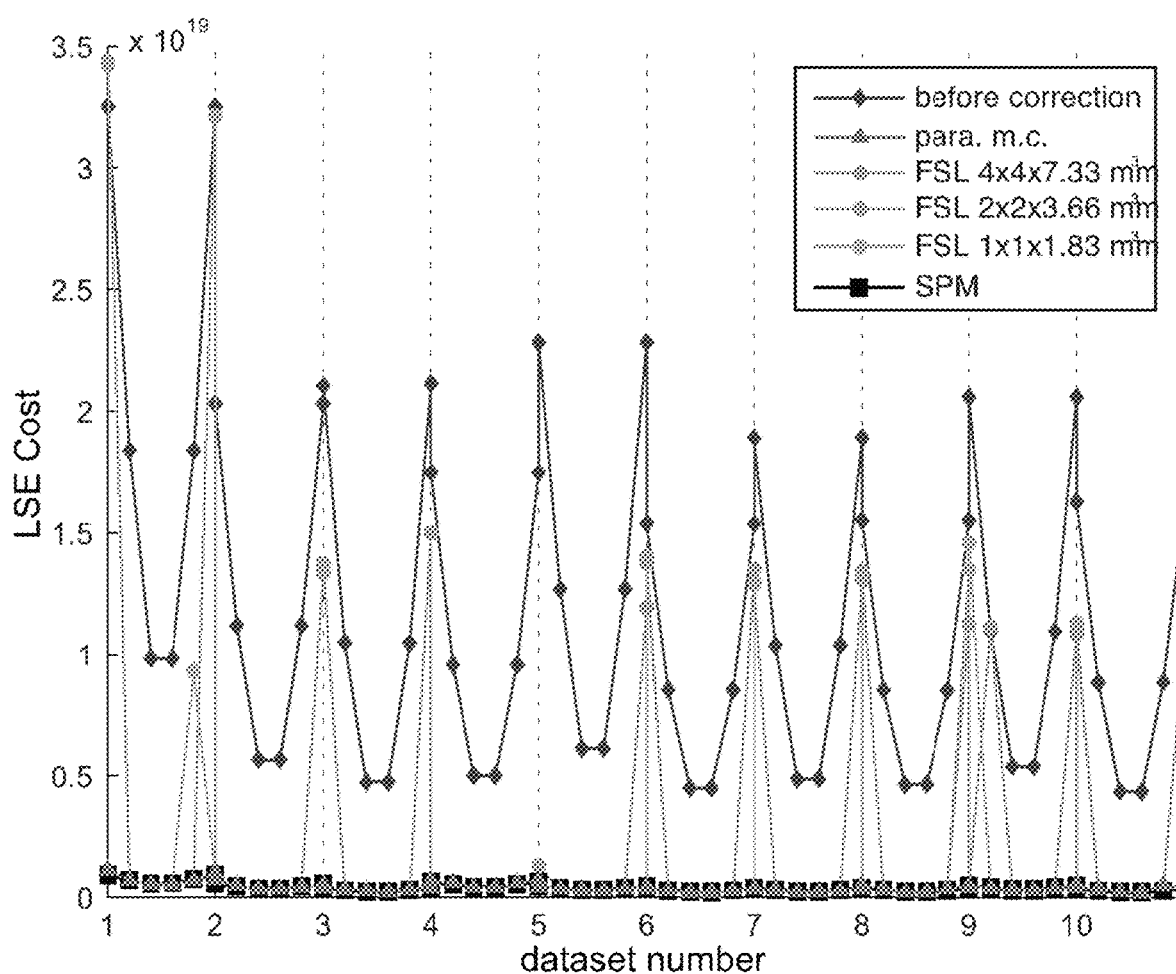

FIG. 51: Robustness test with 10 different images at 6 different rotation angles. 10 different images acquired during different experiments are rotated to six different angles around the z-axis: $-\pi/6, -\pi/12, -\pi/24, \pi/24, \pi/12, \pi/6$. Only the proposed GPU-based parallel motion correction algorithm and SPM successfully corrected all images. FSL fails in the test but shows less failure when the image is downsampled.

Figure 52:
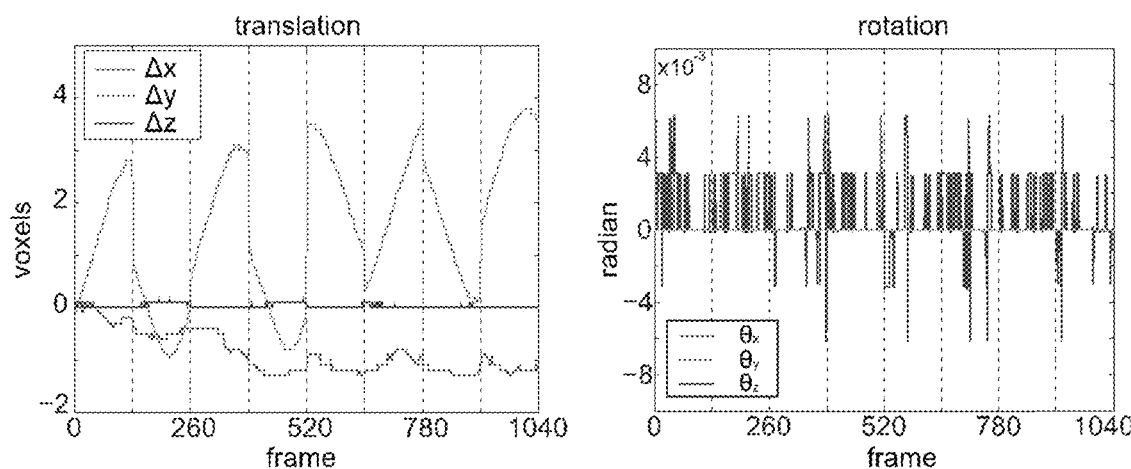
Figure 52:
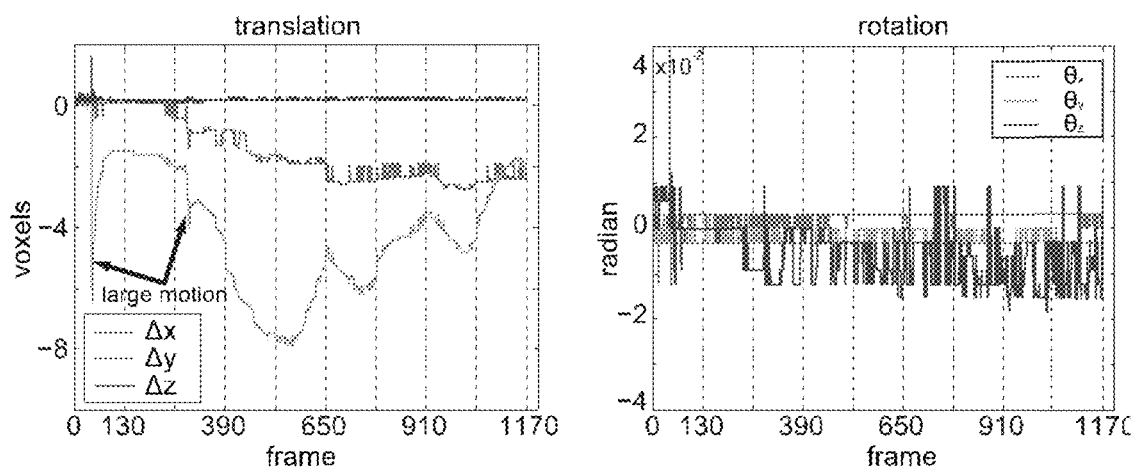

FIG. 52: Estimated motion of ofMRI datasets. a. 0.5× 0.5×0.5 mm³ resolution, motor cortex pyramidal neuron stimulated dataset with 8 repeated scans. The dataset shows drift motion in the x- and y-axes, which is introduced mainly by scanner drift. No rotational motion is observed since $\theta_x$, $\theta_y$, $\theta_z$ only fluctuated within the preset precision angles ($\pi/1000$). b. $0.357 \times 0.357 \times 0.5$ mm$^3$ resolution, hippocampal pyramidal neuron stimulated ofMRI dataset with 9 repeated scans. Two large movements (see arrows) are shown in this dataset. This can be seen from the two large dips in the translation plot.

Figure 53:
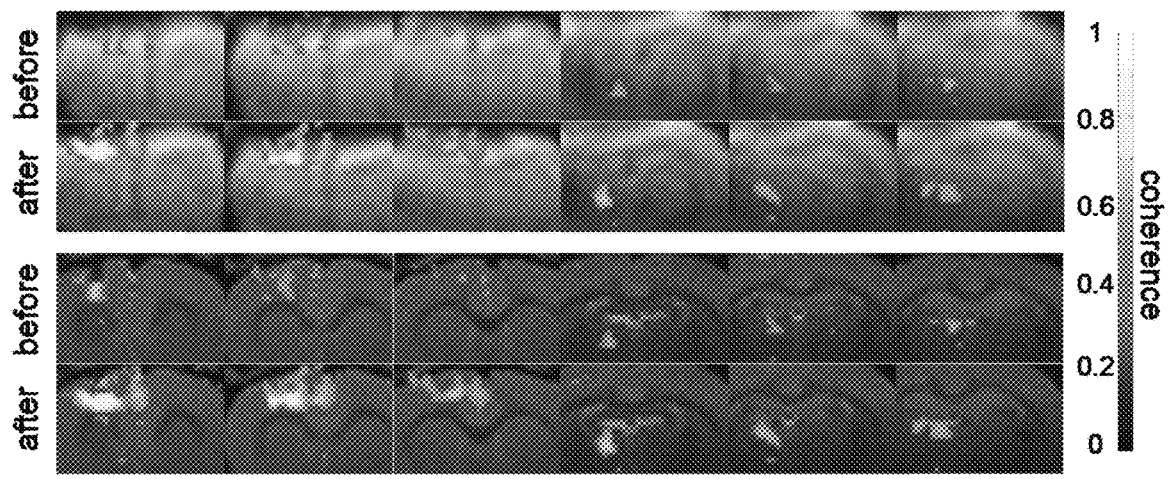
Figure 53:
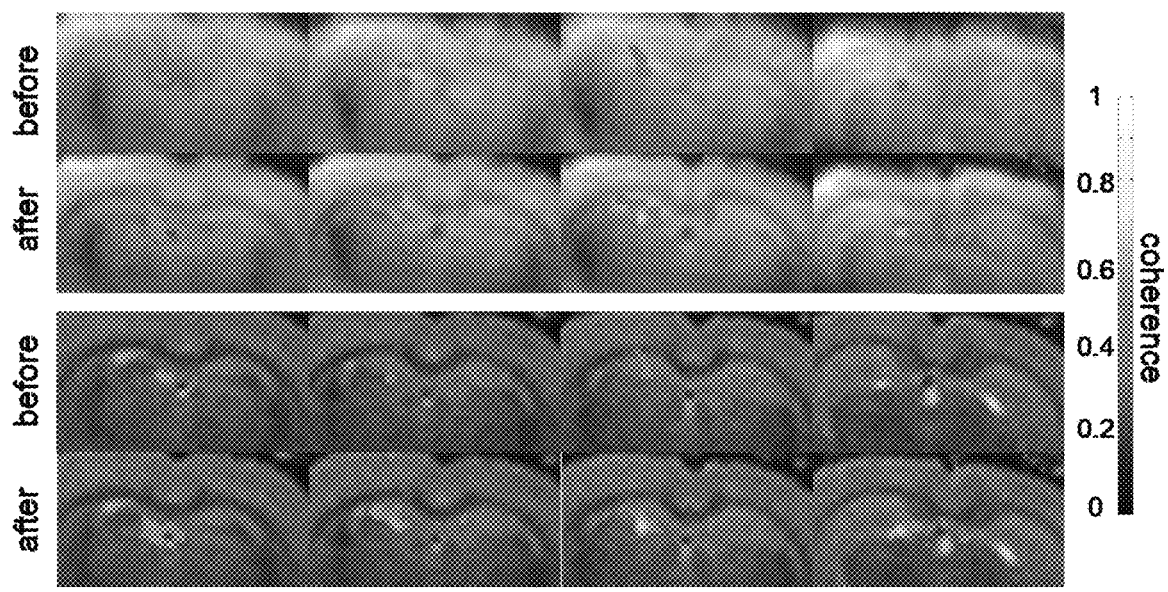

FIG. 53: ofMRI activation maps overlaid onto raw fMRI images and T2 anatomy images before and after motion correction. a. $0.5 \times 0.5 \times 0.5$ mm$^3$ resolution, motor cortex pyramidal neuron stimulated, and b. $0.357 \times 0357 \times 0.5$ mm$^3$ resolution, hippocampal pyramidal neuron stimulated ofMRI activation maps overlaid onto raw fMRI images and T2 anatomy images before and after motion correction. After correction, activated region volume and activation coefficient values are increased. Compared to uncorrected images, the corrected images are sharper and show more visible details.

Figure 54:
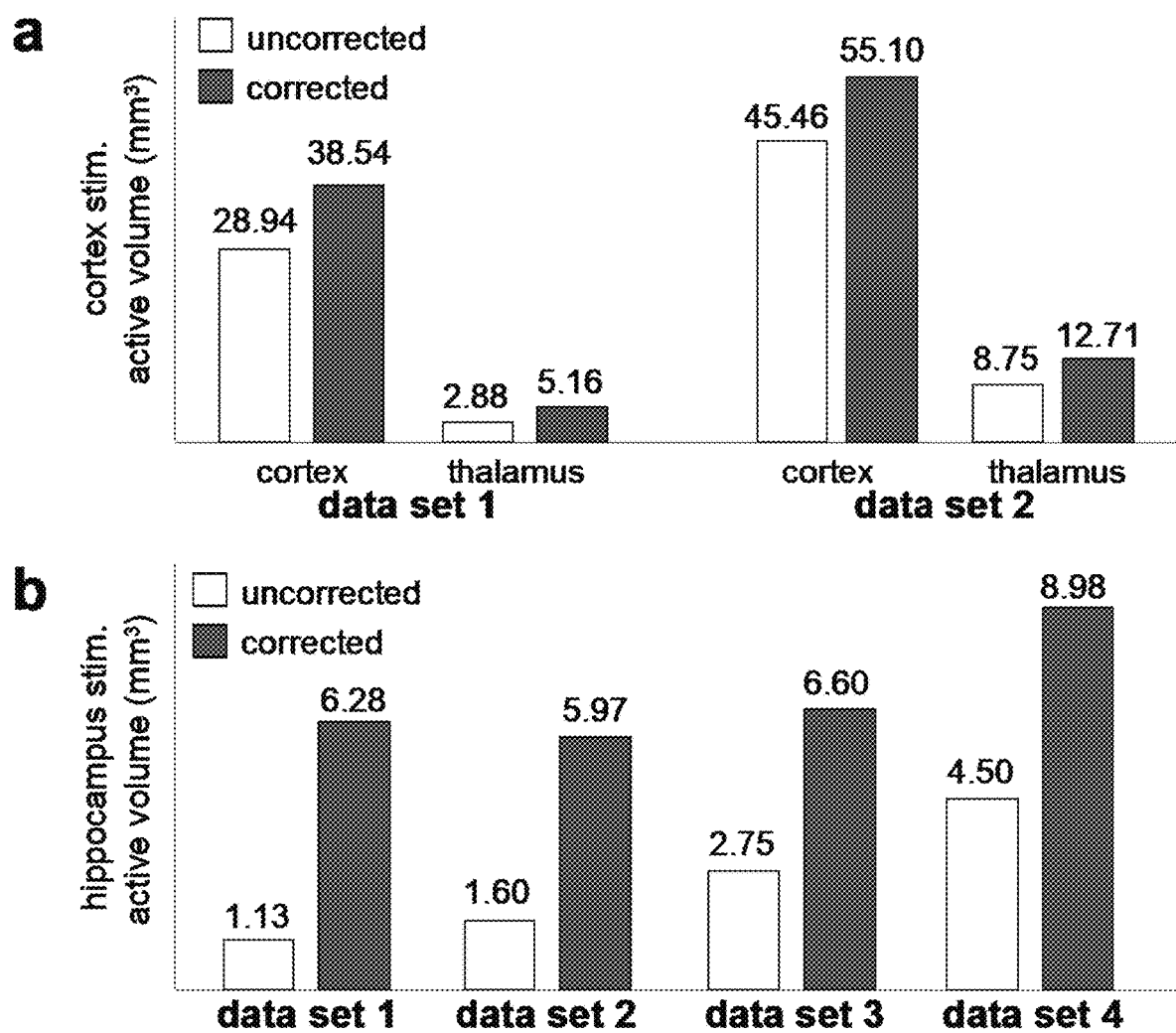

FIG. 54: Comparison of detected active volume before and after motion correction. a. $0.5 \times 0.5 \times 0.5$ mm$^3$ resolution, motor cortex pyramidal neuron stimulated, and b. $0.357 \times 0.357 \times 0.5$ mm$^3$ resolution, hippocampal pyramidal neuron stimulated active volume before and after motion correction. For all datasets, there is a clear increase in active volume after motion correction. High-resolution ofMRI results show greater improvements because it is more sensitive to motion.

Figure 55:
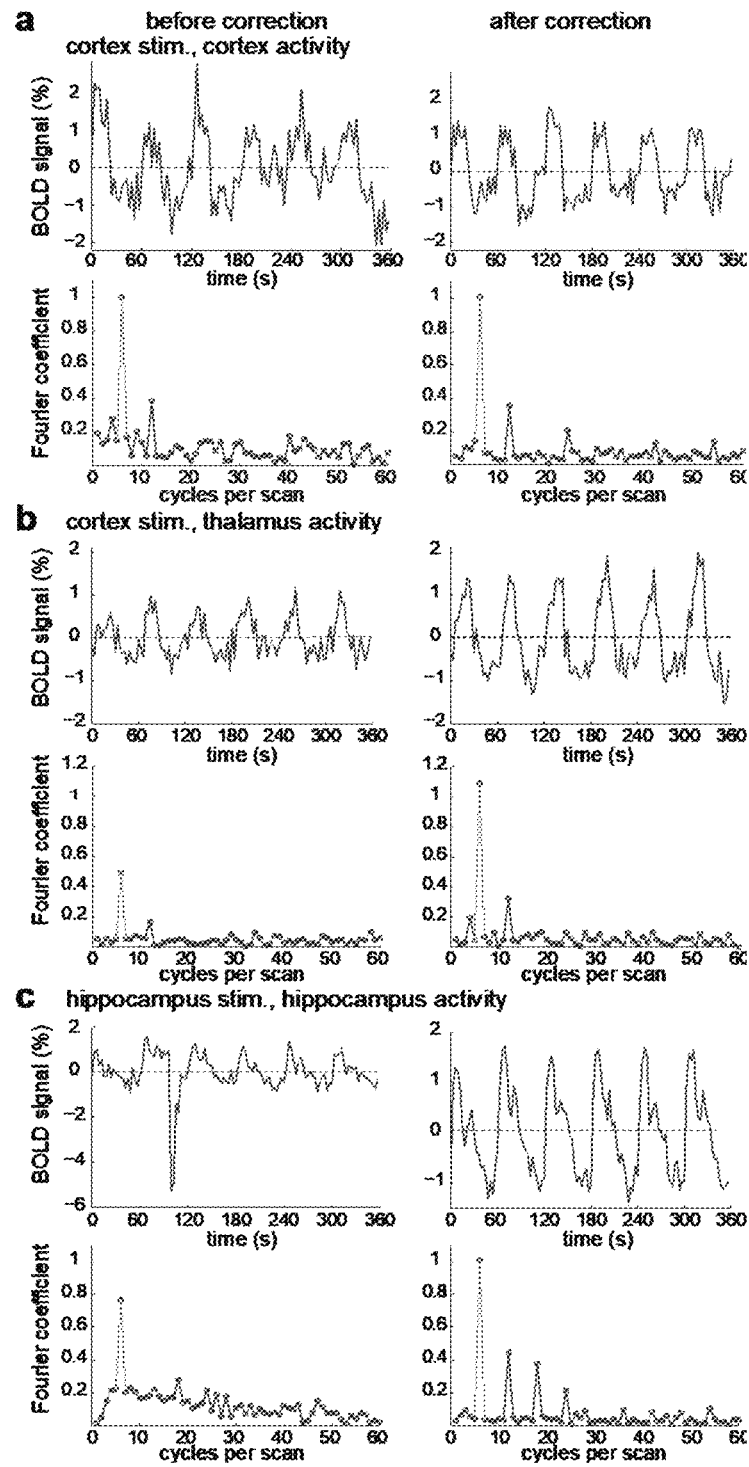

FIG. 55: Comparison of activated voxel time-series and its Fourier transform (FT). a. $0.5 \times 0.5 \times 0.5$ mm$^3$ resolution, motor cortex pyramidal neuron stimulated ofMRI shows the most prominent activation in the motor cortex and the thalamus. The time-series and its FT at the activated region in the motor cortex show that the motion correction removes noise in the time-series and its FT. b. The time-series and its FT at the activated region in the thalamus shows noise filtering and signal amplitude enhancement. The FT value representing the 6-cycle component also increases from 0.5 to 1.1. c. $0.357 \times 0.357 \times 0.5$ mm$^3$ resolution, hippocampus pyramidal neuron stimulated ofMRI shows the most prominent activation in the hippocampus. The motion correction algorithm successfully removes the large motion around 90-120 seconds and improves the 6-cycle FT coefficient from less than 0.8 to more than 1. All time-series are calculated from the averaged signal from each ROI. For each region, the common activated voxels from before and after the motion corrections were chosen for fair comparison.

Figure 56:
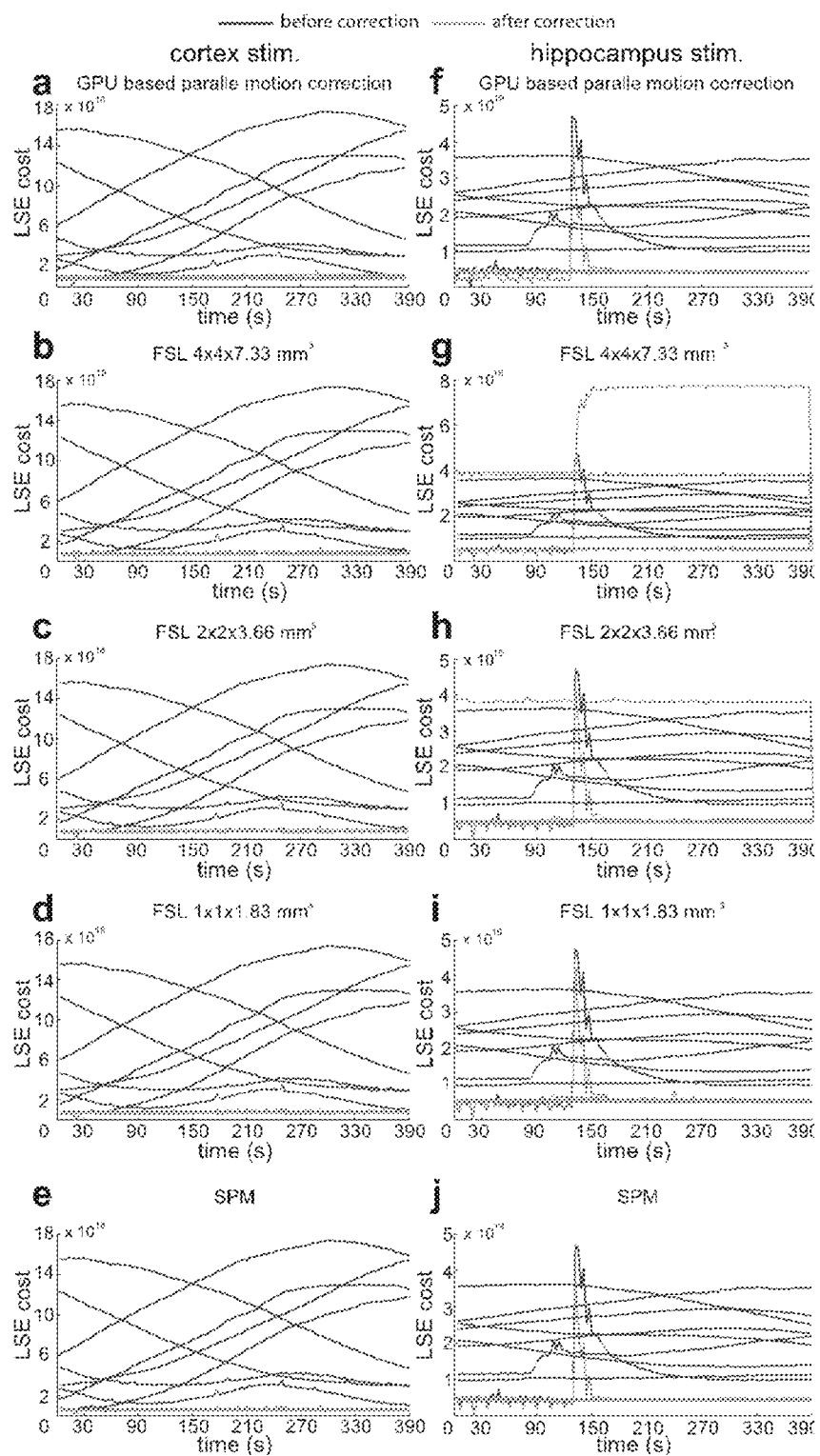

FIG. 56: a-e. $0.5 \times 0.5 \times 0.5$ mm$^3$ resolution ofMRI dataset LSE cost function value before and after motion correction. All algorithms successfully corrected the dataset with small drift motion. f-j. $0.357 \times 0.357 \times 0.5$ mm$^3$ resolution ofMRI dataset LSE cost function value before and after motion correction. Images are successfully corrected in plot f (the proposed GPU-based parallel motion correction algorithm), i (FSL with the $1 \times 1 \times 1.83$ mm$^3$ labeled resolution) and j (SPM). FSL failed at the $4 \times 4 \times 733$ mm$^3$ (plot g) and $2 \times 2 \times 3.66$ mm$^3$ (plot h) labeled resolution datasets. This result is consistent with our robustness test, which shows that when the labeled resolution is low, FSL is more likely to get trapped into a local minimum.

Figure 57:
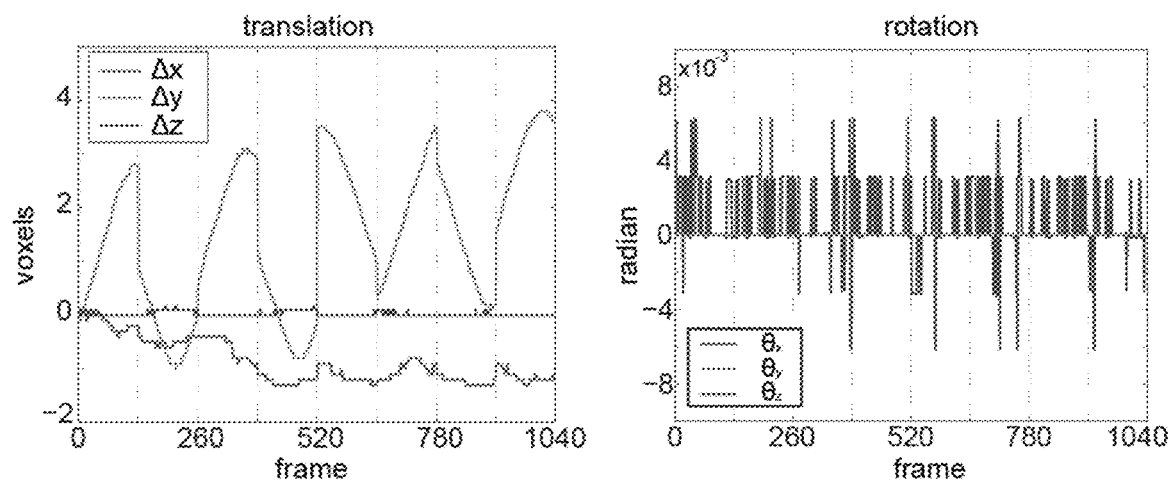

FIG. 57: Plots tracing the motion of the images. Lower resolution cortex stimulation dataset.

Figure 58:
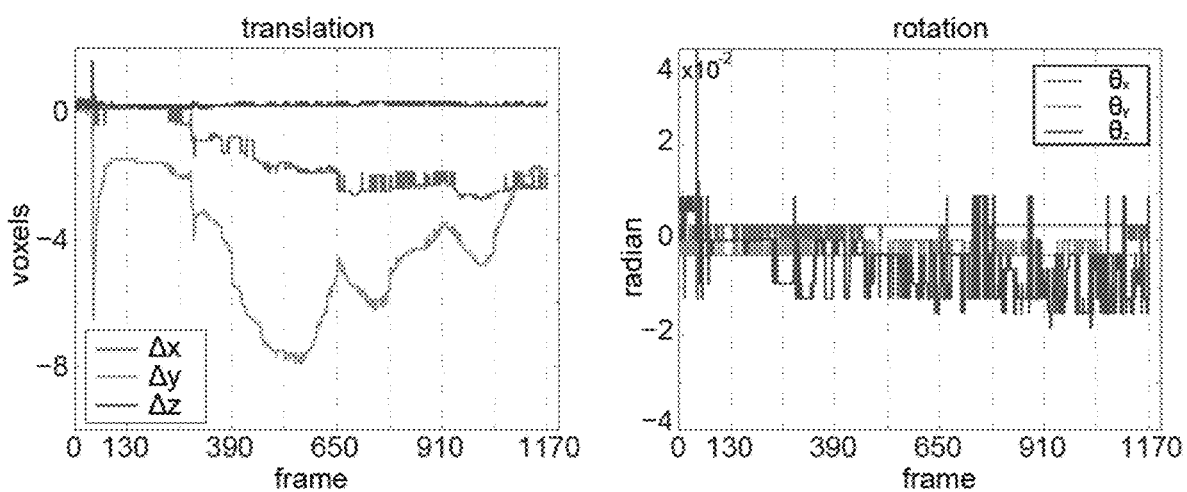

FIG. 58: Plots tracing the motion of the images. Higher resolution thalamus stimulation dataset.

DETAILED DESCRIPTION

The present invention describes how the ofMRI technology can be used to understand diseases, design therapies and be used for therapeutic outcome monitoring.

ofMRI Approach to the Study of Pathological Changes in Neural Circuits

Identify Network Communication Patterns (Visualization): in normal and pathological circuit
Interactive Therapy Design (Control)
  Deep Brain Stimulation (DBS): select stimulation target by monitoring the capability to reverse pathological conditions
  Drug Screening: validate in vivo impact of drug candidates
  Stem Cell Therapy: develop imaging strategies to evaluate the functional integration of transplanted stem cells in vivo
  Prosthetics (BMI): design prosthetics based on comprehensive understanding of circuit function
Translation to Human Patients: guided resting-state fMRI interpretation with ofMRI, direct ofMRI In some embodiments, the method involves generating a phenotype of normal and diseases neurological circuitry network communication patterns to understand the disease. Then, using this information to screen for deep brain stimulation, drugs, stem cell therapy, prosthetics, and brain machine interface design.

EXAMPLES

The following examples are offered to illustrate, but not to limit the claimed invention.

Example 1: Real-Time Brain Circuit Debugging with Optogenetic Functional Magnetic Resonance Imaging (ofMRI)

We aim to develop a revolutionary new method to debug the brain circuit in real time.

To understand the brain circuit, we believe that an approach analogous to electronic circuit debugging will be highly beneficial, where you take various elements in the circuit and precisely control them while monitoring its output in real-time. This is a highly innovative and challenging task that nobody has been able to address to date.

To achieve this, we will be using three technologies (optogenetics [1], passband b-SSFP fMRI [2], optogenetics fMRI (ofMRI) [3]). In the present invention, we combine these technologies with a new parallel processing design using graphics processing unit (GPU)s to achieve its real-time capabilities.

Background

The human brain forms a highly complex circuit that uses electrical and chemical signals to communicate. It consists of approximately 100 billion neurons and 300 billion glial cells that support the activity of neurons. Furthermore, the hundreds of billions of neurons and glial cells also come in various different cell types, which can be categorized based on their shape, location, genetic properties, and the chemicals used for communication. These brain circuit elements are densely packed with complex wiring that connects each other which makes it extremely difficult to understand the circuit's connection topology and function.

Figure 1:
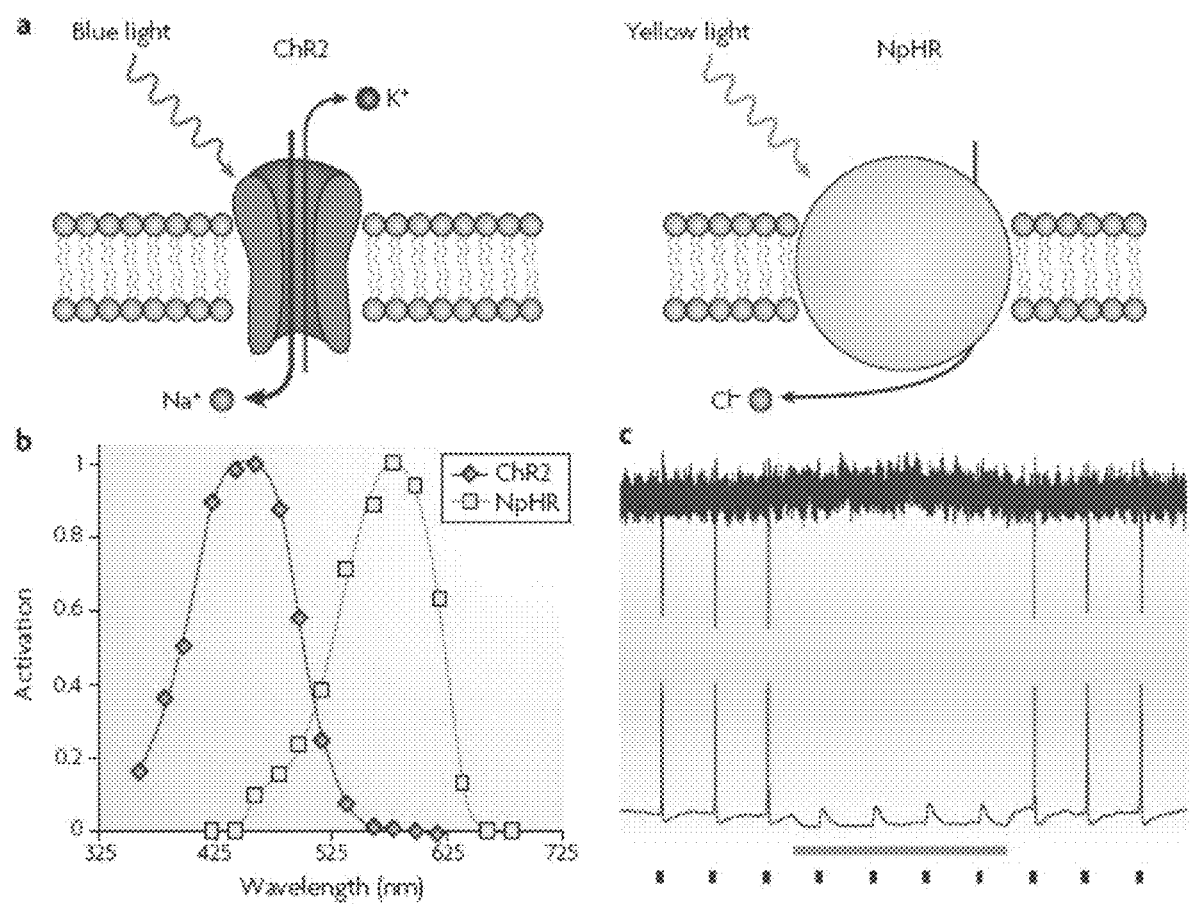
FIG. 1: Optogenetic tools: ChR2 and NpHR. a, Schematic of channelrhodopsin-2 (ChR2) and the halorhodopsin (NpHR) pump. Following illumination with blue light (activation maximum 470 nm), ChR2 allows the entry of cations into the cell. NpHR is activated by yellow light illumination (activation maximum 580 nm) and allows the entry of Cl anions. b, Action spectra for ChR2 and NpHR. The excitation maxima for ChR2 and NpHR are separated by 100 nm, making it possible to activate each opsin independently with light. c, Cell-attached (top) and whole-cell current clamp (bottom) traces from hippocampal neurons showing all-optical neural activation and inhibition. The pulses represent the blue light flashes used to drive ChR2-mediated activation and the bar denotes NpHR-mediated inactivation.

Different state-of-the art methods to understand the brain circuit include microscopic approaches looking at small scale connections with electron and light microscopy, and large scale connection topologies using neuronal tracers and diffusion tensor MRI. These approaches are again analogous to many approaches used by electronic circuit testing. However, methods to debug the brain circuit by triggering specific circuit element while non-destructively monitoring the circuit are not available. The invention of ofMRI is starting to enable such process. The ofMRI approach utilizes the optogenetics technology to genetically modify specific target circuit element to make it sensitive to light for triggering (FIG. 1) while non-invasive monitoring is performed through passband b-SSFP fMRI that allows accurate monitoring of the causal circuit response in a non-invasive manner. The ofMRI process, however, while being highly innovative groundbreaking by enabling precise debugging, is limited in the current form since the complex data acquisition, reconstruction, and analysis needs to be done off-line. This significantly limits its capability since triggering parameters cannot be adaptively adjusted while monitoring its outcome.

Impact of Research

Enhancing the understanding of the brain circuit's function by providing a precise circuit debugging mechanism in real time, has enormous implications. Immediate impact will include understanding of major brain diseases (circuit malfunction) such as Parkinsons's, Depression, Autism, Schitzophrenia, Altzheimers, Traumatic Brain Injury, and Learning Disabilities, allowing development of new device, drug, cell and gene therapies. Therapeutic devices that can be developed by having such quantitative circuit debugging information will also include advanced brain stimulation and recording devices for robotic prosthetics development (robotic limbs, eyes, and ears).

REFERENCES

[1] Zhang, F., et al., Circuit-breakers: optical technologies for probing neural signals and systems. Nat Rev Neurosci, 2007. 8(8): p. 577-81.
[2] Lee, J. H., et al., Full-brain coverage and high-resolution imaging capabilities of passband b-SSFP fMRI at 3T. Magn Reson Med, 2008. 59(5): p. 1099-1110.
[3] Lee, J. H., et al, Global and local fMRI signals driven by neurons defined optogenetically by type and wiring, Nature, 2010. 465(10): p. 788-792.

Example 2: A New In Vivo Brain Circuit Analysis Method Using Real-Time, High-Resolution Ontogenetic fMRI Introduction: Brain Circuit Analysis The human brain forms a highly complex circuit that uses electrical and chemical signals to communicate. It consists of approximately 100 billion neurons and 300 billion glial cells that support the activity of neurons. Furthermore, hundreds of billions of neurons and glial cells also come in various different cell types, which can be categorized based on their shape, location, genetic properties, and the chemicals used for communication. These brain circuit elements are densely packed with complex wiring that connects each other which makes it extremely difficult to understand the circuit's connection topology and function.

Different methods to understand the brain circuit include methods looking at the anatomical connectivity and its functional activity. Connectivity studies are divided into microscopic approaches looking at small scale connections with great precision using light and electron microscopy over a small volume, and macroscopic approaches where large scale connection topologies are studied using neuronal tracers and diffusion tensor MRI. Approaches looking at the brain function include electrophysiological recordings where microelectrodes are used to stimulate and/or record electrical activities in cell-culture, brain slices, and in vivo. Magnetoencephalography (MEG), Electroencephalography (EEG), Near-infrared (NIR) imaging, positron emission tomography (PET) and functional Magnetic resonance imaging (fMRI) [4] also provide information relating to the brain activity by measuring quantities that arise as a result of neural activity.

While all of these approaches add valuable information to the understanding of the brain circuit, the lack of a method that can monitor causal responses to precise triggering of separate neural circuit elements poses a significant limitation to the understanding of the brain. Drawing an analogy with the electronic circuit verification, testing, and debugging methods, in addition to microscopy testing each elements junction, and large scale connection topology imaging, one of the key methods in testing and debugging electronic circuits is to be able to monitor the circuit's causal response to triggering of specific circuit elements. Understanding the brain circuit architecture in normal and dysfunctional state can also tremendously benefit from this approach. However, methods to debug the brain circuit by triggering specific circuit element while non-destructively monitoring the circuit was not available. Electrophysiological triggering results in non-selective stimulation of all cell types (excitatory, inhibitory, glial cells, axons, fibers of passage) only providing localization based on electrode location while sensory stimulation only allows triggering though sensory input which goes through complex pathways before reaching the brain area of interest. Electrophysiological recordings are invasive in nature while lacking spatial information and EEG, MEG, PET, fMRI all suffer from ambiguity of the source signal partly due to the non-specific stimulation and party due to the lack of understanding of the coupling between neural activity and the measured signal.

Figure 5:
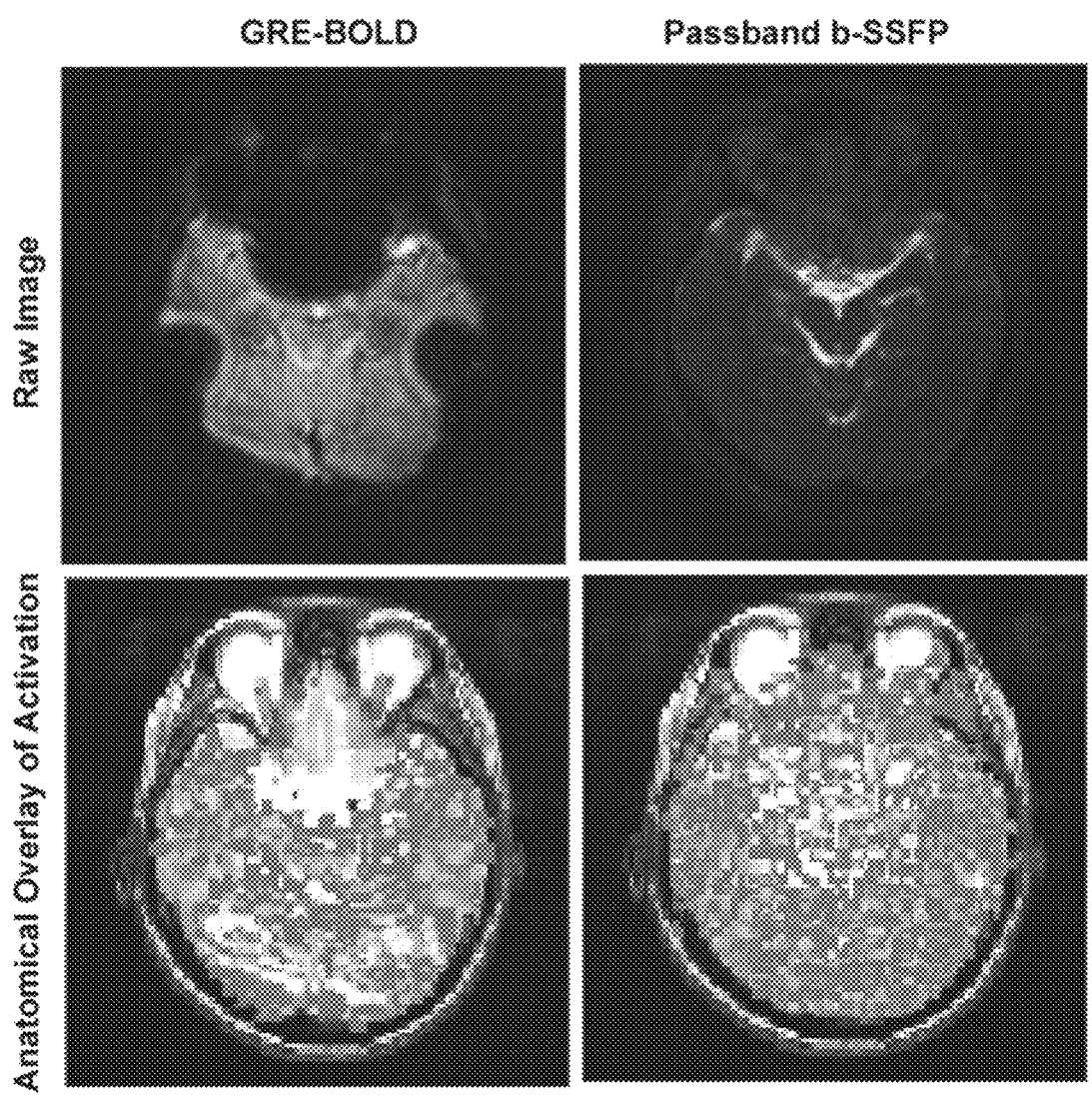
FIG. 5: Human fMRI during a breath-holding task shows large distortions in the conventional GRE-BOLD images while no such distortions are observed in the passband b-SSFP fMRI images. The corresponding anatomical overlay of the activity, as a result, shows significant missing activity regions for GRE-BOLD while no such dropouts are present in passband b-SSFP fMRI.
Figure 6:
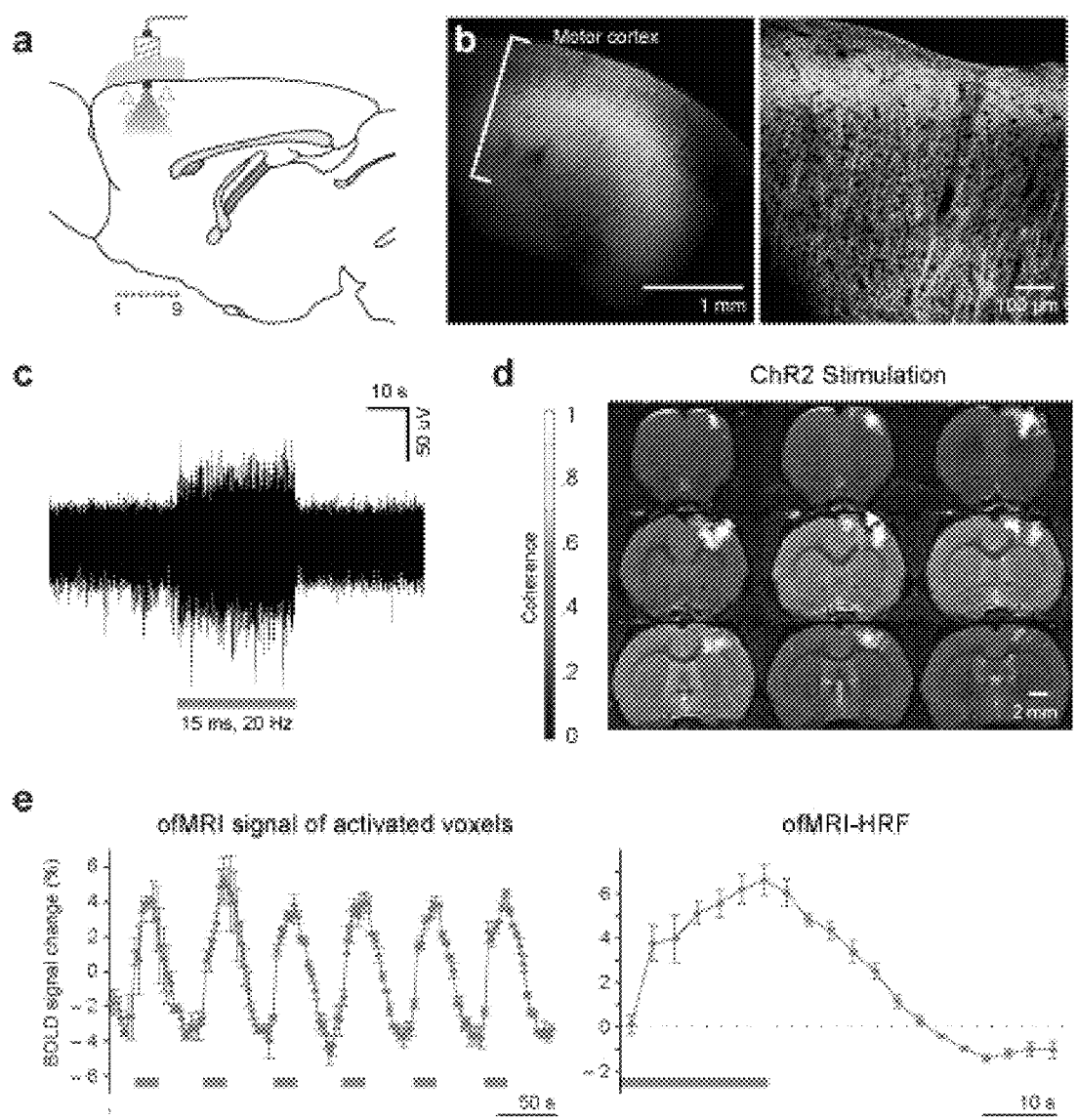
FIG. 6: ofMRI: optically-driven local excitation in defined rodent neocortical cells drives positive BOLD. a, Experimental schematic: transduced cells (triangles) and blue light delivery shown in M1 at cannula implantation and stimulation site. Coronal imaging slices shown in (d) marked as "1 . . . 9". b, Confocal images of ChR2-EYFP expression in M1 (left); higher magnification reveals transduced neuronal cell bodies and processes (right). c, Extracellular optrode recordings during 473 nm optical stimulation (20 Hz/15 ms pulsewidth). d, BOLD activation is observed at near the site of optical stimulation (right) in animals injected with AAV5-CaMKIIα::ChR2-EYFP (p<0.001; arrowhead: injection/stimulation site). Coronal slices are consecutive and 0.5 mm thick. e, ofMRI hemodynamic response during 6 consecutive epochs of optical stimulation (left); stimulus paradigm was 20 s of 20 Hz, 15 ms 473 nm light stimulation repeated every 60 s (bars). Hemodynamic response was averaged across all voxels with coherence coefficient>0.35 in motor cortex. Right, Mean of all stimulation epochs; baseline corresponds to mean pre-stimulation signal magnitude.
Figure 7:
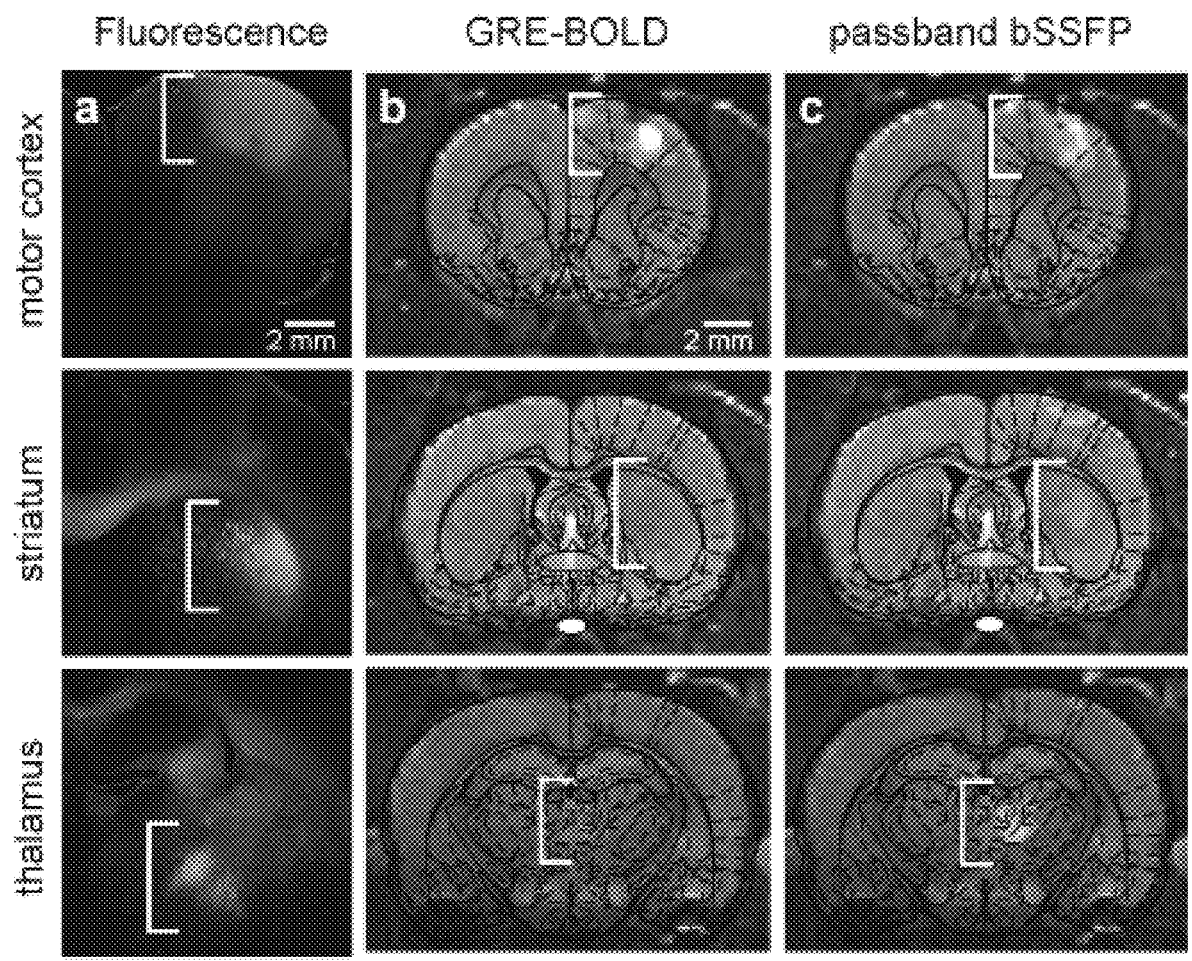
FIG. 7: ofMRI circuit mapping: conventional BOLD and passband bSSFP-fMRI. a, Injection of CaMKIIα::ChR2-EYFP in M1, as expected, leads to opsin visualization in motor cortex, striatum, and thalamus, i.e. the primary site of injection and sites where axons of expressing neurons extend. b, Hemodynamic response following M1 stimulation: conventional BOLD fMRI superimposed onto appropriate atlas image. c, Imaging the same hemodynamic response with passband bSSFP-fMRI, which more fully captures circuit-level activity.

The present invention of optogenetic fMRI (ofMRI) [2] (FIG. 6), however, is starting to enable specific stimulation of each circuit element with non-invasive monitoring of the causal response. The ofMRI approach utilizes the optogenetics [3, 5] technology to genetically modify specific target circuit element to make it sensitive to light for triggering (FIG. 4) while non-invasive monitoring is performed through passband b-SSFP fMRI [1] (FIG. 5) that allows accurate monitoring of the causal circuit response in a non-invasive manner (FIG. 6).

This approach has the potential to shift the paradigm in the efforts to study the brain circuit. Circuit elements can be triggered based on their spatial location of cell body, axonal projection targets, and genetic identity while its causal effects on the circuit can be monitored with spatial and temporal precision. This means we can now start to analyze and debug the brain circuit with precision and large degree of freedom. With such tools, we have the ability to start to parse out specific roles of each circuit elements and how they work together in a non-destructive manner. In addition, assessment of functionality in vivo can allow behavioral and longitudinal studies to be performed in the same animal removing inter-animal dependent variations. This can significantly improve the accuracy, reduce cost and time for many studies. Finally, non-invasive techniques that allow functional assessment in intact whole brain have the potential to be translated into functional assessment of human patients.

However, in its current form, there are important limitations of this ground-breaking new technology. In order to parse through the massive combination of the brain circuit's response, it is necessary for the process of stimulation and response monitoring to be in real time. Currently, the process involves an ofMRI scanning session, which is followed by an off-line reconstruction and analysis. Since animal physiology, experiment setup, light delivery system can have a certain degree of variation between scanning sessions, in order to compare subtle conditional differences, it requires multiple scanning sessions for each condition with averaging. Furthermore, since the trend in the signal change cannot be immediately captured, iterations in choosing experimental conditions will have a large delay, making it impossible to utilize the full potential of this ofMRI technology.

Spatial resolution is another major limitation. While the current spatial resolution of 0.5×0.5×0.5 mm³ covering most of the brain is quite impressive, it is not sufficient to capture signals from small brain structures with reliability. For example, in a rat brain, with such resolution, structures such as the substantia nigra (Stn) will be barely covered by 1 to 2 pixels with a lot of partial volume effects. Therefore, to capture the circuitry with sufficient accuracy to distinguish and detect activities from small brain regions require higher spatial resolution.

Enhancing the understanding of the brain circuit's function by providing a precise circuit debugging mechanism in real time and high resolution has enormous implications. Immediate impact will include understanding of major brain diseases (circuit malfunction) such as Parkinsons's, Depression, Autism, Schitzophrenia, Altzheimers, Traumatic Brain Injury, and Learning Disabilities, allowing development of new device, drug, cell and gene therapies. Therapeutic devices that can be developed by having such quantitative circuit debugging information will also include advanced brain stimulation and recording devices for robotic prosthetics development (robotic limbs, eyes, and ears).

Background: Opotogenetic fMRI

The present invention builds on three technologies. One is the imaging technology called passband b-SSFP fMRI method (FIG. 5) [6] and the other is the optical-neuromodulation technology called optogenetics (FIG. 6) [3, 7-9], and the third is optogenetic fMRI technology.

Figure 2:
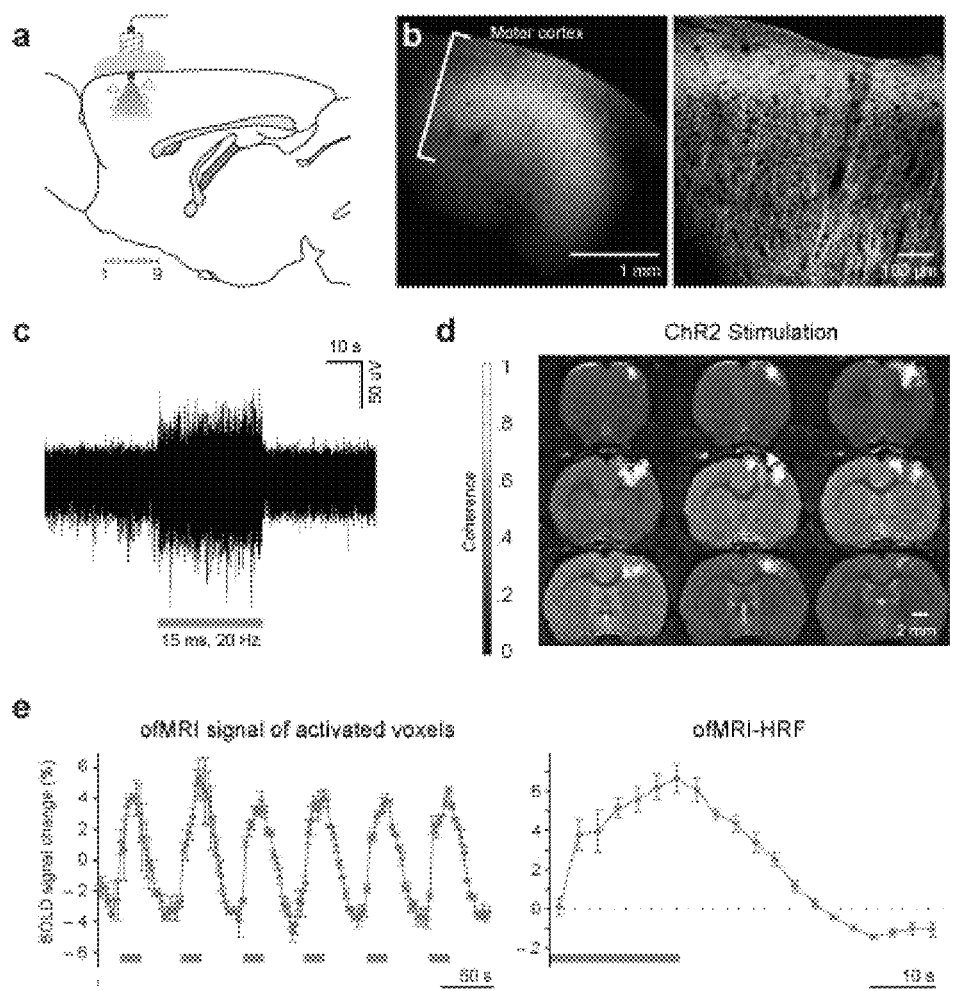
FIG. 2: Optogenetic functional MRI (ofMRI): optically-driven local excitation in defined rodent neocortical cells drives positive BOLD. a, Experimental schematic: transduced cells (triangles) and blue light delivery shown in M1. Coronal imaging slices shown in (d) marked as "1 . . . 9". b, Confocal images of ChR2-EYFP expression in M1 (left); higher magnification reveals transduced neuronal cell bodies and processes (right). c, Extracellular optrode recordings during 473 nm optical stimulation (20 Hz/15 ms pulsewidth). d, BOLD activation is observed at near the site of optical stimulation (right) in animals injected with AAV5-CaMKIIα::ChR2-EYFP. Coronal slices are consecutive and 0.5 mm thick. e, ofMRI hemodynamic response during 6 consecutive epochs of optical stimulation (left); stimulus paradigm was 20 s of 20 Hz, 15 ms 473 nm light stimulation repeated every 60 s (blue bars). Hemodynamic response was averaged across all voxels with coherence coefficient>0.35 in motor cortex. Right, Mean of all stimulation epochs; baseline corresponds to mean pre-stimulation signal magnitude.

Passband b-SSFP fMRI as a more accurate alternative to Conventional fMRI. Passband b-SSFP fMRI is an fMRI method that utilizes rapid radiofrequency excitation pulses combined with fully-balanced gradient pulses during each excitation repetition interval ($T_R$) [10]. Due to its short readout time and $T_R$, b-SSFP provides distortion-free 3D imaging suitable for full-brain, high-resolution functional imaging. While the conventional fMRI is a highly successful technique that provides a non-invasive means to study the whole brain including deep-brain structures, it has significant limitations for the accurate assessment of neural function in its current form. Due to large spatial distortions, large portions of the brain cannot be imaged (FIG. 2, left) while the spatial resolution needs significant improvement to provide information necessary for the state-of-the art neuroscience. Passband b-SSFP fMRI, by providing a way to obtain distortion-free 3D isotropic resolution images (FIG. 5, right), opens a new window for fMRI's role to become a more quantitatively accurate method.

Figure 4:
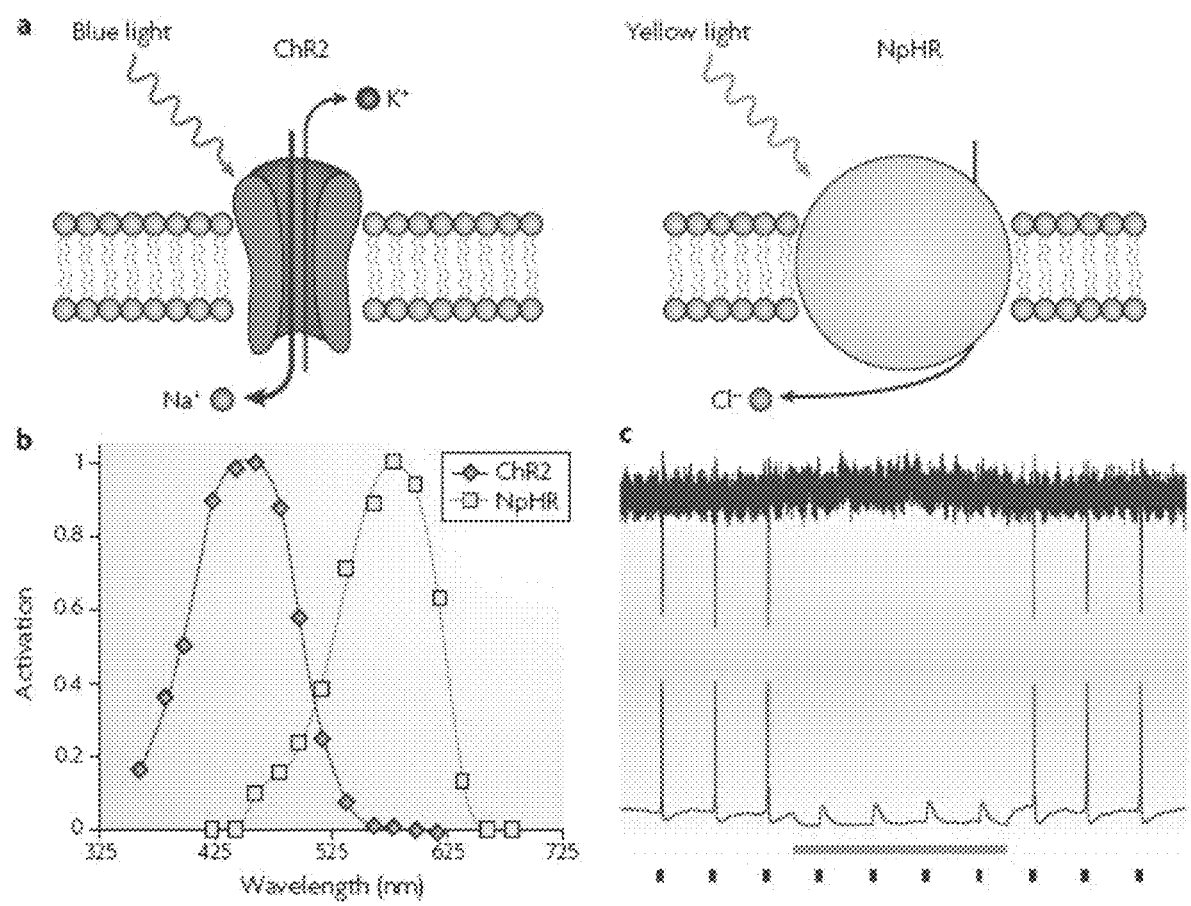
FIG. 4: Optogenetic tools: ChR2 and NpHR. a, Schematic of channelrhodopsin-2 (ChR2) and the halorhodopsin (NpHR) pump. Following illumination with blue light (activation maximum 470 nm), ChR2 allows the entry of cations into the cell. NpHR is activated by yellow light illumination (activation maximum 580 nm) and allows the entry of Cl anions. b, Action spectra for ChR2 and NpHR. The excitation maxima for ChR2 and NpHR are separated by 100 nm, making it possible to activate each opsin independently with light. c, Cell-attached (top) and whole-cell currentclamp (bottom) traces from hippocampal neurons show in all-optical neural activation and inhibition. The pulses represent the blue light flashes used to drive ChR2-mediated activation and the bar denotes NpHR-mediated inactivation.

Optogenetic Control of Genetically Targeted Neurons. Optogenetics [3, 7-9], is a neuro-modulation technology in which single-component microbial light-activated transmembrane conductance regulators are introduced into specifically targeted cell types and circuit elements using cell type specific promoters to allow millisecond-scale targeted activity modulation in vivo [11] (FIG. 4). ChR2 [1] is a monovalent cation channel that allows Na+ ions to enter the cell following exposure to 470 nm blue light, whereas the NpHR [1] is a chloride pump that activates upon illumination with 580 nm yellow light. As the optimum activation wavelength of these two proteins are over 100 nm apart, they can be controlled independently to either initiate action potential firing or suppress neural activity in intact tissue, and together may modulate neuronal synchrony. Both proteins have fast temporal kinetics, on the scale of milliseconds, making it possible to drive reliable trains of high frequency action potentials in vivo using ChR2 [1] and suppress single action potentials within high frequency spike trains using NpHR. Thus far, one of the greatest challenges in neuroscience has been the difficulty of selectively controlling different circuit elements of the brain to understand its function.

Optogenetic Functional Magnetic Resonance Imaging (ofMRI). A new molecular, functional imaging method that combines optogenetic [3, 7-9] control of the brain with the passband b-SSFP fMRI [1] method is described in the present application.

FIG. 6 shows the result from selective optical modulation of CamKIIa-promoted excitatory neurons in the motor cortex of a normal adult rat, which results in spatially resolved local activity, successfully detected using ofMRI while increased local activity is confirmed with electrode recordings. FIG. 4 shows resulting activity in other areas of the brain while demonstrating that the neural activity is more accurately mapped throughout the brain in striatum and thalamus using the passband bSSFP fMRI technique [2] compared to the conventional GRE-BOLD fMRI technique. These preliminary results successfully demonstrate ofMRI technology's capability to map excitatory-neuron-specific neural connectivity between motor cortex, striatum, and thalamus.

Figure 8:
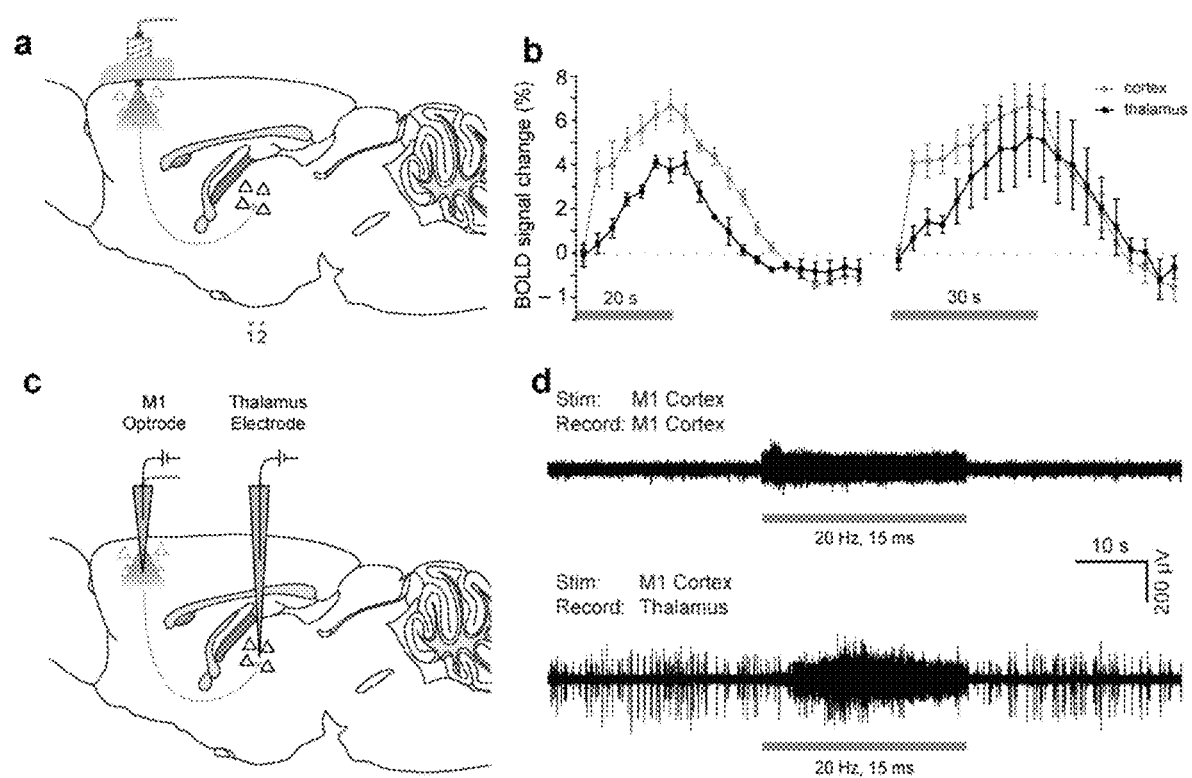
FIG. 8: Long-range functional brain mapping with ofMRI. a, Schematic shows CaMKIIα::ChR2-EYFP viral injection, cannula implantation, and optical stimulation sites in M1. "1" and "2" mark slice locations where thalamic signal was observed. b, ofMRI-HRFs obtained from cortical and thalamic BOLD activation areas (gray: cortical ofMRI-HRF; black: thalamic ofMRI-HRF resulting from optical stimulation of M1) for 20 s (left) or 30 s (right) of optical stimulation Thalamic ofMRI-HRF displayed a slower rate of signal rise compared with M1 ofMRI-HRF, while the offset of the signal timing was similar in both cases. c, Schematic for optical stimulation and electrical recording paradigm using an optrode and an electrode. Optical stimulation was performed in the motor cortex in the setting of simultaneous recording in both motor cortex and thalamus. d, Recordings in M1 and thalamus during M1 optical stimulation mapped well onto BOLD responses; note slow thalamic recruitment.

In addition, electrophysilogical recordings in motor cortex and thalamus reveal striking similarity in neuronal activity and ofMRI hemodynamic response function (HRF) (FIG. 8) Immediate increase in the spiking at the site of direct optical stimulation results in fast increase of ofMRI-HRF signal while slower recruitment of neural activity in thalamus results in slower increase in ofMRI-HRF signal. This close correlation suggests that ofMRI-HRF can be used to evaluate temporal characteristics of neural activity.

Since true functional outputs of genetically defined neurons in a brain region can be globally mapped with ofMRI (FIG. 8,9), it is conceivable that additional levels of specificity could also be achieved. For example, M1 excitatory pyramidal neurons form a genetically- and anatomically-defined class of cell, but within this class are cells that each project to different areas of the brain and therefore have fundamentally distinct roles. Genetic tools may not advance far enough to separate all of these different cell classes. But ofMRI raises the possibility of globally mapping the roles of these cells, accessing them by means of connection topology—i.e. by the conformation of their functional projection patterns in the brain.

We therefore sought to test this possibility by selectively driving the M1 CaMKIIα-expressing cells that project to thalamus. An optical fiber was stereotactically placed in thalamus of animals that h6d received M1 cortical viral injections (FIG. 9*a*); posthoc validation of ChR2 expression (FIG. 9*b*) confirmed ChR2-YFP in cortical neurons and in cortico-thalamic projection fibers. ChR2 readily triggers spikes in illuminated photosensitive axons, that both drive local synaptic output and back-propagate throughout the axon, to the soma of the stimulated cell [12-14]; note that unlike the case with electrical stimulation, specificity is maintained for driving the targeted (photosensitive) axons, and therefore this configuration in principle allows ofMRI mapping during selective control of the M1 cortical cells that project to thalamus. Indeed, robust BOLD signals were observed both locally in thalamus (FIG. 9c: coronal slices 7-12) and also in M1 (FIG. 9d: coronal slices 1-6), consistent with the recruitment of the topologically targeted cells both locally and distally. These data demonstrate that ChR2-expressing axonal fiber stimulation alone is sufficient to elicit BOLD responses in remote areas, and illustrate the feasibility for in vivo mapping of the global impact of cells defined not only by anatomical location and genetic identity, but also by connection topology.

Figure 9:
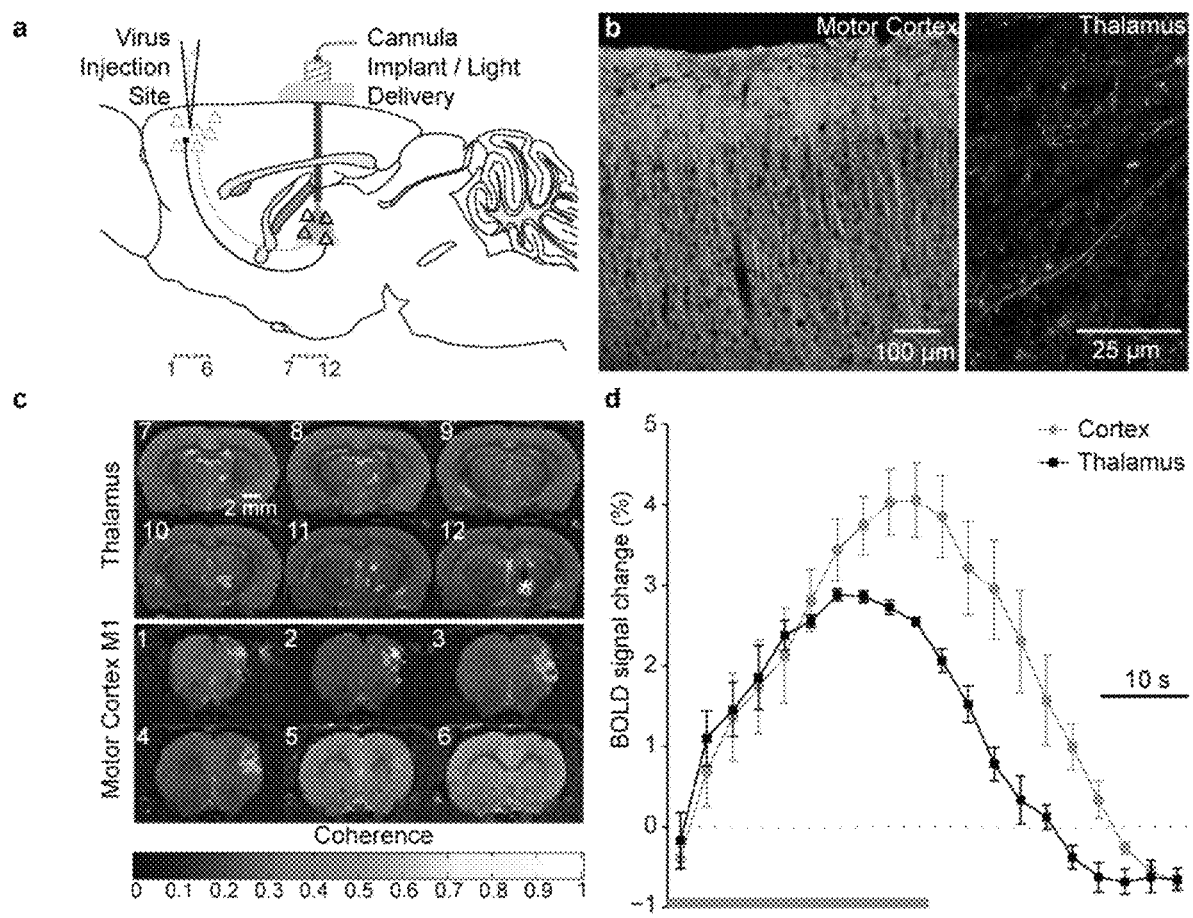
FIG. 9: Control of cells defined by location, genetic identity, and wiring during ofMRI. a, M1 injection of AAV5-CaMKIIα::ChR2-EYFP and optical stimulation of thalamus. Coronal slices shown in (c) marked as "1 . . . 6" and "7 . . . 12". b, ChR2 expression pattern confirming expression in cortical neurons (left) and cortico-thalamic projections. c, BOLD ofMRI data obtained in thalamus (above) and cortex (below). d, ofMRI-HRF for cortical (gray) and thalamic (black) BOLD signals elicited by optical stimulation of cortico-thalamic fibers in thalamus. Both ofMRI-HRFs ramp slowly by comparison with intracortical results in FIG. 1.
Figure 10:
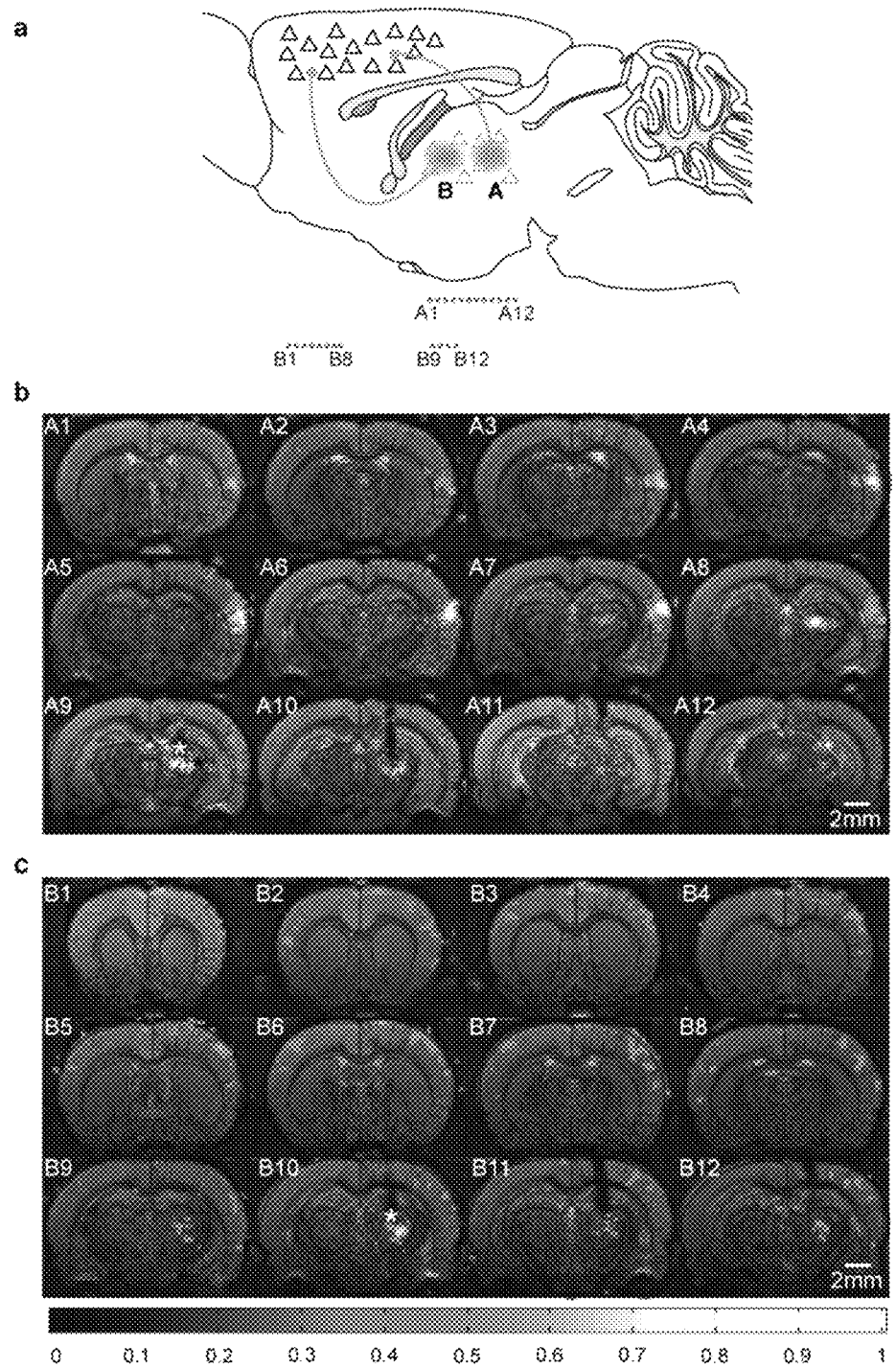
FIG. 10: Recruitment of bilateral cortices by anterior thalamus. a, Thalamic injection of AAV5-CaMKIIα::ChR2-EYFP and optical stimulation in posterior and anterior locations. Coronal slices marked as "A1 . . . A12" and "B1 . . . B12". b, Fluorescence overlaid onto bright-field (left) and confocal image (right) illustrating transduction in thalamus (left) and cortical projections in internal and external capsule (right). c, Stimulation of posterior thalamus evoked ofMRI signal in ipsilateral thalamus and somatosensory cortex. Excited volume was 5.5±1.3 mm$^3$ for thalamus and 8.6±2.5 mm$^3$ for somatosensory cortex (n=3). Stimulation of anterior thalamus evoked ofMRI signal in ipsilateral thalamus and bilateral motor cortex. Excited volume was 1.5 mm$^3$ for thalamus, 10.1 mm$^3$ for ipsilateral cortex, and 3.7 mm$^3$ for contralateral cortex.

We further explored the global mapping capabilities of ofMRI. It has been suggested that thalamic projections to motor cortex may be more likely than those to sensory cortex, to involve both ipsilateral and contralateral pathways, since in many cases motor control and planning must involve bilateral coordination. This principle is challenging to assess at the functional level, since electrode-based stimulation will drive antidromic as well as orthodromic projections, and hence may mistakenly report robust cortico-thalamic rather than thalamocortical projections. We therefore sought to globally map functional connectivity arising from initial drive of anterior or posterior thalamic nucleus projections, employing ofMRI. After injecting CaMKIIα::ChR2 into thalamus (FIG. 9a), we found that optical stimulation of posterior thalamic nuclei resulted in a strong BOLD response, both at the site of stimulation and in the posterior ipsilateral somatosensory cortex (S2) (FIG. 9b). Optically stimulating excitatory cell bodies and fibers in the more anterior thalamic nuclei resulted in BOLD response at the site of stimulation and also significant ipsilateral and contralateral cortical BOLD responses (FIG. 10c), consistent with the proposed bilaterality of anterior thalamocortical nuclei involvement in motor control and coordination.

Now, with the successful demonstration of the feasibility of the ofMRI technology, the next steps involve taking this technology into a whole new direction by enabling real-time, high resolution imaging. This technology will then be used to study the effects of different patterns of temporal modulation with an added specificity of targeting each cortical layer. These effects will be studied in areas known to be relevant to Parkinson's disease such as substantia niagra (Stn), striatum, and motor cortex (M1) [12].

The present methods describe a direct, cell-specific, and in vivo functional interrogation and visualization of neural circuitry in real-time with high spatio-temporal resolution. These methods will enable decoding of temporal encoding schemes of neural activity in intact brain over a large field-of-view (FOV), with the spatial precision that can deconstruct functional roles of cortical layers. Different cortical layers are known to have distinct roles in the neural circuitry. In order to deconstruct the neural circuit function, understanding the temporal coding dynamics with high spatial precision is important. Precisely controlling while monitoring the whole brain with temporal and spatial precision, will revolutionize our understanding of the brain.

The present invention provides for three aims as follows.
Aim 1. Develop Real-Time Optogenetic Functional MRI (ofMRI) Technology to Allow Interactive Imaging and Data Analysis.

Real-time ofMRI will allow parameters of the experiment, such as the optical stimulation frequency and timing, and stimulation location to be adjusted based on the resulting response. This feature is important for precise control of the experiment condition. This situation can be analogous to looking at electrophysiological readings from electrodes in real time to adjust the electrode location as well as the stimulation paradigm. Without such real-time feedback, it would be impossible to record from areas of interest in a realistic timescale. Likewise, enabling real-time interactive ofMRI would revolutionize its capability to rapidly sort through experimental conditions that are of interest with precision.

ofMRI experiments consists of the optical stimulation unit, the image acquisition unit, image reconstruction unit, and the data analysis unit. These units, in its current form, all function separately. The optical stimulation is controlled with a pre-programmed function generator, the acquisition algorithm is programmed into the MRI system host computer, image reconstruction and data analysis is performed using separate programs that run on a Linux machine. We will integrate all of these processes to be operated though the control of one Linux computer while parallelizing the computation associated with each unit using a graphics processing unit (GPU). In particular, we will utilize the Nvidia CUDA GPU.

Figure 11:
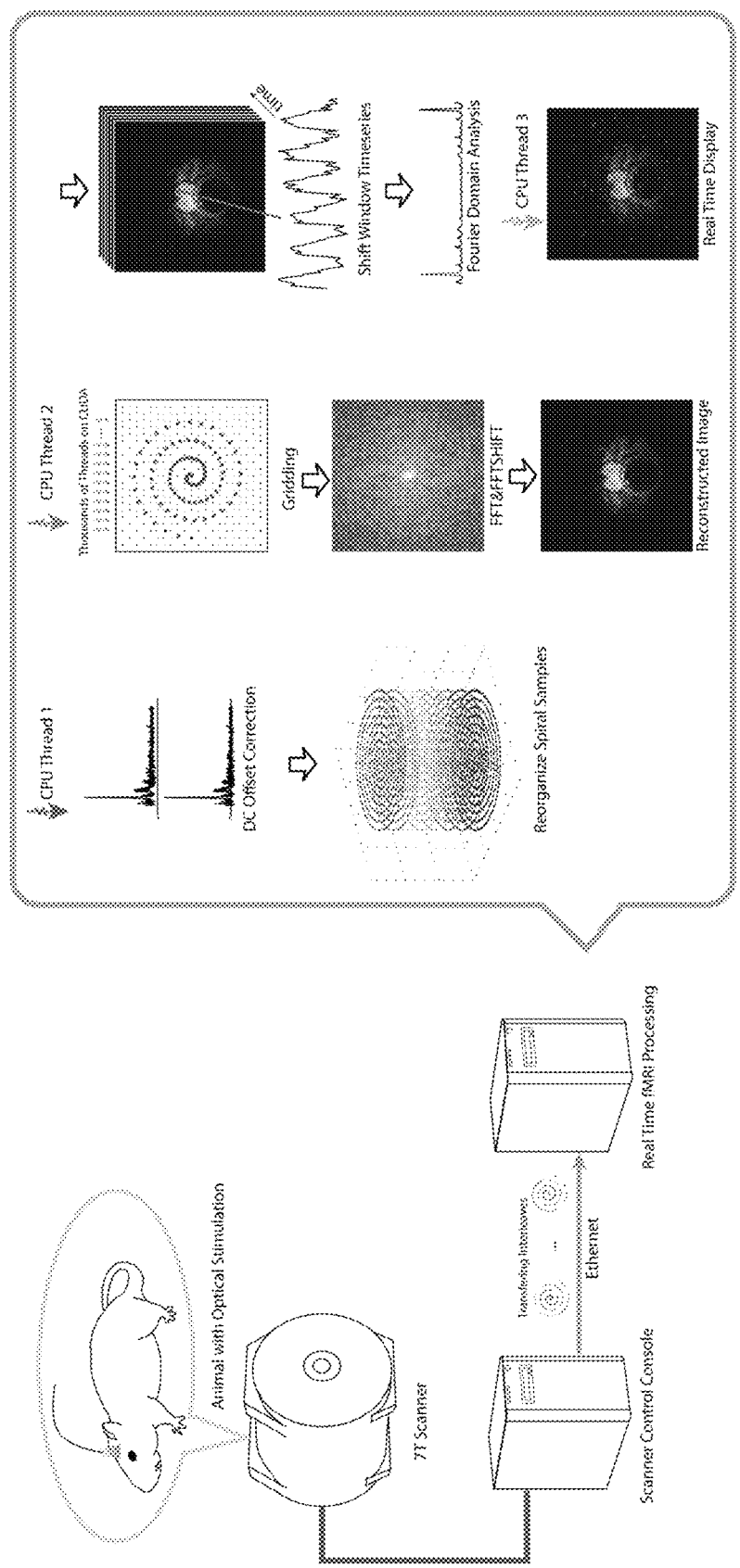
FIG. 11: Real-Time Interactive ofMRI with parallel processing using CUDA. Real time ofMRI allows adaptive optogenetic control of brain circuit with feedback from the resulting activity that is monitored in real time. Acquired data is updated every interleave and processed on a workstation. There are 3 threads running on the workstation. In thread 1, interleaves are first corrected for DC-offset and reorganized into spiral stacks. In thread 2, k-space gridding for data acquired with spiral sampling, Fast Fourier Transform and activation analysis are all calculated in parallel on a Nvidia CUDA video card. In thread 3, the Graphic User Interface handles all user inputs and enables real time display.
Figure 12:
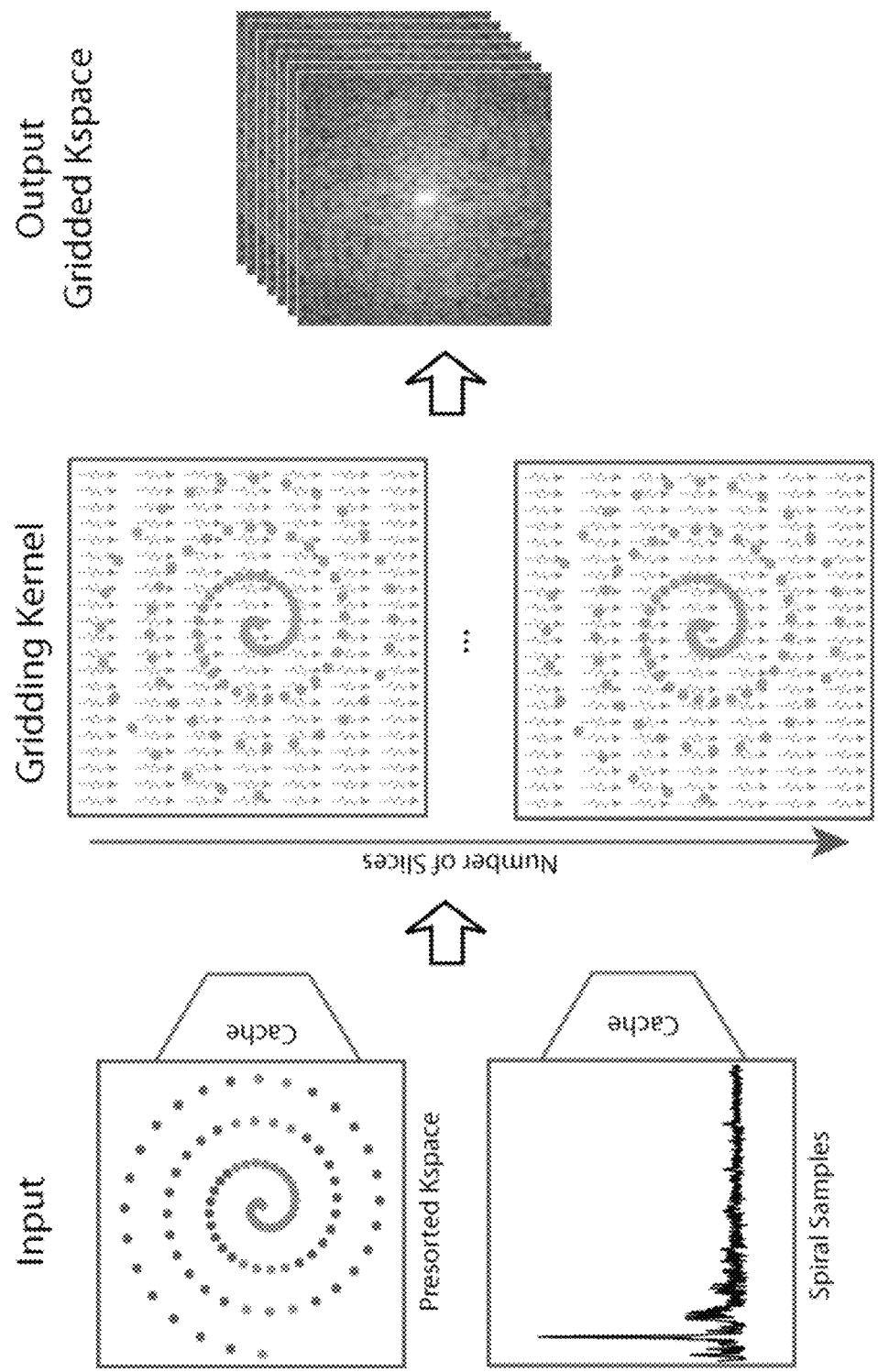
FIG. 12: Parallel data reconstruction. The non-Cartesian sampled data is gridded through grid driven design and limited search space. Allowing each thread to handle a single grid point parallelizes this process. Each thread searches a presorted k-space, and finds the contribution to its grid. The presorted k-space data and spiral samples are stored in input memory and cached by texture memory for fast retrieving. After gridding, the gridded k-space is stored back in the output memory.
Figure 13:
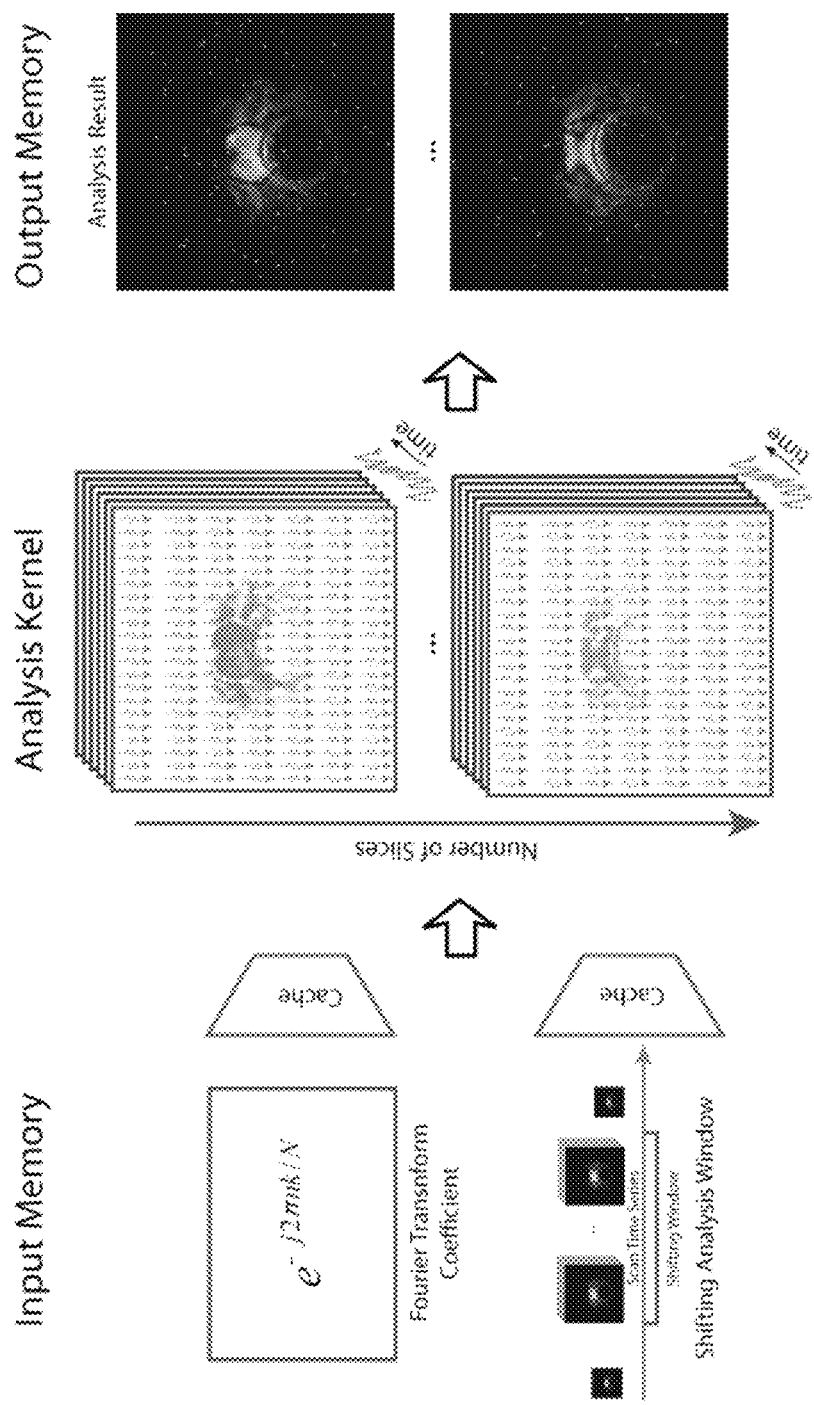
FIG. 13: Parallel data analysis. Using CUDA, each pixel's time series can be handled by independent threads. The threads first Fourier analyzes the time series, which is then used to produce a brain activation map. The analysis result is stored in the output memory for display. Fourier transform coefficients and the windowed image series are stored in the input memory and cached by texture memory on GPU for fast retrieving.

The outline of the data flow design is shown in FIG. 11. A computer will control optical stimulation while the animal sits in the MRI scanner. The same computer will instruct the MRI scanner to acquire the data using the specified algorithm. Then, the received data will go through parallel processing that consists of 3 CPU threads. First thread will take the data and perform tasks such as DC offset correction, data organization Second thread will do data reconstruction tasks such as gridding, FFT&FFTshift, and data analysis, and the third thread will conduct data display tasks. We will first take such a multi-threaded approach to speed up the process. In addition, three main algorithms within the reconstruction and analysis pathway will be massively parallelized utilizing the GPU; Gridding (FIG. 12), Fast Fourier Transform (FFT), and the Fourier analysis of the 4-dimensional ofMRI data (FIG. 13). Preliminary implementation of the algorithm shows the following performance enhancement comparing CUDA GPU and regular CPU performance (CPU: Intel Core i5 750, GPU: Nvidia 9800 GTX+, 128Cores, 512 MB memory, Memory: Quad-Core, 2.66 GHz, 4 GB DDR3 1333 MHz).

| GPU & CPU Performance Comparison | | | |
| --- | --- | --- | --- |
|  | GPU (ms) | CPU (ms) | Speedup Factor |
| Gridding | 10.08 | 85.22 | 8.454365 |
| FFT&FFTSHIFT | 8.78 | 161.4 | 18.38269 |
| Analysis | 4.07 | 1271.55 | 312.4201 |

These speedup factors will allow the whole process of data acquisition, image reconstruction, data analysis, and real time interactive display to happen within tens of milliseconds, allowing real-time visualization of optogenetically elicited neural activity.

Aim 2. Increase Spatial Resolution of the ofMRI Using Compressed Sensing (CS) Algorithms.

Magnetic resonance image acquisition speed and resolution are limited by the need to sample the Fourier Transform domain in a serial fashion. Dense sampling results in larger FOV while large area sampling results in high resolution. The sampling of this Fourier domain can be sped up by efficiently utilizing the imaging gradient waveforms. Another approach to reduce scan time would be to reconstruct images from undersampled data sets.

CS Background

Reconstruction of MR images from undersampled k-space (Fourier domain) information can be viewed as the problem of finding a solution to an underdetermined problem.

Let $x \in C^n$ be an image, $y \in C^m$-k-space data, and $F \in C^{m \times n}$ the Fourier transform matrix. Since k-space is undersampled, F is "fat", and there are infinitely many x satisfying y=Fx. Typically, in these cases, a minimum energy solution is chosen by "zero-filling" unknown k-space samples. This leads to undesirable aliasing artifacts, and the resulting image isn't a faithful representation of the actual object. CS demonstrates that out of infinitely many "wrong" solutions, the "correct" one (that is, the actual image) can be found efficiently, if the following conditions are satisfied.

CS requires the signal to be sparse or compressible under some transform. In other words, the transform representation of the signal only contains few significant terms—rest are very small or zero. This is a very weak requirement, as real-world signals are indeed compressible, as evidenced by success of mp3, JPEG, and MPEG compression schemes, operating on audio, images, and videos. There are also few restrictions on choice of such sparsifying transform: for example, if signal is known be composed of sinusoidal terms, Fourier transform will convert them to sparse Diracs, and thus is a good choice. Similarly, finite differences sparsify piecewise constant signals. In MR-related CS applications, DCT, wavelet, and finite differences are usually chosen.

Moreover, the formulation requires samples to be chosen irregularly, with each sample being a linear combination of underlying signal values. In MR, latter is achieved trivially because imaged objects are acquired in Fourier domain: signals from all image voxels are mixed in each k-space sample. Irregular sampling is readily accomplished by appropriately choosing the sampling trajectory. For example, in 2D-DFT imaging, phase encode lines are randomly sampled, generating artifacts along one dimension [15, 16]. In 3D-DFT, success is reported by randomly sampling phase encode plane, with sampling density decreasing with the distance from center [17]. Non-Cartesian trajectories combine time-efficient sampling of k-space with full freedom of the sampling pattern. Promising results have been reported using undersampled variable density spirals [15] and radial projections [18].

Irregular sampling is desirable to create incoherent, noise-like aliasing artifacts in transform domain Reconstruction proceeds by delicately suppressing these artifacts, while constraining k-space representation of the guessed image to match measured k-space samples. Such procedure is iterative and nonlinear. Formally, one solves:

$$\text{minimize} \|\Psi x\|_1 \text{ subject to } Fx=y \qquad (1)$$

where $\Psi$ is the above mentioned sparsifying transform. It is now well known that $\ell_1$ norm promotes sparsity. The solution finds the sparsest transform representation of the image—that is $\Psi x$—that's also consistent with measured k-space.

This is a convex optimization problem that can be efficiently solved by interior point methods when the size of the problem is small. In large scale situations, it is more practical to solve a relaxed, unconstrained problem $$\text{minimize} \|Fx-y\|_2^2 + \lambda \|\Psi x\|_1 \qquad (2)$$

In this formulation, data consistency holds approximately, and the solution is still sparse. The trade-off parameter $\lambda$ can be used to modify "weights" placed on each term: for example, large $\lambda$ indicates our "displeasure" with a non-sparse $\Psi x$.

CS fMRI

Because images can be sparsified and sampling occurs in an alternate domain (k-space), MRI is an application of CS. Initial applications of CS to MRI demonstrate that acquisitions can be accelerated without degrading image quality. More acceleration can be gained in dynamic MR setting where temporal redundancy can be exploited.

In case of functional brain imaging, a sequence of brain images is rapidly acquired over the course of several minutes. The signal of interest-blood oxygenation level changes-manifests itself as small changes in signal intensity in regions of neuronal activity. Ideally, acquisition proceeds without any subject motion, and the acquired image does not change significantly from frame to frame. Therefore, the captured dataset contains an enormous amount of redundancy and can be compressed temporally, as well as spatially.

Several aspects of functional imaging differentiate it from other applications of CS to MRI. Rapid MRI acquisitions are noisy. While SNR can be improved by longer sampling durations, in fMRI it is traded off for high temporal resolution. Low SNR leads to worse compressibility—one can't hope to sparsify noise. Although the acquired data corresponds to a sequence of brain images, primary interest lies with tracking blood oxygenation level dependen (BOLD) fluctuations. This signal is inherently weak, with amplitude of ~2-8%—on the same order as noise in the data. It is well known that CS algorithms are very quick and successful at recovering high contrast features in images; however, the details are often lost. Here the aim is to reconstruct details—temporal variations engulfed in noise. Moreover, for the method to be of practical use, reconstructions must correctly localize regions that exhibit BOLD, and accurately represent its temporal response.

Prior applications of CS to dynamic MRI dealt with cardiac imaging. There, periodic heart motion made it possible to temporally compress the signal using a Fourier transform. In block design fMRI experiments, BOLD signal follows periodic stimulation, and some "activated" voxels do exhibit a distinct spike at the activation frequency. However, low amplitude of BOLD and low SNR challenges the assumption of frequency sparsity. Instead, we choose to compress the signal temporally by finite differences, since consecutive images in an fMRI sequence are very similar. Finite differences are used to compress the signal along the three spatial directions as well. Regularization by finite differences (also referred to as Total Variation) has been well known since [19], and is popular in image processing applications. In CS-MRI, it's been used in [15-18]. Surprisingly, regularization performs well even when the assumption is not strictly true for the underlying signal.

Our problem formulation is then:

$$\text{minimize } \|Fx - y\|_2^2 + \sum_{i=1}^{4} \lambda \|D_i x\|_1 \qquad (3)$$

Here x is the sought image-domain representation of the entire acquisition. Similarly, y represents the collection of k-space samples acquired during the entire experiment. When we write Fx, it is understood that each image in the sequence is Fourier transformed separately. Since k-space isn't sampled on a Cartesian grid, Fourier transforms are performed using a non-uniform FFT; we use the implementation by Sutton and Fessler [20].

Denoted by $D_i$, i=1, ..., 4 are the finite difference operators along each of the four physical dimensions of the dataset (x, y, z, and t). One can assign individual penalty weighting factors (that is, $\lambda_1, \lambda_2$ ...) to each of the four $\|D_i x\|_1$ terms; in this implementation, separate penalties are assigned to temporal and spatial terms.

The non-differentiable $\|\cdot\|_1$ terms in the penalty function are approximated by a smooth function $\|x\|_1 \cong \Sigma(\sqrt{|x_i|^2 + \hat{\sigma}^2} - \hat{\sigma})$ with $\hat{\sigma}$ on the order of $10^{-4}$. The problem is solved by gradient descent method, details of which can be found in [21].

Figure 14:
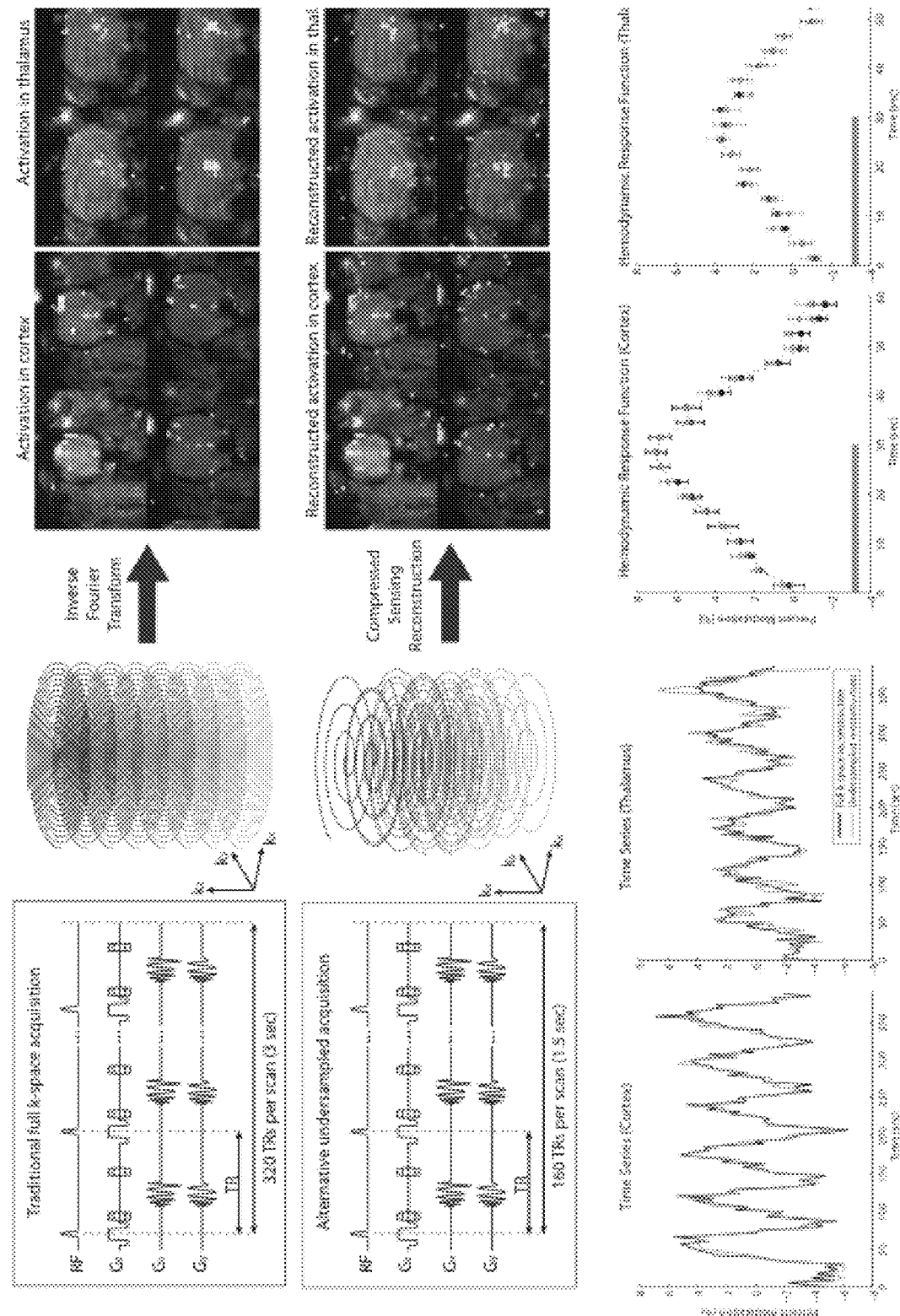
FIG. 14: Compressed Sensing for ofMRI. Top left shows pulse sequence timing diagram. Top row shows the case where k-space is uniformly sampled according to the Nyquist sampling rate using stack-of spirals trajectories. The middle row shows sparse k-space sampling by 50%. Ground truth (top) and CS-reconstruction (middle) from 50% data shows nicely corresponding activation phase map on the right. Reconstruction preserves distinct ROIs in correct locations. On the bottom left, the time course of ofMRI signal in cortex and thalamus regions of interest demonstrate close agreement for the fully sampled and 50% sampled and CS-reconstructed case. Bottom right image shows hemodynamic response functions (HRF) computed by averaging the six repetitions, which also shows close agreement.
Figure 15:
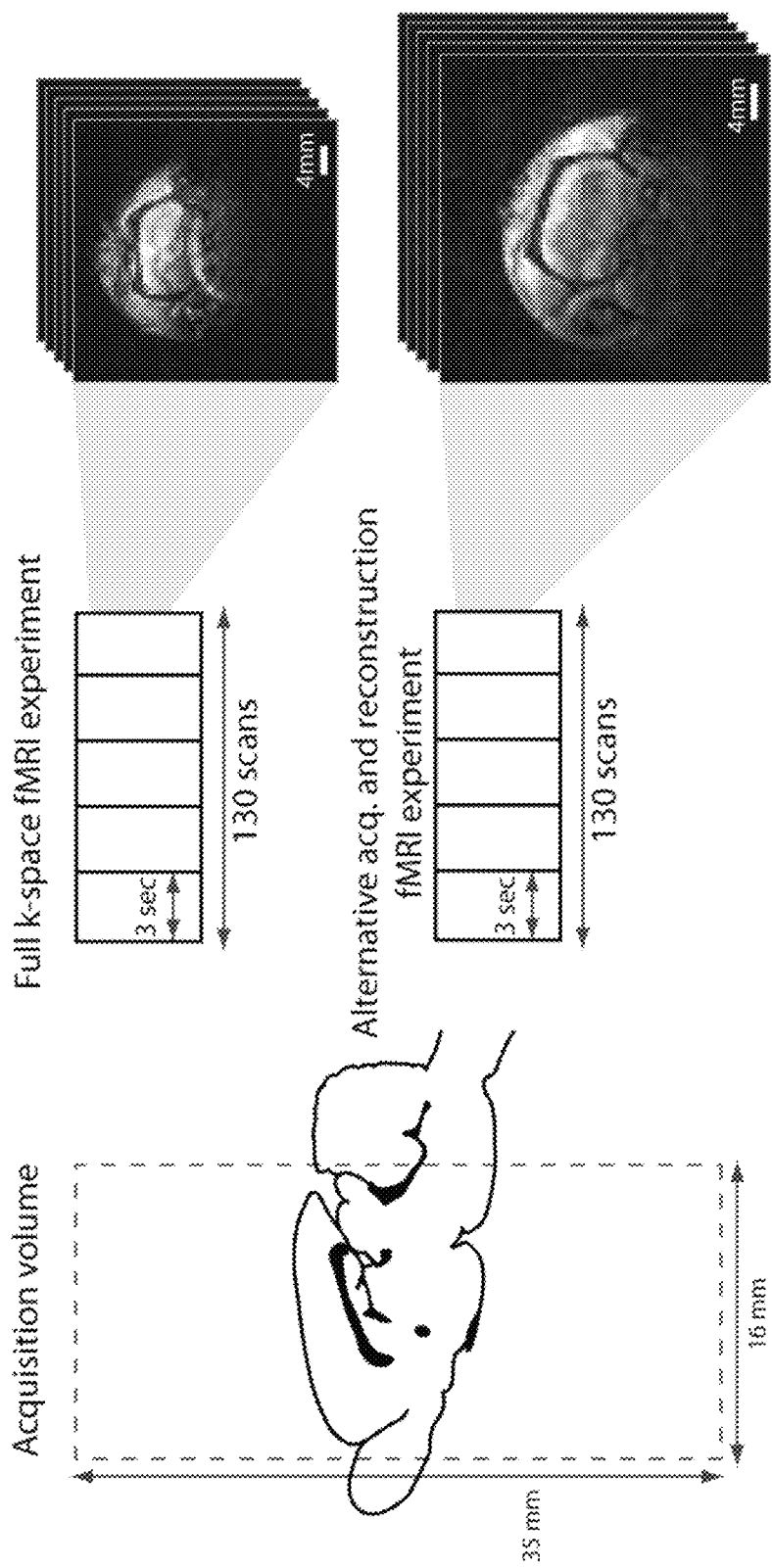
FIG. 15: High-Resolution acquisition enabled by CS. Top row shows acquisition and reconstruction from a fully sampled 500×500×500 um$^3$ acquisition over 3 s, while bottom row shows and 400×400×400 um$^3$ resolution achieved using compressed sensing over the same acquisition period.

FIG. 14 shows accurate reconstruction of the ofMRI activation with 50% data and FIG. 15 shows that high-resolution images with approximately 50% voxel size can be reconstructed using CS reconstruction. By using optimized trajectory design combined with CS algorithm, we aim to achieve in-plane resolution of 200×200 um². and 500 um through-plane resolution.

Aim3. Study Frequency Modulation Effects with Cortical Layer Specificity Using Real-Time, High-Resolution ofMRI.

The brain's communication through the vast network of neurons can be described by neuronal type (cell body location, axonal projection target, neurotransmitter type, genetic identity) and its temporal signaling pattern. For the first time, with the development of ofMRI and the methods in the present application, we will be able to study the brain's communication scheme with high precision in intact brain. Stimulations can be designed to target specific cell type with millisecond scale temporal precision while monitoring the whole brain response in real time at high resolution. As evidenced by different rates of spiking measured in the brain for different brain regions and cell type, the brain obviously has a coding scheme that is used for different communication purposes. In this aim, we will study how such coding scheme relates to propagation of information in the whole brain.

As a testing ground for the capability for this technology to elicit precise information of the communication mechanism, we will test the circuit response in these areas that are known to be relevant to the motor symptoms of Parkinson's disease. We will stimulate four different regions of the brain; the motor cortex (M1), the striatum, the thalamus, and the substantia niagra (Stn). Excitatory neurons, targeted by CamKIIa promoters optically stimulated at frequencies ranging from 0-100 Hz while light exposures are limited to individual cortical layers for M1 and individual nuclei for the thalamus. With real-time high-resolution imaging, the optical stimulation frequency and stimulation location will be adaptively controlled. Activation signal amplitude, region, temporal response shapes will be compared for each stimulation paradigm.

REFERENCES

1. Lee, J. H., et al., *Full-brain coverage and high-resolution imaging capabilities of passband b-SSFP fMRI at 3T.* Magn Reson Med, 2008. 59(5): p. 1099-1110.
2. Lee, J. H., et al., *Global and local fMRI signals driven by neurons defined optogenetically by type and wiring.* Nature, 2010. 465(7299): p. 788-92.
3. Zhang, F., et al., *Circuit-breakers: optical technologies for probing neural signals and systems.* Nat Rev Neurosci, 2007. 8(8): p. 577-81.
4. Ogawa, S., et al., *Oxygenation-sensitive contrast in magnetic resonance image of rodent brain at high magnetic fields.* Magn Reson Med, 1990. 14(1): p. 68-78.
5. Boyden, E. S., et al., *Millisecond-timescale, genetically targeted optical control of neural activity.* Nat Neurosci, 2005. 8(9): p. 1263-8.
6. Lee, J., et al. *Full-brain coverage and high-resolution imaging capabilities of passband SSFP fMRI at 3T.* in *ISMRM.* 2007. Berlin.
7. Zhang, F., et al., *Red-shifted optogenetic excitation: a tool for fast neural control derived from Volvox carteri.* Nat Neurosci, 2008. 11(6): p. 631-3.
8. Zhang, F., et al., *Channelrhodopsin-2 and optical control of excitable cells.* Nat Methods, 2006. 3(10): p. 785-92.
9. Zhang, F., et al., *Multimodal fast optical interrogation of neural circuitry.* Nature, 2007. 446(7136): p. 633-9.
10. Carr, H., *Steady-State free precission in nuclear magnetic resonance.* Physical Review Letters, 1958. 112: p. 1693-1701.
11. Aravanis, A. M., et al., *An optical neural interface: in vivo control of rodent motor cortex with integrated fiberoptic and optogenetic technology.* J Neural Eng, 2007. 4(3): p. S143-56.
12. Gradinaru, V., et al., *Optical deconstruction of parkinsonian neural circuitry.* Science, 2009. 324(5925): p. 354-9.
13. Gradinaru, V., et al., *Targeting and readout strategies for fast optical neural control in vitro and in vivo.* J Neurosci, 2007. 27(52): p. 14231-8.
14. Petreanu, L., et al., *Channelrhodopsin-2-assisted circuit mapping of long-range callosal projections.* Nat Neurosci, 2007. 10(5): p. 663-8.
15. Lustig, M., et al. *Faster Imaging with Randomly Perturbed, Undersampled Spirals and L1 Reconsfruction.* in *ISMRM.* 2005.
16. Lustig, M., D. Donoho, and J. M. Pauly, *Sparse MRI: The application of compressed sensing for rapid MR imaging.* Magn Reson Med, 2007. 58(6): p. 1182-95.
17. Kim, Y. C., S. S. Narayanan, and K. S. Nayak, *Accelerated three-dimensional upper airway MRI using compressed sensing.* Magn Reson Med, 2009. 61(6): p. 1434-40.
18. Chang, R. C., L. He, and T. Fang. *MR Image Reconsfruction from Sparse Radial Samples using Bregman Iteration.* 2005.
19. Rudin, L. I., S. Osher, and E. Fatemi, *Nonlinear Total Variation Based Noise Removal Algorithms.* Phys. D, 1992: p. 259-268.
20. Sutton, B. P. and J. A. Fessler, *Nonuniform Fast Fourier Transforms using Min-Max Interpolation.* IEEE Trans. Signal Processing, 2003: p. 560-574.
21. Boyd, S. and L. Vandenberghe, *Convex Optimization.* 2004, New York, N.Y.: Cambridge University Press.
22. Lee, J. H., et al., *Fast 3D imaging using variable-density spiral trajectories with applications to limb perfusion.* Magn Reson Med, 2003. 50(6): p. 1276-85.
23. Lee, J. H., et al., *Broadband multicoil imaging using multiple demodulation hardware: a feasibility study.* Magn Reson Med, 2005. 54(3): p. 669-76.
24. Seo, W. S., et al., *FeCo/graphitic-shell nanocrystals as advanced magnetic-resonance-imaging and near-infrared agents.* Nat Mater, 2006. 5(12): p. 971-6.
25. Lee, J. H., et al., *High-Contrast In-Vivo Visualization of Micro-Vessels using Novel FeCo/GC Magnetic Nanocrystals.* Magn Reson Med, 2009: p. in press.

Example 3: In Vivo Biomarker Development for the Design and Evaluation of Alzheimer's Disease Treatment There are increasing evidences that the brain functions as an integrated circuit with network communication across diverse brain circuit elements and that disorders result in network level dysfunction of the brain [1-3]. Therefore, while genetics, molecular and cellular neuroscience approaches search for the cause that leads to the disruption of the circuit elements, the understanding of how the brain network is functionally altered as a result is crucial in order to sort through the roles of each candidate genetic, biomolecular elements and to design therapeutic options that can reverse the functional changes.

Figure 16:
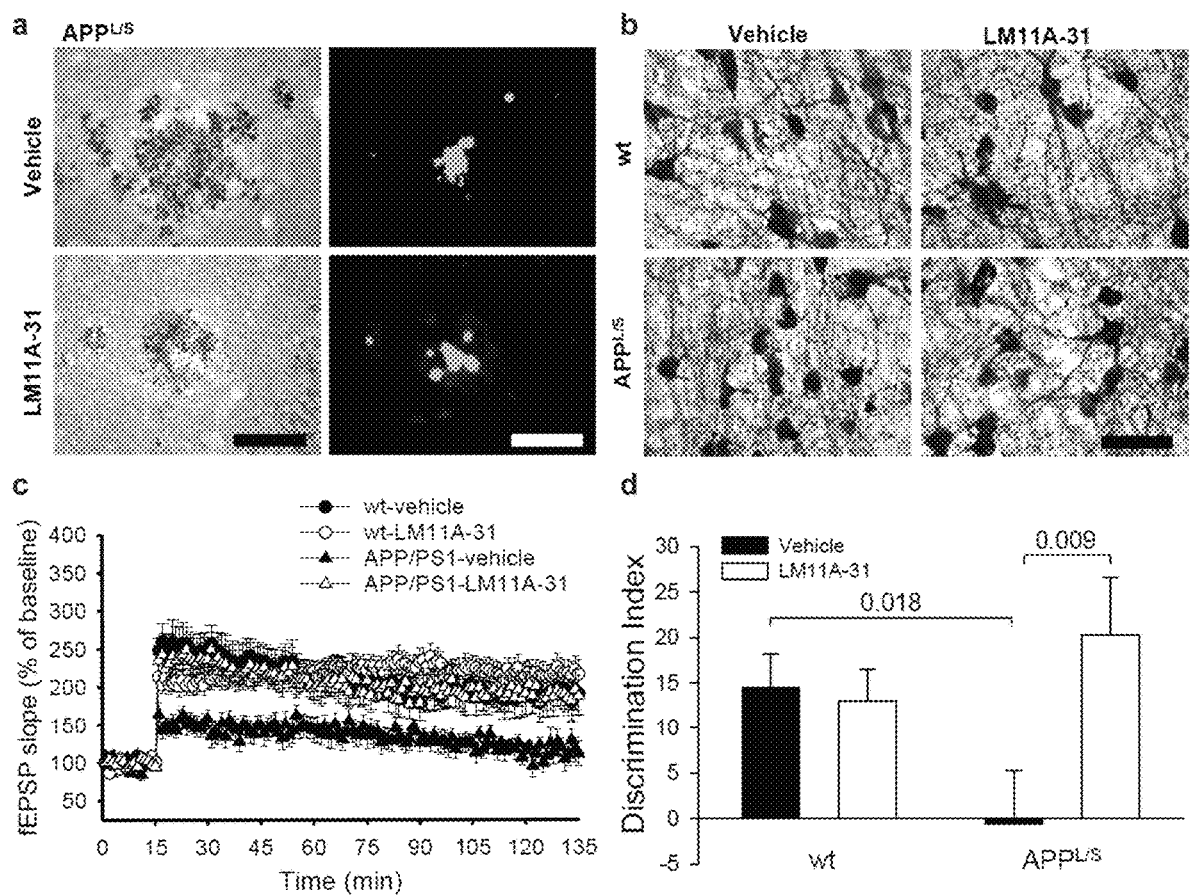
FIG. 16: Transgenic mouse model of AD shows dystrophic neurites and amyloid plaque formation in the hippocampus, reduction of cholinergic neurite length, volume and branching in the basal forebrain, reduction in LTP in the hippocampus, and object recognition deficits, which are all rescued significantly by the administration of a novel drug candidate, LM11A-31. a, Photomicrograph of APP immunolabeling for dystrophic neurites (left) and Thioflavin S staining for amyloid plaques (right) in hippocampus of APP$^{L/S}$ mice given vehicle or LM11A-31 as indicated. Scale bars=25 µm. b, Photomicrograph of choline acetyltransferase-immunostained basal forebrain sections. Treatment of APP$^{L/S}$ mice with LM11A-31 was associated with increased length, volume, and branching of cholinergic neurites. c, LM11A-31 normalizes LTP in APP/PS1 mice: APP/PS1-vehicle vs. wt-vehicle, p=0.003; APP/PS1-vehicle vs. APP/PS1-LM11A-31, p=0.02; wt-vehicle vs. wt-LM11A-31, NS. d, LM11A-31 prevented object recognition deficits in APPL/S mice. Statistical significance was determined using ANOVA and post-hoc Student-Neuman-Keuls testing.
Figure 17:
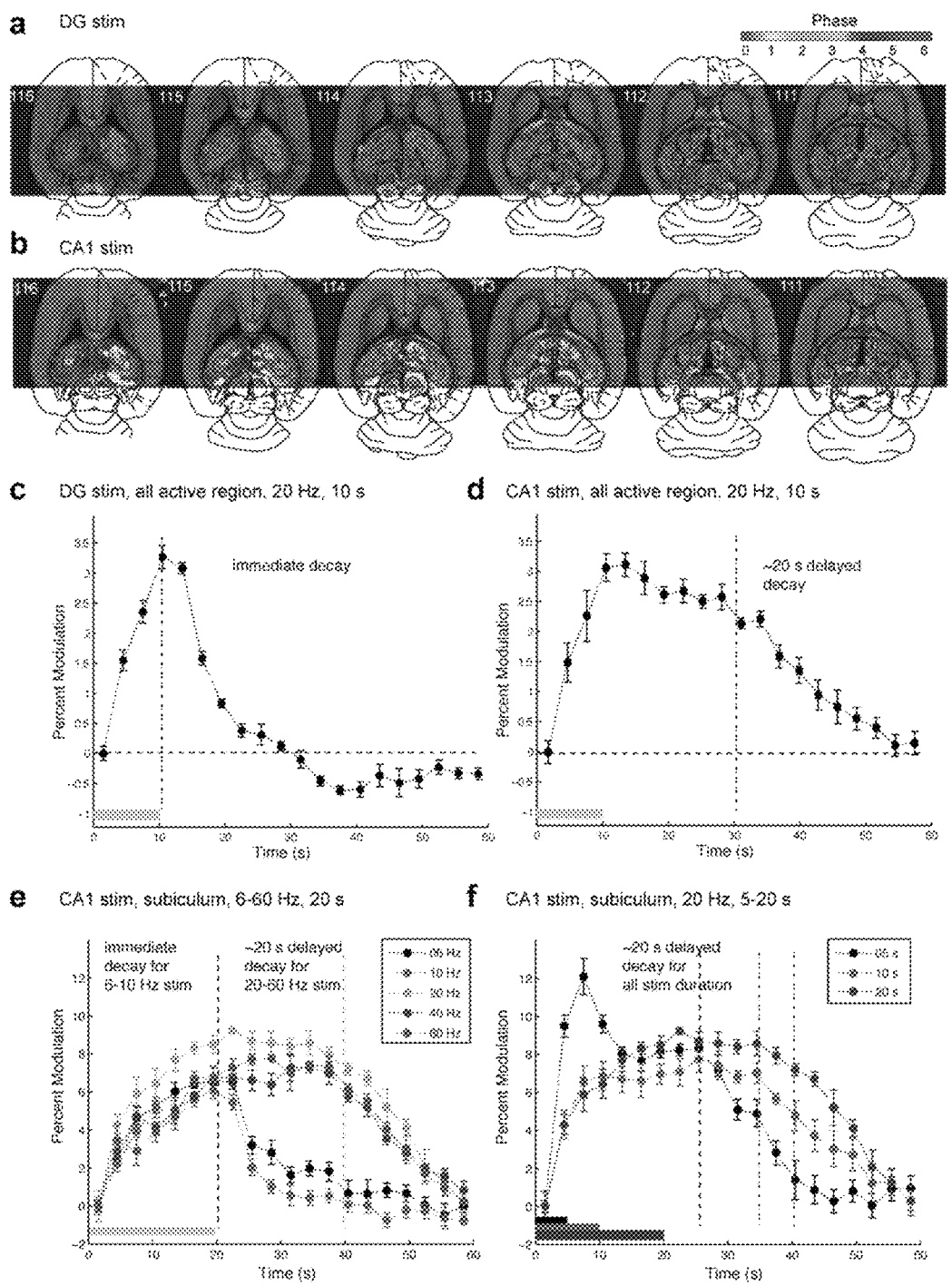
FIG. 17: ofMRI with pyramidal neuron stimulation in the hippocampus reveals frequency-dependent, cell-type-specific responses with full spatial information. a, 20 Hz, 10 s-stimulation of pyramidal neurons in DG shows unilateral activation, b, while identical stimulation of pyramidal neurons in CA1 shows bilateral activation. The phase map color difference also indicates the difference in the ofMRI-HRF shape. c, DG stimulation ofMRI-HRF averaged across all active voxels show immediate decay upon stimulation offset, while d, CA1 stimulation ofMRI-HRF shows sustained signal for an additional ~20 s period. e, Closer examination of the spatial activity pattern reveals the subiculum as the center of the sustained activity. 20 s stimulation of CA1 with frequencies ranging from 6 Hz to 100 Hz shows that stimulation frequencies above 20 Hz give rise to sustained ofMRI-HRF in the subiculum, while lower frequency stimulation leads to immediate decay of the ofMRI-HRF. ofMRI-HRF in the subiculum is also of higher magnitude compared to that of the overall average in d. f, ~20 s sustained activity in the subiculum is consistent across multiple durations of stimulation.

Despite the overwhelming need, currently, there is a relatively large gap in our ability to assess network level dysfunction. The complex dense wiring of the brain makes it extremely challenging to specifically control and trace the neural activity beyond a few synapses. The present invention provides methods to close this crucial gap in our ability to understand the large-scale dynamic changes in the brain network associated with the Alzheimer's disease (AD) (FIG. 16). We envision that such in vivo methods to assess the network communication will provide unprecedented synergy with the discoveries in genetics, molecular and cellular neuroscience allowing fast translation of the findings into the clinic. Our approach builds on and improves recently developed technologies called optogenetic [4] functional magnetic resonance imaging (ofMRI) [5] (FIG. 17) and passband b-SSFP fMRI [6], and novel high-resolution imaging approaches that are currently under development. The revolutionary features will include 3-dimensional (3D) [7] non-invasive evaluation of specific cell-type triggered network communication changes with precision across the whole brain. We believe this approach will greatly accelerate the understanding and search for cure of AD by allowing fast, longitudinal, and systematic evaluation of the circuit dysfunction associated with AD and by allowing quantitative screening and feedback for the design of therapeutic options.

The specific aims are to,

Aim1. Evaluate Normal Neural Network Response to the Stimulation of Key Circuit Elements Implicated in AD.

Neural circuit elements implicated in AD include the hippocampus (FIG. 16a, c), the basal forebrain and its cholinergic projections (FIG. 16b). To elucidate each circuit element's large-scale functional role in vivo, we will first stimulate specified group of pyramidal neurons in the hippocampus while monitoring its global functional response in normal mice using ofMRI. Local field potential and spiking activity will be subsequently measured in ofMRI active regions to confirm the source of the ofMRI signal. Normal, wild type mice will be used with CamKIIa::ChR2 viral injection [5].

Initial studies in the rats show unprecedented accuracy in detecting in vivo, spatially resolved, frequency dependent signaling using ofMRI. Upon above 20 Hz stimulation of pyramidal neurons in CAL long sustained, bilateral ofMRI-hemodynamic response function (HRF) with the most distinct sustained activation in the subiculum is observed (FIG. 17d-f). ofMRI-HRF in the subiculum also shows more than two fold larger peak amplitude compared to the overall average (~3.5% vs. ~9%, FIG. 2d vs. e, f) and was found to be independent of the stimulation duration (5-20 s, FIG. 17f).

Given the anatomical evidence showing prominent degeneration of the basal forebrain's cholinergic system in mouse model of AD (FIG. 16b), Chat-Cre mice in combination with (DIO) ChR2-EYFP virus [8] will also be used to selectively stimulate cholinergic neurons in the basal forebrain while monitoring the global network response.

ofMRI spatial activity map, and ofMRI-HRF resulting from the selective stimulation of pyramidal neurons in the hippocampus and cholinergic neurons in the basal forebrain will reveal communication patterns that are potentially altered in AD.

Aim 2. Establish ofMRI Response as a Bio-Marker for AD Using Transgenic Mouse Model of AD.

A well-characterized mouse model of AD, $APP^{L/S}$ [9] will be used to characterize the difference in ofMRI response compared to normal mice. Taking advantage of the non-invasive, in vivo nature of ofMRI, the response will be monitored every month, from 1 month to 12 months. Spatial activation patterns, and ofMRI-HRF shape will be compared to the wild type response, and throughout the progress of AD in $APP^{L/S}$.

ofMRI response will be distinct in wild type and AD model mice. With ofMRI's proven capability to measure intricate cell type, frequency dependent responses (FIG. 17), the progressive functional degeneration will be captured with good sensitivity across different disease state.

Aim3. Develop ofMRI as a Platform to Test Promising Drug Candidates.

A promising drug candidate for AD, LM11A-31 [10, 11] (FIG. 16) will be used to test ofMRI's capability to evaluate treatment outcome. LM11A-31 will be continuously administered starting at 1, 3, 6, 9 months while ofMRI is conducted every month to evaluate treatment-stage dependent functional reversal.

ofMRI response during treatment will quantitatively visualize treatment outcome. Longitudinal monitoring capability will elucidate the critical therapy time points, and key functional elements related to the behavioral outcome. This will in turn serve as design feedback for further improved drug candidates. Such process will greatly accelerate design and evaluation of AD treatment.

REFERENCES

1. Gradinaru, V., et al., *Optical deconstruction of parkinsonian neural circuitry*. Science, 2009. 324(5925): p. 354-9.
2. Cardin, J. A., et al., *Driving fast-spiking cells induces gamma rhythm and controls sensory responses*. Nature, 2009. 459(7247): p. 663-7.
3. Kravitz, A. V., et al., *Regulation of parkinsonian motor behaviours by optogenetic control of basal ganglia circuitry*. Nature. 466(7306): p. 622-6.
4. Zhang, F., et al., *Circuit-breakers: optical technologies for probing neural signals and systems*. Nat Rev Neurosci, 2007. 8(8): p. 577-81.
5. Lee, J. H., et al., *Global and local fMRI signals driven by neurons defined optogenetically by type and wiring*. Nature. 465(7299): p. 788-92.
6. Lee, J. H., et al., *Full-brain coverage and high-resolution imaging capabilities of passband b-SSFP fMRI at 3T*. Magn Reson Med, 2008. 59(5): p. 1099-1110.
7. Lee, J. H., et al., *Fast 3D imaging using variable-density spiral trajectories with applications to limb perfusion*. Magn Reson Med, 2003. 50(6): p. 1276-85.
8. Sohal, V. S., et al., *Parvalbumin neurons and gamma rhythms enhance cortical circuit performance*. Nature, 2009. 459(7247): p. 698-702.

9. Rockenstein, E., et al., *Early formation of mature amyloid-beta protein deposits in a mutant APP transgenic model depends on levels of Abeta*(1-42). J Neurosci Res, 2001. 66(4): p. 573-82.
10. Longo, F. M. and S. M. Massa, *Neurotrophin receptor-based strategies for Alzheimer's disease*. Curr Alzheimer Res, 2005. 2(2): p. 167-9.
11. Massa, S. M., et al., *Small, nonpeptide p75NTR ligands induce survival signaling and inhibit proNGF-induced death*. J Neurosci, 2006. 26(20): p. 5288-300.

Example 4: In Vivo Visualization and Control of Disease-Caused Neural Circuit Modifications There are increasing evidences that the brain functions as an integrated circuit with network communication across diverse brain circuit elements and that disorders result in network level dysfunction of the brain [1, 2]. For example, while the Parkinson's disease (PD) is prominently characterized by the death of dopaminergic neurons in substantia nigra pars compacta (SNc), one of the most significant functional outcomes is the disruption of motor control pathway involving motor cortex, striatum, globus pallidus, sub-thalamic nuclei (Stn), and substantia nigra pars reticula (SNr) [1, 2]. Circuit element failure such as the death of dopaminergic neurons causes the communication pattern across these diverse brain circuit elements to change, which can be directly linked to the disease phenotype. Approaches such as deep brain stimulation (DBS) [3] to artificially restore the functional disruption show promising outcomes, and more specific targeting using optogenetic stimulation based on circuit topology resulting in more precise therapeutic efficacy [1] further supports the importance of accurate understanding and restoration of the brain network communication. Therefore, while genetics, molecular and cellular approaches search for the cause that leads to the disruption of the circuit elements, the understanding of how the brain network is functionally altered is crucial in order to sort through the roles of each candidate genetic, biomolecular element and to design therapeutic options that can reverse the changes in network function.

Despite the overwhelming need, currently, there is a relatively large gap in our ability to assess network level dysfunction. Complex dense wiring of the brain makes it extremely challenging to trace the neural function beyond a few synapses. The present invention provides methods to close this crucial gap in our ability to understand the large-scale dynamic changes in the brain network associated with the neurological diseases. Our method will find its initial building blocks from the technologies that we recently developed called optogenetic functional magnetic resonance imaging (ofMRI) [4] and passband b-SSFP fMRI [5], and novel high-resolution, real-time imaging methods currently under development. The revolutionary features will include 3-dimensional (3D) non-invasive evaluation of the network communication changes with precision across the whole brain. This approach will greatly accelerate the understanding and search for cure of brain disorders by allowing fast, longitudinal, and systematic evaluation of the circuit dysfunction associated with the disease and by enabling quantitative screening and feedback for the design of therapeutic options. The approaches outlined below are generally applicable to the study of a wide range of neurological diseases including PD, Alzheimer's disease (AD), epilepsy, stroke, addiction, and depression.

The specific aims are to,

Aim 1: Develop High-Resolution, Real-Time, Awake, Behaving ofMRI of Mice in Virtual Reality.

To enable investigation at the sub-nucleus, layer specific level, the spatial resolution will be improved to approximately ~200 um while covering the whole brain. Our first published study was conducted with 500 um, isotropic resolution. Novel parallel imaging and compressed sensing algorithms are currently under development to facilitate such high spatial resolution. Furthermore, to improve study throughput and enable interactive stimulation parameter control, real-time ofMRI imaging method is under development with robust real-time acquisition, reconstruction, analysis, and motion correction. Currently, our parallel computation algorithms under development is able to reduce computations that normally require 1.5 s to be performed in under 22 ms. Awake, behaving studies will then be enabled to investigate brain function under motor behavioral states by combining the high-resolution, real-time imaging approach with head-fixed, virtual-reality [6] ofMRI method development.

Aim 2: Understanding the Neural Circuit's Network Communication Patterns Associated with PD.

Figure 18:
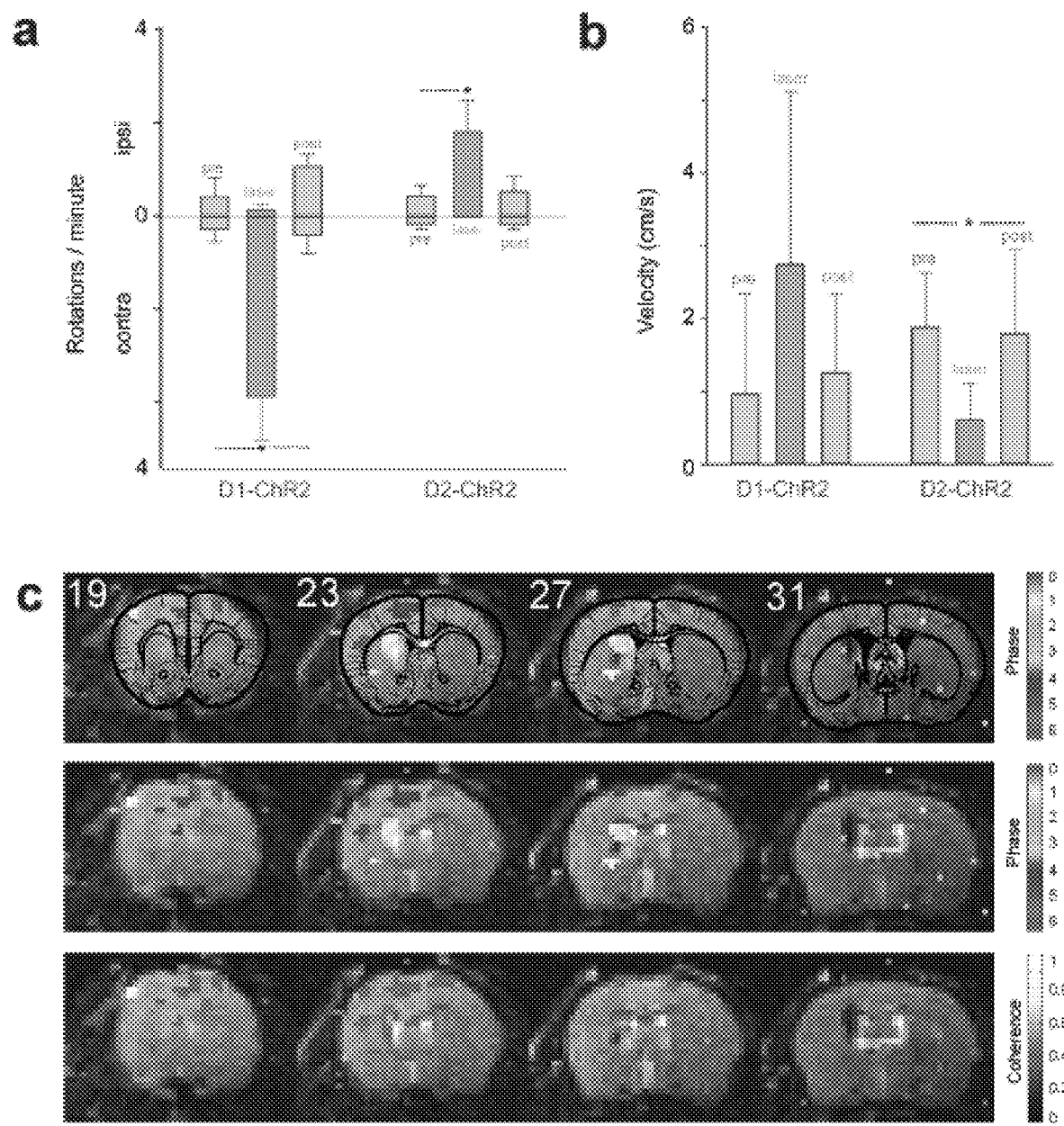
FIG. 18: Unilateral striatal D1-, D2-MSN stimulation driven behavioral response and corresponding neural network response measured using ofMRI. a, D1-MSN stimulation drives contralateral rotation while D2-MSN stimulation drives ipsilateral rotation. b, Velocity of motion increases with D1-MSN stimulation, while it decreases with D2-MSN stimulation. c, ofMRI in anesthetized mice at 0.5 mm isotropic resolution with D2-MSN stimulation shows robust positive BOLD at stimulation site and robust negative BOLD in cortical regions. First row: Paxino's atlas overlay on color-coded phase map with upper left corner showing coronal slice numbers from atlas. Second, third rows: phase and amplitude maps of activity.

With such powerful new ofMRI imaging platform, PD will be investigated by visualizing the role of striatal D1 and D2 Medium Spiny Neurons (MSN). A recent study using optogenetic control combined with electrophysiology and behavioral tests showed that the dorso-medial D1- and D2-MSN play opposite roles in generating motor output through the hypothesized direct and indirect pathways [2]. The control imbalance of D1 and D2 MSN is potentially directly linked to the motor output dysfunction observed in PD. With the ofMRI approach, we aim to identify the D1 and D2 MSN downstream targets and their function across the whole brain. Tracing anatomical connections and/or activity through multiple synapses is a highly challenging task especially when it goes through complex structures such as the thalamus and/or the neocortex. Our preliminary results (FIG. 18) show ofMRI's ability to visualize neural activity with accuracy, where inhibitory D2-MSN neural activity gives positive blood oxygenation level dependent (BOLD) signal while the hypothesized decreased neural activity in the cortical regions gives negative BOLD response. Cortical output regions were accurately identified where negative BOLD effects are observed throughout many regions related to the motor system. This unprecedented capability to accurately pinpoint downstream functional communication partners that are many synapse away will allow us to get a comprehensive understanding of PD related circuitry while also serving as an important in vivo quantitative biomarker.

Aim 3. Interactive Deep Brain Stimulation Target Selection and Novel Drug Screening for PD.

The rodent model of PD will then be used to causally link the disease phenotype with global functional changes in the brain. Identified communication changes will then be used to screen for therapeutic options that can reverse this effect. We plan to establish a platform for the test and interactive development of DBS and drug therapy. 6-hydroxydopamine (6-OHDA) will be injected unilaterally into the medial forebrain bundle (MFB) to create hemiparkinsonian D1-, D2-Cre, and Thy1 transgenic mice. They will be used to stimulate striatal D1-, D2-MSN, and afferent fibers going into Stn. These targets were chosen since D1, D2-MSN control imbalance has been implicated as the source of PD motor symptoms while Stn [3] is a major clinical DBS target. With the ofMRI approach, downstream communication target of the stimulation will be identified in the disease model. Based on where altered communication is observed, optogenetic DBS target will be iteratively designed to better restore normal communication.

Then, we plan to test drug efficacy in restoring the communication starting with levodopa. Utilizing the non-invasive nature of ofMRI, the impact of drug administration will be monitored longitudinally in the same animal Short and long term impact of the drug on circuit function will be quantitatively assessed allowing comprehensive evaluation and treatment design. The ultimate goal is to enable a systematic selection of a DBS target and iterative design of novel drug candidates.

In summary, this present method suggests a paradigm-shifting approach to the study of the mechanisms underlying neurological diseases: a direct, in vivo method to visualize and control disease-caused neural circuit alterations. This approach will enable rapid, synergetic developments in genetics, drug discovery, stem cell therapy, neural interface, prosthetics design, and human neuroimaging by providing a comprehensive understanding of the brain circuit mechanism.

REFERENCES

1. Gradinaru, V., et al., *Optical deconstruction of parkinsonian neural circuitry. Science,* 2009. 324(5925): p. 354-9.
2. Kravitz, A. V, et al., *Regulation of parkinsonian motor behaviours by optogenetic control of basal ganglia circuitry. Nature.* 466(7306): p. 622-6.
3. Rodriguez-Oroz, M C., et al., *Bilateral deep brain stimulation in Parkinson's disease: a multicentre study with 4 years follow-up. Brain,* 2005. 128(Pt 10): p. 2240-9.
4. Lee, J. H, et al., *Global and local fMRI signals driven by neurons defined optogenetically by type and wiring. Nature.* 465(7299): p. 788-92.
5. Lee, et al., *Full-brain coverage and high-resolution imaging capabilities of passband b-SSFP fMRI at 3T. Magn Reson Med,* 2008. 59(5): p. 1099-1110.
6. Dombeck, D. A., et al., *Functional imaging of hippocampal place cells at cellular resolution during virtual navigation. Nat Neurosci.* 13(11): p. 1433-40.

Example 5: In Vivo Control and Functional Visualization of Stem Cell-Driven CNS Regeneration This proposal suggests a consilience of multidisciplinary lines of research to address a singular question that could never be tapped previously: a direct, cell-specific, and in vivo functional interrogation and visualization of neural circuitry regenerated by stem cell transplantation. Stem-cell mediated therapy is a promising candidate for an extensive array of central nervous system (CNS) diseases including, spinal cord injuries, Parkinson's disease, Alzheimer's disease, multiple sclerosis, and stroke. Despite their debilitating nature and urgent calls for cure, the very complexity and functional nature of neural fabric underlying CNS diseases substantially negate successful therapeutic options to date. Here, the ability of stem cells to potentially regenerate non-dividing cells, including neurons, gives fresh impetus for a whole new class of innovative treatments aimed at directly restoring entire neural circuits, which in turn will functionally substitute those lost during CNS disease etiology. Recent development of induced pluripotent stem cells (IPSC) [1] further increased the societal viability of such therapeutic strategies by removing the ethical concerns inherent with embryonic stem cells (ESC). IPSCs are derived from cells that form the bodies of organisms as opposed to sperm or egg cells and despite its origin, they differentiate more readily and survive better upon transplantation than adult stem cells. They also offer the advantage of the possibility of being derived from the patients receiving the treatment, and therefore remove the risk of rejection, requiring no immunosuppressive drugs.

Figure 19:
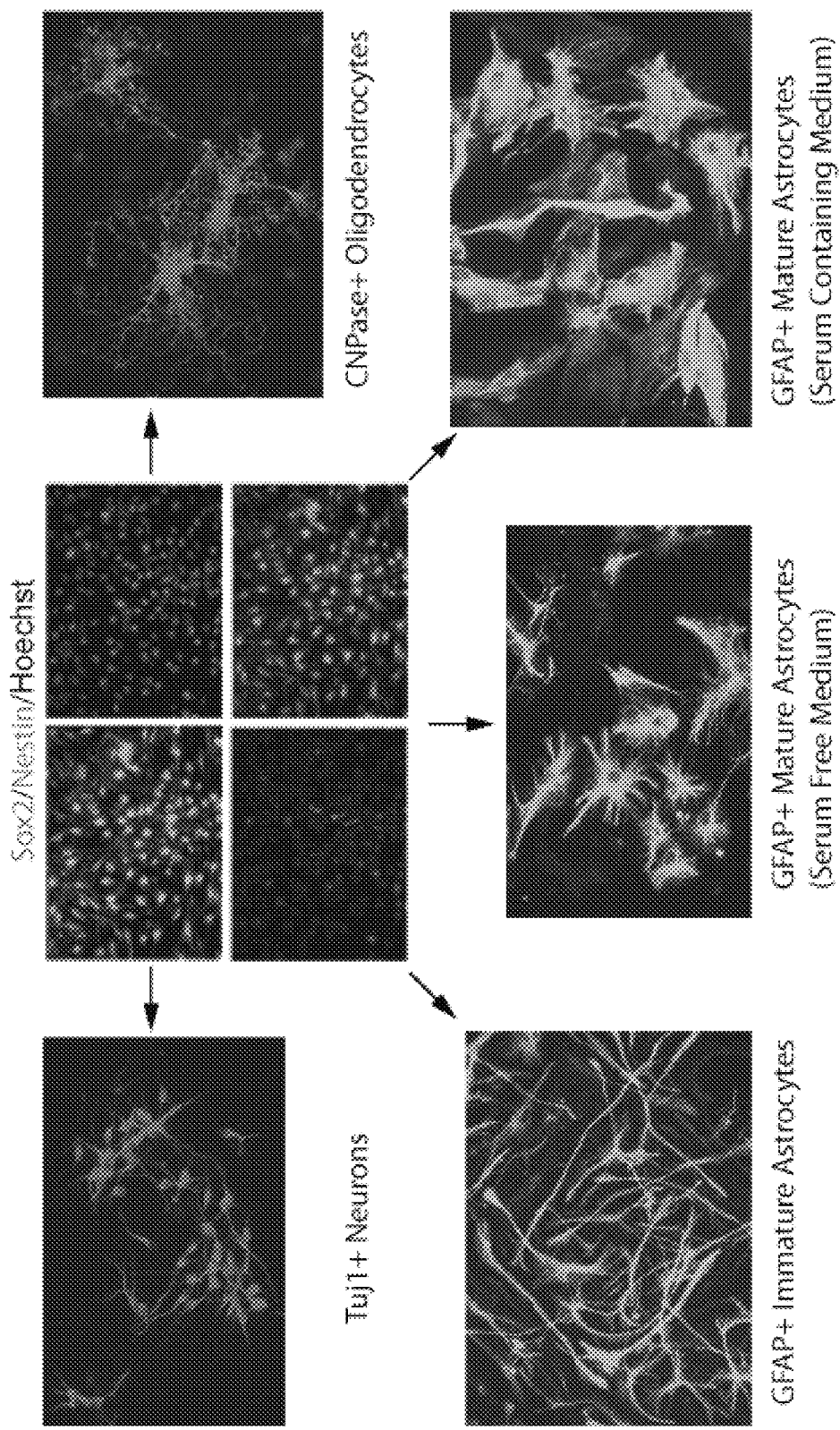
FIG. 19: Neural progenitor stem cells (middle column on top) and their differentiation in to various nerve cells. To explore the full potential of stem cell transplantation therapy, it is essential to be able to evaluate the functional outcome of the transplantation of various neural circuit components at different stages of development, and in different target regions in live intact CNS.

Despite the paradigm-shifting potential for stem cell guided CNS repair, the actual number of approved stem cell therapies to date remains insignificant and mostly outside of the United States. Primary reasons for this underutilized potential include the highly varying therapy efficacy and the possibility of serious side effects resulting from interference with normal CNS functions. The question then becomes, "How can we get an objective and direct measure of stem cell induced CNS perturbations?" Current efforts to more precisely understand the regeneration processes include: guided differentiation of the stem cells before transplantation (FIG. 19) [2-4], and ex vivo live and fixed microscopy/imaging techniques. While these techniques provide valuable information on stem cell survival, phenotypical renormalization of CNS cells and connectivity, cell survival and phenotype similarity are merely indicative of normal CNS functions, but do not necessarily imply restitution of normal neuronal function. Direct elucidation of neuronal functionality of regenerated CNS neurons as well as their communication partners linked by local and distal synaptic connections, remain the holy grail for the future of CNS stem cell therapy.

In order to bring stem cell therapy to its full-blown potential, important developments have to take place. Most importantly, neuronal function has to be assessed in vivo in intact brain with a large field-of-view (FOV), in some embodiments covering the whole brain and the spinal cord, as needed. The functionality of neurons assessed in cell culture and slice setting—especially those established through stem-cell induced regeneration—may significantly deviate from those in an intact, whole brain with its exceedingly large number of precisely switched local and long-range connections. Moreover, one would ideally seek for a way of probing such functionalities in a cell-type and spatio-temporally accurate manner. Advances in molecular biology and genetics provide us with building blocks that can potentially lead to ground-breaking therapies. Yet, without a way to quantitatively assess the functional changes in the intact brain, sorting through the massive possibilities of how the complex CNS might respond to the potential therapeutic options are quite challenging, greatly hampering the development of new therapies.

In addition, assessment of functionality in vivo can allow behavioral and longitudinal studies to be performed in the same animal removing inter-animal dependent variations. This can significantly improve the accuracy, reduce cost and time for many studies assessing neural function post-transplantation of stem cells. Finally, non-invasive techniques that allow functional assessment in intact whole brain have the potential to be translated into functional assessment of human patients.

In vivo circuit function assessment is conventionally done with electrophysiological measurements in animals, while non-invasive options for animal and humans are made possible by electroencephalography (EEG), magnetoencephalography (MEG), positron emission tomography (PET), and functional magnetic resonance imaging (fMRI) [6]. To this end, electrophysiological measurements are limited by its lack of spatial information, while EEG, MEG fMRI suffer from the ambiguity of the source of the signal observed, and their relatively low spatial and/or temporal resolution. Due to these limitations, these in vivo techniques in its current form are deemed unsuitable to provide conclusive information on stem cell-driven functional changes.

Another important challenge is that in the ideal case, causal relationships between the transplanted stem cells' activity and the resulting functionality change should be assessed. Without causal relations established between the activity of the transplanted cells and the resulting circuit activity, it will be difficult to isolate the direct cause of the functional change, thus leaving room for ambiguity. For example, in many cases where stem cell therapy leads to transient improvements in function, it is important to know whether it is due to changes in the direct signaling role of the transplanted cells or whether is it due to the secondary effects from the transplantation. In short, in order to address such questions, it is imperative to devise a way to directly control the transplanted cells and visualize its effects of the controlled changes on the CNS circuit.

For transplantation, wild-type Sprague-Dawley and/or Fischer rats can be employed. In some embodiments, nude rats can be employed. In some embodiments, a stem cell line derived from humans can be used as the transplanted stem cell line. In some embodiments, stem cell lines derived from rodents can be employed as the transplanted cell line.

Therefore, one could imagine a technology enabling precise selective manipulation of the transplanted stem cells based on the stem cell developmental outcome along with high quality visualization of functional changes resulting from such control. This technology should also provide a way to selectively control any CNS circuit element based on genetic and topologic identity to be able to analyze the functional restoration and circuit level activity change resulting from the stem cell therapy. For example, if stem cell therapy were to be used for Parkinson's disease by transplanting stem cells in the striatum, one can separately stimulate transplanted stem cells that developed into excitatory, inhibitory neurons, and astrocytes to observe the functional changes arising from selectively stimulating them. In addition, it would be important to look at what effects, stimulating different types of neurons in areas known to be relevant to Parkinson's disease such as substantia niagra (Stn), striatum, and motor cortex (M1) [7] has on the overall CNS circuit.

In this application, we describe such a technology based on genetically engineered probe for optical control and visualization of regenerating neurons, which in-turn will greatly accelerate new stem cell therapy development by allowing fast, longitudinal, and systematic evaluation of all the therapeutic options.

The evolutionary features this application described can be summarized as follows.

1. Stem cells will have genetically engineered built-in modulators and/or reporters which will be expressed only in cells that develop into specific neuronal types (excitatory, inhibitory, astrocyte, etc.). The modulators will have high genetic precision, excitation or inhibition capability, and temporal precision. The reporters will be designed to have high genetic precision and sensitivity for anatomical localization of stem cells.
2. High quality, high-resolution fMRI images will be acquired, reconstructed, analyzed in real-time to visualize the functional changes associated with in vivo neural circuit modulation. Reporter-provided anatomical localization will be combined with alternate image contrast mechanism to enable tracking of a small number of stem cells, which will compliment the functional information.
3. Characterizing different neuro-modulation frequency in association with the fMRI signal changes. Different connections within the CNS can potentially have distinct signaling mechanism. To allow precise characterization of the observed fMRI signal in relations to the underlying signaling mechanism, temporally precise optical neuro-modulation technique will be utilized to emulate different frequency modulation while fMRI signal is observed.

Figure 20:
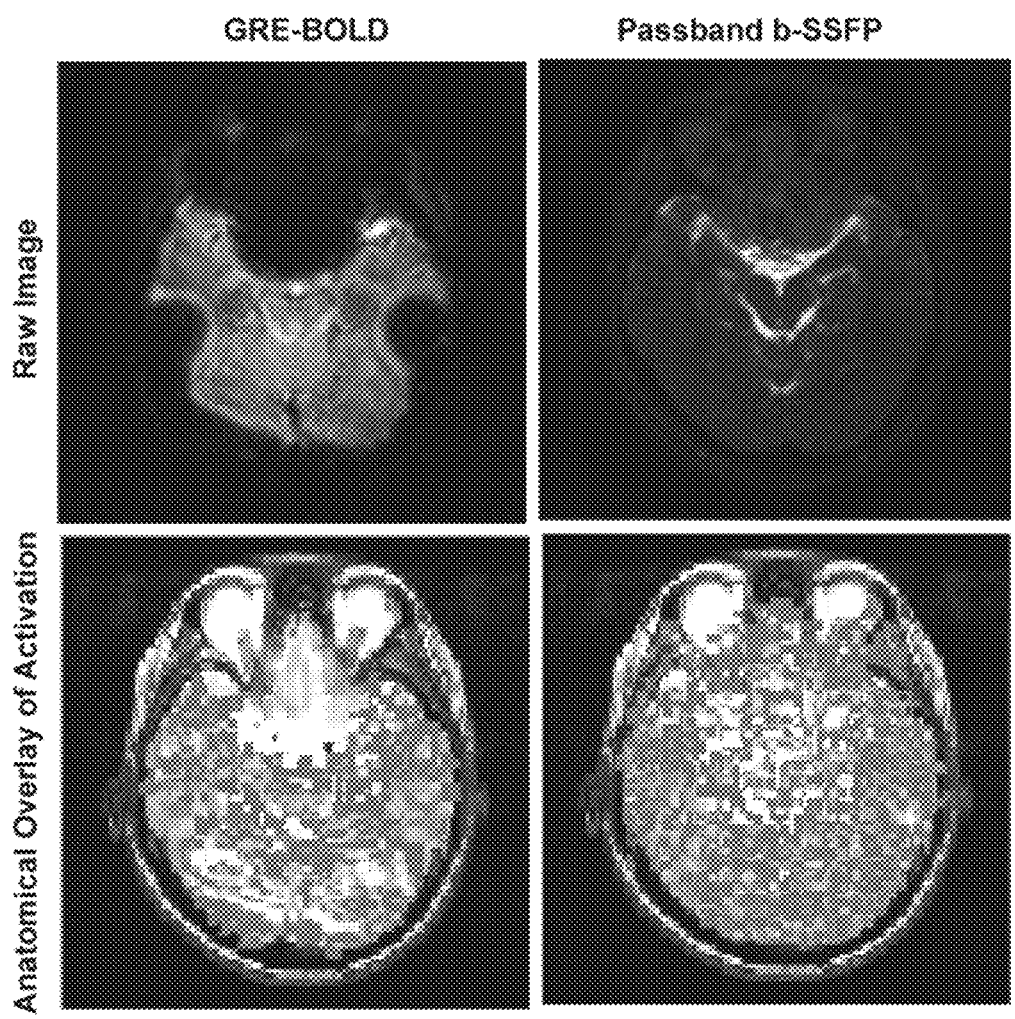
FIG. 20: Human fMRI during a breath-holding task shows large distortions in the conventional GRE-BOLD images while no such distortions are observed in the passband b-SSFP fMRI images. The corresponding anatomical overlay of the activity, as a result, shows significant missing activity regions for GRE-BOLD while no such dropouts are present in passband b-SSFP fMRI.
Figure 21:
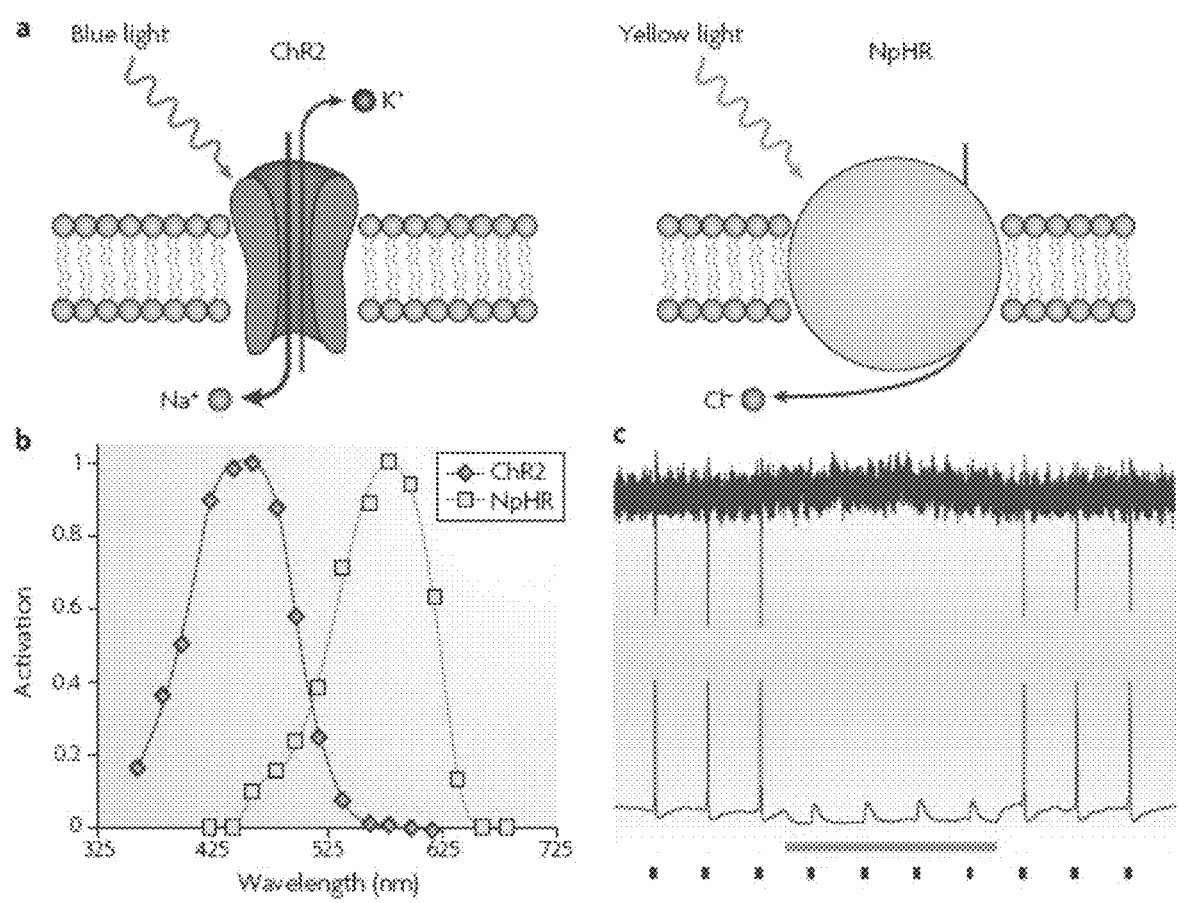
FIG. 21: Optogenetic tools: ChR2 and NpHR. a, Schematic of channelrhodopsin-2 (ChR2) and the halorhodopsin (NpHR) pump. Following illumination with blue light (activation maximum 470 nm), ChR2 allows the entry of cations into the cell. NpHR is activated by yellow light illumination (activation maximum 580 nm) and allows the entry of Cl anions. b, Action spectra for ChR2 and NpHR. The excitation maxima for ChR2 and NpHR are separated by 100 nm, making it possible to activate each opsin independently with light. c, Cell-attached (top) and whole-cell currentclamp (bottom) traces from hippocampal neurons show in all-optical neural activation and inhibition. The pulses represent the blue light flashes used to drive ChR2-mediated activation and the bar denotes NpHR-mediated inactivation.

The present method builds on two state-of-the-art technologies. One is the imaging technology called passband b-SSFP fMRI method (FIG. 20) [8] and the other is the optical-neuromodulation technology called optogenetics (FIG. 21) [5, 9-11]. Passband b-SSFP fMRI is a novel fMRI method that utilizes rapid radiofrequency excitation pulses combined with fully-balanced gradient pulses during each excitation repetition interval ($T_R$) [12]. Due to its short readout time and $T_R$, b-SSFP provides distortion-free 3D imaging suitable for full-brain, high-resolution functional imaging. While the conventional fMRI [6] is a highly successful technique that provides a non-invasive means to study the whole brain including deep-brain structures, it has significant limitations for the accurate assessment of neural function in its current form. Due to large spatial distortions, large portions of the brain cannot be imaged while the spatial resolution needs significant improvement to provide information necessary for the state-of-the art neuroscience. Passband b-SSFP fMRI, by providing a way to obtain distortion-free 3D isotropic resolution images, opens a new window for fMRI's role to become a more quantitatively accurate method. Optogenetics [5, 9-11], on the other hand, is a neuro-modulation technology in which single-component microbial light-activated trans-membrane conductance regulators are introduced into specifically targeted cell types and circuit elements using cell type specific promoters to allow millisecond-scale targeted activity modulation in vivo [13]. Thus far, one of the greatest challenges in neuroscience has been the difficulty of selectively controlling different circuit elements of the brain to understand its function. Optogenetics, enables in vivo control of genetically targeted circuit elements.

Figure 22:
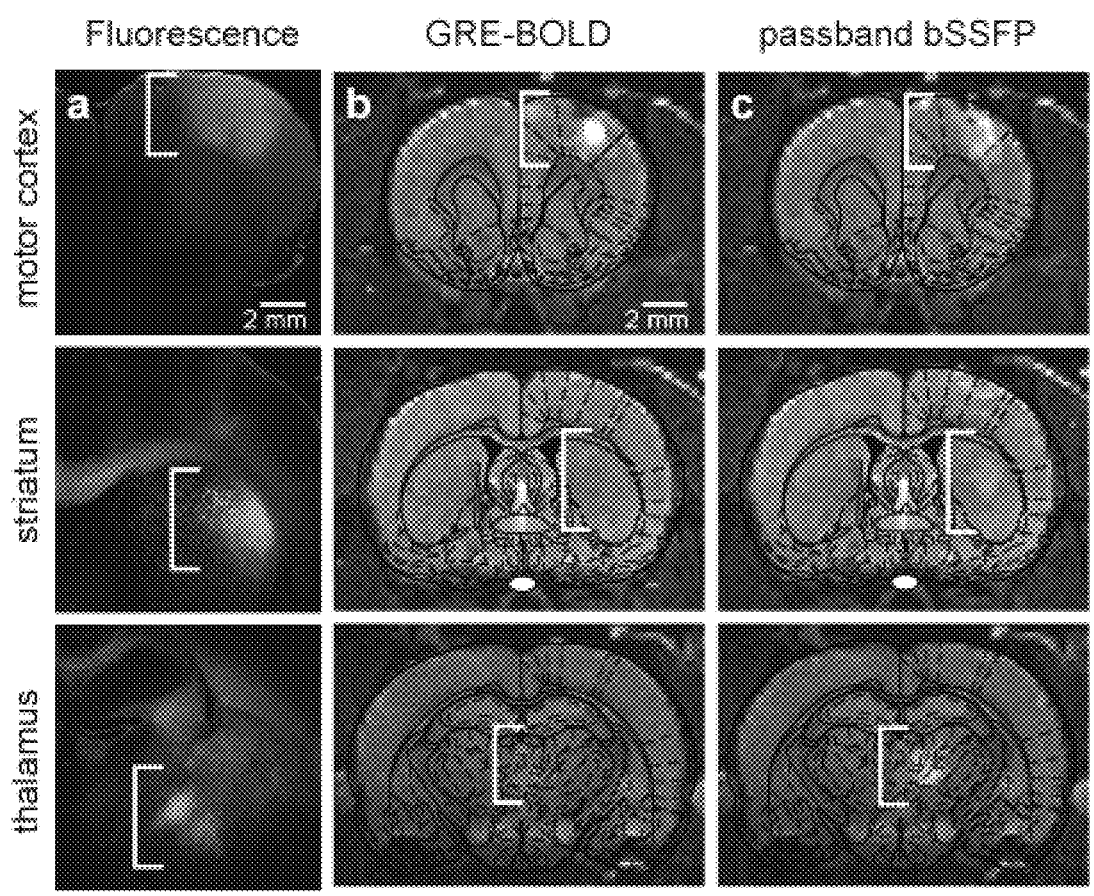
FIG. 22: ofMRI circuit mapping: conventional BOLD and passband bSSFP-fMRI. a, Injection of CaMKIIα::ChR2-EYFP in M1, as expected, leads to opsin visualization in motor cortex, striatum, and thalamus, i.e. the primary site of injection and sites where axons of expressing neurons extend. b, Hemodynamic response following M1 stimulation: conventional BOLD fMRI superimposed onto appropriate atlas image. c, Imaging the same hemodynamic response with passband bSSFP-fMRI, which more fully captures circuit-level activity.

The successfulness and feasibility of small animal optogenetic fMRI has been demonstrated (FIG. 22). Now, with the successful demonstration of the feasibility of such technology, the next step is to use this technology to evaluate and design new stem cell therapy options, capabilities that cannot be achieved through simple improvements of existing technology. Currently available technologies only allow studies with precisely controlled ex vivo environment or poorly controlled in vivo environment. Closing this gap and enabling precise control and measurements in vivo require a paradigm shift, a clear vision, and multi-disciplinary technological expertise combined with carefully planned research over several years.

Stem Cell Genetic Engineering

Figure 23:
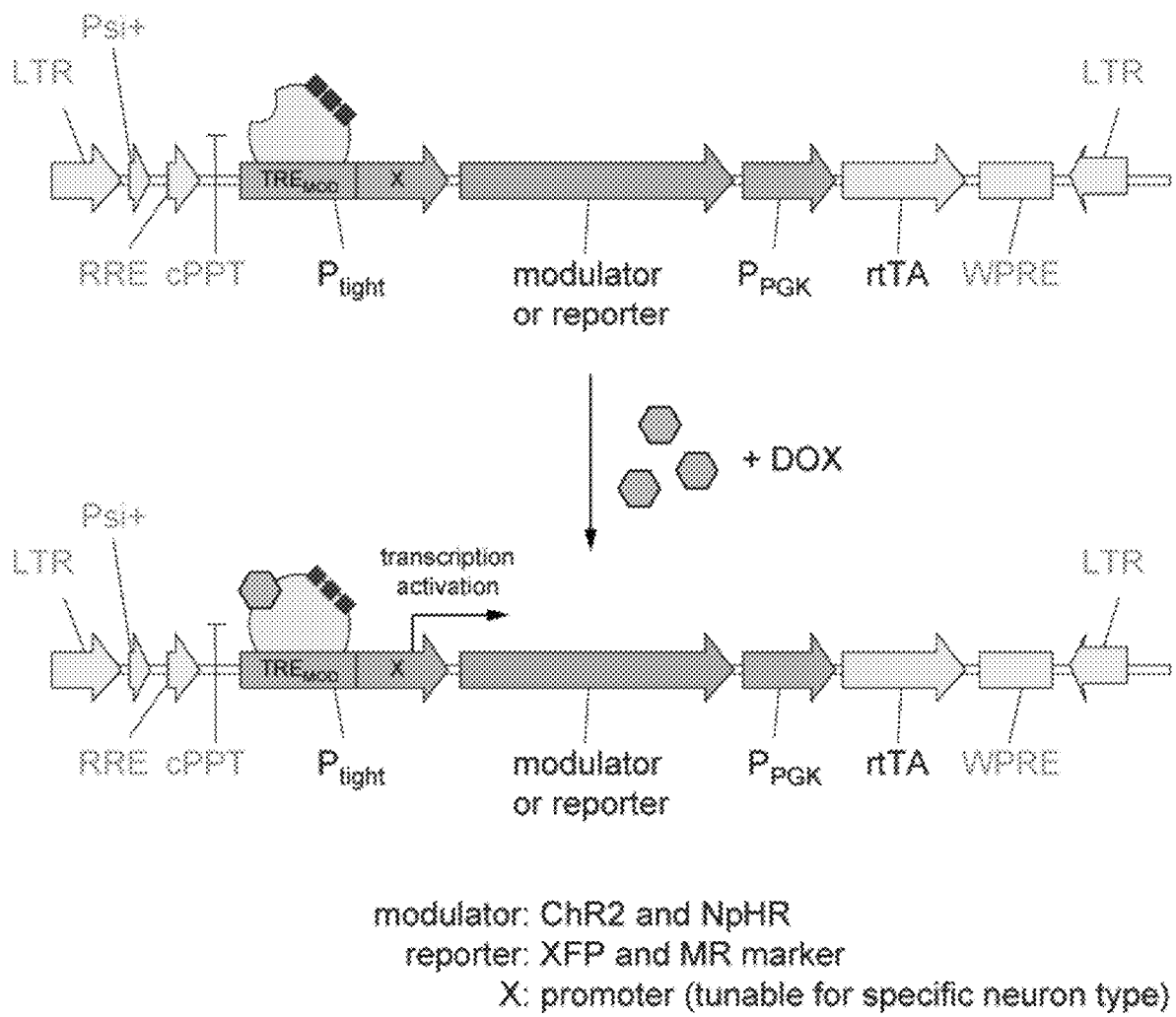
FIG. 23: Inducible lentiviral expression system. By infecting stem cells with the proposed lentiviral construct before transplantation, the goal is to express modulators and/or reporters in cells that develop into a certain type of cell specified by the promoter.

Evaluating the causal role of stem cells in the overall functional changes upon transplantation. To this end, the ability to selectively modulate the transplanted cells would be a feature. To selectively modulate the transplanted cells, lentiviral vectors will be introduced to stem cells prior to transplantation Lentiviral vectors will be designed to express microbial opsins, channelrhodopsin-2 (ChR2) and/or halorhodopsin (NpHR) in the infected cells. ChR2 is a monovalent cation channel that allows Na+ ions to enter the cell following exposure to ~470 nm blue light, whereas the NpHR is a chloride pump that activates upon illumination with ~580 nm yellow light. Furthermore, linking the opsin expression with a specific promoter allows the expression to be confined to specific cell types enabling cell-type specific neuromodulation. However, expressing such opsins in stem cells hold a special challenge. Initial attempts infecting stem cells in its early developmental stage has been found to interfere with its development and causes toxicity. Therefore, creative ways to overcome such issues to allow selective expression of opsins in specific neuronal types only after its differentiation has to be devised. There are various genetic engineering tools available in order to achieve this goal. Initially, we plan to use the strategy outlined in FIG. 23. Abbreviations in the figure can be summarized as follows. LTR=long terminal repeat, Psi+=packaging sequence, RRE=Rev Response Element, cPPT=central polypurine tract, WPRE=Woodchuck Hepatitis Virus Post-transcriptional Element, Ptight=Tet regulation sequence, Ppgk=PGK promoter, rtTA=reverse tetracycline-controlled transactivator. Among these elements, LTR, Psi+, RRE, cPPT, and WPRE are all standard lentiviral components. The creative component of this approach is the use of drug inducible elements (Ptight) which will allow transcription of ChR2 and/or NpHR only if the drug is induced. The drug (tetracycline) can be induced after the differentiation of stem cells avoiding toxicity related to early expression.

In addition to this selective modulation feature, the present methods also try to add additional reporting capabilities (in addition to fluorescent markers) to the stem cells, which can serve as a contrast mechanism visible with MR imaging. This can be a useful feature to have in order to anatomically visualize the location of the transplanted stem cells that differentiated into specific neuronal types. This anatomical information would supplement functional data by allowing primary source of activation to be isolated. Functional data will show a mixture of activity caused by the transplanted cells and the secondary neuronal population activated and/or deactivated by these neurons, not necessarily giving isolated information on the location of the transplanted cells. These reporters, however, will be designed to provide MR contrast based on their identity, making identity-specific localization feasible. Combined with the functional information, this will be a powerful technique in understanding transplanted stem cell functionality. Initially, we plan to try expressing Ferritin, to increase iron levels within the stem cells which can potentially be visible under MRI [14].

MRI Technology Development

For a comprehensive assessment of the stem cell-driven functional restoration in vivo, three different fMRI evaluation strategies could be used.

First, transplanted stem cells will be selectively activated and/or inhibited based on their differentiated identity while the whole brain functional activity resulting from such stimulation is monitored. This approach will directly identify causal functional roles of the transplanted cells.

Figure 24:
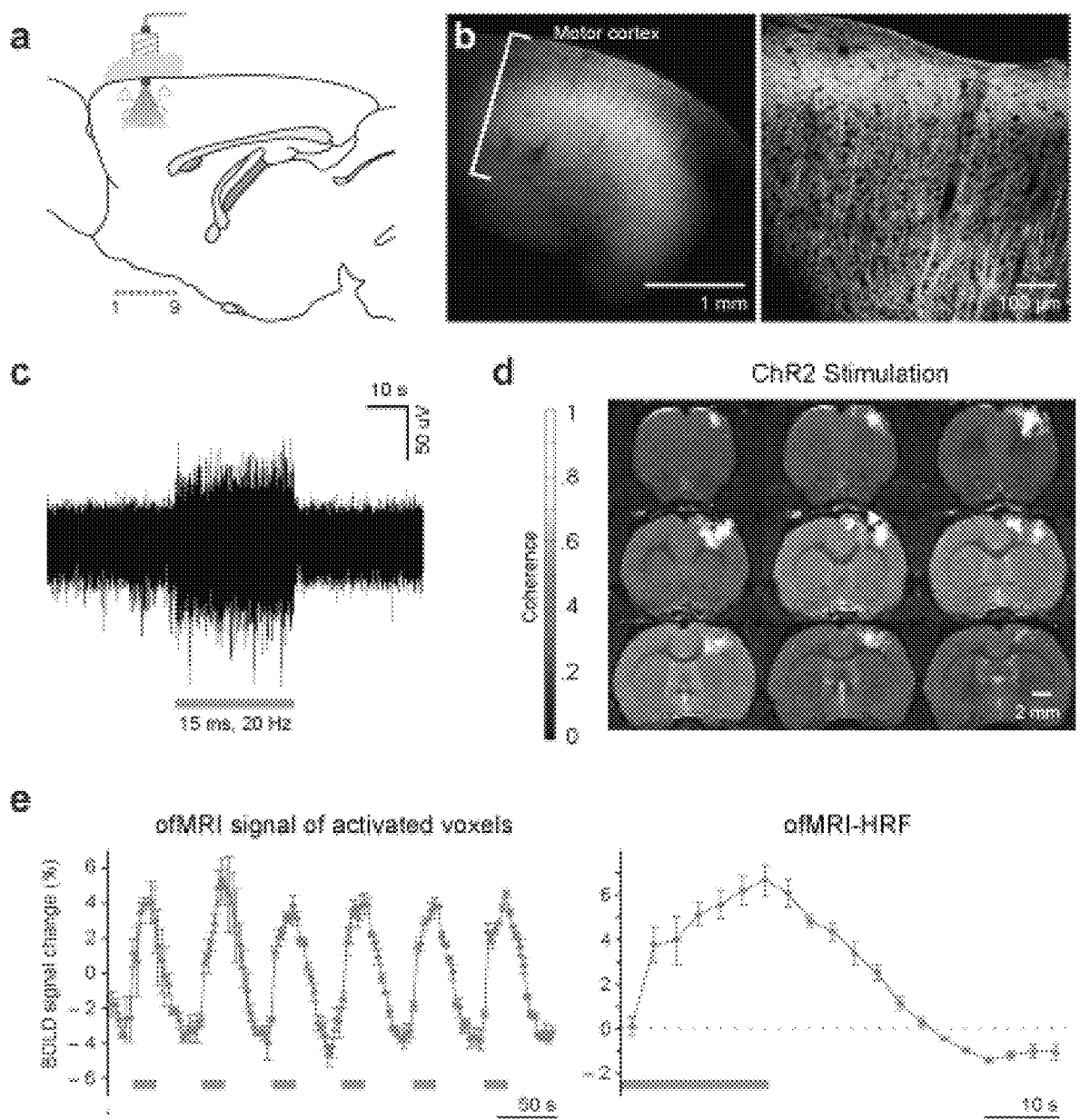
FIG. 24: ofMRI: optically-driven local excitation in defined rodent neocortical cells drives positive BOLD. a, Experimental schematic: transduced cells (triangles) and blue light delivery shown in M1 at cannula implantation and stimulation site. Coronal imaging slices shown in (d) marked as "1 . . . 9". b, Confocal images of ChR2-EYFP expression in M1 (left); higher magnification reveals transduced neuronal cell bodies and processes (right). c, Extracellular optrode recordings during 473 nm optical stimulation (20 Hz/15 ms pulsewidth). d, BOLD activation is observed at near the site of optical stimulation (right) in animals injected with AAV5-CaMKIIα::ChR2-EYFP (p<0.001; arrowhead: injection/stimulation site). Coronal slices are consecutive and 0.5 mm thick. e, ofMRI hemodynamic response during 6 consecutive epochs of optical stimulation (left); stimulus paradigm was 20 s of 20 Hz, 15 ms 473 nm light stimulation repeated every 60 s (blue bars). Hemodynamic response was averaged across all voxels with coherence coefficient>0.35 in motor cortex. Right, Mean of all stimulation epochs; baseline corresponds to mean pre-stimulation signal magnitude.
Figure 25:
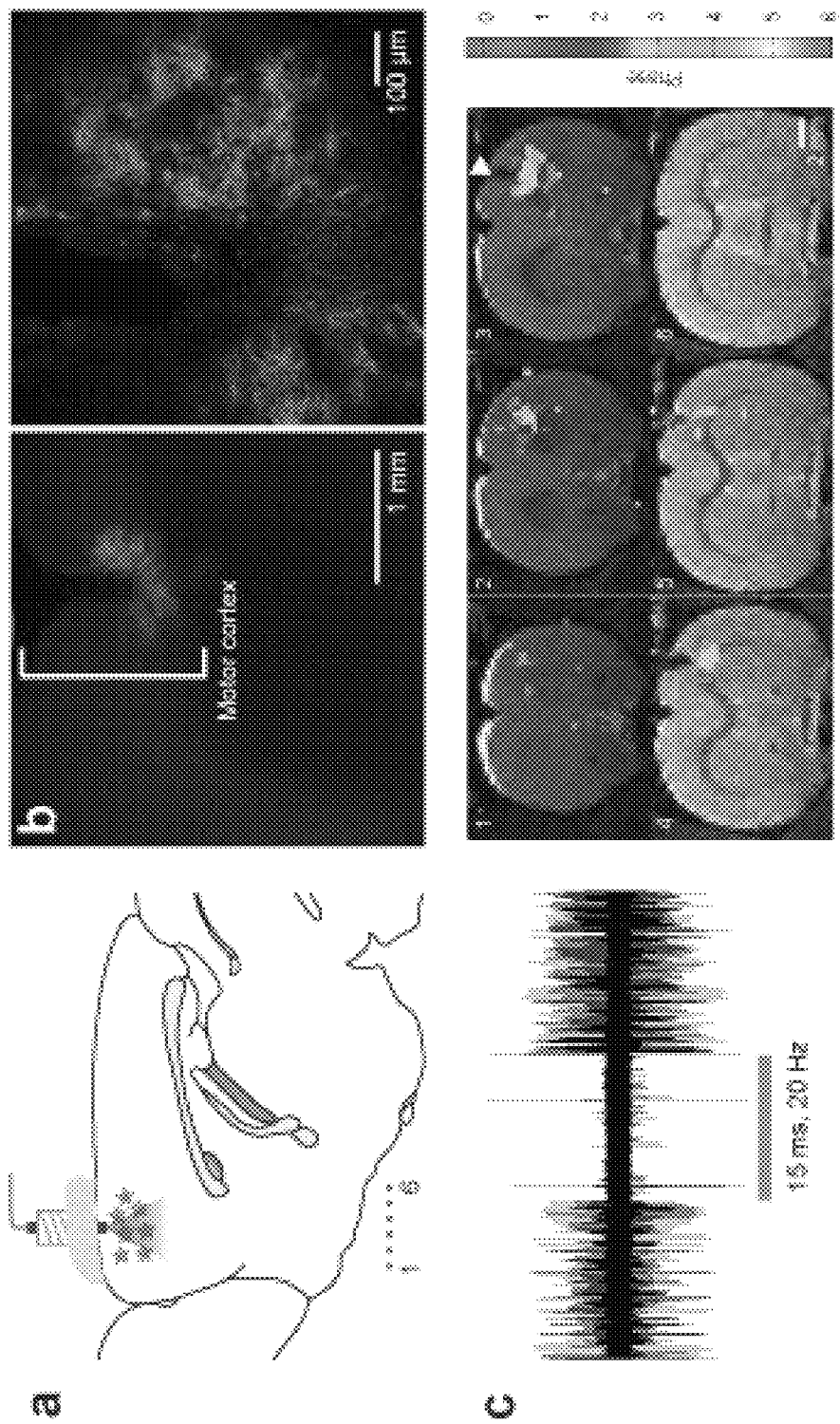
FIG. 25: Optical recruitment of resident astroglia inhibits local circuit neurons and evokes negative BOLD. a, Schematic of AAV1-GFAP::ChR2-mCherry injection, cannula implantation and light stimulation site. Coronal imaging slices shown in (d) marked as "1 . . . 6". b, GFAP promoter-driven ChR2::mCherry expression visualized with confocal imaging. c, Optrode recordings from the injection/stimulation site; optical drive of ChR2-expressing astroglia potently reduces local-circuit neuronal activity. BOLD signal resulting from optogenetic control of ChR2-expressing astroglia in M1. Astroglial BOLD responses were confined to the immediate vicinity of the probe (median radius 1 mm), without the non-local BOLD signals seen earlier from CaMKIIα::ChR2.

Next, CNS circuit elements (FIG. 24, 25) believed to be important for a specific disease (e.g. Stn, striatum and M1 for Parkinson's disease [15]) will be selectively modulated while the functional changes arising from these modulations are monitored across the whole brain. Through such evaluation, the effects of stem cell driven regeneration on these networks can be evaluated which is likely to have a close correlation with the treatment outcome.

Finally, resting-state activity change that results from the transplantation will be monitored. Resting-state fMRI is a technique that looks at brain modulation, network connectivity by monitoring fMRI signal changes at rest without any external stimulation. There are two advantages to using resting-state fMRI monitoring. The fact that it does not require any prior knowledge on the disease mechanism and the completely non-invasive nature, which eliminates any viral vector or optical probe use.

These three approaches might have synergic effects in designing experiments and interpreting results. For example, the first approach might lead to identification of regions that could potentially be part of an interesting circuit that underlies the disease mechanism. In another case, the functionally relevant regions identified through the first and second approach can be selectively analyzed in the resting-state fMRI data to reduce the ambiguity that results from a blind search for a meaningful circuit. Furthermore, the three methods provide independent information that reveals different aspects of the regeneration mechanism, which will all play a key role in the evaluation.

All three fMRI methods dedicated to small animal imaging will be developed. The three fMRI methods share the MRI acquisition and reconstruction technology while data analysis and experiment setup will be developed separately. We aim to achieve, ~0.2 mm isotropic spatial resolution, 3 s temporal resolution, and FOV covering the whole brain. In addition, real-time data reconstruction and data analysis methods will be developed. Real time data reconstruction and data analysis allows a more dynamic approach to the visualization potentially revealing more information. For example, stimulus paradigm can be dynamically changed to see the effect of combining different stimulations back to back.

Initial strategies for data acquisition technique development to achieve the stated spatio-temporal resolution, will involve using non-Cartesian sampling methods, parallel imaging methods, and compressed sensing algorithms. Real-time data reconstruction will be attempted with parallel computing while real-time data analysis would be first implemented through the implementation of the window correlation method. Data analysis methods will be developed separately for each of the fMRI methods with the aid of results obtained in the next aim looking at fMRI signal characteristics associated with different brain modulation modes.

In addition to the fMRI technology development, alternate methods to identify reporters expressed in the stem cells will be investigated. Sensitivity and specificity of detecting such reporters might be enhanced through approaches such as those used to detect off-resonance frequency spectrum generated by nanocrystals. Additionally, methods involving limiting the expression until the cells are fully differentiated may be employed.

Interpretation Method Development

Figure 26:
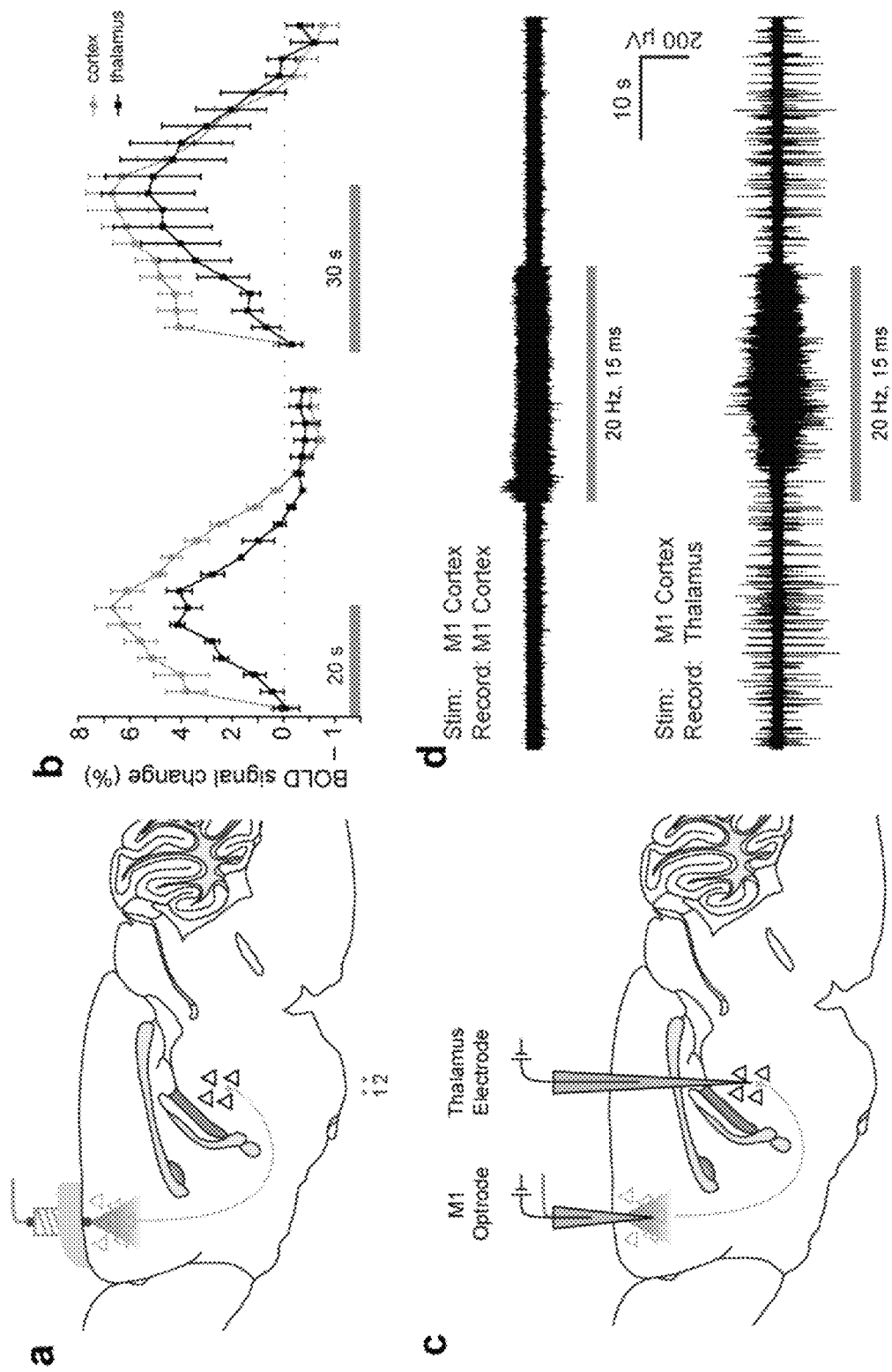
FIG. 26: Long-range functional brain mapping with ofMRI. a, Schematic shows CaMKIIα::ChR2-EYFP viral injection, cannula implantation, and optical stimulation sites in M1. "1" and "2" mark slice locations where thalamic signal was observed. b, ofMRI-HRFs obtained from cortical and thalamic BOLD activation areas (gray: cortical ofMRI-HRF; black: thalamic ofMRI-HRF resulting from optical stimulation of M1) for 20 s (left) or 30 s (right) of optical stimulation Thalamic ofMRI-HRF displayed a slower rate of signal rise compared with M1 ofMRI-HRF, while the offset of the signal timing was similar in both cases. c, Schematic for optical stimulation and electrical recording paradigm using two optrodes. Optical stimulation was performed in the motor cortex in the setting of simultaneous recording in both motor cortex and thalamus. d, Recordings in M1 and thalamus during M1 optical stimulation mapped well onto BOLD responses; note slow thalamic recruitment.

Initial studies with optogenetics show that different frequency modulation leads to different propagations of the cell-type specific modulation throughout the brain [7]. Therefore, in order to accurately interpret the fMRI signal arising from optogenetically modulated signal as well as resting state signal, it is important to define the relationship between fMRI signal characteristic and the associated modulation frequency [16]. Due to our technical advantage of using temporally precise direct stimulation mechanism, we can precisely generate different modulations targeting specific neuronal groups while obtaining fMRI data. This will allow us to first, look at local signal characteristic differences based on the modulation type. In addition, it will reveal differences in signal propagation characteristics to remote locations of the brain based on the modulation. For example, preliminary optogenetic fMRI studies show that 20 Hz modulation of excitatory neurons in motor cortex in layer 5-6 lead to delayed fMRI hemodynamic response in the thalamus which corresponds to group delay in the spiking activity. Whether different modulation frequency plays a role in the fMRI signal difference will be investigated to provide a accurate basis for data interpretation (FIG. 26).

REFERENCES

1. Takahashi, K. and S. Yamanaka, *Induction of pluripotent stem cells from mouse embryonic and adult fibroblast cultures by defined factors.* Cell, 2006. 126(4): p. 663-76.
2. Wu, H., et al., *Integrative genomic and functional analyses reveal neuronal subtype differentiation bias in human embryonic stem cell lines.* Proc Natl Acad Sci USA, 2007. 104(34): p. 13821-6.
3. Kohyama, J., et al., *Epigenetic regulation of neural cell differentiation plasticity in the adult mammalian brain.* Proc Natl Acad Sci USA, 2008. 105(46): p. 18012-7.
4. Hsieh, J., et al., *IGF-I instructs multipotent adult neural progenitor cells to become oligodendrocytes.* J Cell Biol, 2004. 164(1): p. 111-22.
5. Zhang, F., et al., *Circuit-breakers: optical technologies for probing neural signals and systems.* Nat Rev Neurosci, 2007. 8(8): p. 577-81.
6. Ogawa, S., et al., *Oxygenation-sensitive contrast in magnetic resonance image of rodent brain at high magnetic fields.* Magn Reson Med, 1990. 14(1): p. 68-78.
7. Gradinaru, V., et al., *Optical deconstruction of parkinsonian neural circuitry.* Science, 2009. 324(5925): p. 354-9.
8. Lee, J., et al. *Full-brain coverage and high-resolution imaging capabilities of passband SSFP fMRI at 3T.* in *ISMRM.* 2007. Berlin.
9. Zhang, F., et al., *Red-shifted optogenetic excitation: a tool for fast neural control derived from Volvox carteri.* Nat Neurosci, 2008. 11(6): p. 631-3.
10. Zhang, F., et al., *Channelrhodopsin-2 and optical control of excitable cells.* Nat Methods, 2006. 3(10): p. 785-92.
11. Zhang, F., et al., *Multimodal fast optical interrogation of neural circuitry.* Nature, 2007. 446(7136): p. 633-9.
12. Carr, H., *Steady-State free precission in nuclear magnetic resonance.* Physical Review Letters, 1958. 112: p. 1693-1701.
13. Aravanis, A. M., et al., *An optical neural interface: in vivo control of rodent motor cortex with integrated fiberoptic and optogenetic technology.* J Neural Eng, 2007. 4(3): p. S143-56.
14. Jasanoff, A., *MRI contrast agents for functional molecular imaging of brain activity.* Curr Opin Neurobiol, 2007. 17(5): p. 593-600.
15. Gradinaru, V., et al., *Targeting and readout strategies for fast optical neural control in vitro and in vivo.* J Neurosci, 2007. 27(52): p. 14231-8.
16. Sohal, V. S., et al., *Parvalbumin neurons and gamma rhythms enhance cortical circuit performance.* Nature, 2009. 459(7247): p. 698-702.
17. Lee, J. H., et al., *Fast 3D imaging using variable-density spiral trajectories with applications to limb perfusion.* Magn Reson Med, 2003. 50(6): p. 1276-85.
18. Lee, J. H., et al., *Broadband multicoil imaging using multiple demodulation hardware: a feasibility study.* Magn Reson Med, 2005. 54(3): p. 669-76.
19. Lee, J. H., et al., *Full-brain coverage and high-resolution imaging capabilities of passband b-SSFP fMRI at 3T.* Magn Reson Med, 2008. 59(5): p. 1099-1110.
20. Seo, W. S., et al., *FeCo/graphitic-shell nanocrystals as advanced magnetic-resonance-imaging and near-infrared agents.* Nat Mater, 2006. 5(12): p. 971-6.
21. Lee, J. H., et al., *High-Contrast In-Vivo Visualization of Micro-Vessels using Novel FeCo/GC Magnetic Nanocrystals.* Magn Reson Med, 2009: p. in press.
22. Saritas, E. U., et al., *DWI of the spinal cord with reduced FOV single-shot EPI.* Magn Reson Med, 2008. 60(2): p. 468-73.
23. Wu, H. H., J. H. Lee, and D. G. Nishimura, *MRI using a concentric rings trajectory.* Magn Reson Med, 2008. 59(1): p. 102-12.
24. Wu, H. H., J. H. Lee, and D. G. Nishimura, *Fat/water separation using a concentric rings trajectory.* Magn Reson Med, 2009. 61(3): p. 639-49.
25. Cukur, T., et al., *Non-contrast-enhanced flow-independent peripheral MR angiography with balanced SSFP.* Magn Reson Med, 2009. 61(6): p. 1533-9.
26. Berndt, A., et al., *Bi-stable neural state switches.* Nat Neurosci, 2009. 12(2): p. 229-34.
27. Zhao, S., et al., *Improved expression of halorhodopsin for light-induced silencing of neuronal activity.* Brain Cell Biol, 2008. 36(1-4): p. 141-54.
28. Kim, D. S. and T. Bonhoeffer, *Reverse occlusion leads to a precise restoration of orientation preference maps in visual cortex.* Nature, 1994. 370(6488): p. 370-2.

Example 6: Functional Magnetic Resonance Imaging (fMRI)

Functional Magnetic Resonance Imaging (fMRI) [2-5] is a technique that provides a noninvasive means to study the brain function. Unlike other invasive procedures that involve electrical probes, radioactive tracers or even slicing of the brain, fMRI provides non-invasive mapping throughout the brain. The non-invasive nature combined with its ability to provide relatively high resolution spatial information including areas of deep brain structures, make fMRI a very powerful tool for neuroscience. Such properties allow whole-brain coverage and longitudinal imaging; e.g. the ability to repeatedly scan the same animal to follow up the kinetics of neural plasticity.

However, fMRI has significant limitations in its current form. Due to spatial distortions, large portions of the brain cannot be imaged while the spatial resolution needs significant improvement to provide information more relevant to the state-of-the art neuroscience. In this application, we will address these issues by using the passband SSFP approach which is described in the present invention. The technique has been demonstrated to have the capability of imaging the whole brain without distortions while also allowing high resolution encoding which is difficult with the conventional method. While this capability of passband SSFP has been demonstrated in human fMRI studies, its significant potential for high resolution imaging in animals is yet to be exploited. Another aspect of the present invention will be to further develop this method to allow high quality studies of brain activity in small animals.

Brain functions are mostly studied by stimulating the brain and observing the changes in the brain corresponding to the perturbation. One of the most important features of such stimulation is to provide precise control over the stimulation of the neurons. In humans, the stimulation has been largely limited to indirect methods using sensory input. In animals, more invasive methods such as electrode stimulations are used but the control is still limited to spatially grouped set of neurons and it doesn't necessarily stimulate the neuronal circuitry since it is an artificially generated current not initiated by the neurons.

Recently, a technique that allows precise control of neuronal stimulations through molecularly targeted mechanism [6-8] has been developed. The molecularly targeted set of neurons can be selectively excited via optical methods. Such methods have been demonstrated in small animals in-vivo [8] and has a tremendous potential for both the study and treatment of neuropsychiatric diseases. The precisely controlled stimulation mechanism allows the analysis of the neuronal network for diseases such as depression while it can also provide a means to alter such mechanism through excitation or inhibition of part of the network.

The present invention provides methods for developing the passband SSFP fMRI technique in combination with the molecularly targeted optical stimulation to allow monitoring of the brain stimulation results in in-vivo, intact animal brains in order to study the brain circuit on a system level. Specifically, the present invention provides for:

Develop Distortion-Free, High-Resolution fMRI for Small Animals Using Passband SSFP Methods.

With faster, stronger gradients used in animal scanners, higher spatial resolution encoding will be possible within the temporal resolution constraint. Sufficient signal, stability and resolution for small animal brain fMRI can be achieved with the small animal system. Distortion-free, high-resolution (isotropic<200 am) mapping techniques will be developed to allow accurate in-vivo functional brain mapping of the small animals Investigate Neuro-Hemodynamic Coupling Using Specific Photo-Stimulation of Excitatory and Inhibitory Neurons.

Through targeted stimulation of the excitatory and inhibitory neurons, the hypothesized difference in the hemodynamic response can be measured. The small animal fMRI setup developed in aim 1 will be utilized to investigate neuro-hemodynamic coupling related to the linearity of the response and difference in excitatory and inhibitory neuronal response.

Perform In-Vivo Whole-Brain Passband SSFP fMRI Combined with the Photo-Stimulation Method in Animal Model of Depression.

Whole-brain activation mapping with activation in a targeted area of the brain will reveal connectivity of the brain circuitry. The whole brain view of the activations with precise stimulation control in animal depression models will show depression mechanism on a circuit level. The technique developed and the hemodynamic function analysis described above will be utilized to obtain high resolution activation maps of the whole animal brain while the optical neuronal stimulation is applied. These methods will focus on understanding the neuronal pathway for depression.

The methods described in this application provide the means to study the neuronal network in the system level by combining the high quality functional neuroimaging technique and molecularly targeted precise control of neuronal activations. Furthermore, the methods of the present invention will allow investigation of the neuro-hemodynamic coupling specific to neuronal types in order to aid more complex experimental studies such as the evaluation of the depression mechanism. These methods can also be used to study the depression mechanism through whole brain monitoring.

Background

B.1 Functional Neuroimaging

Functional Neuroimaging Methods.

Currently, a variety of tools are used to probe the brain function, each of which comes with different benefits and shortcomings. Direct measurements of the neuronal currents can be made with electrical probes. However, such methods are highly invasive and it is difficult to obtain spatial information due to the invasive nature. Electroencephalography (EEG) [9, 10], magnetoencephalography (MEG) [11] and event-related potentials (ERP) [12, 13] can be used to non-invasively monitor electrical activity in the brain with excellent temporal resolution. However, spatial resolution is severely limited in these methods due to the small number of sensors and ill-conditioned reconstruction which often results in inaccurate localization Optical flowmetry methods [14-16] are intractable for large-scale mappings and can only provide information about the surface of the brain due to limited penetration depth. Positron emission tomography (PET) [17, 18] can create reasonable spatial maps of a number of relevant physiological parameters; however, the limited spatial resolution often makes it difficult to register with anatomy. Furthermore, due to the use of radioactive probes, it is somewhat invasive while the need for a cyclotron to generate the probes makes PET scanning very expensive.

Functional MRI.

While all these methods have a place in neuroscience, MRI has become the dominant tool for functional neuroimaging, primarily because it has a useful compromise of spatial and temporal resolution. The ability to acquire non-invasive data over the entire brain with MRI is also a powerful advantage over other methods. A number of functional MRI (fMRI) methods exist, including BOLD [2-5], arterial spin labeling (ASL) [19-21], and cerebral blood volume measurements [22-24]. In particular, the BOLD technique has gained wide acceptance because it provides signal statistics that are more robust to experimental uncertainties than other fMRI methods.

BOLD fMRI.

BOLD fMRI contrast is based on the change in blood oxygenation as oxygen is consumed in converting glucose into usable energy. Oxygen is transported to tissues by red blood cells via the hemoglobin molecule, which can either be oxygenated (oxyhemoglobin) or deoxygenated (deoxyhemoglobin). During activation, increased need for oxygen leads to an increase in deoxyhemoglobin. This increase in deoxyhemoglobin is immediately followed by an even larger increase in blood flow. The dominant effect of neuronal activity is then counter-intuitively a net decrease in the concentration of deoxyhemoglobin within the blood.

These physiological dynamics are of interest in MRI because the deoxyhemoglobin molecule is paramagnetic [25], making it an endogenous MRI contrast agent. Because it is paramagnetic, deoxyhemoglobin becomes more magnetized by the main magnetic field than the surrounding water [26], which is slightly dia-magnetic. The non-uniform magnetic fields surrounding deoxyhemoglobin in the blood introduce a spread in resonance frequency within and around blood vessels that causes the MRI signal to decay more rapidly than normal. In BOLD fMRI, data acquisition is delayed following the RF excitation to allow signal loss to occur. During activation, the signal increases due to the decreased concentration of deoxyhemoglobin, reflecting a rise in oxygen metabolism, and therefore an increase in brain activity.

Limitations of BOLD fMRI.

However, BOLD fMRI has a number of limitations that stem from the fact that the contrast is based on signal dephasing (signal loss). A long echo time is necessary to allow dephasing to occur, which has some important negative implications. Intense gradients of off-resonance in the brain lead to focal regions of signal loss [27], creating "black holes" in the images (regions with little or no signal, see FIG. 1a). To maintain reasonable scan times with such a delay, BOLD studies are most commonly performed with single-shot echo-planar imaging (EPIBOLD). This increases sensitivity to off-resonance [28] due to the long read-out, causing significant image distortion [29, 30]. These artifacts are particularly prominent near regions with strong susceptibility gradients, as occur near air-tissue boundaries.

The achievable spatial resolution in conventional BOLD is poor relative to other MRI methods. The poor resolution is party due to the severe image artifacts resulting from the long echo time and readout length. The distortions and blurring that occur in BOLD images effectively reduce the resolution. Furthermore, the 2D multi-slice approach makes it difficult to encode isotropic high resolution voxels due to its limitations on reducing slice thickness and low SNR.

Another important limitation of BOLD is that the contrast is fundamentally sensitive to oxygenation level changes in all vessel sizes with emphasis on larger vessels [31]. Larger vessels are expected to be further away from the site of neuronal activity. Therefore, BOLD activations are expected to have components that are not localized to the area of interest.

The image artifacts, limited resolution and lack of specificity of BOLD fMRI are all intrinsically tied to the use of a contrast mechanism that is based on signal dephasing. While BOLD data is of sufficient quality for a large number of studies, these limitations make it difficult to study regions with strong susceptibility such as the orbitofrontal cortex [32] or small nuclei. Furthermore, sensitivity to oxygenation level changes in larger vessels is expected to result in mis-representation of the activated brain region.

Overcoming the Challenges of BOLD fMRI.

Many different approaches have been proposed to address these limitations, notably z-shimming to correct for through-plane susceptibility gradients, and acquiring and combining several different z-shimmed acquisitions expand coverage [27, 33-36]. These methods still suffer from in-plane distortions. In addition, as single-shot multi-slice sequences, they are not easily adaptable to isotropic, high-resolution acquisitions. Another alternative is spiral in/out [37, 38], which improves the signal in areas of susceptibility, but still suffers dropouts.

However, passband SSFP in particular provides complete coverage in the presence of susceptibility distortion with only two-frequency shifted acquisitions while also showing great promise in isotropic high-resolution imaging capabilities. The contrast mechanism of passband SSFP fMRI also has the potential to provide more specificity through vessel size selective activation. For the proposed study of circuit level brain function study in animals, some of the most important features will be whole brain coverage including the areas close to the sinus, high spatial resolution and high specificity. Therefore, passband SSFP fMRI is an ideal fit.

The highest resolution animal fMRT images obtained to date include 50×50 $\mu m^2$ resolution over a 1.28×1.28 $cm^2$ FOV with a 2 mm slice [40]. These images are obtained with a 10 s temporal resolution using a 1.6 cm diameter surface coil and a 11.7 T MRI system. The study demonstrates fMRI's capability to resolve signals across the cortical layer.

While this study shows how high resolution animal fMRT is possible, there are a number of limitations that include single slice imaging which prohibits volume coverage, highly anisotropic voxel shape, and low temporal resolution. Very high field strength systems such as 11.7 T is also not readily available in most imaging sites. The use of high field and thick slices are largely motivated to improve SNR. With passband SSFP imaging, the image SNR is inherently much higher due to 3D acquisitions. The 3D encoding also allows isotropic voxel size imaging.

B.2 Neuronal Circuit Manipulation

Limitations of Conventional Stimulation Methods.

Figure 28:
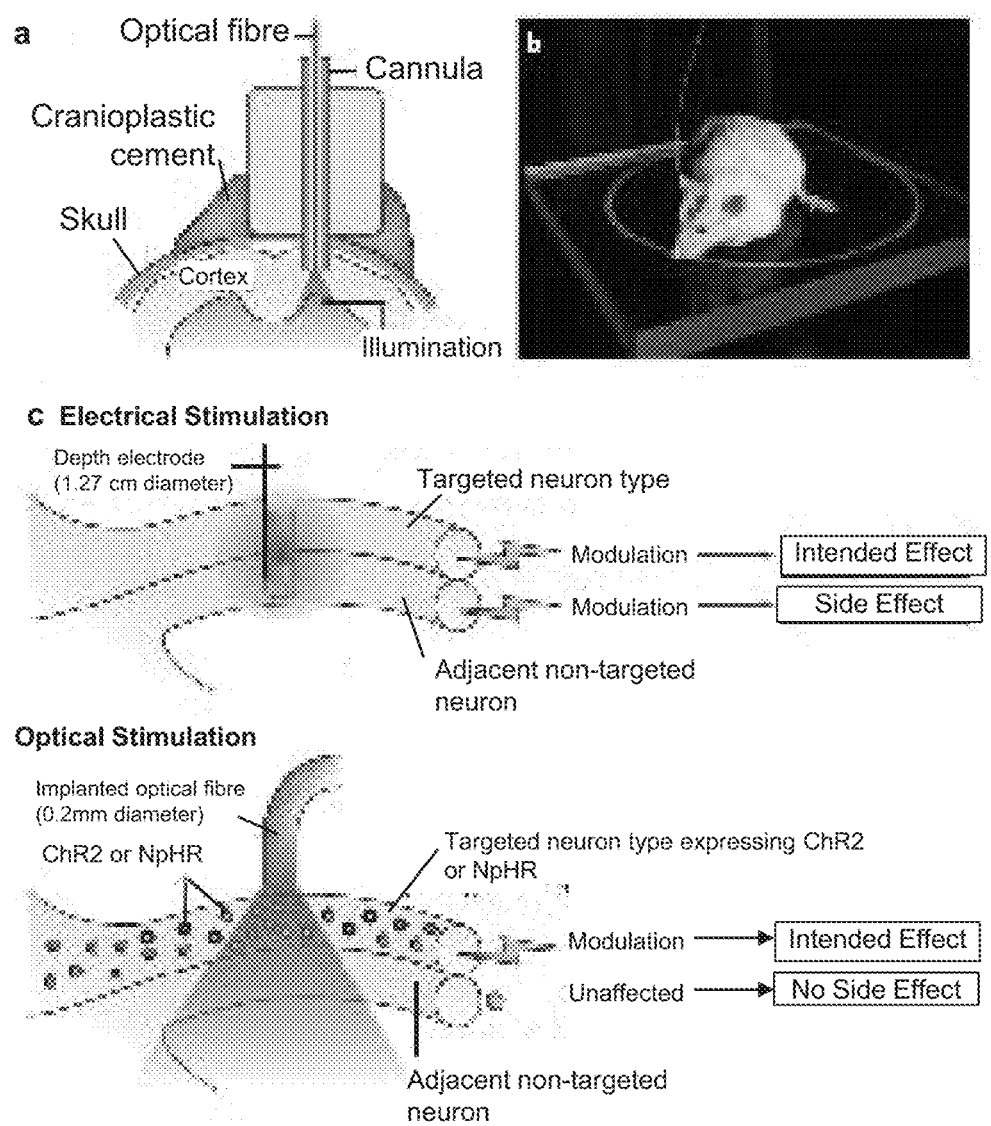
FIG. 28: Small Animal fMRI For animal fMRI dedicated small bore systems are used with field strengths ranging from 4.7 T to 11.7 T [39]. Such use of dedicated small bore systems is to take advantage of the capability to incorporate higher main field strength and faster, stronger gradients. These features allow fast, high resolution imaging.

For research, diagnosis and treatment, the brain circuitry is often stimulated as a controlled input to the brain. The most common, non-invasive stimulation method is through sensory input. While such methods are essential for many neuroscience studies, there is often a need to more directly stimulate the brain. For such direct intervention, electrodes are inserted to create artificial electrical signal. However, there are a number of important limitations. First of all, the stimulation can only be localized based on the spatial location of the electrode (see FIG. 28c). Different types of neurons such as excitatory, inhibitory and modulatory neurons are expected to all have a different roles within the neural circuitry. The inability to selectively excite/inhibit these different types of neurons makes it difficult to analyze and manipulate the neuronal circuit. Furthermore, the fact that the stimulation based on the electrode is not initiated by the neurons often result in signal that does not necessarily propagate through the neuronal network.

Limitation of Non-Selective Stimulation for fMRI.

There is currently no evidence that the metabolic demands differ greatly between excitatory and inhibitory synapses. Fundamentally, both the excitatory (EPSP) and inhibitory (IPSP) synaptic inputs could be expected to cause similar metabolic and hemodynamic events ultimately giving rise to similar fMRT contrasts. However, on the site of the spiking output activity, they have an opposite effects: accumulation of EPSPs will increase the probability for spike generation (and therefore also the metabolic demand), while IPSPs will decrease it. Assuming that the fMRI response predominantly reflects changes in synaptic subthreshold activity, it remains elusive whether excitatory and inhibitory cortical events can be differentiated using the fMRI response in any single region. Previously, one group proposed that inhibition, unlike excitation, elicits no measurable change in the fMRT signal [41]. They hypothesized that because of the lower number of inhibitory synapses, their strategically superior location, and increased efficiency, there could be lower metabolic demand during inhibition compared to excitation. The validity of this claim notwithstanding, both empirical and theoretical studies suggest that excitatory and inhibitory neurons in the cortex are so tightly interconnected in local circuits that one is unlikely to be able to observe an increase in excitation without an increase in inhibition. The tight interconnection of neurons within the local cortex and spatially localized stimulation prohibits selective excitatory input delivery to excitatory or inhibitory neurons. Stimulation methods that provides targeting of neuronal types, therefore, are needed to understand the neuronal mechanisms and its contribution to fMRI signal.

Genetically Targeted Optical Stimulation.

Recently, a method to interrogate the neural circuitry through molecularly targeted mechanism has been developed [6-8]. This method overcomes the aforementioned limitations of electrode based stimulations. The genetically targeted mechanism allows selective targeting (see FIG. 28c) of neurons while the stimulation and inhibition is also designed to be initiated by the neurons through light activated proteins. Laser radiation is used to selectively activate/inhibit the neurons of interest. This creates an enormous opportunity for the study of neural circuits in fine detail. With the present methods, we investigate the difference in the hemodynamic response of excitatory and inhibitory neurons through this genetically targeted stimulation mechanism. Furthermore, whole brain activity imaging will be performed to investigate depression mechanisms.

B.3 Potential Translational Applications

While there are numerous efforts to understand and treat many neuropsychiatric disorders [42, 43] such as depression, Parkinson's disease, obsessive-compulsive disorder (OCD), chronic pain, and Epilepsy, the precise mechanism of such disorders remains elusive. To better understand the contribution of specific cell types to the physiology of neuropsychiatric disease, it is important to be able to control activation or inhibition with millisecond precision while probing of the downstream circuit-level effects of turning specific cells on and off. Furthermore, the ability to control the activity of targeted neuronal groups could make it possible to generate new models of neuropsychiatric diseases by directly mimicking errant electrical signals in the brain with millisecond precision. Therapies using cell-specific modulation might eventually be employed to selectively regulate malfunctioning neurons, which can potentially optimize treatment efficacy and reduce the side-effects associated with less specific therapeutic interventions.

To accurately evaluate the effect of these circuit level activity and effects of intervention, it is important to monitor the activity resulting from the controlled stimulation throughout the brain in high spatial resolution. Especially for diseases that involve multiple brain areas such as depression, non-invasive high resolution imaging of a fully intact-brain in-vivo allows the full-circuit monitoring and longitudinal studies which will be important to monitor disease progress and therapeutic effects.

B.4 Summary

Passband SSFP fMRI methods which can provide high quality brain activation maps combined with the ability to control the activity of specific neural populations with high precision promises great potential in the understanding and treatment of neuropsychiatric diseases.

C Preliminary Studies

C.1 Passband SSFP fMRI

SSFP fMRI.

Steady-state free precession (SSFP) imaging is an image acquisition technique that uses rapid radio-frequency excitation pulses combined with fully-balanced gradient pulses during each excitation repetition interval ($T_R$) [44]. Due to its short readout time and $T_R$, SSFP provides distortion-free 3D imaging suitable for full-brain, high-resolution functional imaging.

Figure 3:
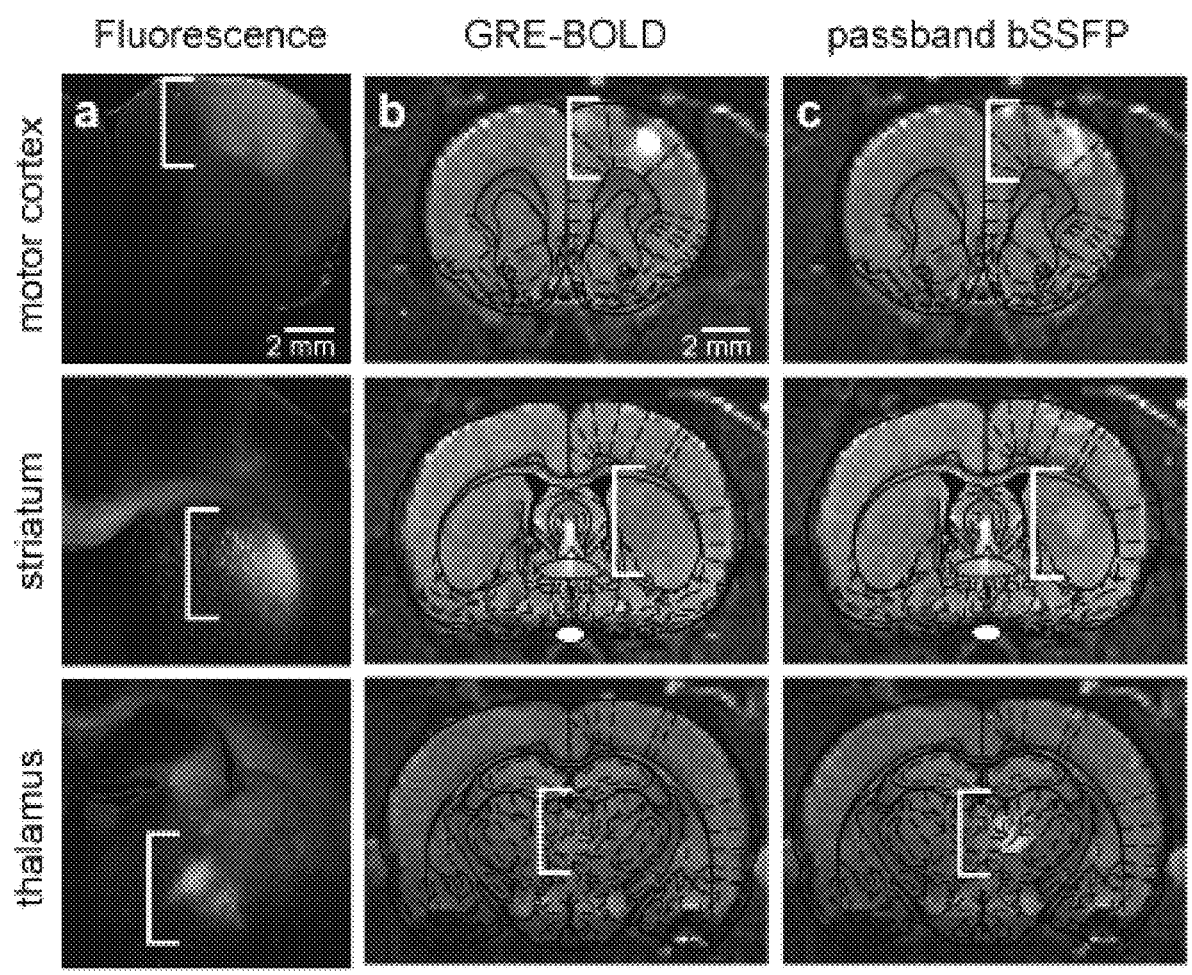
FIG. 3: ofMRI circuit mapping: conventional BOLD and passband bSSFP-fMRI. a, Injection of CaMKIIα::ChR2-EYFP in M1, as expected, leads to opsin visualization in motor cortex, striatum, and thalamus, i.e. the primary site of injection and sites where axons of expressing neurons extend. b, Hemodynamic response following M1 stimulation: conventional BOLD fMRI superimposed onto appropriate atlas image. c, Imaging the same hemodynamic response with passband bSSFP-fMRI, which more fully captures circuit-level activity.

Use of SSFP for functional magnetic resonance imaging (fMRI) was proposed by Scheffler et al. [45] (FIG. 3a), which used the steep magnitude transitional portion of the SSFP off-resonance spectrum to generate oxygen contrast based on the resonance frequency shift induced by deoxy-hemoglobin. Another acquisition scheme using the steep phase transition of the SSFP off-resonance spectrum was subsequently proposed by Miller et al. [46] (FIG. 3b). We refer to these techniques as "transition-band SSFP fMRI" methods. Transition-band SSFP fMRI combines the advantages of SSFP imaging with a functional contrast mechanism sensitive to the deoxyhemoglobin frequency-shift following neuronal activations. In contrast, in conventional gradient-echo (GRE) blood oxygenation level dependent (BOLD) functional MRI signals [2, 3, 47] with long $T_E$, venous signal dephasing due to deoxygenation is both the source of functional signals, as well as the main source for image distortions and signal dropouts. Despite its potential for functional imaging, the use of the transition-band SSFP can be challenging. Transition-band SSFP methods produce oxygenation sensitive contrast only in a very narrow range of frequencies near resonance. This requires the use of multi-frequency acquisitions even for a small volume coverage [48].

Figure 29:
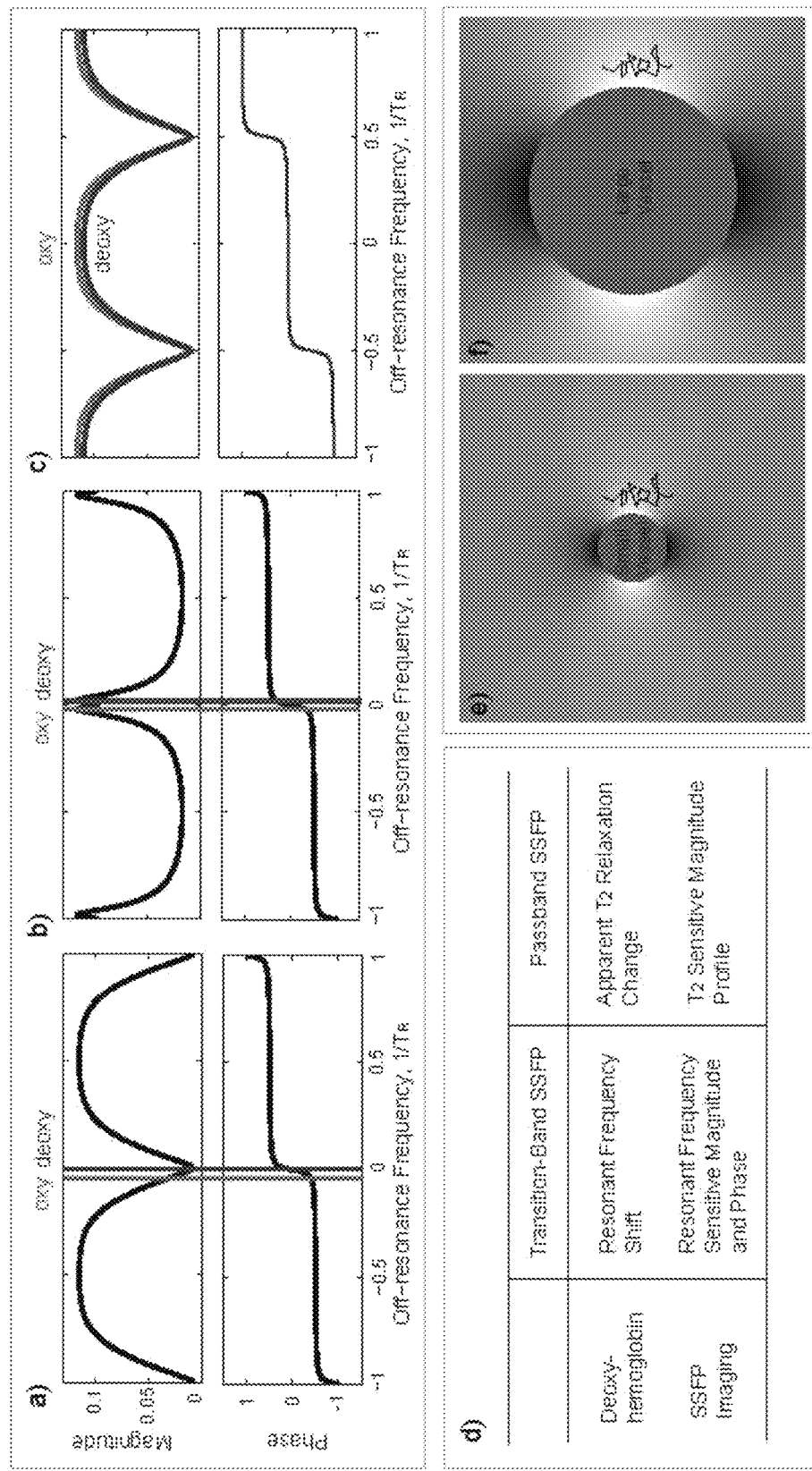
FIG. 29: SSFP fMRT methods. The two transition-band SSFP fMRT methods (a, b) depend on the sharp magnitude and phase transition of the SSFP off-resonance response while the passband SSFP fMRI method (c) utilizes the flat portion of the SSFP off-resonance profile. Differences between transition-band and passband SSFP properties are summarized in (d). (e) The contrast is expected to be maximized near small vessels where water molecules experience rapid off-resonance frequency change during each $T_R$. (f) For larger vessels, water diffuses in a relatively uniform field during each $T_R$. The wiggly lines in (e) and (f) represent the typical water diffusion distances.
Figure 30:
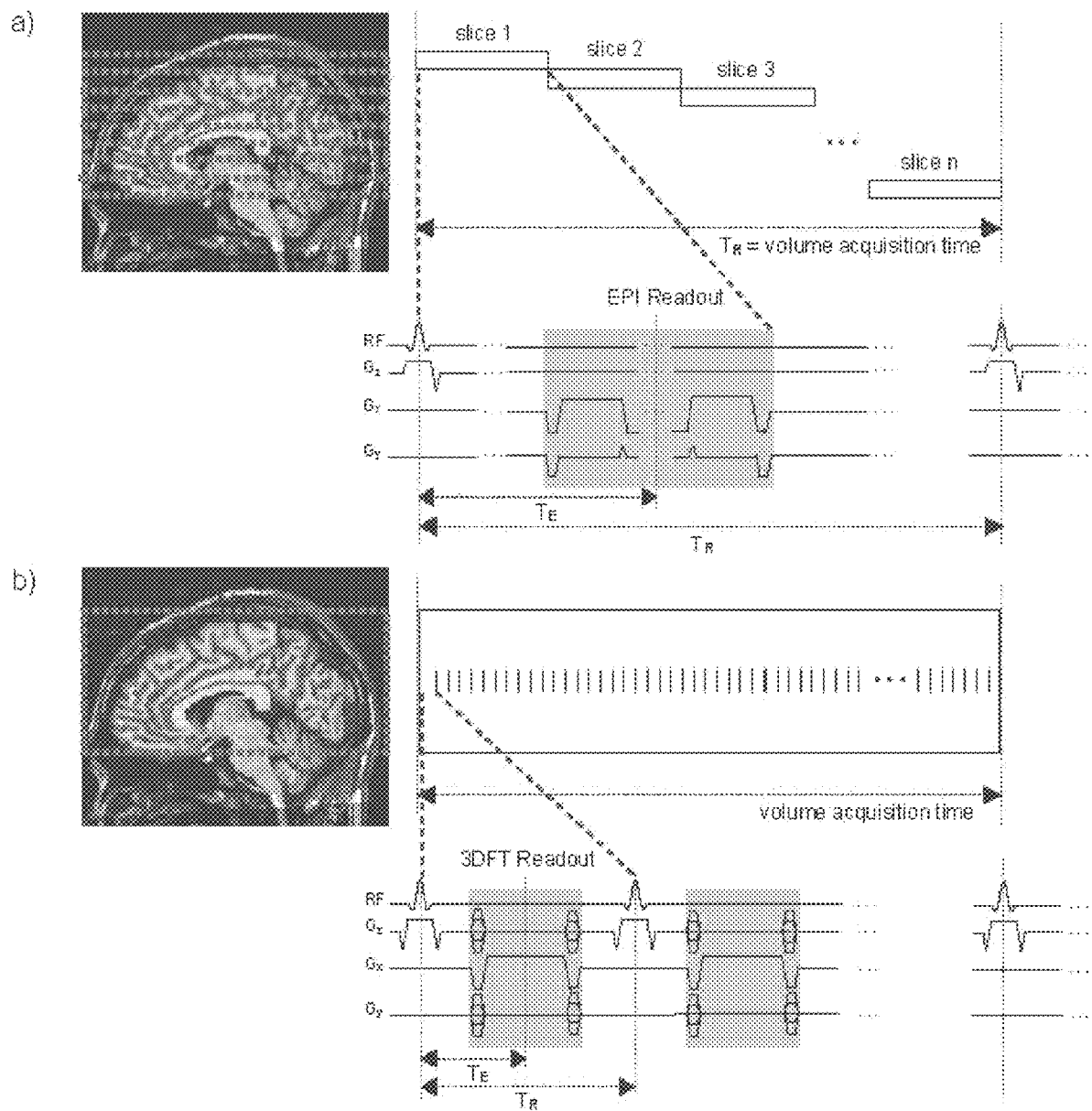
FIG. 30: Pulse sequences for GRE-BOLD and SSFP fMRI. The GRE-BOLD pulse sequences (a) involve long $T_E$ and long $T_R$ with interleaved multi-slice acquisitions while the SSFP fMRT pulse sequences (b) are volumetric multi-shot acquisitions with short $T_E$, short $T_R$ and fully balanced gradients for every $T_R$.

An alternative approach, termed "passband SSFP fMRI" [49-59], has the potential to provide distortion-free, high spatial resolution fMRI studies under practical imaging conditions. The passband SSFP fMRI utilizes the flat portion of the SSFP off-resonance profile, instead of the steep transitional portion (see FIG. 3c). Here, the rapid refocusing of SSFP imaging suppresses larger scale off-resonance effects. This refocusing degrades when the off-resonance is spatially in the scale of the water diffusion distances (compare FIGS. 29e and 29f). The resulting dephasing is expected to produce oxygenation contrast predominantly in parenchymal regions near small vessels with steep off-resonance changes. This mechanism is assumed to be similar to that of spin-echo (SE) based fMRI. The difference in contrast mainly comes from the signal augmenting stimulated echo pathways that exist in SSFP acquisitions. Imaging constraints such as acquisition speed, distortion properties and signal-to-noise ratio (SNR) add further advantages for passband SSFP based fMRI. Bowen et al. [49,50] demonstrated pass-band SSFP fMRI's potential to sensitize itself to signal changes arising from the smaller vessel size of interest, while Lee et al. [51, 52, 57] proposed passband SSFP schemes combined with 3D imaging trajectories and multiple-acquisition techniques. The functional contrast mechanisms of passband SSFP techniques were investigated and compared to more conventional GREBOLD contrast by several groups through experimental and/or simulation studies [55, 56, 58, 59].

Advantages of Passband SSFP fMRI.

From the imaging perspective, passband SSFP's unique features make it well suited for distortion-five, high-resolution functional signal acquisitions. Distortion-free, high-resolution acquisitions are important for brain function studies since gray matter voxels separated by only a few millimeters can have highly distinct functional properties [60, 61]. Spatial distortions can therefore lead to erroneous inference of the brain's functional architecture. With conventional GRE-BOLD acquisitions, a variety of methods have been proposed to reduce spatial distortions [30], including spiral in-out acquisitions [38], z-shimming to correct for through-plane susceptibility gradients, acquiring and combining several different z-shimmed acquisitions to expand coverage [33] and post-processing methods [62]. While most of these methods are also compatible with SSFP acquisitions, the inherently distortion-free nature of the SSFP acquisition circumvents the aforementioned needs for improving distortion characteristics. In pass band SSFP fMRI, the rapid excitation repetition intervals allow short segmented readouts that result in images with distortion levels similar to that of the $T_1$ weighted anatomical acquisitions (compare sequences for GRE-BOLD and SSFP fMRI in FIGS. 4a and 4b). This distortion-free acquisition allows full-brain coverage including areas of the brain that are traditionally difficult to image with conventional GRE-BOLD such as the prefrontal and ventro-temporal cortices. In the presence of spatial distortions, even with high nominal encoding resolutions, the effective spatial resolution can be greatly reduced. Neighboring voxels may not be accurately identified and assigned in the image space. Furthermore, spatial distortions limit the readout length, further constraining the acquisition resolution itself. This reduced distortion in conjunction with 3D acquisitions gives passband SSFP the potential for high-resolution functional images with isotropic voxels.

Imaging with Passband SSFP fMRI.

Figure 31:
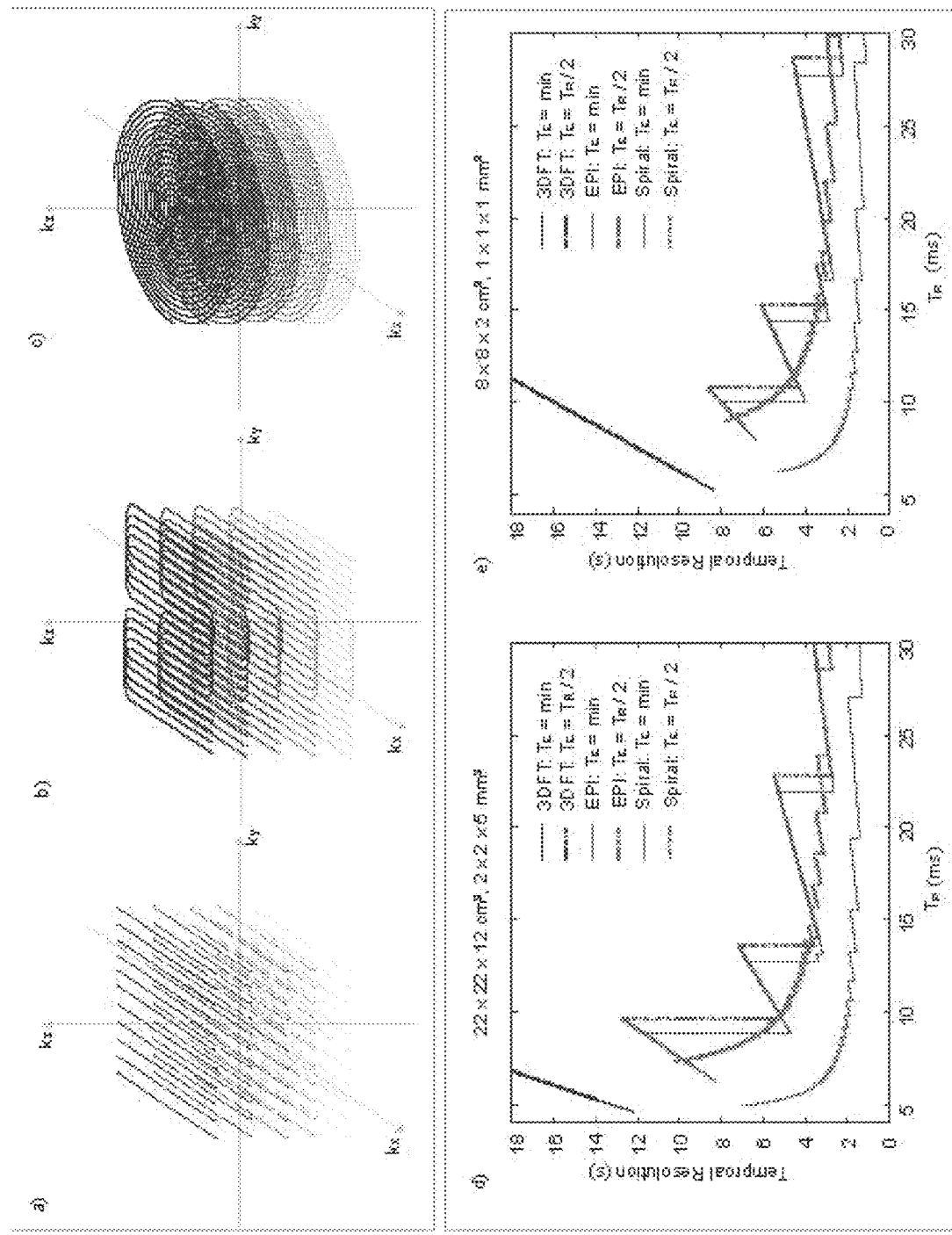
FIG. 31: 3D k-space trajectories and scan time for SSFP fMRI. (a) Any 3D imaging trajectories can be incorporated into an SSFP acquisition including a simple 3DFT readout. To allow fast acquisitions for high spatial and temporal resolution, stack-of-EPI (b) and stack-of-spirals (c) trajectories can be used. Scan time was calculated for different k-space sampling strategies for the whole brain imaging protocol (d) and the high-resolution imaging protocol (e). Since $T_R$ is an important design parameter for spatial scale selectivity, scan time was calculated for a range of $T_R$s.

For 3D acquisitions, the most straightforward strategy is to use 3D Cartesian (3DFT) trajectories (FIG. 31a). Because the $T_R$s are short, the acquisition time using 3DFT is feasible for a relatively low-resolution and small-volume coverage. However, to obtain high-resolution acquisitions with practical volume coverage, an alternative acquisition strategy is necessary. To achieve such a goal, we chose interleaved stack-of-EPI and interleaved stack-of-spiral acquisitions (FIG. 31b, c).

To compare the efficiency of different acquisition strategies, scan times were compared in FIGS. 31d and 31e. The comparison was performed for two different cases with different coverage and resolution (see legends to FIGS. 31d and 31e for further details). The first case was for whole-brain coverage and the second case was for high-resolution acquisition of a small volume of interest. Scan time was calculated as a function of $T_R$. The choice of $T_R$ can potentially determine the spatial scale sensitivity as well as the overall functional contrast. Therefore, the comparison is valid for identical $T_R$s.

Functional brain imaging studies often target a specific brain area such as the primary visual cortex. In such cases, it is only necessary to image a localized region of the brain. To cover a certain localized region using passband SSFP fMRI methods, one simply needs to select the region of interest, shim around that region and then perform the acquisition. To fine tune the volume of interest, phase-cycling angles can also be adjusted to shift the passband region of the SSFP response. Due to the relatively large volume coverage provided by the large flat portion of the SSFP off-resonance profile, a single acquisition is often sufficient for targeted region of interest scans.

Figure 32:
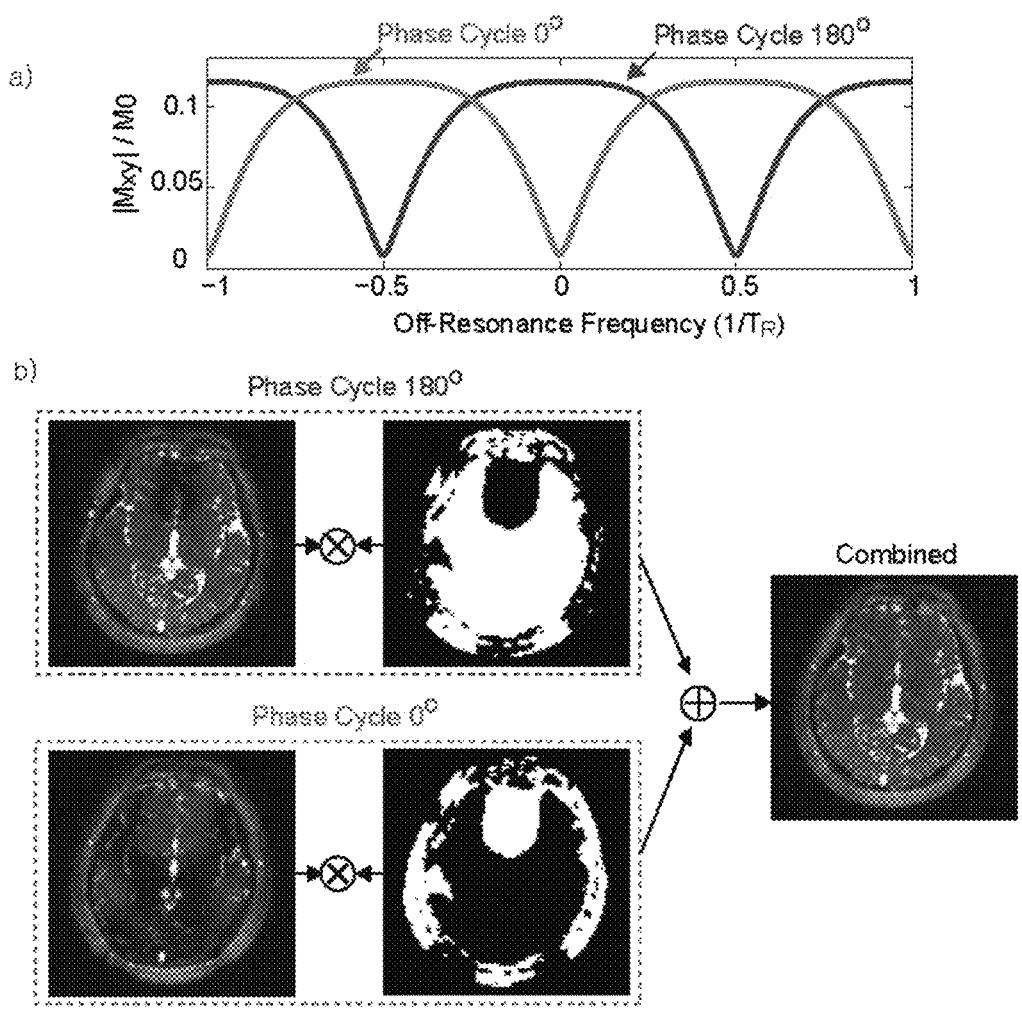
FIG. 32: Two-acquisition method for passband SSFP fMRI. (a) By combining the 180° phase cycled image and the 0° phase cycled image, the passband of the two acquisitions cover the entire off-resonance spectrum. (b) The two images are combined using MIP (instead of methods such as sum-of-squares) to select regions with pure passband contrast.

However, when whole-brain coverage is required, two acquisitions with different phase-cycling angles [63] can be combined (see FIG. 32). With two acquisitions at a 180° phase-cycling angle and a 0° phase-cycling angle, the entire off-resonance spectrum can be covered with the passband region of at least one of the two acquisitions [52, 57, 63]. To avoid mixing contrast from the passband region and the transition band region, a maximal intensity projection (MIP) method was chosen for the combination. The pass-band (flat) portion of the SSFP off-resonance spectrum has a higher signal level. Therefore by selecting pixels from the image that have higher signal intensity, the passband acquired portion can be selected. The pixel selection was performed with the temporally averaged image from the whole fMRI acquisition so that each pixel is selected from one phase-cycling angle image throughout the time series. The MIP selection was then low-pass filtered to generate a selection mask that has a more continuous region unaffected by noise.

It is important to note that while the two-acquisition method can cover the whole brain with just two acquisitions, in some cases, it may not be possible to repeat two identical exams. For example, the novelty of stimuli may be crucial for the experimental design. To avoid such problems, alternating between the two steady-states can be a useful approach. However, there will be scan time overhead during the transition, which could limit the temporal resolution.

Evaluation of Passband SSFP fMRI

Figure 27:
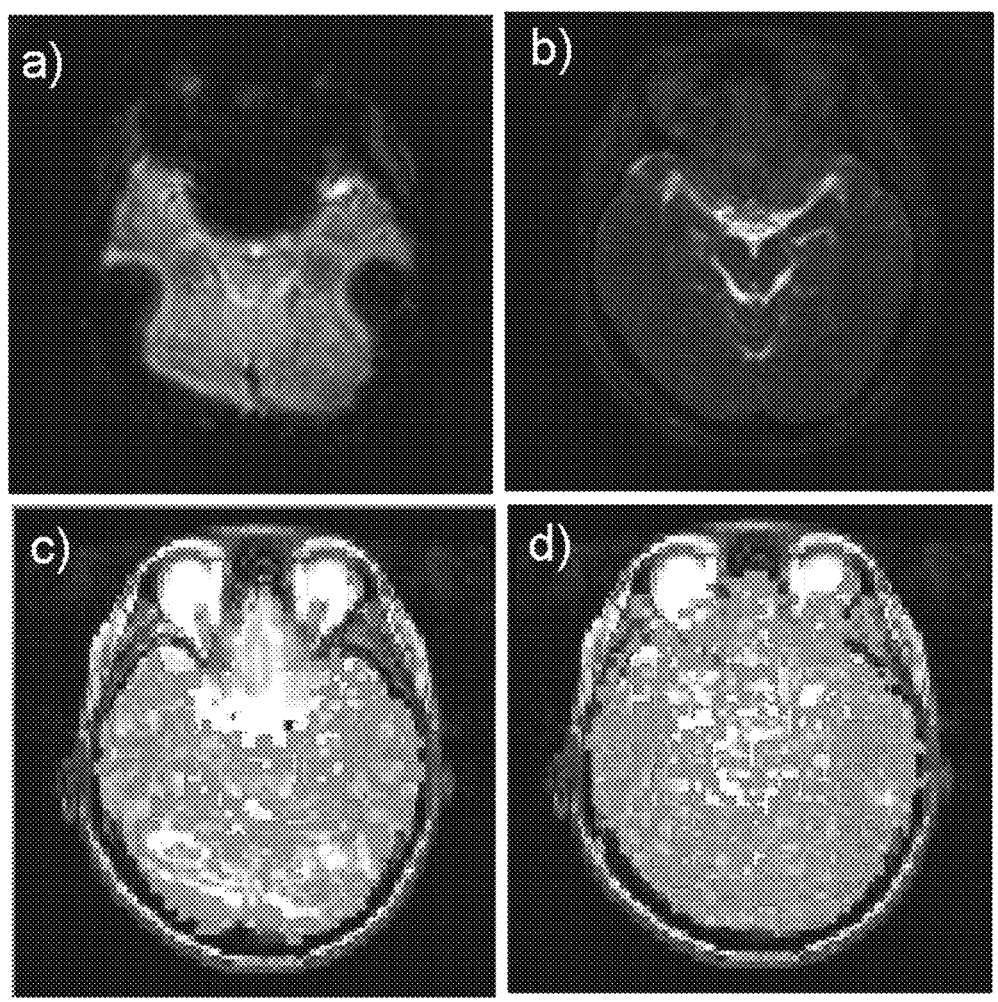
FIG. 27: Functional MRI a) Conventional BOLD fMRI methods are limited due to the spatial distortions and signal dropout that is fundamentally linked to the contrast mechanism b) With Passband SSFP fMRI methods such distortions can be avoided. c) The resulting map from the whole brain activating hypercapnia experiment shows lots of missing areas for the conventional BOLD fMRI while d) the passband SSFP fMRI method shows full brain activation with no missing areas.
Figure 33:
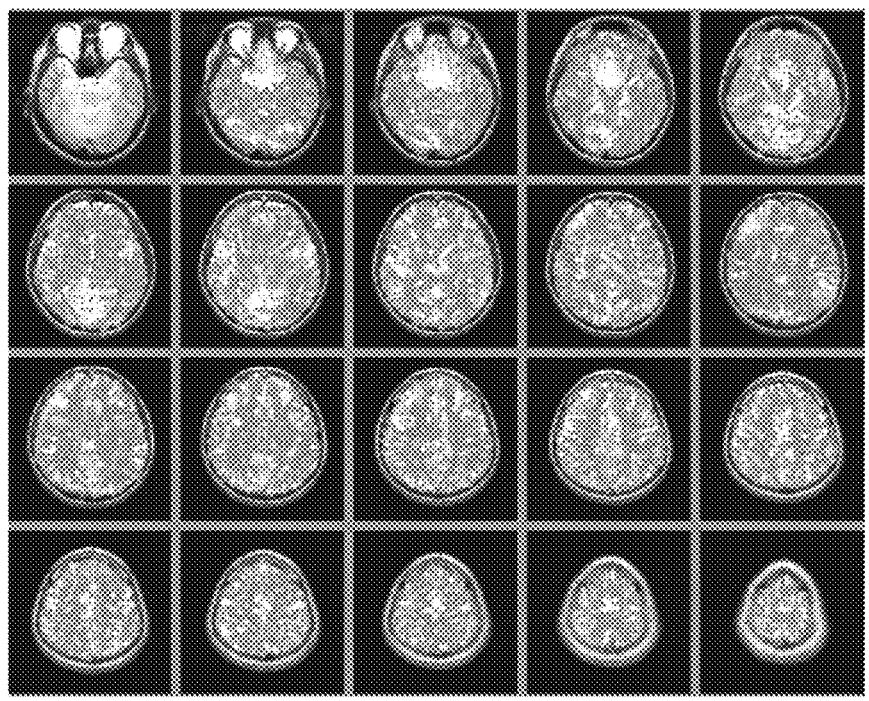
FIG. 33: Hypercapnia experiment result. T2 anatomical overlay of the activation pattern of the whole-brain breath-holding experiment using (a) GRE-BOLD and (b) Passband SSFP fMRI. Severe distortions and signal dropout for GRE-BOLD results in missing activation areas while the passband SSFP result shows no such effect.
Figure 33:
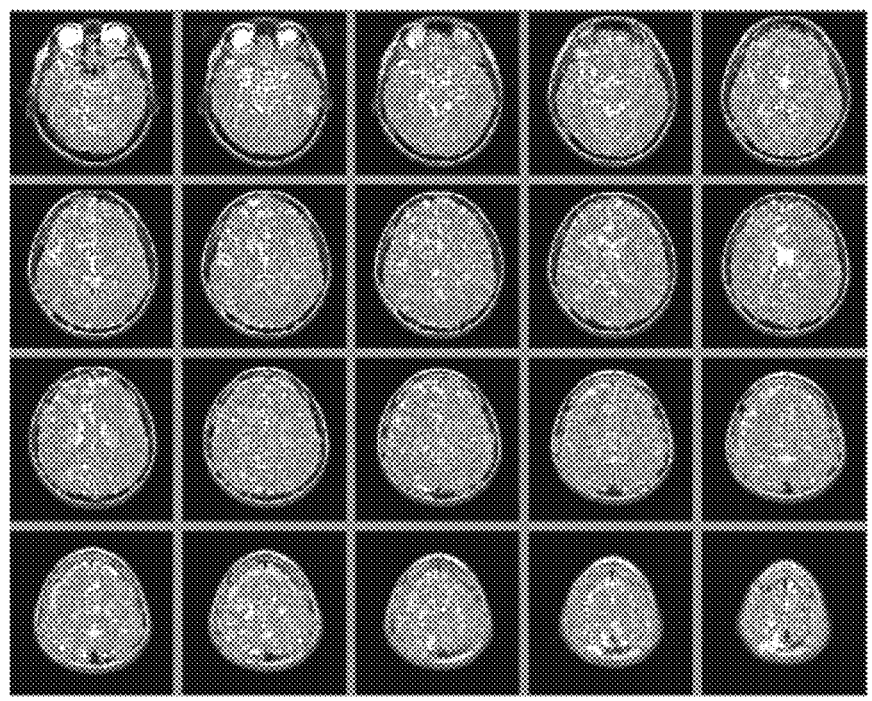

Several experiments were performed to demonstrate the viability and unique capabilities of passband SSFP based functional imaging. All experiments were conducted using a GE 3.0 T EXCITE system with a maximum gradient of 40 mT/m and maximum slew rate of 150 T/m/s. Breath-holding experiments were designed to demonstrate the capability of passband SSFP fMRI for distortion-free full-brain coverage. Hypercapnia induced by breath-holding increases cerebral blood flow (CBF), resulting in increased oxygenation across the entire brain [64]. Breath-holding is thus a simple and robust method to elucidate the extent to which a particular functional imaging technique can measure the degree of oxygenation saturation across the whole brain. The breath-holding experiment results, as shown in FIG. 33, demonstrate passband SSFP fMRI's capability to capture activations in the regions that are traditionally difficult to study using GRE-BOLD. The same axial slices covering the whole brain are displayed for GRE-BOLD (FIG. 33a) and passband SSFP (FIG. 33b), respectively. With GRE-BOLD, a large portion of the prefrontal cortex cannot be robustly imaged due to signal dropout (FIG. 33a). Passband SSFP on the other hand resulted in whole brain oxygenation contrast without marked spatial distortions or signal dropout, including in ventral-most prefrontal cortex. Panels in FIG. 27 demonstrate more clearly the differences in spatial distortions and coverage between the two techniques. The left two axial images display the GRE-BOLD results (top: thresholded activity map overlaid on T2 anatomy; bottom: raw GRE-BOLD image) obtained from one of the ventral-most slices.

Whole-brain retinotopy data acquired using pass-band SSFP fMRI at 3 T. (a) Thresholded activation in the primary visual cortex displayed on an inflated representation the gray matter region (FIG. 34).

Figure 34:
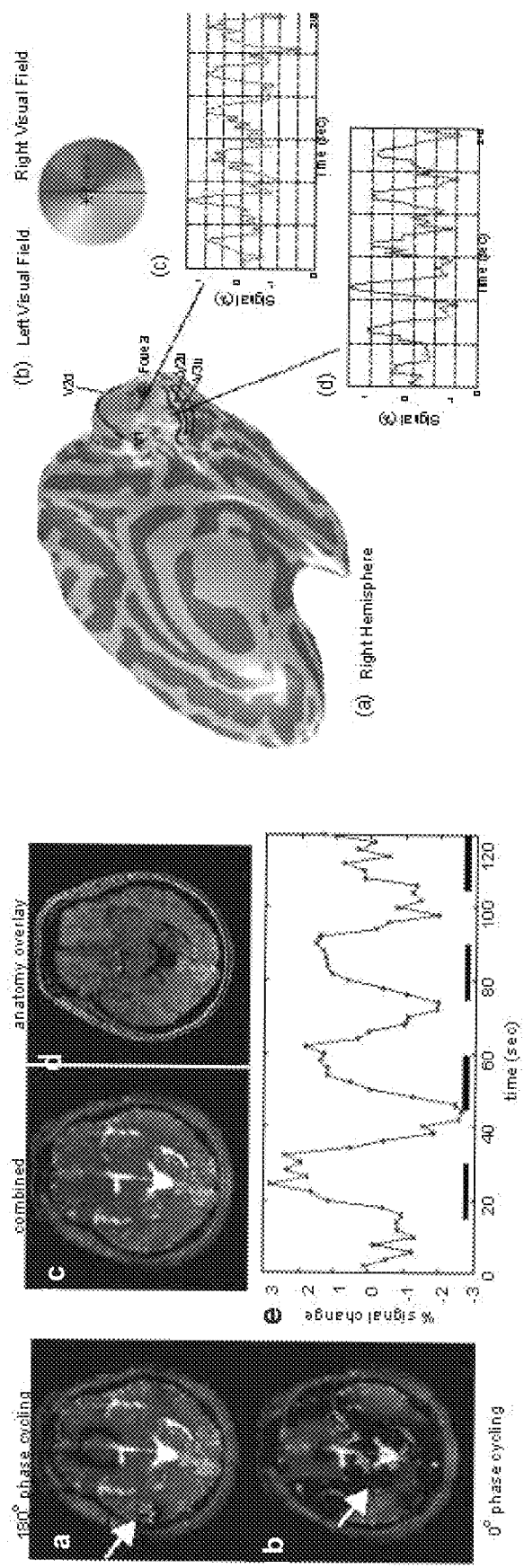
FIG. 34: Full visual field on/off experiment result. (a) 180° and (b) 0° phase cycled SSFP acquisitions and corresponding activation maps. The individual images (a and b) show artifactual activations (white arrows) that occur in the banding areas where the signal exhibits strong frequency sensitivity. (c) These artifactual activations can be eliminated by appropriately combining the two images. (d) Due to the reduced distortion of SSFP, high-quality anatomical registration can be done with simple translations. (e) Signal average over all activated voxels. The horizontal bars indicate the stimulus-on period.

FIG. 34 also depicts results from a full visual field stimulation experiments. Axial slices centered around the primary visual cortex are shown in this figure. Note that a single 180° phase cycled acquisition (FIG. 34a) was sufficient to cover the primary visual cortices, as banding-related artifactual activities occurred only in localized regions outside of the visual cortex (marked by arrows in panels a) and b) in FIG. 34). However, to demonstrate the applicability of the two-acquisition method (see FIG. 32), another set of data was acquired with a 0° phase-cycling angle (FIG. 34b). In both the 180° and the 0° acquisitions, false-positive activations were detected in the banding areas where the signal was unstable due to the rapid magnitude and phase transitions. After combination of the two phase-cycled images using maximum intensity projection, most of the false activations were removed (FIG. 34c). FIG. 34c also shows the lack of any noticeable spatial distortion for passband SSFP functional image. This becomes more evident when the passband SSFP image is compared with the corresponding anatomical image from the same subject (FIG. 34d): the outlines of the two brains closely match with each other such that the passband SSFP functional image can be co-registered with the anatomical images with a simple translation (FIG. 34d). FIG. 34e shows the signal average time course for all activated voxels from FIG. 34c.

Visual field mapping [65-68] produces extra temporal phase information that can be used to verify the passband SSFP fMRI technique's capability to accurately track the time course of the oxygenation signal. Visual field mapping [65-68] across the whole visual cortex is shown in FIG. 34. Then, high-resolution visual field mapping [68] was performed to demonstrate the high-resolution imaging capability of the passband SSFP fMRI. Visual field mapping experiments involved a stimulus with a contrast pattern comprising a rotating wedge (90°) that slowly rotated around fixation, completing a cycle in 42 sec. The wedge rotated around 6 times (total duration 4 min 12 s).

Figure 35:
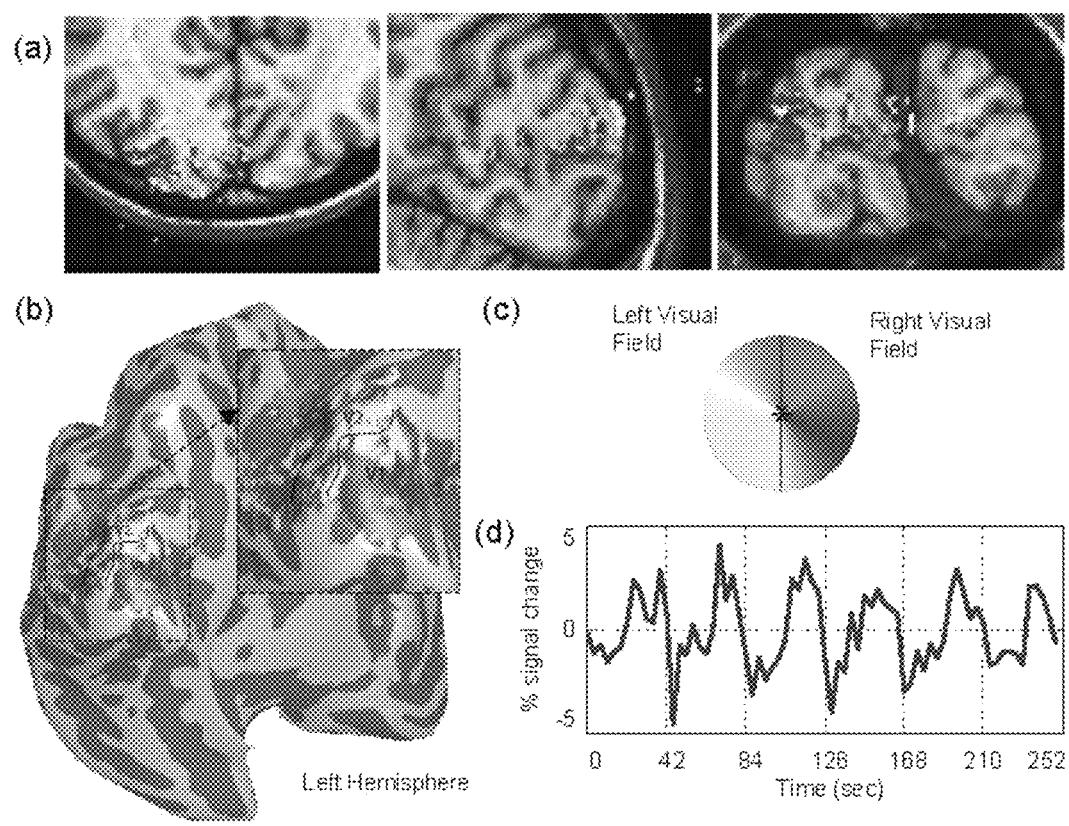
FIG. 35: Visual field mapping at isotropic 1 mm resolution. The phase of the thresholded voxels was overlaid on a T1 anatomical image (a). The thresholded activation shows good correlation with the gray matter. The phase overlaid onto an inflated brain (b) shows the V1/V2 boundary Color coding used for the visual field map is shown in (c). And a graph of % signal charge vs. time is shown in (d).
Figure 39:
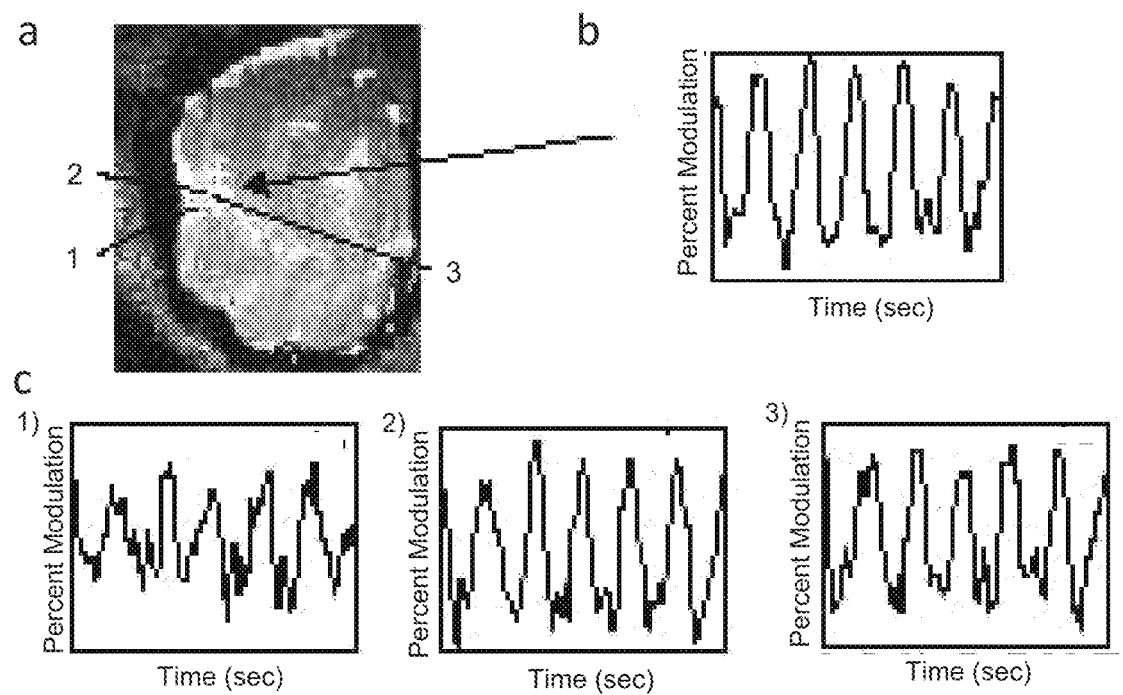
FIG. 39: Visual field mapping in isotropic 0.9 mm resolution. (a) The thresholded coherence map is overlaid onto a coronal T2anatomical image. (b) The average signal intensity in a randomly selected ROI shows robust activation. (c) To further demonstrate the high-resolution nature of the data, three single voxel signal intensities were plotted. The voxel locations are marked in (a). For voxel number 2, the voxel immediately posterior to the marked voxel was plotted. The signal shows robust activations with highly distinct activations levels.

FIGS. 35 and 39 show the result of our high resolution visual field mapping studies. Here, a 1-inch custom single loop surface coil positioned on top of the primary visual cortex was used for localized functional imaging. In FIG. 35a, the phase of the coherence-thresholded activation maps were overlaid on the $T_1$ anatomical images (axial, sagittal and coronal views, respectively) of the same spatial resolution (voxel size=1 mm$^3$). Note how the activated voxels tightly follow the cortical gray matter, indicating that they reflect predominantly neuronal activity. The panels in FIG. 35a further demonstrate that passband SSFP retains adequate functional signals even at an isotropic 1 millimeter spatial resolution. Likewise, the thresholded activation map overlaid on an inflated brain (FIG. 35b) displays a typical visual field map representation of the brain obtained with our distortion-free passband SSFP functional data. The boundaries between V1 and V2 were identified using standard criteria.

C.2 Molecularly Targeted Optical Stimulation

Light Sensitive Proteins and Control of Neuronal Activity.

Figure 36:
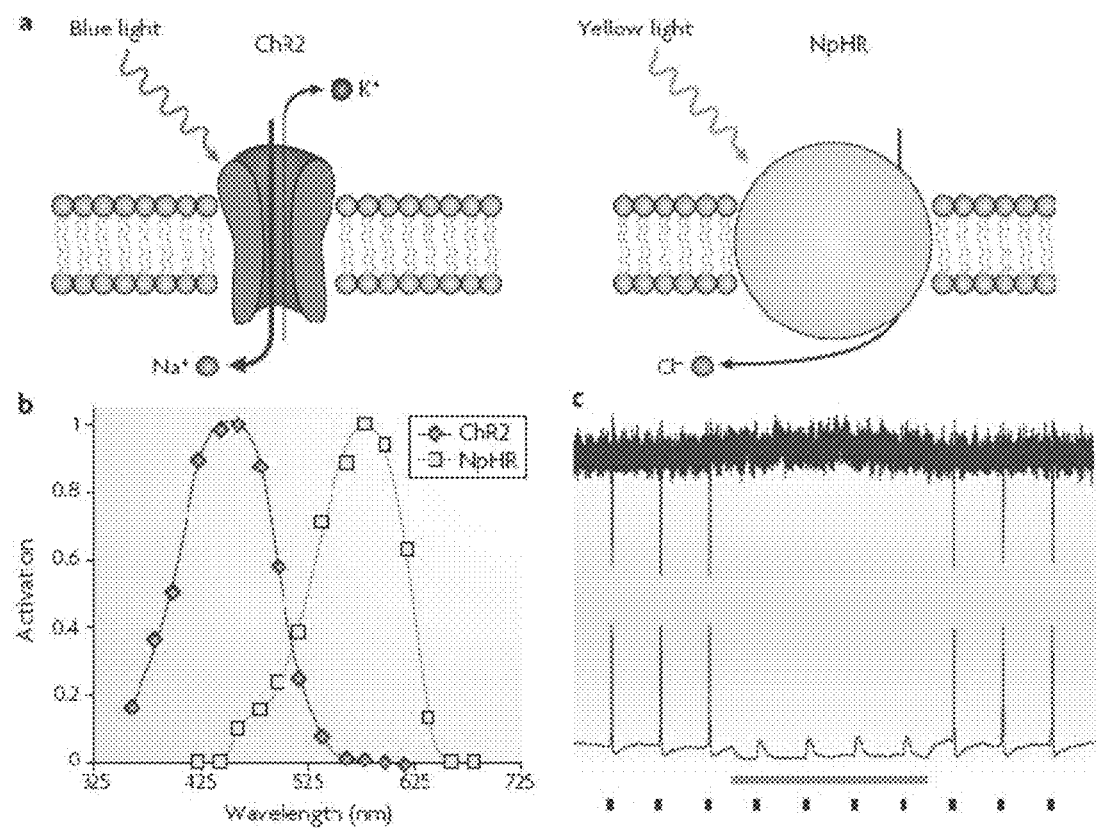
FIG. 36: Optogenetic tools: ChR2 and NpHR. a) Schematic of channelrhodopsin-2 (ChR2) and the halorhodopsin (NpHR) pump. Following illumination with blue light (activation maximum 470 nm, REF.23), ChR2 allows the entry of cations (mostly Na+ and very low levels of Ca2+) into the cell. NpHR is activated by yellow light illumination (activation maximum 580 nm) and allows the entry of Cl. anions. b) Action spectra for ChR2 and NpHR. The excitation maxima for ChR2 and NpHR are separated by 100 nm, making it possible to activate each opsin independently with light. c) Cell-attached (top) and whole-cell current-clamp (bottom) traces from hippocampal neurons showing all-optical neural activation and inhibition. The pulses represent the blue light flashes used to drive ChR2-mediated activation and the bar denotes NpHR-mediated inactivation.
Figure 37:
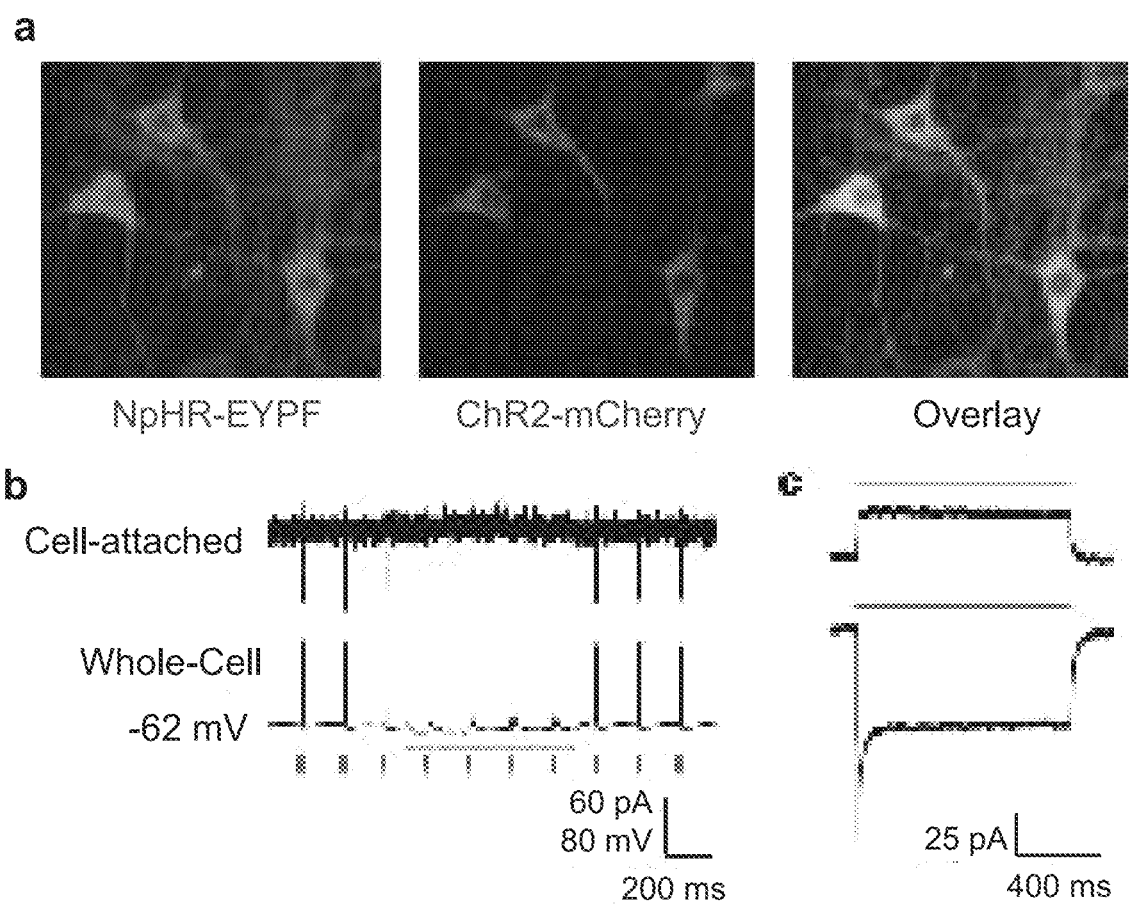
FIG. 37: Combining NpHR with ChR2 noninvasive optical control. a) Hippocampal neurons coexpressing NpHR-EYFP under control of the EF1a promoter and ChR2mCherry under control of the synapsin I promoter. b) Cell-attached and whole-cell recording of neurons coexpressing NpHR-EYFP and ChR2-mCherry. Action potentials are evoked by brief pulses of blue light (473 nm, 15 ms per pulse; length of bars is not to scale for ease of visualization). Simultaneous illumination with yellow light inhibited spike firing. c) Voltage-clamp recording from a single neuron coexpressing NpHR-EYFP and ChR2-mCherry, showing independently addressable outward and inward photocurrents in response to yellow and blue light, respectively.

ChR2 [69] is a monovalent cation channel that allows Na$^+$ ions to enter the cell following exposure to 470 nm blue light, whereas the NpHR [70] is a chloride pump that activates upon illumination with 580 nm yellow light (FIG. 36a). As the optimum activation wavelength of these two proteins are over 100 nm apart (FIG. 36b), they can be controlled independently to either initiate action potential firing or suppress neural activity in intact tissue (FIG. 36c shows implementation of this protocol in hippocampal neurons using cell-attached and whole-cell patch clamp), and together may modulate neuronal synchrony. Both proteins have fast temporal kinetics, on the scale of milliseconds, making it possible to drive reliable trains of high frequency action potentials in-vivo using ChR2 [71] and suppress single action potentials within high frequency spike trains using NpHR. Because NpHR remains active for many minutes when exposed to continuous light and deactivates quickly when light is turned off, it can be used to mimic lesions in a rapid, stable and reversible manner. Stability in general is particularly important. It has long been known that many archaebacterial species express red-shifted light-activated halorhodopsins that can pump chloride ions and modulate membrane potential (e.g. *H. salinarum, H. halobium,* and *N. pharaonis*), but we selected the *Natronomonas halorhodopsin* to experimentally develop for neural control, as NpHR has enhanced stability and chloride affinity. Moreover, halorhodopsin does not require the addition of the cofactor all-transretinal (ATR) to function in intact mammalian tissue, a result that is consistent with previous findings with the homologous opsin ChR2. The ability to functionally express ChR2 and NpHR without the addition of any exogenous cofactor is crucial for applications to basic science investigations, preclinical disease models and possible clinical translation.

Light Delivery to the Brain

To modulate the activity of ChR2 and NpHR expressing neurons, light must be delivered to the brain region of interest. Recently, a fiber-optic system was developed that is suitable for delivering light in-vivo to both superficial and deep brain structures. In this approach, a thin optical fiber (approximately 0.1 to 0.2 mm in diameter) is inserted through a cannula guide (see FIG. 28a) that is targeted precisely to the light-sensitized neurons, to deliver photostimulation to specific neuronal subtypes in the brain of freely moving rats (see FIG. 28b). The optical fiber is coupled to a bright light source such as a diode laser to deliver enough power.

Viral Gene Delivery and Targeting of Specific Neuronal Type

For animal models and clinical applications, viral gene delivery is a convenient and quick approach for mediating ChR2 and NpHR expression. Viral vectors carrying the genes that encode ChR2 or NpHR can be stereotactically delivered into targeted brain regions [72]. So far, recombinant lentiviral and adeno-associated viral (AAV) vectors [72, 73], have been popular choices for gene transfer into patients. Lentiviral vectors integrate into the genome of the target cell and confer permanent gene expression. AAV-mediated expression are expected to be less stable because a much smaller portion (<1%) of the virus is integrated into the target cell.

These vectors can also be made cell-type-specific by the choice of promoter or viral receptor. The targeting of excitatory neurons have been successfully implemented and inhibitory neuron targeting is currently under development.

C.3 Study of Depression

Animal Model of Depression

A chronic mild stress (CMS) paradigm was used as an animal model of depression. Group housed rats were allowed to acclimate for 1 week and then subject to 5-7 weeks of mild stressors that were pseudo-random in nature, duration, frequency, and order. The stressors included inversion of day/night light cycle, continuous illumination, damp cage bedding, 45° tilted cage, restraint, white noise, stroboscopic illumination, and difficult access to food. The duration of each stress ranged from 20 minutes to overnight. During the course administered. Body weight gain (physiological endpoint) and general behavior were monitored consistently throughout the course of the protocol. Unstressed controls were handled only for weight measurements, injections, and during cage changes.

The induced depression is tested using the forced swim test, tail suspension test, and open field test. The forced swim test involved placing the rat in a transparent cylinder (25 cm diameter, 60 cm tall) filled to a depth of 40 cm with room temperature water (25±2° C.). On the first day, the animals were placed the cylinder for a 15-minute pre-exposure. Data were collected during a second test conducted 24 hours later. The animals were observed for a period of 5 minutes by trained observers, and immobility time was recorded. Immobility was defined as the cessation of all movements except those necessary to keep afloat. Long immobility time indicates depression.

Imaging Studies of Depression

To map the brain network involved in depression, neuronal activity needs to be spatially resolved in multiple brain areas. Areas involved in depression include a large portion of the brain in remote locations. The areas that are believed to be involved include portions of the hippocampus (detategyrus(DG), CA1), basolateral amygdale (BLA), pre-frontal cortex (PFC), and subgenual cingulate area 25 (Cg25).

For many neuroscience studies, the brain function is monitored using electrodes that show high temporal resolution data ex-vivo and in-vivo. However, the inability to monitor large areas of the brain with spatial information is limiting, especially for studies involving diseases that is expected to involve complex brain circuitry such as depression. Methods such as voltage sensitive dye imaging (VSDI) allows high spatiotemporal imaging of the brain activity.

The method is still limiting since the brain needs to be sliced before imaging and the spatial coverage only spans a single slice.

Figure 38:
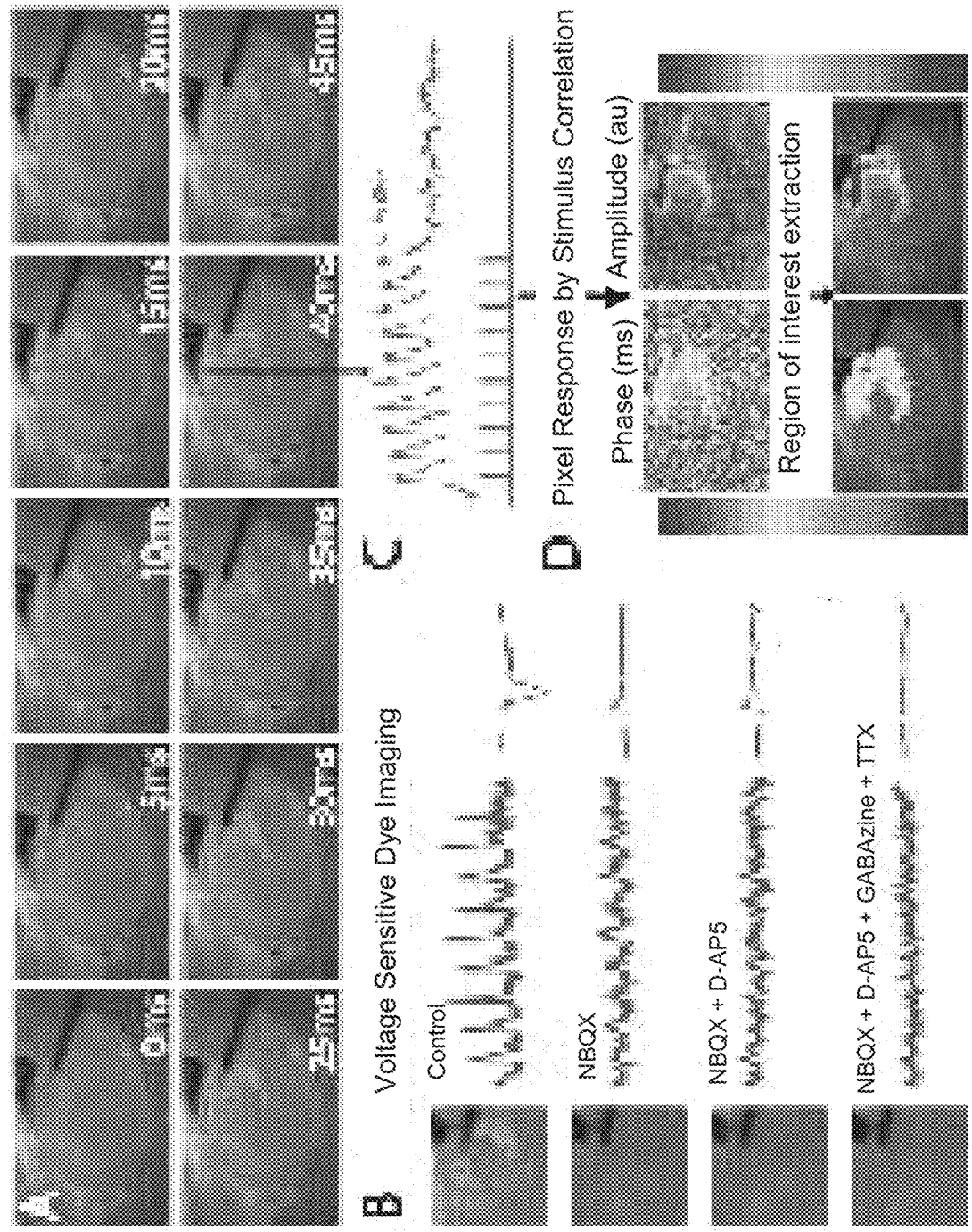
FIG. 38: Voltage sensitive dye imaging (VSDI) of hippocampal network activity. a) Representative filmstrip acquired using VSDI. Times relative to a single stimulus pulse applied to DG; warmer colors indicate greater activity. Data represent the average of four individual acquisitions. b) VSDI signal is abolished by blockers of excitatory synaptic transmission (10 μM NBQX and 25 μM D-AP5). GABAzine (20 μM) and TTX (1 μM) application subsequently confirmed signal extinction. c) Single-pixel response from the indicated region to the given stimulus train (bottom). d) Phase (top left) and amplitude (top right) of maximal correlation between the stimulus and response at each pixel. The region responding to the stimulus was extracted computationally based on similar phase values of responding pixels (bottom).

Prior studies using the animal model of depression combining measurements in the hippocampus DG and CA1 areas are shown in FIG. 38. VSDI from a 400 µm-thick ventral hippocampal slice shows spatially resolved activity in the brain. While the findings from these studies are significant, the lack of whole brain coverage and in-vivo imaging capability prohibits whole brain circuit analysis as well as longitudinal studies with repeated measurements.

C.5 Summary

Passband SSFP fMRI method's effectiveness in delivering distortion-free, high-resolution brain activation maps have been verified through various experiments. The implementation and verification has been on human 3.0 T scanners. The transition to a 7.0 T animal system for small animals is also contemplated by our methods. The optical neural stimulation methods also have been fully implemented and tested in small animals for basic neuronal excitation and inhibition. Combining the pass-band SSFP method and the optical stimulation method and measuring basic hemodynamic function associated with different types of stimulation is also contemplate by our methods. The animal models for depression has also been contemplated for the study of depression.

D Research Design and Methods

D.1 Passband SSFP fMRI Development for Small Animals 7.0 T Animal fMRI Initial Setup.

The final installation of the 7.0 T animal system i consisted of a GE console, RRI gradients instead of the Varian system, and Magnex Scientific superconducting magnet. The RRI gradients had a spec with maximum gradient amplitude of 770 mT/m and maximum slew rate of 7700 T/m/s. This was a significant gradient speed improvement over the originally planned Varian gradients with a maximum gradient amplitude of 600 mT/m and a maximum slew rate of 4000 T/m/s. The inner diameter of the gradient system has also changed to 9 cm instead of 12 cm which was still sufficient for rat studies. The maximum gradient amplitude and slew rate at which the system was stable was 770 mT/m and 2500 T/m/s with approximately 50% duty cycle.

For small animal fMRI, one of the first concerns is whether a proper spatial resolution can be obtained in order to look at the small brains of rodents. The passband SSFP fMRI method's capability to deliver robust activations in high resolution has been previously demonstrated with the retinotopic imaging studies in the human visual cortex (FIG. 39). Here, 900 micron isotropic functional voxel resolution was achieved. Activations tightly confined to the cortical gray matter and robust signal modulation for voxels with less than a 0.73 µl volume demonstrates the high quality of the SSFP fMRI data.

Figure 40:
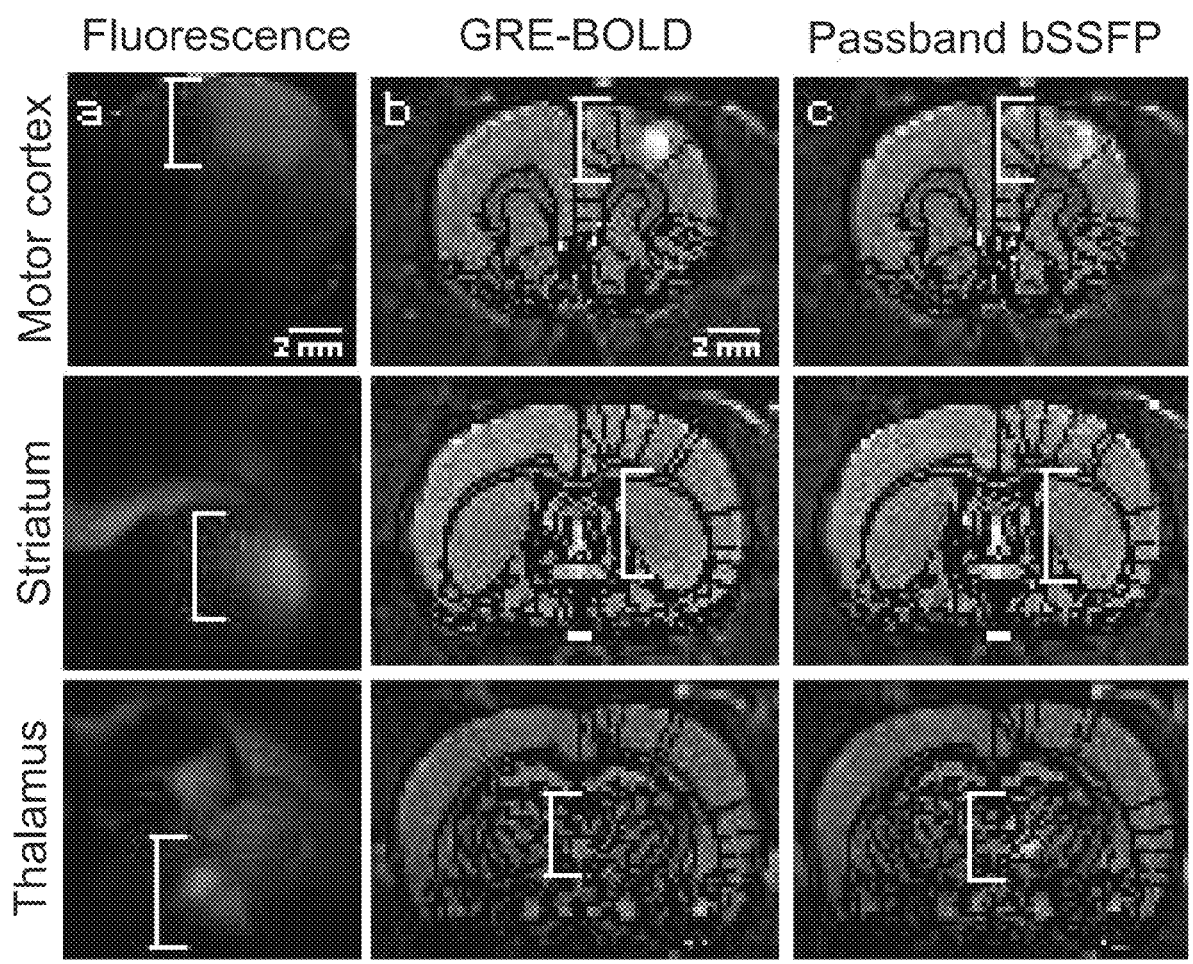
FIG. 40: ofMRI circuit mapping: conventional BOLD and passband bSSFP-fMRI. a, Injection of CaMKII::ChR2-EYFP in M1, as expected, leads to opsin visualization in motor cortex, striatum, and thalamus, i.e. the primary site of injection and sites where axons of expressing neurons extend. b, Hemodynamic response following M1 stimulation: conventional BOLD fMRI superimposed onto appropriate atlas image. c, Imaging the same hemodynamic response with passband bSSFP-fMRI, which more fully captures circuit-level activity.

Initial fMRI implementation at the Stanford small animal imaging system included conventional gradient-echo (GRE)-BOLD fMRI and passband bSSFP fMRI. Both pulse sequences were designed to have 3.5×3.5 cm² in-plane field of view (FOV), 500×500×500 µm³ spatial resolution and 3 s temporal resolution. GRE-BOLD fMRI was designed to be a two-dimensional, multi-slice, gradient-echo sequence with four-interleave spiral readout; 750 ms repetition time ($T_R$) and 12 ms echo time (IL) resulting in 23 slices covering 1.15 cm slice direction volume. This specific design allowed large-volume mapping of the brain during optogenetic control with high temporal resolution. Passband bSSFP-fMRI was designed to be a 3D volumetric, bSSFP sequence with stack-of-spirals readout [78] trajectory. To get good slab selection for the passband bSSFP-fMRI scans, a time-bandwidth (113 W) of 12 pulse was designed with a duration of 1 ms. 10 interleave in-plane spirals with 32 stack locations, 9.372 ms $T_R$ 2 ms $T_E$ resulted in 30 slices (2 slices discarded due to 3D slice direction excitation profile roll-off margin) and 1.5 cm slice direction volume coverage (FIG. 40).

Compared to a 900×900×900 µm³ isotropic resolution image obtained for the human visual cortex, the voxel size decrease (increase in spatial resolution) results in a 5.8-fold signal-to-noise ratio (SNR) hit. This can be potentially compensated by SNR gain from higher field strength going from 3.0 T to 7.0 T (×2.3), reduced body noise, and signal averaging. The contrast which is expected to quadratically increase with higher field strength [79] (×5.5) will also allow higher tolerance to lower SNR for a given CNR necessary for stable signal detection (2.3×5.5=12.7). Theoretically, the analysis above suggests the temporal resolution and SNR is adequate for a 70×70×32 matrix size encoding, which is larger than conventional image matrix size (64×64×32) for human BOLD fMRI. Furthermore, it suggests that further increase in spatial resolution would be supported by the SNR and CNR using the small animal dedicated imaging system.

In addition to the initial implementation of GRE-BOLD and passband SSFP fMRI, a full imaging protocol that includes the localizer, in-plane $T_2$ anatomy (500×500 µm² in-plane spatial resolution, 500 µm at the animal 7.0 T scanner. For the testing of the initial development, approximately 10 rats were used.

The dedicated animal imaging system, is a 7.0 T field strength Bruker BioSpec 70/30 system with a 30 cm bore. Rat insert gradient (BGA 12S) has 11.6 cm inner diameter, 660 mT/m maximum gradient, and 4570 T/m/s slew rate. The spiral gradient designs are slew rate limited for the given imaging FOV. Therefore, the higher slew rate supported by this system compared to the previously described system will support faster, higher spatial resolution imaging. The bore size is suitable for rats while the field strength also matches the previously described system.

Spatial resolution can be further improved, utilizing the higher performance gradients and compressed sensing algorithms. We plan to achieve 200×200×400 µm³ spatial resolution.

Improving Stability.

While the initial studies show that proper spatial and temporal resolution for fMRI studies can be achieved, further improvement in image quality can significantly benefit the study. Some of the factors that can be further improved includes SNR, main field inhomogeneity, radio frequency (RF) field inhomogeneity, eddy currents, and temporal center frequency drift.

Figure 41:
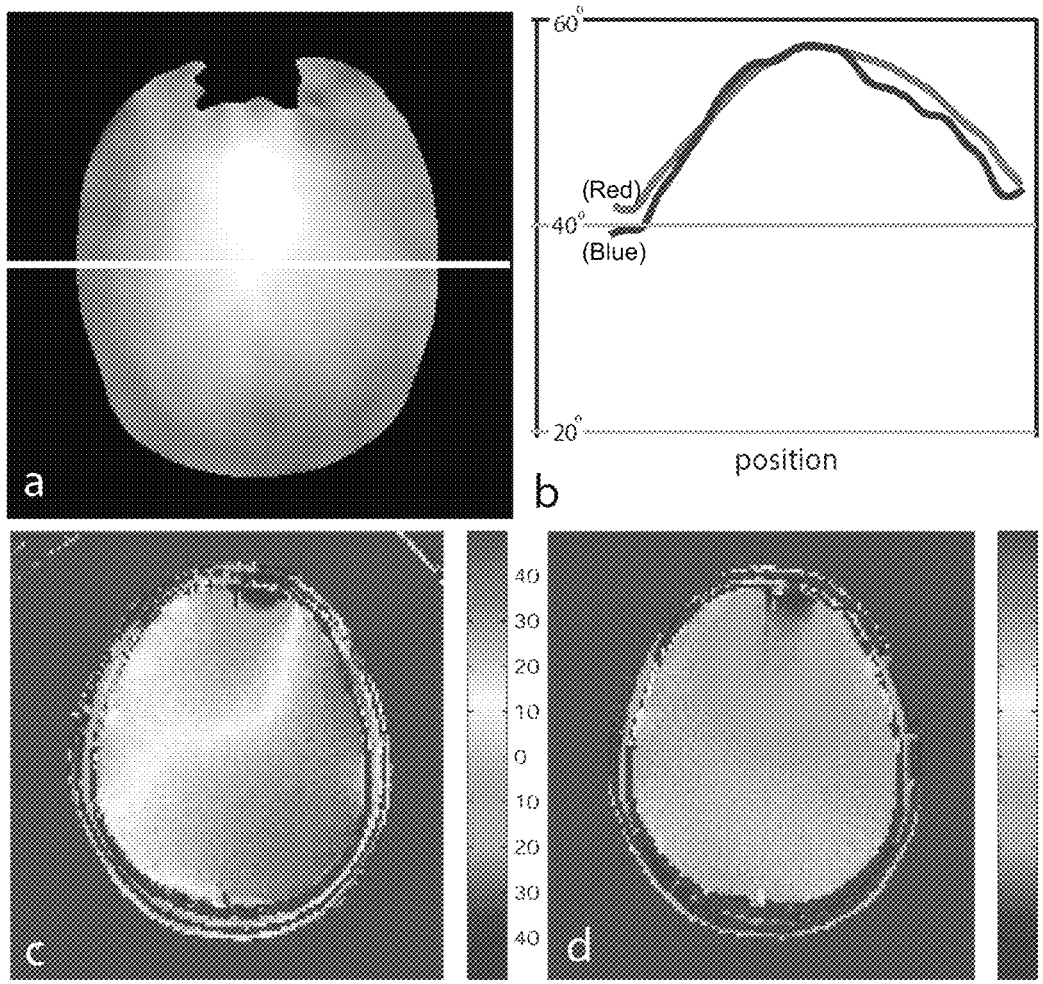
FIG. 41: One slice (a) of a 3 T $B_1$ map covering the entire head in 10 seconds. In (b) a cross section plot through (a) shows the agreement between acquisitions with a 400 ms TR (blue) and a 2000 ms TR (red). Volumetric B0 maps (c) are acquired in several hundred milliseconds, and corrected dynamically using shims (d).

SNR of the passband SSFP image acquisition can be measured with the animal brain. If the SNR is not sufficiently high for the fMRI study, efforts will be put into improving the coil SNR. Using smaller coil elements or cooling the coils can also be considered. Next, the main field inhomogeneity can be tested by measuring the phase map with a animal brain in place. The main field off-resonance effect corrections will be done through improving shimming algorithms or using susceptibility matching foams. With passband SSFP fMRI, the homogeneity will improve the stability of the signal. The RF field inhomogeneity will be measured through rapid B1 mapping techniques developed at MRSRL [80] (see FIG. 41). The B1 mapping will provide a measure of the flip angle reliability.

Eddy current and temporal frequency drift related effects can also be measured and corrected if needed. Eddy current induced gradient errors will be measured [81] and then used to pick proper delay parameters for the three gradient axis. The remaining errors can be corrected through the use of k-space trajectories calculated with the corresponding gradient measurements. To improve the temporal stability of the passband SSFP fMRI method, algorithms to correct for temporal drift in center frequency can also be considered. The temporal frequency drift will be first measured and if the drift is significant enough to corrupt our signal of interest, a real-time feedback algorithm [82] will be implemented to actively is section.

Improving Resolution.

While the initial achievement of 500×500×500 $\mu m^3$ spatial resolution in 3 s temporal resolution is a significant achievement, further efforts will be put into improving the spatial and temporal resolution. The spatial and temporal resolution can have a limit imposed by SNR, image encoding speed (temporal resolution), subject motion, and the spatial extent of the hemodynamic response.

The limit of the achievable resolution will be determined while relaxing the temporal resolution constraint. The temporal resolution constraint will be relaxed by using long lasting stimulations and by encoding for small number of slices. Under this relaxed constraint, several passband SSFP fMRI acquisitions with varying resolutions will be obtained and compared to test the limit of the spatial resolution imposed by SNR, subject motion, and hemodynamics. The spatial resolution limit will be determined by identifying the resolution at which no significant change in activation pattern occurs with spatial smoothing.

After the determining the spatial resolution limit, acquisitions will be optimized to achieve the target resolution over the whole rat brain in reasonable temporal resolution. Methods of interleaving acquisitions of different k-space location [40] will also be considered to achieve target resolution. Three rats will be used for these experiments.

Improving Data Analysis.

Methods for improving the data analysis methods are also contemplated. Motion correction, incorporating the measured hemodynamic function will be some of the most important developments. Hemodynamic function, in particular, will be used to generate HRF models for the analysis and different response to neuronal types will be incorporated through multi-dimensional analysis using various HRF models [83].

Small Animal Imaging Setup. For fMRI studies in small animals, the preparation of the animal to keep the body temperature and anesthesia level constant while limiting motion is important. We will use rats (female adult Sprague-Dawley, 250-350 g) for distortion free functional MRI during/after neuro-moleculartargeted photo-stimulation.

Rats will be initially anesthetized by i.p. injection (90 mg ketamine and 5 mg xylazine per kg of rat body weight) Animal will be intubated, ventilated (Harvard Apparatus) and kept under isoflurane anesthesia during the duration of the preparation and fMRI scans Animal will be placed in a custom-designed cradle made of MRI compatible plexiglass padded with soft forms for the animal's comfort Animal's head will be placed in a custom-designed non-ferromagnetic stereotaxic frame, and a custom-designed optical neural interface (ONI) placed on the animal's head following standard procedures as developed in the mentor's laboratory. To minimize head motion, a MRI-compatible head holder (Kopf and Crist) will be installed on the frame.

The ONI consists of an optical fiber guide stereotactically mounted to the skull with an optical fiber inserted through the guide. The fiber guide is composed of a long cannula embedded in a mounting pedestal. The ONI will serve two purposes. First, for viral transduction of neurons, the fiber guide serves as an injection cannula to deliver the viral vector to the cortex. Then following expression of ChR2, the cannula will be used to guide the optical fiber to the correct location, positioning the tip so the light beam is registered with the ChR2+ neurons. By using the same cannula for viral delivery and positioning of the optical fiber, it is ensured that the light beam will be correctly registered to the ChR2+ neurons.

Subsequently, the cradle with the animal will be inserted to the iso-center of the magnet, and the end of the ONI cannula will be accessible from the outside of the 7.0 T animal MRI scanner. Expiratory CO2 content will be monitored continuously by a capnometer (Datex Ohmeda), and kept at about 3.5% by varying ventilation volume and frequency. Gaseous anesthesia (isoflurane (0.6-1.5%) in a mixture of 70% nitrous oxide and 30% oxygen) will be induced and maintained through the scan. Heated waterbed and rectal temperature probe will be used to maintain the animal's body temperature at physiological levels.

D.2 Neuro-Hemodynamic Coupling Measurement

There are two major purposes for measuring the hemodynamic response function (HRF). One is to figure out necessary information for future data analysis. Accurately understanding the hemodynamic response is very important for the understanding of the resulting functional MRI data. The knowledge of response time, response magnitude and response shape plays an important role in the data analysis for more complicated experimental paradigms. Furthermore, response to impulses with different temporal duration and stimulus strength will be analyzed to test whether the response is linear.

Another purpose of this measurement is to test whether activation of excitatory and inhibitory neurons result in different HRF. With the molecularly targeted control mechanism, we can selectively stimulate different types of neurons to test this hypothesis. Whether there is any difference in the hemodynamic response or not, this will be an important measurement in understanding the characteristics of the neuro-hemodynamic coupling as well as a useful information for data analysis when studying the depression mechanism.

HRF Measurement Method.

Figure 42:
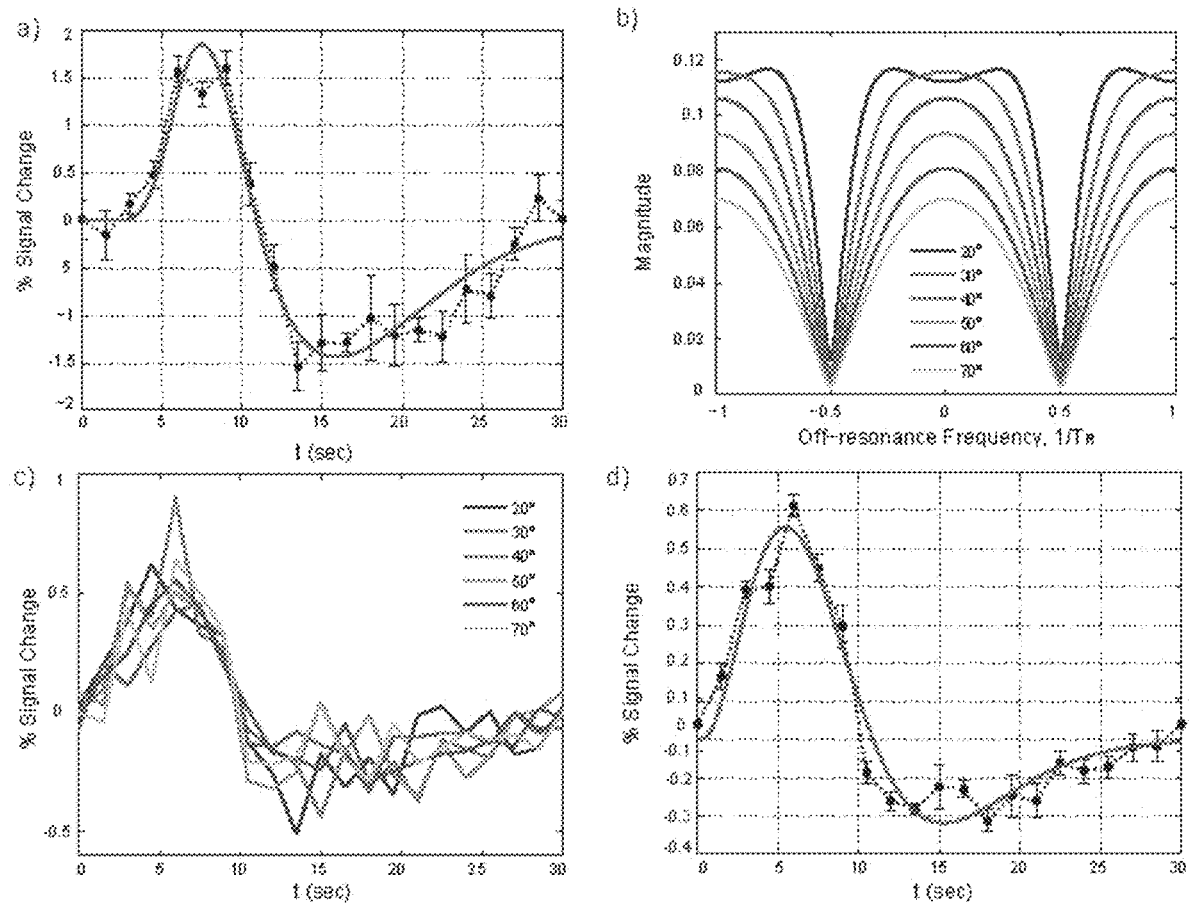
FIG. 42: (a) GRE-BOLD hemodynami response function matches a typical response. The two-gamma function fit resulted in T-value of 15.8423, maximum amplitude of 1.8644 at 7.5 s. Rise to half time was 5.4 s. (b) Passband SSFP fMRI utilizes the flat portion of the SSFP off-resonance profile. Therefore, to obtain robust contrast over a large off-resonance region, the flat portion has to be wide. The flip angle dependency of the off-resonance profile is plotted here for gray matter with T1,T2 values at 3T (T1=1820 ms, T2=99 ms) obtained from a recent paper [85].

An example of a hemodynamic response function (HRF) analysis, a measurement result of human visual cortex stimulation is shown in FIG. 42. A brief visual stimulation is applied and the response is measured over a defined period long enough to capture all the delayed response. For this experiment, the goal was to measure HRF in the human visual cortex V1 using conventional BOLD methods and the passband SSFP method. The signal intensity for all the voxels from V1 were averaged. The measurement results (FIG. 42a, c, d) show characteristic delayed oxygenation followed by signal reversal and undershoot [84].

A similar methodology will be used for the HRF measurements in the small animal brain with the optical stimulations. The difference will be that the stimulation in this case will be the laser radiation of the molecularly targeted neurons and the signal intensity will be averaged across the region of interest. Since this experiment is partially to aid the interpretation of data in the study of depression, HRF measurements will be performed in the prefrontal cortex (PFC) and the basolateral amygdala (BLA) (see section D.3). The stimulations will be delivered to the PFC while the measurement of the HRF will be in both the PFC and BLA. Signal in all of PFC and BLA will be separately averaged as a measurement of the hemodynamic response. While the measurements will be conducted in depression related brain areas, normal rats without CMS will be used.

HRF Linearity Measurement.

On the fourth year, the linearity of the HRF [86] will be tested. To test linearity, three different stimulation duration (3 s, 6 s, 12 s), and three different stimulus amplitude will be used as input. The amplitude of the stimulation will be controlled by the strength of the optical laser radiation. The hemodynmics will be recorded during and for an additional 30 s following the stimulation period.

The viral delivery will be targeted for excitatory neurons with the expression of both ChR2 and NpHR. First, the blue light will be used to simply stimulate the PRF with different duration and amplitude. Then, yellow light will be kept on constantly to see if the hemodynamics change at the presence of yellow light which will block the blue light induced activation. After that, another experiment with alternating intervals of blue light stimulations with and without the yellow light and with the yellow light will be repeated to verify whether the interleaved hemodynamics resemble the individually measured hemodynamics. For all the experiments, the HRF will be measured in two regions of interest, PRF and BLA. The linearity test will be performed in 3 rats. Each rat will be used for the full set of experiments outlined above.

HRF Measurement Specific to Targeted Neurons.

The difference in HRF for excitatory and inhibitory neurons will be measured. Initial measurements of excitatory neuron HRF shows similar shape as conventional fMRI hemodynamic response (FIG. 43). This experiment will also be conducted by stimulating the PFC region. In this case, excitatory neurons and inhibitory neurons will be separately targeted while they both express ChR2. Four rats will be used for this experiment. Two with excitatory neurons expressing ChR2 and 2 with inhibitory neurons expressing ChR2. For each case, blue light radiation will be performed. The duration and strength of the radiation will be selected based on the experiment results from the linearity study. The parameters that give the most robust response with high CNR will be chosen. The HRF will be measured during the stimulation and the 30 s period following the stimulation. The signal will be averaged in PFC and BLA, respectively.

HRF Analysis

During the fourth year, HRF parameters will be estimated. Models such as two-gamma function [27] fitting will be used to calculate parameters including peak amplitude, rise-to-peak time, rise-to-half-peak time. The model of choice will highly depend on the resulting HRF and corresponding adjustments to the model to best describe the response will be made as needed.

D.3 fMRI Study in Animal Model of Depression

The present methods provide for observing high-resolution whole-brain activity during precisely controlled optical stimulation. The need for such mechanism has been highly motivated by the study of neural dysfunction in a system level for diseases such as depression. In some embodiments, the developed technology's capability through applications to the study of brain circuitry involved in depression are contemplated.

Whole-Brain fMRI with Optical Stimulations.

Initial fMRI measurements with the optical stimulations were performed with a block design starting with a 30 sec on/off paradigm. In the fourth year, the block duration will be varied (10 sec, 15 sec, 30 sec) in order to determine a proper duration that gives the most robust signal. The robustness of the signal will be determined based on the CNR of the response.

The experiment will consist of the following steps. We will first start by delivering lentivirus carrying excitatory neuron specific expression of ChR2 to the pre-frontal cortex (PFC) of normal rats. The block design stimulation will be applied with blue laser radiation in 10, 15, 30 s on/off interval. Passband SSFP fMRI measurements will be conducted over the whole brain while the signal in the PFC and BLA will be averaged respectively and used for the calculation of robustness of activation measurement. The measurements will be repeated for 3 rats.

Study of Prefrontal Cortex Input to the Basolateral Amygdala in Animal Model of Depression. The basolateral amygdala (BLA) is believed to be involved in depression and other disorders that display affective components [87]. The neuronal activity of the BLA, and BLA-mediated affective behaviors, are driven by sensory stimuli transmitted in part from sensory association cortical regions. These same behaviors may be regulated by prefrontal cortical (PFC) inputs to the BLA.

By optically stimulating excitatory neurons in PFC, behavioral changes in animal depression model can be observed. The initial experiment results from mice are shown in FIG. 44. For this experiment, virus specific to excitatory cells are used to target ChR2 expression in excitatory neurons. Blue laser (Crystal Laser, wavelength=473 nm, power=40 mW) with 200 um diameter multi-mode optical fiber is used to insert into the brain, through a cannula obtained from Plastics 1 (www.plastics1.com). The results clearly demonstrate that the light activation in PFC leads to behavioral changes in the tail suspension test (TST).

Similar experimental setup will be used with rats. Excitatory neurons will be targeted to express ChR2 and blue light laser will be used to stimulate the neurons in the prefrontal cortex. For the proposed experiment, passband SSFP will be conducted during the experimental period and the fMRI data will be analyzed using models constructed from the HRF measurements.

fMRI studies will be followed by electrode measurements in the same animals used for the fMRI study. The goal of this measurement is to validate fMRI measurements in some of regions of relevance. The electrodes will be placed in the areas of known relevance such as PFC and BLA. The electrode measurements will be made with the same stimulation setup as in the case of fMRI. At the conclusion of the MR recording session, the animal will be transferred to the physiological recording room. Control of anesthesia will be within the same limits necessary to achieve good hemodynamic signals. Single-unit activity will be recorded with standard tungsten micro-electrodes with a tip diameter of 5-7 Am and impedance of 2-4 MΩ, and amplified 10000× with standard equipment (Bak Electronics, Germantown, Md.). The analog signal and stimulus sequence will be recorded continuously (Power1401, Cambridge Electronics Design) allowing for off-line spike discrimination and filtering. Neuronal signals will be collected and stored as an analog waveform at 20 kHz. Activity in pass bands of 0.3.0.7, 0.1.0.3, and 20.80 Hz will be used to estimate neuronal activity over increasingly large areas around the electrode. The higher-frequency band will be used as an estimate for multiunit activity of cells near the electrode tip (MUA), and the lower-frequency band will be used as an approximation of the local field potential activity (LFP).

This study can be summarized as follows.
1. Prepare 3 normal rats and induce CMS in 3 rats.
2. TST for all 6 rats to confirm the behavioral change as observed in the earlier experiment in mice.
3. Viral delivery of ChR2 to PFC for all 6 rats.
4. Laser radiation of blue light in the predetermined blocked interval (10, 15 or 30 s) and the full 14 min interval as was done for the mice experiment in FIG. 20. Passband SSFP fMRI imaging throughout the laser radiation on/off period.
5. Electrode measurements in BLA and PFC for the same animals used in fMRI with the same laser radiation
6. Data analysis using the earlier HRF measurements for fMRI and correlation studies with electrode measurements.

D.4 Data Analysis and Interpretation

Data analysis and interpretation criteria for the testing of the methods described in the present application are discussed. How the results from each experiment will be interpreted is discussed.

Passband SSFP fMRI Development for Small Animals

With faster, stronger gradients used in animal scanners, higher spatial resolution encoding will be possible within the temporal resolution constraint. This will be tested by evaluating the small animal scanner's gradient capability of encoding 200×200×400 $\mu m^3$ resolution in 2 s which is the initial goal set for the resolution. If the image in phantoms show reasonable image quality without blurring or distortion, then the use of faster, stronger gradients used in animal scanners, higher spatial resolution encoding will be possible within the temporal resolution constraint.

Sufficient signal, stability and resolution for small animal brain fMRI can be achieved with the small animal system. If the same resolution image in rat brain is delivered without blurring or distortion and if the temporal stability is reasonable for fMRI signal detection, sufficient signal, stability and resolution for small animal brain fMRI will be achieved with the small animal system.

Neuro-Hemodynamic Coupling Measurement

The optical stimulation gives rise to a linear hemodynamic response. If HRF linearly increases its duration and amplitude proportional to the stimulus duration and amplitude, the HRF will be considered to be linear.

Through targeted stimulation of the excitatory and inhibitory neurons, the difference in the hemodynamic response can be measured. The HRF will be measured from exciting the excitatory neurons and the inhibitory neurons to show significant difference measured by the model parameters such as the peak amplitude and rise-to-peak time.

fMRI Study in Animal Model of Depression

Whole-brain activation mapping with activation in a targeted area of the brain will reveal connectivity of the brain circuitry. If the initial study of activating the PFC in normal rats show correlated activations in BLA or other distinct areas of the brain, then whole-brain activation mapping with activation in a targeted area of the brain reveals connectivity of the brain circuitry.

The whole brain view of the activations with precise stimulation control in animal depression models will show depression mechanism on a circuit level. If the activations in the PFC result in different activations in other parts of the brain comparing normal and CMS induced rats, then whole brain view of the activations with precise stimulation control in animal depression models shows depression mechanism on a circuit level.

D.5 Summary

The small animal fMRI with distortion-free, high-resolution characteristics will be developed and hemodynamics will be measured to look into its linearity and the HRF dependency on neuronal types as described by the methods of the present invention. Depression related circuit level analysis utilizing the HRF measurements are also contemplated and can in some case be employed to demonstrate the technique's capability. For the experiments described, a total of 27 rats will be used over 5 years.

F Vertebrate Animals

Rats (male adult Sprague-Dawley, 250-350 g, http://aceanimals.com/SpragueDawley.htm) will be used for distortion free functional MRI during/after neuro-molecular-targeted photo-stimulation. All animal studies will be performed with the approval of the Stanford University Institutional Animal Care and Use Committee (IACUC). A total of 41 rats will be used for the study.

Rats will be anesthetized by i.p. injection (90 mg ketamine and 5 mg xylazine per kg of rat body weight) Animal will be intubated, ventilated (Harvard Apparatus) and kept under isoflurane anesthesia during the duration of the preparation and fMRI scans Animal will be placed in a custom-designed cradle made of MRI compatible plexi-glass padded with soft forms for the animal's comfort Animal's head will be placed in a custom-designed non-ferromagnetic stereotaxic frame, and a custom-designed optical neural interface (ONI) placed on the animal's head following standard procedures as developed in the mentor's laboratory.

The ONI consists of an optical fiber guide stereotactically mounted to the skull with an optical fiber inserted through the guide. The fiber guide is composed of a long cannula embedded in a mounting pedestal. The ONI will serve two purposes. First, for viral transduction of neurons, the fiber guide serves as an injection cannula to deliver the viral vector to the cortex. Then following expression of ChR2, the cannula will be used to guide the optical fiber to the correct location, positioning the tip so the light beam is registered with the ChR2+ neurons. By using the same cannula for viral delivery and positioning of the optical fiber, it is ensured that the light beam will be correctly registered to the ChR2+ neurons.

Subsequently, the cradle with the animal will be inserted to the iso-center of the magnet, and the end of the ONI cannula will be accessible from the outside of the 7.0 T animal MRI scanner. Expiratory CO2 content will be monitored continuously by a capnometer (Datex Ohmeda), and kept at about 3.5% by varying ventilation volume and frequency. Gaseous anesthesia (isoflurane (0.6-1.5%) in a mixture of 70% nitrous oxide and 30% oxygen) will be induced and maintained through the scan. Heated waterbed and rectal temperature probe will be used to maintain the animal's body temperature at physiological levels.

REFERENCES

[1] J. H. Lee, R. Durand, V. Gradinaru, F. Zhang, I. Goshen, D. S. Kim, L. E. Fenno, and C. Ra-makrishnan K. Deisseroth. Global and local fmri signals driven by neurons defined optogenetically by type and wiring. Nature, page doi:10.1038/nature09108, 2010.

[2] K. K. Kwong, J. W. Belliveau, D. A. Chesler, I. E. Goldberg, R. M. Weisskoff, B. P. Poncelet, D. N. Kennedy, B. E. Hoppel, M. S. Cohen, R. Turner, H.-M. Cheng, T. J. Brady, and B. R. Rosen. Dynamic magnetic resonance imaging of human brain activity during primary sensory stimulation. Proc Natl Acad Sci USA, 89:5675-5679, 1992.

[3] S. Ogawa, D. W. Tank, R. Menon, J. M. Ellermann, S-G. Kim, H. Merkle, and K. Ugurbil. Intrinsic signal changes accompanying sensory stimulation: Functional brain mapping with magnetic resonance imaging. Proc Natl Acad Sci USA, 89:5951-5955, 1992.

[4] P. A. Bandettini, E. C. Wong, R. S. Hinks, R. S. Tikofsky, and J. S. Hyde. Time course EPI of human brain function during task activation. Magn Reson Med, 25:390-397, 1992.

[5] J. Frahm, H Bruhn, K.-D. Merboldt, W. Hanicke, and D. Math. Dynamic MR imaging of human brain oxygenation during rest and photic stimulation. J Magn Reson Imaging, 2:501-505, 1992.

[6] F. Zhang, L.-P. Wang, M. Brauner, J. F. Liewald, K. Kay, N. Watzke, P. G. Wood, E. Bamberg, G. Nagel, A. Gottschalk, and K. Deisseroth. Multi-modal fast optical interrogation of neural circuitry. Nature, 446(5): 633-641, 2007.

[7] F. Zhang, A. M. Aravanis, A. Adamantidis, L. de Lecea, and K. Deisseroth. Circuit-breakers: optical technologies for probing neural signals and systems. Nat Reviews, 8:577-581, 2007.

[8] A. M. Aravanis, L. P. Wang, F. Zhang, L. A. Meltzer, M. Z. Mogri, M. B. Schneider, and K. Deisseroth. An optical neural interface: in vivo control of rodent motor cortex with integrated fiberoptic and optogenetic technology. J Neural Eng, 4:1-14, 2007.

[9] A. S. Gevins, G. M. Zeitlin, J. C. Doyle, C. D. Yin-gling, R. E. Schaffer, E. Callaway, and C. L. Yeager. Electroencephalogram correlates of higher cortical functions. Science, 203(4381):665-668, 1979.

[10] J. D. Bronzino. Principles of electroencephalography. In J. D. Bronzino, editor, The Biomedical Engineering Handbook, volume 1, chapter 15. CRC Press, 2 edition, 2000.

[11] J. Malmivuo. Biomagnetism. In J. D. Bronzino, editor, The Biomedical Engineering Handbook, volume 1, chapter 16. CRC Press, 2 edition, 2000.

[12] D. Brandeis and D. Lehmann Event-related potentials of the brain and cognitive-processes-Approaches and applications. Neuropsychologia, 24(1):151-168, 1986.

[13] M. Kutas and S. A. Hillyard. Event-related potentials in cognitive science. In M S Gazzaniga, editor, Handbook of Cognitive Neuroscience. Plenum Press, New York, 1984.

[14] M. D. Stern. In vivo evaluation of microcirculation by coherent light-scattering. Nature, 254(5495):56-58, 1975.

[15] U. Dirnagl, B. Kaplan, M. Jacewicz, and W. Pulsinelli. Continuous measurement of cerebral cortical blood-flow by Laser-Doppler Flowmetry in a rat stroke model. J Cereb Blood Flow Metabol, 9(5):589-596, 1989.

[16] A. Villringer, R. L. Haberl, U. Dirnagl, F. Anneser, M. Verst, and K. M. Einhaupl. Confocal laser microscopy to study microcirculation on the rat-brain surface in vivo. Brain Research, 504(1):159-160, 1989.

[17] M. E. Raichle. Circulatory and metabolic correlates of brain function in normal humans. In V. B. Mountcastle, F. Plum, and S. R. Geiger, editors, Handbook of physiology—the nervous system, pages 643-674. American Physiological Society, Bethesda, 1987.

[18] J. P. Ollinger and J. A. Fessler. Positron-emission tomography. IEEE Signal Processing Magazine, 14(1): 43-55, 1997.

[19] J. A. Detre, J. S. Leigh, D. S. Williams, and A. P. Koretsky. Perfusion imaging. Magn Reson Med, 23(1): 37-45, 1992.

[20] D. S. Williams, J A Detre, J. S. Leigh, and A. P. Koretsky. Magnetic-Resonance-Imaging of perfusion using spin inversion of arterial water. Proc Natl Acad Sci USA, 89(1):212-216, 1992.

[21] R. R. Edelman, B Siewert, D. G. Darby, V. Thangaraj, A. C. Nobre, M. M. Mesulam, and S. Warach. Qualitative mapping of cerebral blood-flow and functional localization with echo-planar MR-imaging and signal targeting with alternating radio-frequency. Radiology, 192(2):513-520, 1994.

[22] J. W. Belliveau, D. N. Kennedy, R. C. Mckinstry, B. R. Buchbinder, R. M. Weisskoff, M. S. Cohen, J. M. Vevea, T. J. Brady, and B. R. Rosen. Functional mapping of the human visual-cortex by magnetic-resonance-imaging. Science, 254(5032):716-719, 1991.

[23] J. B. Mandeville, J. J. A. Marota, B. E. Kosofsky, J. R. Kellner, R. Weissleder, B. R. Rosen, and R. M. Weisskoff. Dynamic functional imaging of relative cerebral blood volume during rat forepaw stimulation. Magn Reson Med, 39:615-624, 1998.

[24] H. Lu, X. Golay, J. J. Pekar, and P. C. M. van Zijl. Functional magnetic resonance imaging based on changes din vascular space occupancy. Magn Reson Med, 50(2): 263-274, 2003.

[25] K. R. Thulborn, J. C. Waterton, P. M. Matthews, and G. K. Radda. Oxygenation dependence of the transverse relaxation time of water protons in whole blood at high field. Biochem Biophys Acta, 714:265-270, 1982.

[26] L. Pauling and C. Coryell. The magnetic properties and structure of hemoglobin, oxyhemoglobin and carbon monoxyhemoglobin. Proc Natl Acad Sci USA, 22:210-216, 1936.

[27] G. H. Glover. Deconvolution of impulse response in event-related bold fMRI. NeuroImage, 9:416-429, 1999.

[28] F. Farzaneh, S. J. Riederer, and N. J. Pelc. Analysis of T2 limitations and off-resonance effects on spatial-resolution and artifacts in echo-planar imaging. Magn Reson Med, 14(1):123-139, 1990.

[29] J. S. Gati, R. S. Menon, K. Ugurbil, and B. K. Rutt. Experimental determination of the BOLD field strength dependence in vessels and tissue. Magn Reson Med, 38:296-302, 1997.

[30] P. Jezzard and S. Clare. Sources of distortion in functional MRI data. Human Brain Mapping, 8:80-85, 1999.

[31] J. L. Boxerman, P. A. Bandettini, K. K. Kwong, J. R. Baker, T. L. Davis, B. R. Rosen, and R. M. Weisskoff. The intravascular contribution to fMRI signal change: Monte Carlo modeling and diffusion-weighted studies in vivo. Magn Reson Med, 34:4-10, 1995.

[32] J. T. Devlin, R. P. Russell, M. H. Davis, C. J. Price, H. E. Moss, P. M. Matthews, and L. K. Tyler. Comparing PET and FMRI on a semantic task: Applying FMRI to the temporal lobes. NeuroImage, 11:589-600, 2000.

[33] R. T. Constable and D. D. Spencer. Composite image formation in z-shimmed functional MR imaging. Magn Reson Med, 42(1):110-7, July 1999. PMID: 10398956.

[34] Z. Li, G. Wu, X. Zhao, F. Luo, and S. J. Li. Multiecho segmented EPI with z-shimmed background gradient compensation (MESBAC) pulse sequence for fMRI. Magn Reson Med, 48(2):312-21, August 2002. PMID: 12210940.

[35] H. Gu, H. Feng, W. Zhan, S. Xu, D. A. Silbersweig, E. Stern, and Y. Yang. Single-shot interleaved z-shim EPI with optimized compensation for signal losses due to susceptibility-induced field inhomo-geneity at 3 T. Neuroimage, 17(3):1358-64, November 2002. PMID: 12414275.

[36] R. Deichmann, J A Gottfried, C. Hutton, and R. Turner. Optimized EPI for fMRI studies of the orbitofrontal cortex. Neuroimage, 19(2 Pt 1):430-41, June 2003. PMID: 12814592.

[37] A. R. Preston, M. E. Thomason, K. N. Ochsner, J. C. Cooper, and G. H. Glover. Comparison of spiral-in/out and spiral-out BOLD fMRI at 1.5 and 3 T. Neuroimage, 21(1):291-301, January 2004. PMID: 14741667.

[38] G. H. Glover and M. E. Thomason. Improved combination of spiral-in/out images for BOLD fMRI. Magn Reson Med, 51(4):863-8, April 2004. PMID: 15065263.

[39] S. G. Kim and K. Ugurbil. High-resolution functional magnetic resonance imaging of the animal brain. Methods, 30(1):28-41, 2003.

[40] A. C. Silva and A. P. Koretsky Laminar specificity of functional mri onset times during somatosen¬sory stimulation in rat. Proc Natl Acad Sci USA, 99(23):15182-15187, 2002.

[41] D. Waldvogel, P. van Gelderen, W. Muellbacher, U. Ziemann, I Immisch, and M. Hallett. The rela-tive metabolic demand of inhibition and excitation. Nature, 406:995-998, 2000.

[42] K. J. Ressler and H. S. Mayberg. Targeting ab¬normal neural circuits in mood and anxiety dis¬orders: from the laboratory to the clinic. Nat Neuro-science, 10(9):1116-1124, 2007.

[43] H. S. Mayberg, A. M. Lozano, V. Voon, H. E. McNeely, D. Seminowicz, C. Hamani, J M. Schwalb, and S. H. Kennedy. Deep brain stimulation for treatment-resistant depression. Neuron., 45:651-660, 2005.

[44] H. Y. Carr. Steady-state free precession in nuclear magnetic resonance. Phys Rev Let, 112:1693-1701, 1958.

[45] K. Scheffler, E. Seifritz, D. Bilecen, R. Venkatesan, J. Hennig, M. Deimling, and E. M. Haacke. Detec-tion of BOLD changes by means of a frequency-sensitive trueFISP technique: preliminary results. NMR Biomed, 14:490-496, 2001.

[46] K. L. Miller, B. A. Hargreaves, J. Lee, D. Ress, R. C. deCharms, and J. M. Pauly. Functional MRI using a blood oxygenation sensitive steady state. Magn Reson Med, 50:675-683, 2003. PMID: 14523951.

[47] S. Ogawa, T.-M. Lee, A. S. Nayak, and P. Glynn. Oxygenation-sensitive contrast in magnetic reso-nance images of rodent brain at high magnetic fields. Magn Reson Med, 14:68-78, 1990.

[48] K. L. Miller, S. M. Smith, P. Jezzard, and J. M. Pauly. High-resolution FMRI at 1.5T using bal-anced SSFP. Magn Reson Med, 50:161-170, 2006. PMID: 16345040.

[49] C. V. Bowen, R. S. Menon, and J. S. Gati. High field balanced-SSFP FMRI: A BOLD technique with ex-cellent tissue sensitivity and superior large vessel suppression. In Proc 13th ISMRM, page 119, Mi-ami, 2005.

[50] C. V. Bowen, J. Mason, R. S. Menon, and J. S. Gati. High field balanced-SSFP fMRI: Examining a dif-fusion contrast mechanism using varied flip an-gles. In Proc 14th ISMRM, page 665, Seattle, 2006.

[51] J. H. Lee, P. T. Gurney, R. Dharmakumar, G. A. Wright, B. A. Hargreaves, A Shankaranarayanan, K. L. Miller, D. G. Nishimura, and J. M. Pauly. Blood oxygenation (BOX) level dependent func-tional brain imaging using steady-state preces-sion. In Proc 14th ISMRM, page 3291, Seattle, 2006.

[52] J. H. Lee, P. T. Gurney, S. O. Dumoulin, B. A. Wan-dell, A. Shankamnarayanan, D G Nishimura, and J. M. Pauly. BOX fMRI using multiple-acquisition steady-state free precession imaging for full-brain coverage. In Proc 14th ISMRM, page 3297, Seat-tle, 2006.

[53] O. Bieri and K. Scheffler. Microscopic susceptibility-induced steady-state perturba¬tion: Theory and experiment. In Proc 14th ISMRM, page 432, Seattle, 2006.

[54] O. Bieri and K. Scheffler. Effect of diffusion in inhomogeneous magnetic fields on balanced steady-state free precession. NMR Biomed, 20:1-10, 2007.

[55] K. Zhong, J. Leupold, J. Hennig, and O. Speck. fmri activation in human visual cortex measured with steady state free precession at 3 tesla. In Proc 14th ISMRM, page 3296, Seattle, 2006.

[56] K. Zhong, J. Leupold, J. Hennig, and O. Speck. Systematic investigation of balanced steady-state free precession for functional MRI in human visual cortex at 3 Tesla. Magn Reson Med, 57(1):67-73, 2007. PMID: 17191247.

[57] J. H. Lee, S. O. Dumoulin, Gary H. Glover, B. A. Wandell, D. G. Nishimura, and J. M. Pauly. Full-brain coverage and high-resolution imaging capa¬bilities of passband SSFP fMRI at 3T. In Proc 15th ISMRM, page 694, Berlin, 2007.

[58] K. Miller. Characterization of passband SSFP fMRI: A comparison with GRE at multiple field strengths. In Proc 15th ISMRM, page 695, Berlin, 2007.

[59] T. Kim, J. Lee, and J. M. Pauly. Analysis of the BOLD signal characteristics in balanced SSFP fMRI: A Monte-Carlo simulation. In Proc 15th ISMRM, page 696, Berlin, 2007.

[60] C. I. Moore, C. E. Stern, S. Corkin, B. Fischl, A. C. Gray, B. R. Rosen, and A. M. Dale. Segregation of somatosensory activation in the human rolandic cortex using fMRI. J Neurophysiology, 84:558-569, 2000.

[61] K. Ugurbil, L. Toth, and D. S. Kim. How accurate is magnetic resonance imaging of brain function? Trends in Neurosciences, 26(2):108-114, 2003.

[62] C. Studholme, T. Constable, and J. S. Dun-can. Accurate alignment of functional epi data to anatomical MRI using a physics-based distortion model. IEEE Trans Med Imaging, 19:1115-1127, 2000.

[63] N. K. Bangerter, B. A. Hargreaves, S. S. Vasanawala, J. M. Pauly, G. E. Gold, and D. G. Nishimura. Analysis of multiple-acquisition SSFP. Magn Reson Med, 51(5):1038-1047, 2004. PMID: 15122688.

[64] A. Kastrup, T.-Q. Li, A. Takahashi, G H Glover, and M. E. Moseley. Functional magnetic res-onance imaging of regional cerebral blood oxy-genation changes during breath holding. Stroke, 29:2641-2645, 1998.

[65] R. F. Dougherty, V. M. Koch, A. A. Brewer, B. Fis-cher, J. Modersitzki, and B. A. Wandell. Visual field representations and locations of visual areas V1/2/3 in human visual cortex. J Vis, 3(10):586-598, 2003.

[66] S. A. Engel, D. E. Rumelhart, B. A. Wandell, A. T. Lee, Glover G. H., E. J. Chichilnisky, and M. N. Shadlen. fMRI of human visual cortex. Nature, 369(6481):525, 1994.

[67] M. I. Sereno, A. M. Dale, J. B. Reppas, K. K. Kwong, J. W. Belliveau, T. J. Brady, B. R. Rosen, and R. B. Tootell. Borders of multiple human vi-sual areas in humans revealed by functional MRI. Science, 268:889-893, 1995.

[68] S. A. Engel, G. H. Glover, and B. A. Wandell. Retinotopic organization in human visual cortex and the spatial precision of functional MRI. Cereb Cortex, 7(2):181-92, 1997.

[69] Georg Nagel, Tanjef Szellas, Wolfram Huhn, Suneel Kateriya, Nona Adeishvili, Peter Berthold, Doris Ollig, Peter Hegemann, and Ernst Bamberg. Channelrhodopsin-2, a directly lightgated cation-selective membrane channel. Proc Natl Acad Sci USA, 100:13940-13945, 2003.

[70] G. S. H. Soliman and H. G. Truper. *Halobacterium pharaonis*: a new, extremely haloalkaliphilic archaebacterium with low magnesium requirement. Allgemeine, angewandte and okologische Mikrobi-ologie 3, pages 318-329, 1982.

[71] B. Arenkiel, J. Peca, I. Davison, C. Feliciano, K. Deisseroth, G. Augustine, M. Ehlers, and G. Feng. In vivo light-induced activation of neural circuitry in transgenic mice expressing channelrhodopsin-2. Neuron., 54:205-218, 2007.

[72] B. L. Davidson and X. O. Breakefield. Viral vectors for gene delivery to the nervous system. Nature Rev. Neurosci., 4(353-364), May 2003.

[73] P. Osten, V. Grinevich, and A. Cetin. Viral vectors: a wide range of choices and high levels of service Handb Exp Pharmacol., 178:177-202, 2007.

[74] Raag D. Airan, Leslie A. Meltzer, Madhuri Roy, Yuqing Gong, Han Chen, and Karl Deisserothl. High-speed imaging reveals neurophysiological links to behavior in an animal model of depres-sion. Science, 317:819-823, 2007.

[75] D. S. Kim, T. Q. Duong, and S. G. Kim. High-resolution mapping of iso-orientation columns by FMRI. Nat Neuroscience, 3(2):164-169, 2000.

[76] Cheryl Olman, Itamar Ronen, Kamil Ugurbil, and Dae-Shik Kim. Retinotopic mapping in cat visual cortex using high-field functional magnetic resonance imaging. Journal of Neuroscience Methods, 131:161-170, 2003.

[77] Dae-Shik Kim, Itamar Ronen, Cheryl Olman, Seong-Gi Kim, Kamil Ugurbil, and Louis J. Totha. Spatial relationship between neuronal activity and bold functional mri. NeuroImage, 21:876-885, 2004.

[78] J. H. Lee, B. A. Hargreaves, B. S. Hu, and D. G. Nishimura. Fast 3D imaging using variable-density spiral trajectories with application to limb perfusion. Magn Reson Med, 50(6):1276-1285, 2003. PMID: 14648576.

[79] R. Dharmakumar, J Hong, J. H. Brittain, D. B. Plewes, and G. A. Wright. Oxygen-sensitive con-trast in blood for steady-state free precession imaging. Magn Reson Med, 53(3):574-583, 2005.

[80] C. H. Cunningham, J M. Pauly, and K. S. Nayak. Saturated double angle method for rapid B1+ map¬ping. Magn Reson Med, 55(6):1326-1333, 2006. PMID: 16683260.

[81] J. H. Duyn, Y. Yang, J. A. Frank, and J. W. van der Veen. Simple correction method for k-space trajectory deviations in mri. J Magn Reson, 48(153):132-150, 1998.

[82] J. Lee, J. M. Santos, S. M. Conolly, K. L. Miller, B. A. Hargreaves, and J. M. Pauly. Respiration-induced B0 field fluctuation compensation in bal¬anced SSFP: Real-time approach for transition-band SSFP fMRI. Magn Reson Med, 50:1197-1201, 2006. PMID: 16598728.

[83] M. S. Cohen. Parametric analysis of fMRI data using linear systems methods. NeuroImage, 6:93-103, 1997.

[84] R. B. Buxton, E. C. Wong, and L. R. Frank. Dy¬namics of blood flow and oxygenation changes during brain activation: The balloon model. Magn Reson Med, 39:855-864, 1998.

[85] G. J. Stanisz, E. E. Odrobina, J. Pun, M. Escar-avage, S. J. Graham, M. J. Bronskill, and R. M. Henkelman T1, T2 relaxation and magnetization transfer in tissue at 3T. Magn Reson Med, 54:507-512, 2005.

Parallel Computation Based Real-Time Functional Magnetic Resonance Imaging

Parallel computation based Real-time functional magnetic resonance imaging (fMRI) is a technique which is able to reconstruct, motion correct, analyze fMRI images and display brain activations in real-time. To achieve real-time fMRI image acquisition and processing, many algorithms are designed such as spiral sampling sequence, parallel k-space gridding, parallel 3D motion correction, and parallel Fourier domain analysis. Graphic Processing Unit (GPU) is chosen to be the platform for the parallel algorithms because of its high processing power and massive multi-threading ability. The proposed technique is generally applicable to all human/animal fMRI studies, however it was developed specifically with optogenetic fMRI applications in mind. The technique can be distributed as software packages for the applications mentioned above.

Background

There are several software packages (either commercial or open source) developed for real-time fMRI, such as TurboFire, AFNI and TurboBrainvoyager. Many articles about the real-time reconstruction, motion correction, analysis and applications are also published. However, our approach and implementation is unique in utilizing massively parallel computation combined with fast spiral image acquisition, novel robust, real-time motion correction, and Fourier coefficient analysis.

Software Packages include

TurboFire (http://www.flintbox.com/public/project/6205)

AFNI (http://afni.nimh.nih.gov/afni)

Turbo Brainvoyager (http://www.brainvoyager.com/products/turbobrainvoyager.html)

Publications include

Bagarinao et al., 2003; Cohen, 2001; Cox and Jesmanowicz, 1999; Cox et al., 1995; Gembris et al., 2000; Voyvodic, 1999

Bagarinao, E., Matsuo, K., Nakai, T., Sato, S., 2003. Estimation of general linear model coefficients for real-time application. NeuroImage 19, 422-429.

Cohen, M. S., 2001. Real-time functional magnetic resonance imaging. Methods 25, 201-220.

Cox, R. W., Jesmanowicz, A., 1999. Real-time 3D image registration for functional MRI. Magnetic Resonance in Medicine 42, 1014-1018.

Cox, R. W., Jesmanowicz, A., Hyde, J. S., 1995. Real-Time Functional Magnetic Resonance Imaging. Magnetic Resonance in Medicine 33, 230-236.

Gembris, D., Taylor, J. G., Schor, S., Frings, W., Suter, D., Posse, S., 2000. Functional Magnetic Resonance Imaging in Real Time (FIRE): Sliding-Window Correlation Analysis and Reference-Vector Optimization Magnetic Resonance in Medicine 43, 259-268.

Voyvodic, J. T., 1999. Real-time fMRI paradigm control, physiology, and behavior combined with near real-time statistical analysis. NeuroImage 10, 91-106.

Invention

Compared to existing real-time fMRI approaches, our system features higher speed, robustness and more tolerance to unknown temporal brain activity patterns.

Our method uses new architectural design of image acquisition, reconstruction, and analysis utilizing massive parallel processing power. Combining the massively parallel computation power of GPU and our efficient parallel algorithm, our method is able to grid data in 19 ms, motion correct in 31 ms and analyze in 8 ms. This means our method is able to reach 52 frames/s when only gridding and analysis is enabled and 20 frames/s when motion correction is added. The exact number will depend on the GPU and CPU utilized Another important feature is the robustness of our 3D motion correction module. We tested our motion correction module with widely used, goal standard, offline motion correction software such as FSL MCFLIRT and SPM. After testing with both known large motion phantoms and real ofMRI datasets, our method shows higher reliability and speed compared to FSL MCFLIRT and SPM. In addition to the real-time correction capability, our method shows more robustness.

Real-Time fMRI Software Package Components

The real-time fMRI software architecture is composed of two parts: The data sampling unit and the GPU based real-time processing unit (FIG. 45a). The data sampling unit is programmed to run on a third party MRI scanner. The scanner is programmed to sample data with a fast acquisition scheme such as the interleaved spiral readout and sends data interleaf by interleaf (each readout sequence) into a fast ethernet. On another end of the ethernet, the real-time processing workstation receives, processes the interleaved samples and displays the analysis result. (FIG. 45b) There are 3 CPU threads running concurrently to process the received data in streamline. After each interleaf of sample is received, it is first baseline corrected and stored into its memory space by the first thread. After accumulating enough samples, spiral samples are retrieved by the second CPU thread and processed by a GPU. In our model, the GPU is a coprocessor of the second CPU thread: the second CPU thread calls a custom programmed GPU function and asks GPU to help reconstruct, motion correct and analyze the fMRI data through GPU's thousands of threads in real-time. After finishing processing the data, the second CPU thread passes reconstructed images and analysis results to the third CPU thread. The third CPU thread next renders the analysis results on to the reconstructed fMRI images and displays while interactively processes the user inputs and responds the user requests in real-time. The supported operations in the initial implementation include image intensity adjustment, image enlargement, analysis threshold adjustment, and selected voxel time series and corresponding Fourier transform display.

Real-Time Spiral Image Acquisition 2D and 3D spiral sampling based sequences are implemented on a 7 T Bruker (Bruker Corporation, Germany) scanner: 1. Gradient recalled echo (GRE) sequence and 2. Steady state free precession (SSFP) sequence. For the current implementation, the GRE sequence parameters are TR/TE=750/12 ms, with a 30° flip angle. 23 four-interleaf coronal slices (11.5 mm slice direction coverage) are obtained at a 3 s temporal resolution. For the SSFP sequence, the sequence parameters are TR/TE=9.375/1.5 ms, also with a 30° flip angle. 32 ten-interleaf coronal slices (16 mm slice direction coverage) are obtained in 3 s temporal resolution. The in-plane field of view (FOV) equals 35×35 mm$^2$ with 0.5 mm slice thickness for both sequences.

Real-Time fMRI Image Reconstruction

To reconstruct the non-uniform sampled k-space into an ofMRI image, gridding method is utilized. Since the spiral sampling is only performed in 2 dimensional planes (x and y plane) and z direction is uniform sampled, 2D gridding is performed in our real-time reconstruction algorithm. The 2D gridding method is mathematically described by:

$$M_{grid}(u,v) = \{[M(u,v) \times S(u,v)] * [w(u,v) \times C(u,v)]\} \cdot \Delta(u,v)$$

where $M(u,v)$ is the original image k-space, and $$S(u, v) = \sum_{j=1}^{P} \delta(u - u_j, v - v_j)$$

is the spiral sampling function. Thus "$M_{spiral}(u,v) = M(u,v) \times S(u,v)$" is the spiral samples acquired from the scanner. Spiral samples are then convolved with a weighted kernel function $w(u,v) \times C(u,v)$ for interpolation. $C(u,v)$ is the interpolation kernel and the weighting function $w(u,v)$ is calculated from Voronoi diagram. The interpolated image is finally uniform resampled by the Cartesian comb function $$\Delta(u, v) = \sum_m \sum_n \delta(u - m, v - n).$$

Deriving from above method, parallel Grid Driven Gridding method (FIG. 46) is implemented in our real-time reconstruction algorithm. When reconstruction function is called, thousands of GPU thread is allocated and assigned a k-space Cartesian voxel at $x_m$ and $y_m$ to work on. Each thread then searches through the spiral samples $M_{spiral}(u_i,v_i)$ for sample that is within the kernel radius (r). r=1.5 is chosen in our implementation. Eligible samples are then convoluted with the weighted kernel function ($w(u_i,v_i) \times C(m-u_i,n-v_i)$) separately and then summed together. We chose the gridding kernel to be $C(u,v)=\sqrt{u^2+v^2}$. In conclusion each gridded voxel in k-space is calculated by the formula shown below:

$$M_{grid}(m, n) = \sum_i \{M_{spiral}(u_i v_i) \times [w(u_i, v_i) \times C(m - u_1, n - v_i)]\}$$

and $$\sqrt{(m - u_i)^2 - (n - v_i)^2} < r.$$

m and n is fixed for each thread.

Because searching for spiral samples puts a heavy and unnecessary overhead on the calculation, we presorted the spiral samples into groups for each Cartesian line of threads. Only one presorting is required since all real-time images are sampled by the same sequence. For example, when the kernel radius is 1.5 voxels, the outmost spiral sample that will be within the search range is +1.5 voxels and −1.5 voxels. Then for the $k^{th}$ Cartesian line ($M_{grid}(m=k,n)$), spiral samples ($M_{spiral}(u_i,v_i)$) with $|u_i-k|<1.5$ will be categorized into group k. A spiral sample can belong to different groups due to the search ranges are overlapped. The presorted spiral sample locations are then stored onto GPU texture memories for later reference and fast retrieving. The presorting saves a lot of GPU time from searching unnecessary samples. Since GPU texture memory is on-chip, it will also boost the gridding performance dramatically by reducing data retrieving time.

After gridding, the images are Fast Fourier Transformed (FFT) by a free software library CUFFT provided by NVIDIA. The image is then rearranged by moving the brain center to the image center through our custom programmed parallel FFTSHIFT function on GPU.

Real-time fMRI Image Motion Correction

After the fMRI image is real-time reconstructed, it is passed to the real-time motion correction module. This module corrects motion often caused by the subject's motion and/or scanner drift. Two sub-modules are implemented: cost function evaluation and optimization Cost function evaluates the differences between template image and the image under correction. Optimization minimizes the cost function (the difference) by adjusting image positions. 6 degrees of freedom (DOF) is chosen: translations ($\Delta x$, $\Delta y$, $\Delta z$) and rotations ($\theta_x$, $\theta_y$, $\theta_z$) relative to the x, y and z axis. (See, also, Example 7.)

In our implementation, cost functions are evaluated in parallel on the GPU, while the optimization is processed on the CPU. (FIG. 47) When called by CPU for cost function evaluation, GPU will allocate hundreds of processing threads, calculates the cost in parallel, and returns the cost directly back to CPU. To achieve the highest efficiency, both the template image and image under correction are stored in the texture memory on the GPU since texture memory has a cache space for fast data retrieval. Another advantage of the GPU texture memory is its built-in hardware interpolation function, which can linearly interpolate 3D images without loss of speed. Generally, an image will not lie on its original Cartesian grid after shifts and rotations. Therefore, when off-grid voxels are needed during motion correction, texture memory's built-in hardware linear interpolation function is utilized to interpolate based on the nearest 26 neighbors (voxels within the cube (x±1,y±1,z±1)) in high speed.

Least Squared Error (LSE) cost function is utilized for our real-time purpose. LSE can be mathematically written as, $$\rho = \|Y - f(X)\|_2 = \sum_{m=1}^{M}\sum_{n=1}^{N}\sum_{p=1}^{P}(\{Y\}_{m,n,p} - \{f(X)\}_{m,n,p})^2$$

where Y is the template image, X is the image under correction, and $f(X)$ is a function which rotates and shifts image X. Function $f(X)$ can be defined as:

$$\{f(X)\}_{m,n,p} = \{X\}_{m',n',p'}$$

and $$\begin{bmatrix} m' \\ n' \\ p' \end{bmatrix} = R \begin{bmatrix} m \\ n \\ p \end{bmatrix} + \begin{bmatrix} \Delta x \\ \Delta y \\ \Delta z \end{bmatrix}$$

$\{Y\}_{m,n,p}$, $\{X\}_{m,n,p}$ and $\{f(X)\}_{m,n,p}$ are the m×n×p elements of image Y, X and $f(X)$. R is a 3×3 rotation matrix. For our GRE fMRI datasets, M=128, N=128, and P=23. For SSFP fMRI datasets, M=128, N=128, and P=32. The LSE cost function measures the Euclidean distance between two images.

When implementing LSE on GPU for real-time application, single voxel errors ($e_{m \times n \times p} = \{Y\}_{m,n,p} - \{f(X)\}_{m,n,p}$) are calculated simultaneously on the GPU threads. The sum of errors is next calculated by parallel summation algorithm. In this algorithm, errors are linearly organized and separated into blocks on the GPU for parallel summation Blocks work concurrently. Within each block, errors are summed in parallel reducing the data size to half each time. For example, if there are 8 error values waiting to be summed, the first half of the data will be summed with the second half of the data in parallel during the first iteration. The result will then be summed in the same pattern until convergence. Thus, the total number of data will be reduced by a factor of 2 after each iteration. In our implementation, the x-y plane error summations are conducted on GPU through the parallel method showed above. The rest z-direction errors are summed on CPU. The timing test shows that the rest z-direction errors transferring from the GPU to CPU does not add any significant overhead in data transfer time. This is because the hardware loading startup time dominates the overall transfer time when data size is small.

Powell's multi-dimension optimization method and one dimensional line search method were implemented on the CPU for cost function optimization. The optimization is conducted on the CPU because optimization is a serial process with many conditional statements. When implementing the one dimensional line search algorithm, the cost function is not smooth and convex with respect to shifts because of linear interpolation. To overcome this, we split the optimization process into voxel level optimization and sub-voxel level optimization. In the voxel level optimization, translation parameters converge in integer steps, preventing the process from being trapped into a local minimum Voxel level optimization converges very fast (2-3 iterations) and stops when it reaches the region with minimum value (the region between two voxels with the smallest value). In sub-voxel level optimization, the optimization domain is limited within a single voxel, and the correct local minimum is calculated based on the interpolation cost function. For rotation, the cost function is not convex and has two main local minima. The two minima appear around rotation angles of 0 and $\pi$. This is because the ellipsoid-shaped brain has maximum overlapping area around these two rotation values. Therefore, in our optimization process, we assume the rotation variable to be limited to $-\pi/6 - \pi/6$, where the cost function has one global minimum and the line search method holds. This is a reasonable assumption considering the low probability of head rotation being outside of the range given by $-\pi/6 - \pi/6$. We also set the translation precision to be 0.1 voxels and rotation precision to be $\pi/1000=0.18°$. For translation, 0.1 voxels is a proper step since higher precision will not make significant differences in improving image quality and activation map after testing. For rotation, the required precision is higher since the out most voxels (e.g. 64 voxels for a 128×128×23 image) from center will be affected a lot if the precision is low. This is because its shift from the true location is depending on the rotation precision and its radius from the center. Thus to make sure the out most voxel is within acceptable shifts from its true location, we set the rotation precision to be pi/1000 (0.18 degrees), which will make the out most voxel within 0.2 voxels precision (64×π/1000=0.2).

Real-Time Fourier Domain Analysis

After the fMRI image is motion corrected, it is stored sequentially into a GPU memory. The memory is cached by the GPU texture to speedup the program's performance. We implemented Fourier domain analysis method in parallel to achieve the real-time fMRI analysis. The Fourier domain analysis can be written as:

$$\rho_{mnp} = \sqrt{\frac{2 \times f_{mnp,k}^2}{\sum_{l=1}^{N-1} f_{mnp,l}^2}}$$

where $f_{xyz,l}$ is the Fourier coefficient of (m,n,p) voxel at the $l^{th}$ frequency $\rho_{mnp}$ measures the significance of the $k^{th}$ coefficient across all different frequencies. k is usually the number of periods repeated in fMRI experiment. This method requires number of voxels' fast Fourier transform. Thus it is quite time consuming and unwanted for real-time application.

Our algorithm calculates the sum of Fourier coefficients from the image space to avoid redundant FFT calculation. Based on energy conservation equation $$\left(\sum_{l=0}^{N-1} f_{mnp,l}^2 = N \sum_{l=0}^{N-1} x_{mnp,l}^2\right),$$

the interested Fourier coefficient can be calculated as:

$$\rho_{mnp} = \sqrt{\frac{2 \times f_{mnp,k}^2}{\sum_{l=1}^{N-1} f_{mnp,l}^2}} = \sqrt{\frac{2 \times \left(\sum_{l=0}^{N-1} x_{mnp,l} e^{-j2\pi lk/N}\right)^2}{N \sum_{l=0}^{N-1} x_{mnp,l}^2}}.$$

where $x_{mnp,l}$ is the intensity of voxel (m,n,p) at $l^{th}$ time frame. Each voxel time series is first linearly detrended on GPU and then analyzed. When performing the Fourier domain analysis on GPU, each GPU thread is assigned a separate $\rho_{mnp}$ to calculate. Since the calculation is independent between different threads, activation analysis for each voxel is evaluated in parallel. The Fourier transform coefficient $e^{-j2\pi lk/N}$ is also calculated in advance and cached in the texture memory on GPU for higher performance.

In some embodiments, our system is developed to be a real-time fMRI processing workstation that can work seamlessly with existing third-party vendor provided MRI scanner. The scanner end software is installed on the MRI scanner. It controls the fast scanning sequences and sends samples through Ethernet. On another end of the Ethernet, the real-time processing workstation reconstructs, motion corrects, and analyzes the fMRI images with massive multithreading computation on GPU. The real-time workstation is build from a regular computer with high-end video card installed.

A prototype is built for testing purposes. Our prototype works with a 7 Tesla Bruker made animal MRI scanner located in UCLA Brain Mapping Center. The prototype equips with all features described above. We tested our real-time fMRI technology with optogenetic fMRI experiments. Our system is able to show fMRI images and activations in real-time. It is able to track changes of brain activations across time under different optogenetic stimulations on the subject.

EXAMPLES

The following examples are offered to illustrate, but not to limit the claimed invention.

Example 7: Motion Correction Using Parallel Computation with Applications to Optogenetic Functional Magnetic Resonance Imaging Introduction Motion correction for time-series imaging involves registration and alignment of a group of time-series images to a given template. This is of particular importance for applications like fMRI (Jones et al., 2008) since the movement of subjects causes image misalignment that leads to activation signal degradation and even unusable data. Motion correction is of particular importance in animal imaging (Cheng et al., 2011; Dombeck et al., 2007; Scholvinck et al., 2010), due to the difficulty of fully controlling the movement of the test subject. Conventionally, rodent fMRI is conducted with light anesthesia to keep the animal still while also keeping the brain's activity close to physiological levels. Though stereotactic fixation is used to keep the subject's head still during the scan, residual motion (such as motion caused by stimulation of neural circuits governing aspects of arousal or movement) and scanner drift effects can often degrade image quality. When considering awake rodent fMRI, robustness to residual motion becomes even more critical. In addition, high-resolution fMRI scans also rely on robust motion correction methods since a low signal-to-noise ratio (SNR) combined with smaller pixel size make scans more sensitive to motion. Furthermore, a fast motion correction algorithm is increasingly desired in many developing time-series imaging applications, e.g. real-time ofMRI. Real-time ofMRI is a novel technology, which can help scientists analyze brain circuits online by using optogenetic stimulation as input, and real-time fMRI readout as output. A fast motion correction algorithm with real-time capability will undoubtedly enhance the real-time analysis and reveal better online brain circuitry information. Thus, a robust and fast motion correction method will be an essential tool for both conventional and real-time time-series imaging applications.

The majority of motion correction methods are based on optimization theory and the minimization of a cost function between the template and the time-series images. To date, many different cost functions have been proposed including the Woods function (Woods et al., 1993), mutual information (Maes et al., 1997; Pluim et al., 2003; Viola and Wells, 1997), normalized mutual information (Studholme et al., 1999), joint entropy (Studholme et al., 1995), and the correlation ratio (Roche et al., 1998). There are diverse approaches to solving optimization problems including Powell's multi-dimensional optimization method (Press et al., 2007), the global optimization algorithm for affine registration (Jenkinson et al., 2002; Jenkinson and Smith, 2001) and generic registration algorithms (Yeo et al., 2010). These cost functions and optimization algorithms are widely used in fMRI software such as AFNI (Cox, 1996), AIR (Woods et al., 1992; Woods et al., 1998a; Woods et al., 1998b; Woods et al., 1993), FSL (Smith et al., 2001), and SPM (Friston et al., 1995; Friston et al., 1994). These packages are mainly designed for offline data processing where the software itself requires long processing time. Researchers also need to spend a lot of time to carefully convert the image format and parameters when customized fast scanning sequence is used or non-human subjects is involved. Furthermore, most of the methods are designed as CPU algorithms. While the CPU technology and its processing power improved exponentially for many years, such growth is slowing down recently due to the transistor size limitation and high power dissipation. On the other hand, the GPU, which is rapidly evolving for massive parallel computation such as 3D computer graphics, shows increasing potential for new high-speed motion correction algorithms.

In 2006, the Nvidia Corporation released a new graphics card based parallel computation platform called CUDA. Unlike CPUs, GPUs are designed to execute hundreds of threads concurrently, opening up new possibilities for fast, parallel computation based algorithms for imaging. For example, Ruijters et al. demonstrated an efficient GPU B-Spline interpolation method, which can achieve 356×10⁶ cubic interpolations per second as opposed to 0.45×10⁶ cubic interpolations per second on a CPU (Ruijters et al., 2008). Stone et al. designed and implemented an advanced MRI reconstruction method with a GPU and achieved a 21-fold increase in speed compared to a method that used a quad-core CPU (Stone et al., 2008). Chen et al. reported a maximum of 80 times speedup in image registration using mutual information (Chen et al., 2009). Ansorge et al. developed non-linear 3D image registration algorithms and obtained 50-748 times improvement in speed (Ansorge et al., 2009). Fast phase based MRI registration method also has been reported. (Eklund et al., 2010) However, to date, research and development on GPU-based time-series motion correction with real-time capability has not been reported.

With the present invention, describe a novel GPU based parallel motion correction algorithm. It combines advantages of both the CPU and the GPU, making the correction process exceptionally fast and robust. This method dramatically speeds up conventional time-series image processing and allows for real-time applications. First, the methods including our parallel algorithm implementation and cost function optimization are discussed. Speed and robustness tests in comparison with popular existing software such as FSL MCFLIRT and SPM are then presented. These tests demonstrate that our method is much faster and more reliable than the gold-standard software packages. The proposed method was then applied to various ofMRI time-series datasets where significant improvements in both activation volume size and coherence coefficient values were demonstrated.

Method

Software Architecture

Motion correction is a process that aligns a group of time-series images to a single template image. During the process, parameters representing translation, rotation and scaling are adjusted to reduce the cost function value between the time-series image and the template image. Motion correction algorithms consist of two main parts: cost function evaluation and optimization. The cost function evaluates a defined distance between the template image and the image under correction. Optimization then minimizes the cost function (the distance) by adjusting parameters. Considering the fact that translation and rotation are the most common changes between time-series images, we chose parameters with 6 degrees of freedom (DOF): translation ($\Delta x$, $\Delta y$, $\Delta z$) and rotations ($\theta_x$, $\theta_y$, $\theta_z$) relative to the x-, y- and z-axis.

In our proposed algorithm, cost functions are evaluated in parallel on the GPU, while the optimization is processed on the CPU (FIG. 47). In this approach, the GPU is a co-processor of the CPU, which is specifically designed to efficiently calculate the cost function value in parallel (FIG. 48). When the CPU calls the GPU to calculate the cost function value, the GPU allocates hundreds of processing threads, calculates the cost, and returns the result back to the CPU. The cost function can be efficiently calculated in parallel since most of the operations involved are independent of one another.

To achieve the highest efficiency, both the template image and image under correction are stored in the texture memory on the GPU. Texture memory has cache space for fast data retrieval. Another advantage of the GPU texture memory is the built-in hardware interpolation function, which can linearly interpolate 3D images without a loss of speed (Nvidia, 2011). Generally, an image will not lie on its original Cartesian grid after shifts and rotations. Therefore, when off-grid voxels are needed during motion correction, the texture memory's built-in hardware linear interpolation function is utilized to interpolate based on the nearest 26 neighbors (voxels within the cube (x±1, y±1, z±1)) in high speed. We use a linear, rather than cubic or spline-based interpolation method since it can be performed using efficient, hardware built-in operations.

Cost Function Evaluation

Our proposed algorithm utilizes two cost functions: Least Square Error (LSE) and Correlation Ratio (CR).

Least Square Error

LSE can be mathematically written as, $$\rho = \|Y - f(X)\|_2 = \sum_{m=1}^{M}\sum_{n=1}^{N}\sum_{p=1}^{P}(\{Y\}_{m,n,p} - \{f(X)\}_{m,n,p})^2$$

where Y is the template image, X is the image under correction, and $f(X)$ is a function which rotates and shifts image X. Function $f(X)$ can be defined as:

$$\{f(X)\}_{m,n,p} = \{X\}_{m',n',p'}$$

and $$\begin{bmatrix} m' \\ n' \\ p' \end{bmatrix} = R\begin{bmatrix} m \\ n \\ p \end{bmatrix} + \begin{bmatrix} \Delta x \\ \Delta y \\ \Delta z \end{bmatrix}$$

$\{Y\}_{m,n,p}$, $\{X\}_{m,n,p}$ and $\{f(X)\}_{m,n,p}$ are the m×n×p elements of image Y, X and $f(X)$. R is a 3×3 rotation matrix. For our test ofMRI datasets, M=128, N=128, and P=23. The LSE method measures the Euclidean distance between two images.

In our algorithm, single voxel errors ($e_{m \times n \times p} = \{Y\}_{m,n,p} - \{f(X)\}_{m,n,p}$) are calculated simultaneously on the GPU threads. For the calculation of the summation of errors, we utilized a parallel summation algorithm (Kirk and Hwu, 2010). In this algorithm, errors are linearly organized and separated into blocks on the GPU for parallel summation (FIG. 48a), and the blocks work concurrently. Within each block, errors are summed in parallel reducing the data size by one-half each time. For example, during the first summation, if there are eight error values allocated in one block, the first half of the data ($e_1$-$e_4$) will be summed with the second half of the data ($e_5$-$e_8$) in parallel. Each iteration will reduce the total amount of data by a factor of two and the summation will continue until the final sum is calculated (FIG. 48b). In GPU computing, the threads can be executed in parallel only when adjacent threads are assigned the same task. Otherwise, the execution is serialized—this is termed "thread divergence" (Nvidia, 2011) Summation in a pair-wise pattern as described above avoids thread divergence because adjacent threads are continuously assigned the same task. After all the blocks finish summation of assigned errors, many partially summed error values are produced (FIG. 48a). These partial error data are again linearly organized and assigned to new blocks in the next iteration. The iteration continues until all the partial errors get summed. For our 128×128×23 ofMRI dataset, we allocated 2944 (128×23) blocks and 128 threads within each block for summation Since the number of blocks is not a power of two, after seven iterations ($2^7$=128), 23 partially summed errors remain. These 23 values are summed on the CPU. The timing test shows that the transfer time between the GPU and CPU for 23 float variables does not add any significant overhead in data transfer time because the transfer startup time dominates the overall transfer time when data size is small. Compared to algorithms that transfer all errors to the CPU for serial summation, this parallel summation method using the GPU significantly reduces both the cost function calculation time and the data transfer time. In addition, since the cost function is evaluated many times during the optimization process, small amounts of time saved in each cost evaluation can generate a great performance improvement.

Correlation Ratio

CR (Roche et al., 1998) is defined as, $$\rho = \frac{E(\text{Var}(Y \mid X = x))}{\text{Var}(Y)}$$

Where Var(Y) is the variance of image Y with each pixel of Y considered to be a measure of a random variable. E(Var(Y|X=x)) measures the conditional expectation. Mathematically, E(Var(Y|X=x)) measures how much the value of X can predict Y (the predictability is inversely proportional to Var(Y|X=x)). Var(Y) is used to normalize the ratio to a number between 0 and 1 since Var(Y)=Var[E(Y|X)]+E[Var(Y|X=x)]. Thus, the motion correction problem becomes a problem of minimizing the correlation ratio.

To determine the CR, the joint probability distribution function (JPDF) is calculated first. The CR is then calculated through a parallel summation algorithm of JPDF values. In our implementation, we chose to use a 256×256 JPDF. An intensity range of 256 values was chosen because the parallel summation algorithms require the dimension of the JPDF to be a power of two. An intensity range of 256 is a good compromise between calculation speed, memory space, and the precision of the CR. When the JPDF matrix size is large, it requires more parallel summation time and more GPU memory. On the other hand, a JPDF matrix size that is too small would not be sensitive enough to quantify small differences between images. JPDF statistics are calculated by the GPU threads' atomic update. For example, if one thread reads 128 and 200 from voxel ($x_0$, $y_0$, $z_0$) in the template and the image under correction, 1 is atomically added to the JPDF's (128,200) bin. The atomic operation here refers to the smallest irreducible operations performed by the GPU. The operation is guaranteed even when there are memory conflicts. An atomic operation is used to avoid conflicts when the same JPDF location needs to be updated concurrently by different threads. Although the performance of this atomic update method depends on the distribution of data, it is simple and uses memory more efficiently compared to other algorithms such as collision-free histogram algorithms (Shams and Kennedy, 2007). In collision-free algorithms, each thread requires a separate memory space to avoid collisions and these separate memory spaces need to be summed later to obtain the JPDF. Such operations introduce expensive memory and calculation costs, which require more calculation time than the atomic update approach. For instance, if all the threads are assigned separate JPDF space in our example, the total memory size required is 92 GB (number of threads x JPDF size x float size=(128×128×23)×(128×128)×4 bytes), which makes the collision-free method impractical in our case. In addition, due to the increase in GPU processing power, the relatively slower nature of atomic operations has a very limited impact on the overall performance.

After the JPDF was calculated, a parallel summation algorithm was utilized to calculate E(Var(Y|X=x)) and Var(Y) since both terms can now be decomposed into the summation of JPDF values.

Optimization

For optimization, both Powell's multi-dimensional optimization method (Press et al., 2007) and one-dimensional line search method (Boyd and Vandenberghe, 2004) were implemented using the CPU. This choice was made because optimization is a serial process with many conditional statements. For example, "if" statements that is shown often in optimization will cause thread divergence on a GPU, making optimization more suitable for a CPU.

When implementing the one-dimensional line search algorithm, the cost function is not smooth and convex with respect to shifts because of linear interpolation (FIG. 49a, c). To overcome this, we split the optimization process into pixel level optimization and sub-pixel level optimization. In the pixel level optimization, translation parameters converge in integer steps, preventing the process from being trapped in a local minimum Pixel level optimization converges very quickly (two to three iterations) and stops when it reaches the region with the minimum value (the region between two pixels with the smallest value). In sub-pixel level optimization, the optimization domain is limited to a single pixel, and the correct local minimum is calculated based on the interpolation cost function. For rotation, the cost function is not convex and has two main local minima (FIG. 49b, d). The two minima appear around the rotation angles of 0 and $\pi$. This is because the ellipsoid-shaped brain has a maximum overlapping area around these two rotation values. Therefore, in our optimization process, we assume the rotation variable to be limited to $-\pi/6-\pi/6$, where the cost function has one global minimum and the line search method holds. This is a reasonable assumption considering the low probability of head rotation being outside of the range given by $-\pi/6-\pi/6$. We also set the translation precision to be 0.1 voxels and rotation precision to be $\pi/1000$=0.18°. For translation, 0.1 voxels is a proper step since higher precision will not make significant differences in improving image quality and activation maps after testing. For rotation, the required precision is higher since the outermost voxels (64 voxels for a 128×128 image) from center will be significantly affected if the precision is low. This is because the actual shift due to a rotation angle at each location is dependent on its radius from the center. Thus, to make sure the outmost voxel is within acceptable shifts from its true location, we set the rotation precision to be $\pi/1000$ (0.18°), which will make the outmost voxel to be within the 0.2 voxel precision (64×$\pi$/1000=0.2).

ofMRI Data Acquisition and Analysis

All images were acquired on a 7 T Bruker small animal imaging scanner with a custom-designed gradient recalled echo (GRE), multi-slice, four-interleaf spiral readout sequence. Sequence parameters were TR/TE=750/12 ms, with a 30° flip angle. We obtained 23 coronal slices (11.5 mm slice direction coverage) at a 3 s temporal resolution. For the first set of experiments, the in-plane field-of-view (FOV) was designed to be 35×35 mm$^2$ with 0.5 mm slice thickness resulting in a spatial resolution of 0.5×0.5×0.5 mm$^3$. For the second set of experiments, FOV was designed to be 25×25 mm$^2$ with 0.5 mm slice thickness resulting in a spatial resolution of 0.357×0.357×0.5 mm$^3$.

Each fMRI experiment consisted of a 30 s baseline acquisition period, followed by six periods of 20 s of optical stimulation and 40 s of no optical stimulation, resulting in 6 min 30 s of scan with 130 temporal frames. Eight such scans were repeated for each condition per subject. The resulting data was reconstructed into 128×128×23×130 matrix size 4D images by gridding reconstruction (Jackson et al., 1991), and inverse 2D fast Fourier transform (FFT).

The fMRI data were then analyzed using frequency domain analysis (Engel et al., 1997). Each image pixel time-series is Fourier transformed and the significance of the frequency component associated with the stimulation, i.e., the coherence value, is determined. The analysis is mathematically defined as $$\gamma = \sqrt{\frac{2 \times f_k^2}{\sum_{i=0}^{N-1} f_i^2}}$$

where $f_i$ (i=1~N−1) are the values of each frequency components and $f_k$ is the frequency component of interest (e.g. k=6 in our experiment because there are six stimulation cycles). The denominator calculates the total spectrum energy and the numerator determines the energy of the frequency component of interest. The resulting coherence value ($\gamma$) ranges from 0 to 1 and represents the significance of the frequency component of interest. A coherence value of 0.35 was selected as a threshold to determine active voxels for all the results presented in this paper. We chose this analysis method instead of methods like correlation coefficients and general linear models is because this method avoids assuming a particular form for the HRF. Many of our ofMRI experiments find distinct HRF shapes and delay depending on the circuitry and temporal encoding.

Result
Speed Performance

The motion correction method described above was implemented on a workstation with an Intel Core i5 750 quadcore 2.66 GHz CPU, Nvidia Geforce GTX 480 CUDA GPU and 4 GB DDR3 1333 MHz memory. The algorithm was implemented in C++ under Linux and both LSE and CR cost functions were written as CUDA kernel functions. The optimization algorithms are serially executed on the CPU and cost functions are evaluated in parallel on the GPU.

The speed performance was evaluated using various datasets acquired with the two imaging parameters mentioned in the methods section. We first tested the average correction time for a single 3D image. The average correction time for LSE and CR were 30.60 ms and 111.83 ms, respectively. A detailed breakdown of the performance measurement was also conducted. The LSE computation kernel function took 116.34 μs. This short calculation time is mainly attributed to the parallel summation algorithm. The CR computation kernel that calculates the CR cost took 922.22 μs, which can be sub-divided into 762.24 μs of JPDF calculation time and 159.98 μs of CR kernel calculation time. The CR method requires longer computation time compared to the LSE method because the CR cost function involves more complex mathematical computations such as the JPDF calculation. Data transfer overhead for both methods (2.39 μs for LSE and 7.24 μs for CR) is small compared to the kernel computation time. Storing the image in the texture memory facilitates such low data transfer overhead by data caching (FIG. 47).

To compare the performance of the proposed GPU-based parallel algorithm with a serial CPU algorithm, we implemented a CPU-based motion correction method, which evaluates cost functions and interpolations on the CPU. No CPU multi-threading technique was used in this test. Optimization strategies, such as the multi-resolution optimization method used in FSL MCFLIRT, were also not implemented. The CPU implementation was designed to compare the raw speed differences between the serial CPU algorithm and the massive multi-threading GPU method without introducing any other variables. The comparison between the GPU- and CPU-based methods revealed a dramatic speedup in the LSE cost function evaluation time (Table 1) where the GPU-based algorithm was 604 times faster than the CPU counterpart in calculating the cost function for each 3D image. The overall LSE motion correction process was sped up by a factor of 215 (from 14.27 min to 3.98 s for a 4D time-series with 130 time points). For the CR method, a relatively smaller but dramatic speedup was achieved; where each 3D image correction was sped up by a factor of 78 and 4D time-series correction was sped up by a factor of 57 (from 13.79 min to 14.54 s for a 4D time-series with 130 time points). Note that the two CPU implementations had approximately the same cost function evaluation time (70320 μs and. 71590 μs). A detailed profiling showed this was because the majority of CPU time was spent on image traversing in both cases.

We next compared our proposed GPU-based parallel motion correction algorithm with the existing popular software packages which are mainly based on and optimized for CPU computations, such as FSL MCFLIRT utility ver. 4.1.6 (Jenkinson et al., 2002; Jenkinson and Smith, 2001) and SPM8 fMRI realign tools (Friston et al., 1995) (Table 2).

FSL MCFLIRT is an intra-modal motion correction tool that is especially designed for fMRI time-series correction. It utilizes a multi-resolution global optimization method, which motion corrects 3D fMRI images in fixed 8 and 4 mm resolutions. This multi-resolution strategy both speeds up the motion correction process and avoids local minimums. However, MCFLIRT's motion correction speed largely depends on the labeled image's resolution (which is recorded in its NIFTI format image header). If the user manually sets the resolution to different values, motion correction will be conducted with a different speed and precision. For SPM, its optimization resolution is not fixed as with FSL so we tested with the default settings.

For our 0.5×0.5×0.5 mm$^3$ resolution, 130 frame images (the original 3D acquisition matrix size was 70×70×23), we reconstructed them into 128×128×23 matrix size for minimal error in gridding reconstruction and fast FFT. Thus the effective image resolution is 0.273×0.273×0.5 mm$^3$. When testing this dataset with FSL, we manually set the labeled resolution in NIFTI format header to four different values: 4×4×7.33 mm$^3$, 2×2×3.66 mm$^3$, and 1×1×1.83 mm$^3$. These corresponded to matrix sizes of 64×64×21, 32×32×10, and 16×16×5 at an 8 mm sampling size, and 128×128×23, 64×64×21, and 32×32×10 at a 4 mm sampling size in MCFLIRT. Therefore, FSL at a 4×4×733 mm$^3$ resolution uses the same matrix size and precision as our proposed method, and the speedup factor of our parallel motion correction algorithm should be compared to FSL based on the 4×4×7.33 mm$^3$ resolution. We chose to compare 3 different labeled resolutions because FSL MCFLIRT is mainly designed for human subjects and requires the data resolution to properly fit into its fixed optimization resolutions. If the resolution is small, e.g. 0.5×0.5×0.92 mm$^3$ or less, FSL fails because motion correction would be conducted on a matrix as small as 8×8×2 at an 8 mm resolution and 16×16×5 at a 4 mm resolution. If the resolution is large, e.g. 8×8×14.65 mm³ or larger, FSL would be subject to a slow cost function calculation for the large matrix and be trapped in a local minimum with high probability.

As shown in Table 3, our proposed motion correction method corrected 130 time frame 128×128×23 matrix size images in 3.98 s. In comparison, FSL corrected the same matrix size image (FSL header resolution of 4×4×7.33 mm³) in 215.23 s, which is 54.08 times slower. At a resolution of 2×2×3.66 mm³ and 1×1×1.83 mm³, FSL motion corrected the data in 34.81 s and 11.20 s respectively by using much smaller matrix-size images (32×32×10 and 16×16×5 at an 8 mm stage, 64×64×21 and 32×32×10 at a 4 mm stage) compromising its accuracy. We also tested the motion correction speed on SPM; SPM uses no information regarding resolution, thus the resolution header does not affect its performance. After testing, SPM corrected 130 time frame 128×128×23 matrix-size images in 75.06 s, which is 18.86 times slower than our GPU based parallel motion correction algorithm. For all our speed performance tests, we visually checked the corrected images and all motions were removed.

CR motion correction speed tests showed similar results. Our proposed method corrected 130 time frame 128×128×23 matrix-size ofMRI time-series images in 14.54 s, while FSL took 153.14 s (FSL header resolution of 4×4×7.33 mm³) with the same matrix size. Our method was 10.53 times faster than FSL. When the NIFTI format resolution header was set to 2×2×3.66 mm³ and 1×1×1.83 mm³, FSL corrected the images in 26.55 s and 10.06 s, using a much smaller matrix size than our method. SPM uses only the LSE method, thus the CR result was not available. The speedup of the GPU CR method compared to LSE method decreased because the CR cost parallelism was not as high as the LSE cost.

Robustness Test

We first tested the robustness of our GPU-based parallel motion correction algorithm with 3 different artificially generated datasets: In the first dataset, the brain rotated from $-\pi/6$ to $\pi/6$ about the z-axis. In the second dataset, the brain moved from −20 voxels to 20 voxels on the x-axis. In the third dataset, a 20 voxel abrupt movement was introduced at the 30th frame after which the brain then moves slowly back to its original location. All datasets had 130 time frames. This test was designed to evaluate the algorithm's performance under different translation and rotation situations. We also conducted the same test on FSL MCFLIRT and SPM for comparison. In the rest of this section, we only show results from using the LSE cost function since CR corrected datasets showed similar and indistinguishable results.

In the rotation test, the dataset with $-\pi/6$ to $\pi/6$ rotation about the z-axis was successfully corrected by our proposed parallel motion correction algorithm (FIG. 50a). The algorithm reduced the cost to almost zero compared to the original value before correction. Visual inspection also shows no movement. We also tested the dataset with FSL MCFLIRT at three different resolutions. The 2×2×166 mm³ and 1×1×1.83 mm³ resolution datasets are successfully corrected by FSL. For the 4×4×7.33 mm³ resolution dataset, all frames except the last one were properly registered. When the rotational angle was large, the zero padded value (at four corners) introduced a local minimum for FSL with the 4×4×7.33 mm³ resolution setting. SPM was also tested with this dataset and it successfully corrected all frames at a slower speed than our proposed method. Compared to the result of our proposed algorithm and SPM, FSL is less robust when it uses a large matrix size.

The translation test showed a similar result to the rotation test (FIG. 50b). Our proposed parallel motion correction algorithm, FSL working on 2×2×3.66 mm³, 1×1×1.83 mm³ labeled resolution images, and SPM successfully corrected the dataset with −20 voxels to 20 voxels translation in x direction. FSL failed to correct the last frame of the 4×4×733 mm³ resolution dataset. In addition to the zero padding, part of the muscle tissue was outside of FOV when the movement was 20 voxels. This produced a local minimum which caused the error in FSL.

In the abrupt movement test (FIG. 50c), the dataset was designed to have 20-voxel abrupt translation at frame 30. The brain then slowly moves back to its original position. This test is necessary since abrupt motion is common in fMRI, especially in small animal fMRI. As shown in FIG. 50c, our proposed parallel motion correction algorithm, FSL under 2×2×3.66 mm³ and 1×1×1.83 mm³ labeled resolutions, and SPM successfully corrected the large motion. FSL failed to correct the dataset at the 4×4×7.33 mm³ resolution. From tests above, we can see that FSL is prone to getting trapped into a local minimum when the labeled resolution is low and the matrix size is large.

We then tested the our GPU-based motion correction algorithm with 10 different rodent ofMRI images acquired in different experiments and with different subjects. For each of the ofMRI image, we rotated it to six different orientations ($-\pi/6$, $-\pi/12$, $-\pi/24$, $\pi/24$, $\pi/12$, and $\pi/6$ radians) about the z-axis. Our algorithm, FSL MCFLIRT and SPM were then applied to the generated dataset. In FIG. 51, we show the LSE cost of the test results. As can be seen in FIG. 51, only the proposed parallel motion correction algorithm and SPM corrected all the datasets, while our method ran at a much higher speed than SPM. FSL showed fewer mistakes when the labeled resolution was reduced.

As demonstrated through the tests results, our method shows both high speed and robustness. This is further supported by our extensive experience utilizing the proposed method with our ofMRI experiments. The algorithm is robust. Although FSL is consistent in most cases, it has occasional failures in some datasets. It also puts a burden on the user to try different resolutions when the image is not fit into its optimization range. While SPM is robust and passes all our robustness test, it takes longer to correct the dataset. For applications such as the real-time ofMRI study, a fast and robust motion correction algorithm is required.

Motion Correction for ofMRI

We then tested the our motion correction method on real ofMRI datasets acquired with two different experimental settings. The first set of data was acquired at a 0.5×0.5×0.5 mm³ resolution with optical stimulation of pyramidal neurons in the motor cortex. The second group was acquired at a 0.357×0.357×0.5 mm³ resolution with optical stimulation of pyramidal neurons in the hippocampus.

We plotted the estimated motion ($\Delta x$, $\Delta y$, $\Delta z$, $\theta_x$, $\theta_y$, $\theta_z$) of the two datasets in FIG. 52 as a reference. The parameters were estimated by our motion correction algorithm. The cortex stimulation data set shows the estimated motion for 8 repeated scans while the hippocampus data set shows the estimated motion for 9 repeated scans. As shown in FIG. 52a, the 0.5×0.5×0.5 mm³ resolution cortex stimulation datasets showed small and continuous translation in both x- and y-axes, which was potentially caused by scanner drift. These data showed little rotational motion since the estimated rotation angles fluctuated within the rotation precision: $\pi/1000 = 3.14 \times 10^{-3} = 0.18°$. In FIG. 52b, large motion was observed for the 0375×0.375×0.5 mm³ high-resolution datasets. Two large dips were shown in the first and third scan translation plot, which corresponded to two large abrupt motions of the subject.

Two representative ofMRI activation maps overlaid onto the time-averaged raw fMRI image and $T_2$ anatomical image are shown in FIG. 53. Both results shown were obtained using the LSE method. Eight time-series were separately motion corrected and averaged before data analysis. Because CR correction gave similar, indistinguishable image quality and fMRI activation patterns, the faster LSE method was shown. In FIG. 53, one of the first noticeable improvements with our proposed motion correction is larger activation volume with an increased coherence value. Decreased misregistration between temporal frames allows higher accuracy in the analysis leading to a more robust activation map. Another noticeable difference is that the time-averaged raw fMRI image is sharper with more texture after motion correction. This is because after motion correction, the images were better aligned, producing sharper images when the temporal frames were averaged. This is particularly noticeable in the high-resolution ofMRI image (FIG. 53b).

For further quantitative comparison, volume of active voxels were measured. Comparisons were made on several datasets at both low and high resolutions. In FIG. 54a, activation volumes are shown for two datasets acquired at $0.5\times0.5\times0.5$ mm$^3$ resolution. In both cases, activation volumes in motor cortex and thalamus show significant increases after correction. In FIG. 54b, active volumes for four $0.357\times0.357\times0.5$ mm$^3$ resolution datasets are shown. Improvements in the higher-resolution ofMRI images were even more significant. This is because high-resolution images are more sensitive to motion due to smaller voxel size and a lower SNR.

We next compared the time-series and the corresponding Fourier coefficients for the datasets with the activation maps shown in FIG. 53. The time-series was calculated for several regions of interest (ROI) that show significant activity. For example, for the $0.5\times0.5\times0.5$ mm$^3$ resolution motor cortex stimulated dataset, we selected two ROIs: one in the motor cortex and one in the thalamus. For the $0.375\times0.375\times0.5$ mm$^3$ hippocampus-stimulated dataset, one ROI in the hippocampus was selected. For each region, the common activated voxels from before and after the corrections were chosen for unbiased comparison. In FIG. 54, the time-series from all three ROIs show significantly reduced deviations from the 6-cycle curve after the corrections. Such a reduction of noise in the time-series is also reflected well in the increase of the 6-cycle frequency component in the Fourier coefficients.

In order to evaluate the quality of the proposed motion correction algorithm more quantitatively, the LSE cost function value of the corrected and uncorrected ofMRI images are plotted in FIG. 56. The CR cost function value showed similar and indistinguishable results. In FIG. 56a, before correction, the cost function values for the $0.5\times0.5\times03$ mm$^3$ resolution ofMRI dataset fluctuated randomly depending on the scanner drift. After applying our proposed motion correction, the cost function values were significantly reduced, all collapsing into a single line. In FIG. 56f, two of the nine $0.357\times0.357\times0.5$ mm$^3$ resolution time-series datasets showed a particularly large motion at around 90 s. After correction with our proposed motion correction method, the cost function value difference between consecutive time-series images was significantly reduced; the value remained a small constant over all scans except the large-motion frames. The large motion cannot be corrected because the motion blurred the spiral scanned ofMRI image heavily and the image cannot be fully recovered. Thus, in the activation analysis result shown above, the scan with large motion is excluded. For all corrected data, the remaining cost difference after correction is mainly dependent on noise. We also tested the performance of FSL MCFLIRT and SPM for comparison. As shown in FIG. 56b-e, FSL MCFLIRT and SPM successfully corrected all the scanner drift in all resolutions. However, in FIG. 56g-j, FSL MCFLIRT was trapped into a local minima at $2\times2\times3.66$ mm$^3$ and $4\times4\times7.33$ mm$^3$ resolutions. At $4\times4\times7.33$ mm$^3$ resolution, it fails to correct images after the abrupt motion. This result is consistent with our robustness test and shows FSL MCFLIRT is less reliable compared to our algorithm.

Conclusions and Discussion

We present a novel fast and robust motion correction method in this paper. GPU computation is utilized in this method to significantly enhance the speed of time-series imaging motion correction and allows more accurate result with high speed making it compatible with real-time applications.

In our method, the two principal components of motion correction, optimization and cost function evaluation, are computed on CPU and GPU respectively. The CPU controls the optimization process and the GPU is designed to be a co-processor for the CPU. Parallel algorithms such as the parallel summation algorithm and the atomic update method are implemented to boost the cost function calculation and overall process. GPU texture is used for hardware interpolation and caching, which also speeds up the correction dramatically. The transfer overhead between the CPU and the GPU is also reduced to only 6 DOF float parameters and a few cost values (23 float cost values for our datasets). With all of these optimizations, the GPU is able to calculate an LSE cost in 116 μs and a CR cost in 922.22 μs, which are respectively 604 and 77 times faster than a CPU-based serial calculation. The cost function optimization is performed on the CPU because it is a conditional and serial process. The cost function is first optimized at the pixel level to avoid local minima introduced by interpolation. After reaching the optimal region, sub-pixel optimization is conducted and a global minimum is obtained.

Upon testing, the optimization process is able to correct $128\times128\times23$ matrix-size 3D images acquired with 130 time points in 3.98 s (as opposed to 856.22 s with a serial CPU method, 215.23 s with FSL MCFLIRT and 75.06 s with SPM) for the LSE-based method and 14.54 s (as opposed to 827.52 s with a serial CPU method, and 153.14 s with FSL MCFLIRT) for the CR-based method. For the LSE method, this fast correction speed implies the possibility of being incorporated into a real-time fMRI system.

The robustness of the parallel motion correction algorithm was also tested and compared with FSL MCFLIRT and SPM. After testing with known motion profile datasets with translation, rotation or abrupt motion, the parallel motion correction algorithm shows consistency and robustness with high speed. Additionally, FSL MCFLIRT show less robustness than our method and SPM.

The motion correction method was then tested with several ofMRI datasets acquired at two different spatial resolutions. After correction, the time-averaged images show dramatic improvement in sharpness and display more structural details. The activation region also becomes larger with higher coherence coefficient values indicating more robust activity detection. For high-resolution ofMRI, the improvement is particularly significant due to its higher sensitivity to motion.

We have also extensively tested our motion correction method on all ofMRI data sets that are routinely acquired in our lab. After several months of testing, we are confident that our motion correction algorithm is able to successfully correct the datasets. We have also implemented the parallel LSE motion correction module into our real-time ofMRI system under development. The algorithm is able to work accurately within a limited time, and provides significantly improved online analysis results in real time.

REFERENCES

Ansorge, R. E., Sawiak, S. J., Williams, G. B., 2009. Exceptionally Fast non-linear 3D Image Registration using GPUs. 2009 IEEE Nuclear Science Symposium Conference Record, 4088-4094.

Boyd, S. P., Vandenberghe, L., 2004. Convex optimization Cambridge University Press, Cambridge, UK; New York.

Chen, S., Qin, J., Xie, Y., Pang, W., Heng, P., 2009. CUDA-based acceleration and algorithm refinement for volume image registration. 2009 International Conference on Fugure BioMedical Information Engineering, 544-547.

Cheng, Y., Peng, Q., Hou, Z., Aggarwal, M., Zhang, J., Mori, S., Ross, C. A., Duan, W., 2011. Structural MRI detects progressive regional brain atrophy and neuroprotective effects in N171-82Q Huntington's disease mouse model. Neuroimage.

Cox, R. W., 1996. AFNI: software for analysis and visualization of functional magnetic resonance neuroimages. Computers and Biomedical Research 29, 162-173.

Dombeck, D. A., Khabbaz, A. N., Collman, F, Adelman, T L, Tank, D. W., 2007. Imaging large-scale neural activity with cellular resolution in awake, mobile mice. Neuron 56, 43-57.

Eklund, A., Warntjes, M., Andersson, M., 2010. Fast Phase Based Registration for Robust Quantitative MRI. Annual meeting of the International Society for Magnetic Resonance in Medicine.

Engel, S. A., Glover, G. H., Wandell, B. A., 1997. Retinotopic organization in human visual cortex and the spatial precision of functional MRI. Cereb Cortex 7, 181-192.

Friston, K. J., Ashburner, J., Frith, C. D., Poline, J. B., Heather, J. D., 1995. Spatial normalization and registration of images. Human Brain Mapping 3.

Friston, K. J., Jezzard, P., Turner, R., 1994. The analysis of functional MRI time-series Human Brain Mapping 1, 153-171.

Jackson, J., Meyer, C., Nishimura, D. G., Macovski, A., 1991. Selection of a convolution function for fourier inversion using gridding. IEEE Trans Med Imaging 10, 473-478.

Jenkinson, M., Bannister, P., Brady, M., Smith, S., 2002. Improved optimization for the robust and accurate linear registration and motion correction of brain images. Neuroimage 17, 825-841.

Jenkinson, M., Smith, S., 2001. A global optimisation method for robust affine registration of brain images. Med Image Anal 5, 143-156.

Jones, T. B., Bandettini, P. A., Birn, R. M., 2008. Integration of motion correction and physiological noise regression in fMRI. Neuroimage 42, 582-590.

Kirk, D B, Hwu, W.-m. W., 2010. Programming Massively Parallel Processors: A Hands-on Approach.

Maes, F., Collignon, A., Vandermeulen, D., Marchal, G., Suetens, P., 1997. Multimodality image registration by maximization of mutual information. IEEE Transactions on Medical Imaging 16, 187-198.

Nvidia, 2011. Nvidia CUDA C programming guide Ver 3.2.

Pluim, J. P. W., Maintz, J. B. A., Viergever, M. A., 2003. Mutual-information-based registration of medical images: a survey. IEEE Transactions on Medical Imaging 22, 986-1004.

Press, W. H., Teukolsky, S. A., Veterling, W. T., Flannery, B. P., 2007. Numerical Recipes (3rd Edition).

Roche, A., Malandain, G, Pennec, X., Ayache, N., 1998. The correlation ratio as a new similarity measure for multimodal image registration. Proceedings of the Medical Image Computing and Computer Assisted Intervention 1998 1496, 1115-1124.

Ruijters, D., Romeny, B. M. t. H., Suetens, P., 2008. Efficient GPU-Based Texture Interpolation using Uniform B-Splines. Journal of Graphics, GPU, & Game Tools 13, 61-69.

Scholvinck, M. L., Maier, A., Ye, F. Q., Duyn, J. H., Leopold, D. A., 2010. Neural basis of global resting-state fMRI activity. Proc Natl Acad Sci USA 107, 10238-10243.

Shams, R., Kennedy, R. A., 2007. Efficient histogram algorithms for NVIDIA CUDA compatible devices. Proceeding of International Conference on Signal Processing and Communications Systems (ICSPCS) 2007, 418-422.

Smith, S., Bannister, P., Beckmann, C, Brady, M., Clare, S., Flitney, D., Hansen, P., Jenkinson, M., Leibovici, D., Ripley, B., Woolrich, M., Zhang, Y., 2001. FSL: new tools for functional and structural brain image analysis. Seventh Int. Conf. on Functional Mapping of the Human Brain.

Stone, S. S., Haldar, J. P., Tsao, S. C., Hwu, W.-m. W., Liang, Z.-P., Sutton, B. P., 2008. Accelerating Advanced MRI reconstructions on GPUs. Journal of Parallel and Distributed Computing 68, 1307-1318.

Studholme, C., Hill, D. L. G., Hawkes, D. J., 1995. Multiresolution voxel similarity measures for MR-PET registration. Proceedings of Information Processing in Medical Imaging, Brest, France, pp. 287-298.

Studholme, C., Hill, D. L. G., Hawkes, D. J., 1999. An overlap invariant entropy measure of 3D medical image alignment. Pattern Recognition 32, 71-86.

Viola, P., Wells, W. M., 1997. Alignment by maximization of mutual information. International Journal of Computer Vision 24, 137-154.

Woods, R. P., Cherry, S. R., Mazziotta, J. C., 1992. Rapid automated algorithm for aligning and reslicing PET images. Journal of Computer Assisted Tomography 16, 620-633.

Woods, R. P., Grafton, S. T., Holmes, C. J., Cherry, S. R., 1998a. Automated image registration: I. General methods and intrasubject, intramodality validation. Journal of Computer Assisted Tomography 22, 139-152.

Woods, R. P., Grafton, S. T., Watson, J. D. G., Sicotte, N. L., J. C., M., 1998b. Automated image registration: II. Intersubject validation of linear and nonlinear models. Journal of Computer Assisted Tomography 22, 153-165.

Woods, R. P., Mazziotta, J. C., Cherry, S. R., 1993. MRI-PET registration with automated algorithm. Journal of Computer Assisted Tomography 17, 536-546.

Yeo, B. T., Sabuncu, M. R., Vercauteren, T., Holt, D. J., Amunts, K., Zilles, K., Golland, P., Fischl, B., 2010. Learning task-optimal registration cost functions for localizing cytoarchitecture and function in the cerebral cortex. IEEE Trans Med Imaging 29, 1424-1441.

Table 1. Speed comparison of CPU-based and GPU-based parallel motion correction algorithms using LSE and CR as cost functions. In this table, the CPU method uses only single thread and basic calculation method. The comparison shows the difference between serial CPU method and proposed massively multithreading GPU method. Parallel computation on the GPU speeds up the LSE cost calculation for a single 3D image by a factor of 604.03 and optimization for a single 3D image, and the 4D time-series are sped up by a factor of 215.24. CR cost calculation for a single 3D image is sped up by a factor of 77.63 and optimization for a single 3D image, and the 4D time-series are sped up by a factor of 56.92. The speed of the CPU-based CR algorithm (71590 μs) is almost the same as LSE algorithm (70320 μs). This is because the majority of CPU time is spent on image traversing for CPU-based algorithms.

TABLE 1

|     |                              | CPU           | GPU           | Speedup Factor |
| --- | ---------------------------- | ------------- | ------------- | -------------- |
| LSE | cost calc./3D image          | 70320 (μs)    | 116.34 (μs)   | 604.43         |
|     | optimization/3D image        | 6586.33 (ms)  | 30.60 (ms)    | 215.24         |
|     | motion corr./4D time-series  | 856.22 (s)    | 3.98 (s)      | 215.24         |
| CR  | cost calc./3D image          | 71590 (μs)    | 922.22 (μs)   | 77.63          |
|     | optimization/3D image        | 6365.53 (ms)  | 111.83 (ms)   | 56.92          |
|     | motion corr./4D time-series  | 827.52 (s)    | 14.54 (s)     | 56.92          |

TABLE 2

|                              | LSE time(s) | CR time(s) |
| ---------------------------- | ----------- | ---------- |
| GPU Parallel Motion Corr.    | 3.98        | 14.54      |
| FSL 4 × 4 × 733 mm$^3$       | 215.23      | 153.14     |
| FSL 2 × 2 × 3.66 mm$^3$      | 34.81       | 26.55      |
| FSL 1 × 1 × 1.83 mm$^3$      | 11.2        | 10.06      |
| SPM                          | 75.06       | N/A        |

Table 2. Speed comparison of proposed GPU-based parallel motion correction algorithms, FSL MCFLIRT and SPM for 130 framed 4D image. Since FSL uses fixed 8 mm and 4 mm optimization resolution, we tested FSL at three different labeled resolutions. When calculating at the same matrix size (128×128×23), our GPU-based parallel motion correction speeds up the LSE motion correction process by 54.08 times (3.98 s vs. 215.23 s) compared to FSL MCFLIRT, and 18.86 times (3.98 s vs. 75.06 s) compared to SPM. For CR motion correction, there is 10.53 times (14.54 s-153.14 s) speedup compared to FSL MCFLIRT.

Example 8: Additional Algorithm Testing

The invention describes an approach to motion correction using GPU hardware to increase computation speed. After testing our algorithm with FSL MCFLIRT version 4.1.6 and SPM8, we found our proposed method to be both faster and more robust.

We tested the algorithm with test datasets that have known motion profiles that were designed for robustness test and also with real, unknown motion profile datasets. With the known motion profile datasets, we generated 4 different groups of data. The first dataset has 130 time points with $-\pi/6$ to $-\pi/6$ radian rotation about the z-axis. The second dataset has 130 time points with −20 to 20 voxels translation in x-axis. The third dataset has an abrupt (20 voxels in the x-axis) motion starting at the 30th frame. We also generated 10 different groups of images from 10 different rats, respectively, as the fourth dataset Within each group, there are six images which are rotated from one common image by six different angles. These known-motion datasets are designed to test the algorithm's robustness at different rotations and translations across distinct datasets. For the real, unknown motion profile datasets, we choose two ofMRI datasets scanned at two different resolutions. These datasets are meant to demonstrate the performance of different algorithms in the context of a real experiment.

In the known-motion dataset test, our algorithm and SPM corrected all rotations, translations and abrupt motions in all four test datasets, while FSL was subjected to occasional failure while SPM ran at a much slower speed compared to our proposed method. In the real, unknown-motion dataset test, our algorithm also successfully corrected all motions with high speed. FSL failed in some of the scans showing less robustness. SPM also corrected all real datasets but ran at a much slower speed.

The two most desirable features of a motion correction algorithm are robustness and speed. For the majority of motion correction algorithms and experimental paradigms currently used, the main issue is robustness. However, even in the context of robustness, speed is of critical importance since a fast computation platform allows for more accurate motion correction algorithms to be implemented in a reasonable amount of time. Even in a conventional post-processing paradigm, long motion correction times can be prohibiting. Therefore, ideally, robust algorithms with high speed are desirable. Furthermore, keeping in mind advanced applications such as real-time, interventional imaging, including real-time ofMRI approaches, robustness needs to be obtained with high-speed in the order of tens of milliseconds. Upon extensive testing, our proposed algorithm is both faster and more robust than existing algorithms and is sufficiently fast to support real-time applications.

Our CPU implementation's cost function calculation was run on a single CPU thread and no fast calculation method was implemented. In contrast, FSL MCFLIRT utilizes down-sampled images and SPM8 uses CPU multithreading to speed up the motion correction process. Therefore, the speed of our CPU implementation is expected to be slower than the FSL MCFLIRT and SPM implementations. Our CPU implementation, however, is meaningful since it allows us to calculate the raw speedup factor enabled by parallel computation using the GPU.

Regarding FSL, some might argue that FSL MCFLIRT is able to correct 96×96×40 images with 130 timepoints in 45 s on his/her laptop and 10 s on their desktop. In comparison, our GPU-based parallel motion correction algorithm corrects 128×128×23 matrix-size images with 130 timepoints in 11 s (in a previous version) and 3.98 s in our current version. This is important as FSL MCFLIRT uses fixed resolution optimization at 8 mm and 4 mm (http://www.fmrib.ox.ac.uk/fsl/mcflirt/index.html), which makes comparison between FSL MCFLIRT and our algorithm inappropriate. When FSL MCFLIRT conducts motion correction, it downsamples the images into a smaller matrix to avoid local minimum and to improve speed. The sampling rate also depends on the resolution recorded in the image header. For example, if we label our 128×128×23 images with three different resolutions, say 4×4×7.33 mm$^3$, 2×2×3.66 mm$^3$, and 1×1×1.83 mm$^3$ (if labeled at the real voxel resolution of 0.273×0.273×0.5 mm$^3$, the image will be down-sampled to just a few voxels making the algorithm fail), the resulting matrix size used for motion correction will be 64×64×21, 32×32×10, and 16×16×5, respectively at an 8 mm sampling size, and 128×128×23, 64×64×21, and 32×32×10, respectively, at a 4 mm sampling size. The corresponding correction times in that example are 215 s, 35 s and 11 s, respectively. As can be seen from this example, when the images are labeled as high resolution, FSL uses a small, down-sampled matrix. Therefore, fast speed is achieved on the CPU with FSL at the cost of accuracy with significant down-sampling. If FSL were to use the same matrix size as we do in our implementation, it will be 54 times slower than our current version of the proposed parallel algorithm.

On the other hand, FSL's fixed resolution optimization strategy also has a problem in that the user is given a burden in guessing what resolution should be used. If labeled as a lower resolution, for example, the rate gets significantly slower and it becomes more likely to get trapped in a local minimum (we have seen that this is very possible after testing with many scenarios). If labeled as higher resolution, it is often true that the down-sampled image does not have enough information for registration where the matrix size is too small to successfully correct for motion.

We also compared our GPU-based parallel algorithm with SPM and found SPM is 19 times slower than our method.

Although some studies have been reported on GPU-based image registration, they are not designed to speed up time series image registration with real-time capability, and few report the robustness of their algorithm. Our GPU based parallel method is optimized (both the optimization algorithm and the GPU calculation) for time series image registration. Tests with different datasets acquired from several experiments show both high speed and robustness.

As the reviewer notes, the reason why we chose the frequency analysis was to avoid assuming a particular form for the HRF. We continue to use the frequency analysis since many of our experiments find distinct HRF's depending on the circuitry and temporal encoding. From the perspective of motion correction, the most accurate way to compare the time series and its quality would be to compare the time series of the same set of active voxels and also to visually inspect the resulting activation maps. The time series before and after correction were calculated from the same voxels that were active before the motion correction while the activation map was created with frequency analysis and the same threshold. This way, the raw time series and how it is corrected can be properly observed while the quality of correction in the spatial dimension can be judged with the activation map.

Plots tracing the motion of the images were also made. For the lower resolution cortex stimulation dataset, see FIG. 57. For the higher resolution thalamus stimulation dataset, see FIG. 58.

Since our precision is 0.1 voxels for translation and $\pi/1000$ (0.18 degrees) for rotation, there are small glitches observed in the estimated motion of the image. For translation precision, 0.1 voxels was selected as a proper step since higher precision did not make significant differences in improving image quality and activation maps upon testing. For rotation, the required precision is higher since the outermost voxels (64 voxels for a 128×128 image) from center will be significantly affected if the precision is low. This is because the actual shift due to a rotation angle at each location is dependent on its radius from the center. Therefore, to make sure the outermost voxel is within acceptable shift error, we set the rotation precision to be $\pi/1000$ (0.18 degrees), which will make the outermost voxel within 0.2 voxels' precision ($64 \times \pi/1000 = 0.2$). For this dataset, there is no obvious rotation, while it shows x- and y-axis translations. The x-axis motion here is more like scanner and/or a small animal position drift, which cannot be fully avoided in a realistic experiment setup.

There is some z-axis rotation in this dataset, with very large x- and y-axis translations. The translations are more likely to be due to the motion of the animal One reason to believe so is the abrupt motion in the first scan, which blurred the image. Due to the light anesthesia and optogenetic stimulation, motion is very common in ofMRI scans.

In our ofMRI experiments, motion is common even for anesthetized animals since we use light anesthesia. The isoflurane level is usually set around ~1.3%. In addition to the light anesthesia, the optogenetic stimulation also has some impact on the animal generating motion, since it causes certain neural circuits to become activated, such as those governing aspects of arousal or movement. Scanner phase drift, which is hard to avoid, also causes the images to be shifted across time. We tested our motion correction algorithm on datasets with both known and unknown motion profile. Upon both quantitative and visual inspection, all datasets are properly motion corrected. We also compared our algorithm with existing popular software packages. The comparison shows our algorithm is significantly faster and more robust.

ofMRI is a novel technology, which can help scientists analyze brain circuits by using optogenetic stimulation as input, and fMRI readout as output. The present finds use in a real-time ofMRI system, and can be used for online brain circuit analysis and debugging. Due to the light anesthesia, optogenetic stimulation, and equipment imperfections such as scanner phase drift, image misregistration/motion is common in ofMRI experiments. Therefore, in order to enable real-time ofMRI, a rapid and robust motion correction algorithm is required. Currently existing popular software packages such as FSL and SPM cannot be used for the real-time applications because they are mainly designed for offline data processing. Researchers need to spend a large amount of time on data format conversion and the software itself requires long processing time. With our algorithm, we are able to correct our 3D images in ~30 ms, which is much faster than existing packages and is capable of real-time motion correction. The robustness test in comparison with existing packages also show that our method is more robust.

Those skilled in the art will recognize, or be able to ascertain using no more than routine experimentation, many equivalents to the specific embodiments of the invention described herein. Such equivalents are intended to be encompassed by the appended claims.

All publications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the appended claims.

The invention claimed is:

1. A method for cell transplantation design for a living organism, the method comprising:
    selecting a target cell population including stem cells at various developmental stages and types;
    modifying a function of the target cell population by causing cells of the target cell population to express light responsive molecules that can be controlled with targeted light delivery;

transplanting a portion of cells expressing light responsive molecules into a living organism during a cell transplantation;

measuring nervous system responses to targeted energy control using functional magnetic resonance imaging (fMRI), wherein the measuring is conducted via a parallel processing architecture having one or more processors and memory storing instructions defining a plurality of threads for performing respective processes, and the measuring includes:

performing, by a first thread of the plurality of threads, direct circuit current (DC) offset correction;

performing, by a second thread of the plurality of threads, data reconstruction; and performing, by a third thread of the plurality of threads, data display tasks; and determining at least one of neural circuit activity locations and neural circuit activity timings in the living organism.

2. The method of claim 1, further comprising profiling the cells based on differences in measured responses derived from a normal living organism and a diseased living organism to provide a phenotype of disease.

3. The method of claim 1, wherein a cell transplantation location or type is selected to achieve normal brain function.

4. The method of claim 1, wherein the targeted energy control is applied at least one time before, during and after the cell transplantation to improve therapeutic outcome.

5. The method of claim 1, wherein measurements are analyzed for resting connectivity and are used to interpret clinical resting state functional neuroimaging data.

6. The method of claim 1, wherein the targeted light delivery includes delivering blue light of approximately 470 nm or yellow light of approximately 580 nm.

7. The method of claim 1, wherein the light responsive molecules include Channelrhodopsin-2 (ChR2) or halorhodopsin (NpHR).

8. The method of claim 1, wherein the parallel processing architecture includes closed-loop control.

9. The method of claim 1, wherein the measuring is conducted with a high-resolution using a parallel compressed sensing reconstruction.

10. The method of claim 1, wherein performing the data reconstruction includes:

performing gridding, then fast-Fourier transforms (FFTs), and then FFT shifts on data obtained from the measuring, wherein the gridding, FFTs, and FFT shifts are performed in parallel on different portions of the data.

11. The method of claim 10, wherein performing the data reconstruction includes performing motion correction.

12. The method of claim 11, wherein performing the motion correction includes:

evaluating in parallel a plurality of cost functions; and optimizing the plurality of cost functions.

13. The method of claim 12, wherein:

the plurality of cost functions is evaluated in parallel using a graphical processing unit; and the plurality of cost functions is optimized using a central processing unit.

14. The method of claim 12, wherein a cost function of the plurality of cost functions comprises a least square error and a correlation ratio.

15. The method of claim 14, wherein evaluating in parallel the plurality of cost functions includes evaluating the least square error, including:

calculating in parallel a plurality of single voxel errors; and summing in parallel the plurality of single voxel errors.

16. The method of claim 14, wherein the correlation ratio comprises a plurality of joint probability distribution functions summed in parallel.

17. The method of claim 10, wherein performing the gridding comprises:

searching for spiral samples within a plurality of gridding kernels;

convolving the spiral samples found in individuals ones of the plurality of gridding kernels with a weighted kernel function; and summing results of the convolving from the plurality of gridding kernels.

18. The method of claim 17, further comprising presorting the spiral samples.

19. The method of claim 17, wherein the searching for spiral samples for each of the plurality of gridding kernels is performed in parallel by separate threads of a processor.

* * * * *